US012544426B2

(12) United States Patent
Kley et al.

(10) Patent No.: US 12,544,426 B2

(45) Date of Patent: Feb. 10, 2026

(54) COMBINATION THERAPY WITH CD13-TARGETED CHIMERIC PROTEINS OR CHIMERIC PROTEIN COMPLEXES

(71) Applicants: Orionis Biosciences, Inc., Waltham, MA (US); Orionis Biosciences BV, Zwijnaarde (BE); VIB VZW, Ghent (BE); Universiteit Gent, Ghent (BE)

(72) Inventors: Nikolai Kley, Waltham, MA (US); Jan Tavernier, Zwijnaarde (BE); Leander Huyghe, Beernem (BE)

(73) Assignees: Orionis Biosciences, Inc., Waltham, MA (US); Orionis Biosciences BV, Zwijnaarde (BE); VIB VZW, Ghent (BE); Universiteit Gent, Ghent (BE)

( * ) Notice: Subject to any disclaimer, the term of this patent is extended or adjusted under 35 U.S.C. 154(b) by 1087 days.

(21) Appl. No.: 17/620,329

(22) PCT Filed: Jun. 18, 2020

(86) PCT No.: PCT/US2020/038373
§ 371 (c)(1),
(2) Date: Dec. 17, 2021

(87) PCT Pub. No.: WO2020/257412
PCT Pub. Date: Dec. 24, 2020

(65) Prior Publication Data

US 2022/0249609 A1 Aug. 11, 2022

Related U.S. Application Data

(60) Provisional application No. 62/863,447, filed on Jun. 19, 2019.

(51) Int. Cl.

| | |
|---|---|
| ***A61P 35/00*** | (2006.01) |
| ***A61K 9/00*** | (2006.01) |
| ***A61K 9/1271*** | (2025.01) |
| ***A61K 31/704*** | (2006.01) |
| ***A61K 38/17*** | (2006.01) |
| ***A61K 38/19*** | (2006.01) |
| ***A61K 38/21*** | (2006.01) |
| *A61K 39/00* | (2006.01) |

(52) U.S. Cl.
CPC ........ *A61K 38/1774* (2013.01); *A61K 9/0019* (2013.01); *A61K 9/1271* (2013.01); *A61K 31/704* (2013.01); *A61K 38/191* (2013.01); *A61K 38/217* (2013.01); *A61P 35/00* (2018.01); *A61K 2039/505* (2013.01)

(58) Field of Classification Search
None
See application file for complete search history.

(56) References Cited

U.S. PATENT DOCUMENTS

| | | | |
|---|---|---|---|
| 5,914,254 | A | 6/1999 | Mascarenhas et al. |
| 7,993,636 | B2 | 8/2011 | Mayumi et al. |
| 8,450,460 | B2 | 5/2013 | Hill et al. |
| 8,980,267 | B2 | 3/2015 | Grewal et al. |
| 9,139,634 | B2 | 9/2015 | Morrison et al. |
| 9,534,056 | B2 | 1/2017 | Grewal et al. |
| 9,724,390 | B2 | 8/2017 | Gurney |
| 2010/0172868 | A1 | 7/2010 | Morrison et al. |
| 2010/0297076 | A1 | 11/2010 | Morrison et al. |
| 2011/0081341 | A1 | 4/2011 | Honjo et al. |
| 2011/0104112 | A1 | 5/2011 | Morrison et al. |
| 2011/0224407 | A1 | 9/2011 | Langer et al. |
| 2011/0274658 | A1 | 11/2011 | Silver et al. |
| 2012/0288477 | A1 | 11/2012 | Wang |
| 2013/0183298 | A1 | 7/2013 | Le et al. |
| 2014/0348789 | A1 | 11/2014 | Tavernier et al. |
| 2015/0139951 | A1 | 5/2015 | Grewal et al. |

FOREIGN PATENT DOCUMENTS

| | | | | |
|---|---|---|---|---|
| WO | WO 91/02754 | A1 | 3/1991 | |
| WO | WO 03/033720 | A2 | 4/2003 | |
| WO | WO 03/092737 | A1 | 11/2003 | |
| WO | WO 2006/053883 | A1 | 5/2006 | |
| WO | WO 2006/115800 | A2 | 11/2006 | |
| WO | WO 2008/014612 | A1 | 2/2008 | |
| WO | WO 2008/124086 | A2 | 10/2008 | |
| WO | WO 2009/003145 | A1 | 12/2008 | |
| WO | WO 2009/039409 | A1 | 3/2009 | |
| WO | WO 2010/036918 | A1 | 4/2010 | |
| WO | WO 2010/066740 | A1 | 6/2010 | |
| WO | WO 2011/020783 | A2 | 2/2011 | |
| WO | WO 2011/029870 | A1 | 3/2011 | |
| WO | WO 2012/170072 | A1 | 12/2012 | |
| WO | WO 2013/059885 | A2 | 5/2013 | |
| WO | WO 2013/107791 | A1 | 7/2013 | |
| WO | WO 2013/134138 | A1 | 9/2013 | |
| WO | WO 2015/007520 | A1 | 1/2015 | |
| WO | WO 2015/007536 | A2 | 1/2015 | |
| WO | WO 2015/007542 | A1 | 1/2015 | |
| WO | WO 2015/007903 | A1 | 1/2015 | |
| WO | WO-2017134306 | A1 * | 8/2017 | ............. A61K 38/00 |
| WO | WO 2018/144999 | A1 | 8/2018 | |

OTHER PUBLICATIONS

Cho et al. (Seminars in Cancer Biology 59 (2019) 175-186, published online Jun. 27, 2019). (Year: 2019).*
Calcinotto et al. (The Journal of Immunology, 2012, 188: 2687-2694). (Year: 2012).*
Fuchs et al. (J Interferon Cytokine Res. Apr. 2013;33(4):211-25). (Year: 2013).*
Haring et al. (The Journal of Immunology, 2005, 174: 6791-6802). (Year: 2005).*

(Continued)

*Primary Examiner* — Zachary S Skelding
(74) *Attorney, Agent, or Firm* — Morgan, Lewis & Bockius LLP

(57) ABSTRACT

The present invention relates, in part, to chimeric protein or chimeric protein complex comprising a CD13 targeting moiety and a signaling agent (e.g., without limitation TNF or IFN-γ) and methods of treatment using such compositions.

11 Claims, 52 Drawing Sheets

Specification includes a Sequence Listing.

(56) References Cited

OTHER PUBLICATIONS

Acres, et al., "Fusokine Interleukin-2/Interleukin-18, a Novel Potent Innate and Adaptive Immune Stimulator with Decreased Toxicity," Cancer Res., vol. 65, No. 20, pp. 9536-9546, 2005.
Baba, et al., "Identification of CCR6, the Specific Receptor for a Novel Lymphocyte-Directed CC Chemokine LARC," The Journal of Biological Chemistry, vol. 272, No. 23, pp. 14893-14898, 1997.
Barbara, J A, et al., "Dissociation of TNF-alpha cytotoxic and proinflammatory activities by p55 receptor- and p75 receptor-selective TNF-alpha mutants," EMBO Journal, vol. 13, No. 4, pp. 843-850, 1994.
Bork, et al., "Go hunting in sequence databases but watch out for the traps." Trends in Genetics, vol. 12, pp. 425-427, 1996.
Bork, "Powers and Pitfalls in Sequence Analysis: The 70% Hurdle", Genome Research, vol. 10, pp. 398-400, 2000.
Boschert, et al., "Single chain TNF derivatives with individually mutated receptor binding sites reveal differential stoichiometry of ligand receptor complex formation for TNFR1 and TNFR2," Cellular Signaling, vol. 22, pp. 1088-1096, 2010.
Bremer, et al., "Superior Activity of Fusion Protein scFvRit:sFasL over Cotreatment with Rituximab and Fas Agonists," Cancer Res., vol. 68, No. 2, pp. 597-604, 2008.
Camacho, et al., "Structure of an Interleukin-1β Mutant With Reduced Bioactivity Shows Multiple Subtle Changes in Conformation That Affect Protein-Protein Recognition," Biochemistry, vol. 32, No. 34, pp. 8749-8757, 1993.
Cauwels, et al., "Delivering Type I Interferon to Dendritic Cells Empowers Tumor Eradication and Immune Combination Therapies," Cancer Res, vol. 78, No. 2, pp. 463-474, Nov. 29, 2017.
Cauwels, et al., "A safe and highly efficient tumor-targeted type I interferon immunotherapy depends on the tumor microenvironment," Oncoimmunology, vol. 7, No. 3, 13 pages, 2018.
Coulstock, et al., "Liver-Targeting of Interferon-Alpha with Tissue Specific Domain Antibodies," PLOS One, vol. 8, No. 2, pp. 1-11, 2013.
De Bruyn, et al., "Antibody-Based Fusion Proteins to Target Death Receptors in Cancer," Cancer Letters, vol. 332, pp. 175-183, 2013.
Deffar, et al., "Nanobodies—The New Concept in Antibody Engineering" African Journal of Biotechnology, vol. 8, No. 12, pp. 2645-2652, 2009.
Dijkmans, et al., "Murine Interferon-γ Interleukin-1 Fusion Proteins Used as Antigens for the Generation of Hybridomas Producing Monoclonal Anti-Interleukin-1 Antibodies," Cytokine, vol. 3, No. 2, pp. 134-140, 1991.
Dimitrov, "Engineered CH2 Domains (Nanoantibodies)," mAbs, Landes Bioscience, vol. 1, No. 1, pp. 26-28, 2009.
Frey, et al., "Antibody-Based Targeting of Interferon-Alpha to the Tumor Neovasculature: A Critical Evaluation," ntegrative Biology, vol. 3, pp. 468-478, 2011.
Garcin, et al., "High Efficiency cell-specific targeting of cytokine activity," Nature Communications, vol. 5, No. 8, 9 pages, 2014.
Garlanda, et al., "The Interleukin-1 Family: Back to the Future", Immunity, vol. 39, No. 6, pp. 1003-1018, Dec. 12, 2013.
Holler, et al., "Two Adjacent Trimeric Fas Ligands are Required for Fas Signaling and Formation of a Death-Inducing Signaling Complex," Molecular and Cellular Biology, vol. 23, No. 4, pp. 1428-1440, 2003.
Huang, et al., "A Trimeric Anti-HER2/neu ScFv and Tumor Necrosis Factor-[alpha] Fusion Protein Induces HER2/Neu Signaling and Facilitates Repair of Injured Epithelia," The Journal of Pharmacology and Experimental Therapeutics, vol. 316, No. 3, pp. 983-991, 2006.
International Search Report and Written Opinion in PCT/EP2013/050787, dated Jun. 14, 2013.
International Search Report and Written Opinion PCT/EP2014/063976, dated Oct. 29, 2014.
International Search Report and Written Opinion PCT/EP2014/064227, dated Feb. 5, 2015.
International Search Report and Written Opinion PCT/EP2014/064283, dated Oct. 1, 2014.
International Search Report and Written Opinion PCT/EP2014/065554, dated Oct. 30, 2014.
Loetscher, et al., "Human Tumor Necrosis Factor α (TNFα) Mutants with Exclusive Specificity for the 55-kDa or 75-kDa TNR Receptors," The Journal of Biological Chemistry, vol. 268, No. 35, pp. 26350-26358, 1993.
Krippner-Heidenreich, et al., "Single-Chain TNF, a TNF Derivative with Enhanced Stability and Antitumoral Activity," The Journal of Immunology, vol. 180, pp. 8176-8183, 2008.
Masci, et al., "New and Modified Interferon alfas: Preclinical and Clinical Data," Current Oncology Reports, vol. 5, pp. 108-113, 2003.
Ngo, et al., "Computational Complexity, Protein Structure Prediction, and the Levinthal Paradox. The Protein Folding Problem and Tertiary Structure Prediction", Edited by: Mertz et al., (Birkhauser, Boston), (1994), pp. 492-495.
Pan, et al., "Mutation of the IFNAR-1 Receptor Binding Site of Human IFN-α2 Generates Type I IFN Competitive Antagonists," Biochemistry, vol. 47, pp. 12018-12027, 2008.
Patris, et al., "Nanoimmunoassay onto a screen printed electrode for HER2 breast cancer biomarker determination", Talanta, vol. 130, pp. 164-170, 2014.
Penafuerte, et al., "The Human Ortholog of Granulocyte Macrophage Colony-Stimulating Factor and Interleukin-2 fusion Protein Induces Potent Ex Vivo Natural Killer Cell Activation and Maturation," Cancer Res, vol. 69, No. 23, pp. 9020-9028, 2009.
Rafei, et al., "A MCP1 Fusokine with CCR2-Specific Tumoricidal Activity," Molecular Cancer, vol. 10, No. 121, pp. 1-11, 2011.
Rafei, et al., "An Engineered GM-CSF-CCL2 Fusokine Is A Potent Inhibitor of CCR2-Driven Inflammation as Demonstrated in a Murine Model of Inflammatory Arthritis," The Journal of Immunology, vol. 183, pp. 1759-1766, 2009.
Roberts, et al., "Systemic use of tumor necrosis factor alpha as an anticancer agent," Oncotarget, vol. 2, No. 10, pp. 739-751, 2011.
Roisman, et al., "Structure of the Interferon-Receptor Complex Determined by Distant Constraints from Double Mutant Cycles and Flexible Docking," PNAS, vol. 98, No. 23, pp. 13231-13236, 2001.
Rovero, et al., "Insertion of the DNA for the 163-171 Peptide of IL 1 II Enables a DNA Vaccine Encoding p185$^{neu}$ to inhibit Mammary Carcinogenesis in Her-2/neu Transgenic BALB/c Mice," Gene Therapy, vol. 8, pp. 447-452, 2001.
Schutyser, et al., "The CC Chemokine CCL20 and its Receptor CCR6," Cytokine & Growth Factor Reviews, vol. 14, pp. 409-426, 2003.
Vaneycken, et al., "Preclinical Screening of Anti-HER2 Nanobodies for Molecular Imaging of Breast Cancer", The FASEB Journal, vol. 25, pp. 2433-2446, 2011.
Weber, et al., "Single Amino Acid Changes that Render Human IFN-α2 Biologically Active on Mouse Cells," The EMBO Journal, vol. 6, No. 3, pp. 591-598, 1987.
Wells, "Additivity of Mutational Effects in Proteins." Biochemistry, vol. 29, No. 37, pp. 8509-8517, 1990.
Wesolowski, et al., "Single Domain Antibodies: Promising Experimental and Therapeutic Tools in Infection and Immunity", Med Microbiol Immunol. vol. 198, pp. 157-174, 2009.
Zhang, et al., "Site-directed Mutational Analysis of Human Tumor Necrosis Factor-α Receptor Binding Site and Structure-Functional Relationship," The Journal of Biological Chemistry, vol. 267, No. 33, pp. 24069-24075, Nov. 25, 1992.
Curnis, et al., "Enhancement of tumor necrosis factor alpha antitumor immunotherapeutic properties by targeted delivery to aminopeptidase N ($CD_{13}$)," Nat Biotechnol. vol. 18, No. 11, Abstract.
International Search Report & Written Opinion PCT Application No. PCT/US20/038373, dated Nov. 17, 2020, 12 pages.

* cited by examiner

Fig. 14E
Fig. 14F
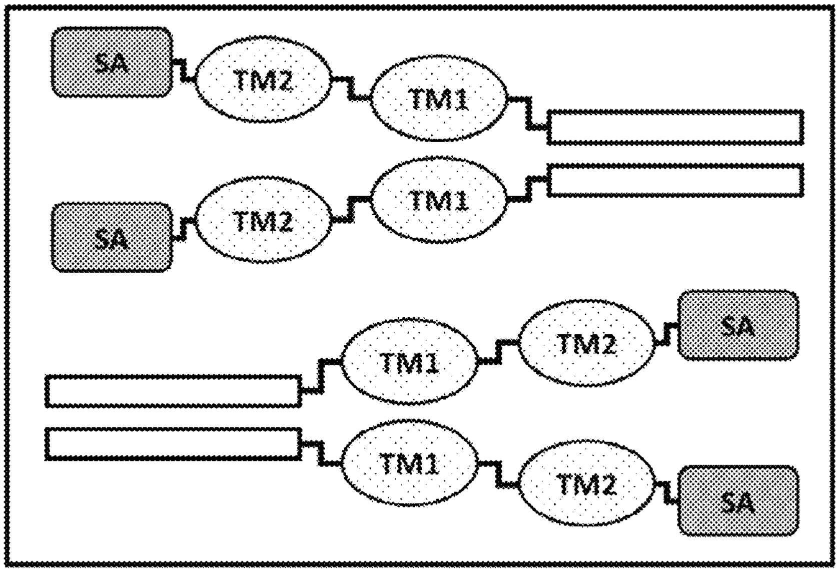
Fig. 14G
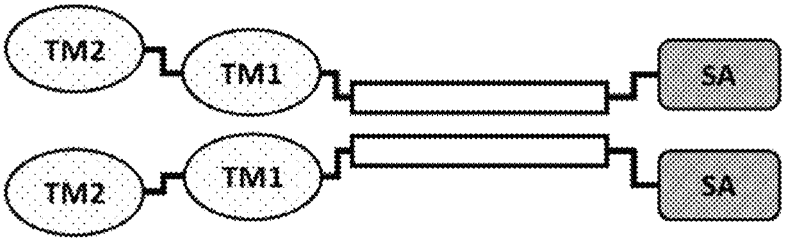
Fig. 14H
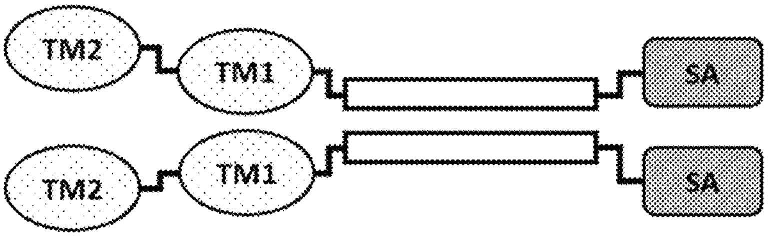

COMBINATION THERAPY WITH CD13-TARGETED CHIMERIC PROTEINS OR CHIMERIC PROTEIN COMPLEXES

RELATED APPLICATIONS

This application is a National Stage Entry of PCT/US20/38373, filed Jun. 18, 2020, which claims the benefit of U.S. Provisional Patent Application No. 62/863,447, filed Jun. 19, 2019, the entire disclosure of which is hereby incorporated by reference in its entirety.

FIELD

The present invention relates, in part, to CD13-targeted chimeric proteins or chimeric protein complexes and their use as therapeutic agents in combination therapy.

DESCRIPTION OF THE TEXT FILE SUBMITTED ELECTRONICALLY

The contents of the text file submitted electronically herewith are incorporated herein by reference in their entirety: a computer readable format copy of the Sequence Listing (filename: ORN-047 Sequence Listing ST25.txt; date recorded: Dec. 17, 2021; file size: 231,649 bytes).

BACKGROUND

Cancer is a global health challenge that causes nearly 7 million deaths each year worldwide and which has, to date, proven largely untreatable despite major advances in medicine. Frustratingly, cancers appear to develop strategies to evade immune detection and destruction thereby sidestepping the body's main protection against the disease. Increased expression of various hydrolytic enzymes like peptidases, esterases, and proteases has been described in several types of human malignancies, especially those characterized by fast-growing and aggressive phenotypes. One of the peptidases involved in cancer is aminopeptidase N (also known as CD13), a $Zn^{2+}$ dependent membrane-bound ectopeptidase that degrades preferentially proteins and peptides with a N-terminal neutral amino acid.

CD13 is highly expressed in multiple human cancers. Its expression is induced and particularly pronounced in endothelial cells of the tumor neovasculature compared to normal vasculature. It can also be expressed on some tumor cells, e.g. from epithelial origin. Multiple regulatory functions have been ascribed to CD13, including regulation of endothelial cell morphology, formation of neovascular blood vessels (neoangiogenesis), cell differentiation, proliferation and motility. Therefore, CD13 is both a marker and a functional regulator of the tumor microenvironment. There remains a need for novel therapeutic agents that can effectively target cancers.

By virtue of its function and, in particular, its disease-associated expression profiles, CD13 represents an intriguing target for various strategies aimed at inhibiting cancer growth and cancer immunoregulation. We describe novel strategies and therapeutic agents targeting CD13 to modulate endothelial cell functions and various processes associated with tumor neovasculature and cancer growth.

Accordingly, there remains a need for novel therapeutic agents that can effectively target cancers, including CD13-driven cancers.

SUMMARY

In various aspects, the present technology relates to therapeutic uses of CD13-targeted chimeric proteins or chimeric protein complexes having at least one targeting moiety that specifically binds to CD13 and at least one signaling agent that is a tumor necrosis factor (TNF). In various embodiments, the TNF signaling agent may be modified to attenuate activity. In some embodiments, the present CD13-targeted chimeric proteins or chimeric protein complexes may directly or indirectly recruit an immune cell to a site of action (such as, by way of non-limiting example, the tumor microenvironment).

In some aspects, the present technology relates to therapeutic uses of CD13-targeted chimeric proteins or chimeric protein complexes having at least one targeting moiety that specifically binds to CD13 and at least one signaling agent that is an interferon (IFN) or a modified form thereof. In various embodiments, the IFN signaling agent may be modified to attenuate activity. In one embodiment, the interferon is IFN-γ or a modified form thereof.

In various aspects, the present technology relates to the co-administration of the CD13-targeted chimeric proteins or chimeric protein complexes with at least one other therapeutic agent. In some embodiments, the other therapeutic agent is a CD8-targeted chimeric protein or chimeric protein complex having at least one targeting moiety that specifically binds to CD8 and at least one signaling agent that is an interferon (IFN) or a modified form thereof. In various embodiments, the IFN signaling agent may be modified to attenuate activity. In some embodiments, the other therapeutic agent is another CD13-targeted chimeric protein or chimeric protein complex having at least one targeting moiety that specifically binds to CD13 and at least one signaling agent that is an interferon (IFN) or a modified form thereof. In various embodiments, the IFN signaling agent may be modified to attenuate activity. In one embodiment, the interferon is IFN-γ or a modified form thereof.

In some embodiments, the at least one other therapeutic agent is one or more agents selected from a phosphoinositide-3-kinase 9 (PI3K) inhibitor, anthracycline, and SMAC mimetic. In some embodiments, the anthracycline is a liposomal anthracycline.

In various embodiments, the co-administration of CD13-targeted chimeric proteins or chimeric protein complexes with at least one other therapeutic agent is useful in the treatment of various diseases or disorders such as cancer, immune disorders, and other diseases and disorders.

In some embodiments, the present invention relates to chimeric protein complexes where the chimeric protein complex includes one or more signaling agents, one or more targeting agents, and one or more fragment crystallizable domains (Fc domains). These Fc-based chimeric protein complexes of the present invention are highly target selective, enable conditional and/or regulated modulation of receptor signaling, and are highly active and/or long-acting active and/or long-acting while eliciting minimal side effects.

BRIEF DESCRIPTION OF DRAWINGS

FIG. 7A: Toxicity of wt sc mTNF and mutant Y86F after injection (T) in naïve C56BU6 mice. First injection was i.v., other injections were i.p. Mean rectal body temperature±SEM and cumulative survival rates are shown (n=4 per group). For continuity of the temperature graphs, dead mice were included with a temperature of 20° C. FIG. 7B: Plasma IL-6 concentrations measured via ELISA. Blood samples were taken 6 hours after i.v. injection of wt sc mTNF or mutant Y86F. ns, non-significant by one-way ANOVA with Bonferroni's multiple comparison test. FIG. 7C: Immunohistochemical staining for PECAM-1 (red), ICAM-1 (green) and DNA (blue) of B16BI6 tumors after p.I. treatment with 7 μg wt mTNF or 50 μg of mCD13-AFR. Scale bar is 50 μm. FIG. 7D: Expression of ICAM-1, E-selectin and VEGF-R2 in B16BI6 tumor 6 h after treatment, by qPCR analysis of whole tumor RNA. Error bars are SEM. ns, non-significant; *, p<0.05; p<0.01; *, p<0.001 by one-way ANOVA with Bonferroni's multiple comparison test. FIG. 7E: Tumor growth and body weight change after daily p.1. injection of 50 μg mCD13-AFR in the B16BI6 melanoma model. The line under the graph represents the treatment period. Tumor growth is shown as mean TSI, error bars are SEM (n=5 per group). *, p<0.001 by two-way ANOVA with Bonferroni's multiple comparison test on day 21.

FIG. 8A and 8B: B16BI6 tumor growth after daily p.1. treatment with 7 μg mTNF, 30 μg hTNF alone or in combination with 10000 IU mIFN-γ in wt C57BL/6 mice (a) or homozygous Flk1 dnIFN-γR transgenic mice. The line under the graph represents the treatment period. Tumor growth is depicted as mean TSI, error bars are SEM (n=5 per group). FIG. 8C: IL-8 concentration in HUVEC supernatant after 24 h stimulation with the indicated concentration of sc hTNF mutant Y87F (Y87F), hCD13-AFR or wt hTNF, alone or in combination with 200 ng/ml hIFN-γ, measured via ELISA. Error bars are SEM. ns, non-significant; p<0.01; *, p<0.001 by one-way ANOVA with Bonferroni's multiple comparison test. FIG. 8D: Schematic representation of AFN-II, consisting of a VHH fused via a 20×GGS linker to an engineered IFN-γ (e-IFN-γ) variant and N-terminal affinity tag. FIG. 8**E: Viability of B16BI6 parental or mCD20-expressing cells after 72 h stimulation with wt mIFN-γ or de18 mutant fused to a BcII10 or mCD20 VHH, in the presence of 60 ng/ml mTNF. Cell viability was measured via an ATP luminescence assay. Each point is the mean of three replicates and error bars are SEM.

FIGS. 9A and 9B: TSI of B16-dnIFN-γR tumor in wt C57BL/6 mice (a) or B16B16 parental tumor in IFN-$\gamma R^{-/-}$ mice (b). In wt mice, the growth rate of a B16-dnIFN-γR tumor was similar to B16B16 parental tumor. Mice were treated daily via p.1. injection of 7 μg mTNF, 30 μg hTNF, or a combination of 30 μg hTNF and 10000 IU mIFN-γ. Error bars are SEM (n=7 per group). The line under the graph represents the treatment period.

FIG. 10A: Cryosections of embryos on day E10.5 were stained with anti-c-Myc Ab, followed by chromogenic detection with Alkaline Phosphatase conjugated anti-mlgG Ab and BCIP/NBT substrate. Nuclei were stained with haematoxylin. Expression was visible in endothelial cells of large veins (v), sinus venosus (sv) and aorta (ao). FIG. 10B: Cryosections of B16B16 tumors inoculated in adult transgenic mice were stained with biotinylated anti-c-Myc Ab and visualised using streptavidin-FITC. Nuclei were stained with DAPI. Tumor endothelial cells showed positive staining. Scale bars are 50 μm.

FIGS. 12A and 12B: Tumor growth, body weight change and rectal body temperature after daily p.1. treatment with mCD13-AFR, mCD13-AFN-II or combination thereof, in the B16BI6 model in C57BL/6 mice (a) or RL model in NSG mice (b).

Tumor growth is shown as mean TSI, error bars are SEM (n=5 per group) (upper panel), or as TSI of individual mice (lower panel). The line under the graph represents the treatment period. FIG. 12C: Immunohistochemical staining for PECAM-1 (red), cleaved Caspase-3 (green) and DNA (blue) of B16BI6 tumors after pi. treatment with 50 μg mCD13-AFR and 23.8 μg mCD13-AFN-II. Scale bar is 100 μm. FIGS. 13A-F, 14A-H, 15A-H, 16A-D, 17A-F, 18A-J, 19A-D, 20A-F, 21A-J, 22A-F, 23A-L, 24A-L, 25A-F, 26A-L, 27A-L, 28A-J, 29A-J, 30A-F, and 31A-F show various non-limiting illustrative schematics of the Fc-based chimeric protein complexes of the present invention. In embodiments, each schematic is a composition of the present invention. Where applicable in the figures, "TM" refers to a "targeting moiety" as described herein, "SA" refers to a "signaling agent" as described herein, ⌐ is an optional "linker" as described herein, the two long parallel rectangles are human Fc domains, e.g. from IgG1, from IgG2, or from IgG4, as described herein and optionally with effector knock-out and/or stabilization mutations as also described herein, and the two long parallel rectangles with one having a protrusion and the other having an indentation are human Fc domains, e.g. from IgG1, from IgG2, or from IgG4 as described herein, with knob-in-hole and/or ionic pair (a/k/a charged pairs, ionic bond, or charged residue pair) mutations as described herein and optionally with effector knock-out and/or stabilization mutations as also described herein.

FIGS. 13A-F show illustrative homodimeric 2-chain complexes. These figures show illustrative configurations for the homodimeric 2-chain complexes.

FIGS. 14A-H show illustrative homodimeric 2-chain complexes with two targeting moieties (TM) (as described herein, more targeting moieties may be present in some embodiments). In embodiments, the position of TM1 and TM2 are interchangeable. In embodiments, the constructs shown in the box (i.e., FIGS. 14G and 14H) have signaling agent (SA) between TM1 and TM2 or between TM1 and Fc.

FIGS. 15A-H show illustrative homodimeric 2-chain complexes with two signaling agents (as described herein, more signaling agents may be present in some embodiments). In embodiments, the position of SA1 and SA2 are interchangeable. In embodiments, the constructs shown in the box (i.e., FIGS. 15G and 15H) have TM between SA1 and SA2 or TM at N- or C-terminus).

FIGS. 16A-D show illustrative heterodimeric 2-chain complexes with split TM and SA chains, namely the TM on the knob chain of the Fc and the SA on hole chain of the Fc.

FIGS. 17A-F show illustrative heterodimeric 2-chain complexes with split TM and SA chains, namely with both TMs on the knob chain of the Fc and with SA on hole chain of the Fc, with two targeting moieties (as described herein, more targeting moieties may be present in some embodiments). In embodiments, the position of TM1 and TM2 are interchangeable. In some embodiments, TM1 and TM2 can be identical.

FIGS. 18A-J show illustrative heterodimeric 2-chain complexes with split TM and SA chains, namely with TM on the knob chain of the Fc and with a SA on the hole chain of the Fc, with two signaling agents (as described herein, more signaling agents may be present in some embodiments). In these orientations and/or configurations, one SA is on the knob chain and one SA is on the hole chain. In embodiments, the position of SA1 and SA2 are interchangeable.

FIGS. 19A-D show illustrative heterodimeric 2-chain complexes with split TM and SA chains, namely the SA on the knob chain of the Fc and the TM on hole chain of the Fc.

FIGS. 20A-F show illustrative heterodimeric 2-chain complexes with split TM and SA chains, namely with SA on the knob chain of the Fc and both TMs on hole chain of the Fc, with two targeting moieties (as described herein, more targeting moieties may be present in some embodiments). In embodiments, the position of TM1 and TM2 are interchangeable. In some embodiments, TM1 and TM2 can be identical.

FIGS. 21A-J show illustrative heterodimeric 2-chain complexes with split TM and SA chains, namely with SA on the knob chain of the Fc and TM on hole chain of the Fc, with two signaling agents (as described herein, more signaling agents may be present in some embodiments). In these orientations and/or configurations, one SA is on the knob chain and one SA is on the hole chain. In embodiments, the position of SA1 and SA2 are interchangeable.

FIGS. 22A-F show illustrative heterodimeric 2-chain complexes with TM and SA on the same chain, namely the SA and TM both on the knob chain of the Fc.

FIGS. 23A-L show illustrative heterodimeric 2-chain complexes with a TM and a SA on the same chain, namely with SA and with TM both on the knob chain of the Fc, with two targeting moieties (as described herein, more targeting moieties may be present in some embodiments). In embodiments, the position of TM1 and TM2 are interchangeable. In some embodiments, TM1 and TM2 can be identical.

FIGS. 24A-L show illustrative heterodimeric 2-chain complexes with a TM and a SA on the same chain, namely with SA and with TM both on the knob chain of the Fc, with two signaling agents (as described herein, more signaling agents may be present in some embodiments). In embodiments, the position of SA1 and SA2 are interchangeable.

FIGS. 25A-F show illustrative heterodimeric 2-chain complexes with TM and SA on the same chain, namely the SA and TM both on the hole chain of the Fc.

FIGS. 26A-L show illustrative heterodimeric 2-chain complexes with a TM and a SA on the same chain, namely with SA and with TM both on the hole chain of the Fc, with two targeting moieties (as described herein, more targeting moieties are present in some embodiments). In embodiments, the position of TM1 and TM2 are interchangeable. In embodiments, TM1 and TM2 can be identical.

FIGS. 27A-L show illustrative heterodimeric 2-chain complexes with a TM and a SA on the same chain, namely with SA and with TM both on the hole chain of the Fc, with two signaling agents (as described herein, more signaling agents may be present in some embodiments). In embodiments, the position of SA1 and SA2 are interchangeable.

FIGS. 28A-J show illustrative heterodimeric 2-chain complexes with two targeting moieties (as described herein, more targeting moieties may be present in some embodiments) and with SA on knob Fc and TM on each chain. In embodiments, TM1 and TM2 can be identical.

FIGS. 29A-J show illustrative heterodimeric 2-chain complexes with two targeting moieties (as described herein, more targeting moieties may be present in some embodiments) and with SA on hole Fc and TM on each chain. In embodiments, TM1 and TM2 can be identical.

FIGS. 30A-F show illustrative heterodimeric 2-chain complexes with two signaling agents (as described herein, more signaling agents may be present in some embodiments) and with split SA and TM chains: SA on knob and TM on hole Fc.

FIGS. 31A-F show illustrative heterodimeric 2-chain complexes with two signaling agents (as described herein, more signaling agents may be present in some embodiments) and with split SA and TM chains: TM on knob and SA on hole Fc.

DETAILED DESCRIPTION

Figure 1:
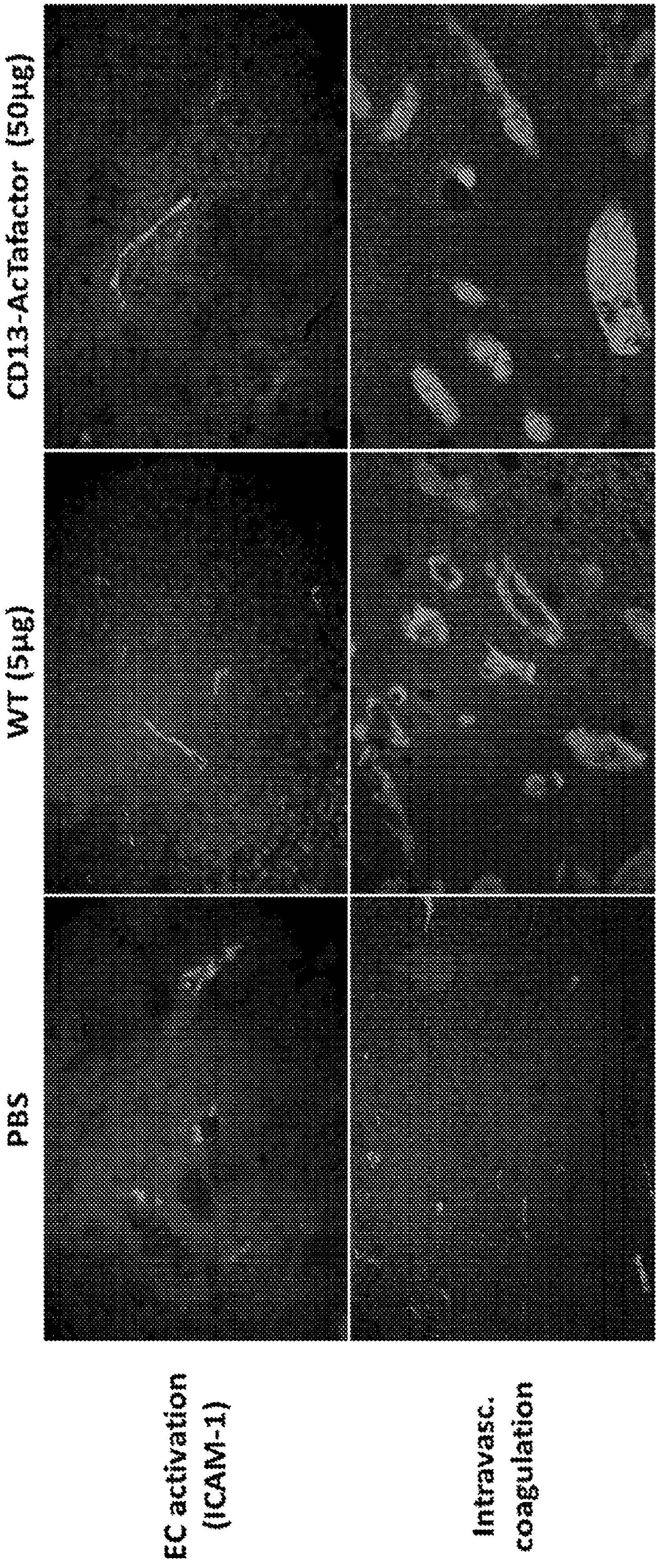
FIG. 1 shows immunohistochemical analysis of B16BI6 tumor after p.I. treatment with 5 μg wild-type sc mTNF or 50 μg of the AcTakine mCD13 VHH-sc mTNF Y114L. The upper panel was taken 4 hours after treatment and stained for mouse ICAM-1. The lower panel was taken 24 hours after treatment and shows aspecific fluorescence in blood clots. Sections were made transverse and pictures were taken close to the skin, near the site of injection.

The present technology is based, in part, on the discovery of the use of CD13-targeted chimeric proteins or chimeric protein complexes in combination with at least one other therapeutic agent in the treatment of diseases and disorders. In some embodiments, the CD13-targeted chimeric proteins or chimeric protein complexes include at least one CD13 targeting moiety and at least one tumor necrosis factor (TNF) signaling agent. In various embodiments, the TNF signaling agent may be modified to have attenuated activity.

In some embodiments, these CD13-targeted chimeric proteins or chimeric protein complexes may bind and directly or indirectly recruit immune cells to sites in need of therapeutic action (e.g. a tumor or tumor microenvironment or tumor vasculature). In some embodiments, these CD13-targeted chimeric proteins or chimeric protein complexes bind to, but do not functionally modulate CD13. In some embodiments, the CD13-targeted chimeric proteins or chimeric protein complexes enhance tumor antigen presentation for elicitation of effective antitumor immune response. In some embodiments, a) the cancer or tumor cells overexpress a CD13 protein or b) endothelial cells of tumor neovasculature overexpress a CD13 protein. In some embodiments, the CD13 protein is overexpressed by neovascular endothelial cells in disease indications associated with increased angiogenesis.

In some embodiments, the chimeric proteins or chimeric protein complexes or their combination with therapeutic agents described herein have a cytotoxic, cell modulatory, or otherwise anti-cellular effect against the tumor vasculature, e.g., they suppress the growth or cell division of vascular endothelial cells of the tumor vasculature, shrink or destroy the developed vasculature around an established tumor, or activate tumor neovasculature endothelial cells and/or endothelial cells associated with neoangiogenesis. The agents described herein can lead to a tumor-localized vascular collapse, depriving the tumor cells, particularly those tumor cells distal of the vasculature, of oxygen and nutrients, ultimately leading to cell death and tumor necrosis. The agents described herein can activate the tumor endothelium (or neoangiogenic endothelium in general) to recruit immune cells and promote immune cell infiltration.

In some embodiments, the chimeric proteins or chimeric protein complexes or their combination with therapeutic agents described herein cause activation of tumor vasculature, e.g. evidenced by expression of leukocyte adhesion markers. In some embodiments, the chimeric proteins or chimeric protein complexes or their combination with therapeutic agents described herein cause disruption of tumor vasculature or tumor necrosis. In some embodiments, the chimeric proteins or chimeric protein complexes or their combination with therapeutic agents described herein cause activation of tumor vasculature, e.g. evidenced by expression of leukocyte adhesion markers and disruption of tumor vasculature or tumor necrosis.

In some embodiments, the chimeric proteins or chimeric protein complexes or their combination with therapeutic agents described herein cause activation of tumor vasculature. In some embodiments, the chimeric proteins or chimeric protein complexes or their combination with therapeutic agents described herein cause activation of tumor vasculature, which is non-injurious. In some embodiments, the chimeric proteins or chimeric protein complexes or their combination with therapeutic agents described herein allow for infiltration of T cells.

In some embodiments, the methods and compositions of the invention are applicable to the treatment or diagnosis of any tumor mass having a vascular endothelial component. Typical vascularized tumors are the solid tumors, particularly carcinomas, which require a vascular component for the provision of oxygen and nutrients. Exemplary solid tumors to which the present invention is directed include but are not limited to carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, neuroblastomas, and the like. In embodiments, the methods and compositions of the invention are applicable to the treatment or diagnosis of a cancer selected from basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

In some embodiments, the methods and compositions of the invention are applicable to the treatment or diagnosis of leukemia or lymphoma. Illustrative leukemias or lymphomas include, but are not limited to, a leukemia or lymphoma selected from B cell lymphoma, non-Hodgkin's lymphoma (NHL) including low grade and intermediate grade non-Hodgkin's lymphomas (NHLs), relapsed Hodgkin's disease, resistant Hodgkin's disease high grade, lymphocyte predominant subtype of Hodgkin's lymphoma, precursor B cell lymphoblastic leukemia/lymphoma, mature B cell neoplasm, B cell chronic lymphocytic leukemia (CLL), small lymphocytic lymphoma (SLL), B cell prolymphocytic leukemia, lymphoplasmacytic lymphoma, mantle cell lymphoma (MCL), follicular lymphoma (FL) including low-grade, intermediate-grade and high-grade FL, cutaneous follicle center lymphoma, marginal zone B cell lymphoma, MALT type marginal zone B cell lymphoma, nodal marginal zone B cell lymphoma, splenic type marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, multiple myeloma, and anaplastic large-cell lymphoma (ALCL). In embodiments, the cancer is a hematologic malignancy, optionally selected from multiple myeloma and 5q-deletion-associated myelodysplastic syndrome (del(5q) MDS). In some embodiments, the cancer is multiple myeloma.

In some embodiments, the methods and composition of the invention are applicable to the treatment or diagnosis of brain metastatic lesions. In some embodiments, the compositions and methods disclosed herein are capable of targeting blood brain barrier at sites of brain metastatic lesions. In some embodiments, the compositions and methods disclosed herein are capable of breaking down the blood brain barrier and/or promote immune cell infiltration. In some embodiments, the chimeric proteins or chimeric protein complexes (whether alone or in combination with therapeutic agents described herein) targeted to CD13 enable selective activation of the tumor neovasculature without detectable toxicity in vivo. In some embodiments, the agents described herein cause upregulation of adhesion markers and support enhanced T cell infiltration leading to elimination of solid tumors. In some embodiments, the chimeric proteins or chimeric protein complexes in combination with the therapeutic agents lead to selective, non-injurious activation of tumor vasculature such that circulating immune cells are attracted to the tumor vasculature.

CD13 Targeting Moieties

In various embodiments, the present CD13-targeted chimeric proteins or chimeric protein complexes comprise a CD13 targeting moiety. In some embodiments, the CD13-targeted chimeric proteins or chimeric protein complexes include a CD13 targeting moiety and a TNF or a modified form thereof. In some embodiments, the CD13-targeted chimeric proteins or chimeric protein complexes include a CD13 targeting moiety and IFN or a modified form thereof. In some embodiments, the present invention relates to a combination of two or more CD13-targeted chimeric proteins or chimeric protein complexes. For example, in some embodiments, the present invention is related to a combination of a first CD13-targeting chimeric protein or chimeric protein complex which includes a CD13 targeting moiety and a TNF or a modified form thereof and a second CD-13 targeting chimeric protein or chimeric protein complex, which includes a CD13 targeting moiety and a IFN or a modified form thereof. In some embodiments, the CD13 targeting moiety is a protein-based agent capable of specific binding to CD13. In various embodiments, the present CD13 targeting moiety is a protein-based agent capable of specific binding to CD13 without functional modulation (e.g., partial or full neutralization) of CD13. CD13 (also known as aminopeptidase N (APN)) is a $Zn^{2+}$ dependent membrane-bound ectopeptidase that degrades, preferentially, proteins and peptides with a N-terminal neutral amino acid. CD13 has been associated with the growth of different human cancers.

In various embodiments, the CD13 targeting moiety of the technology comprises an antigen recognition domain that recognizes an epitope present on CD13. In an embodiment, the antigen-recognition domain recognizes one or more linear epitopes present on CD13. As used herein, a linear epitope refers to any continuous sequence of amino acids present on CD13. In another embodiment, the antigen-recognition domain recognizes one or more conformational epitopes present on CD13. As used herein, a conformation epitope refers to one or more sections of amino acids (which may be discontinuous) which form a three-dimensional surface with features and/or shapes and/or tertiary structures capable of being recognized by an antigen recognition domain.

In various embodiments, the CD13 targeting moiety of the present invention may bind to the full-length and/or mature forms and/or isoforms and/or splice variants and/or fragments and/or any other naturally occurring or synthetic analogs, variants, or mutants of human CD13. In various embodiments, the CD13 targeting moiety of the invention may bind to any forms of the human CD13, including monomeric, dimeric, heterodimeric, multimeric and associated forms. In an embodiment, the CD13 targeting moiety binds to the monomeric form of CD13. In another embodiment, the CD13 targeting moiety binds to a dimeric form of CD13. In a further embodiment, the CD13 targeting moiety binds to glycosylated form of CD13, which may be either monomeric or dimeric.

In an embodiment, the present CD13 targeting moiety comprises a targeting moiety with an antigen recognition domain that recognizes one or more epitopes present on human CD13. In an embodiment, the human CD13 comprises the amino acid sequence of:

```
                                      (SEQ ID NO: 1)
MAKGFYISKSLGILGILLGVAAVCTIIALSVVYSQEKNKNANSSPVAST

TPSASATTNPASATTLDQSKAWNRYRLPNTLKPDSYRVTLRPYLTPNDR

GLYVFKGSSTVRFTCKEATDVIIIHSKKLNYTLSQGHRVVLRGVGGSQP

PDIDKTELVEPTEYLVVHLKGSLVKDSQYEMDSEFEGELADDLAGFYRS

EYMEGNVRKVVATTQMQAADARKSFPCFDEPAMKAEFNITLIHPKDLTA

LSNMLPKGPSTPLPEDPNWNVTEFHTTPKMSTYLLAFIVSEFDYVEKQA

SNGVLIRIWARPSAIAAGHGDYALNVTGPILNFFAGHYDTPYPLPKSDQ

IGLPDFNAGAMENWGLVTYRENSLLFDPLSSSSSNKERVVTVIAHELAH

QWFGNLVTIEWWNDLWLNEGFASYVEYLGADYAEPTWNLKDLMVLNDVY

RVMAVDALASSHPLSTPASEINTPAQISELFDAISYSKGASVLRMLSSF

LSEDVFKQGLASYLHTFAYQNTIYLNLWDHLQEAVNNRSIQLPTTVRDI

MNRWTLQMGFPVITVDTSTGTLSQEHFLLDPDSNVTRPSEFNYVWIVPI

TSIRDGRQQQDYWLIDVRAQNDLFSTSGNEWVLLNLNVTGYYRVNYDEE

NWRKIQTQLQRDHSAIPVINRAQIINDAFNLASAHKVPVTLALNNTLFL

IEERQYMPWEAALSSLSYFKLMFDRSEVYGPMKNYLKKQVTPLFIHFRN

NTNNWREIPENLMDQYSEVNAISTACSNGVPECEEMVSGLFKQWMENPN

NNPIHPNLRSTVYCNAIAQGGEEEWDFAWEQFRNATLVNEADKLRAALA

CSKELWILNRYLSYTLNPDLIRKQDATSTIISITNNVIGQGLVWDFVQS

NWKKLFNDYGGGSFSFSNLIQAVTRRFSTEYELQQLEQFKKDNEETGFG

SGTRALEQALEKTKANIKWVKENKEVVLQWFTENSK.
```

In some embodiments, the CD13 targeting moiety is a protein-based agent capable of specific binding, such as an antibody or derivatives thereof. In an embodiment, the CD13 targeting moiety comprises an antibody. In various embodiments, the antibody is a full-length multimeric protein that includes two heavy chains and two light chains. Each heavy chain includes one variable region (e.g., $V_H$) and at least three constant regions (e.g., $CH_1$, $CH_2$ and $CH_3$), and each light chain includes one variable region ($V_L$) and one constant region ($C_L$). The variable regions determine the specificity of the antibody. Each variable region comprises three hypervariable regions also known as complementarity determining regions (CDRs) flanked by four relatively conserved framework regions (FRs). The three CDRs, referred to as CDR1, CDR2, and CDR3, contribute to the antibody binding specificity. In some embodiments, the antibody is a chimeric antibody. In some embodiments, the antibody is a humanized antibody.

In some embodiments, the CD13 targeting moiety comprises antibody derivatives or formats. In some embodiments, the CD13 targeting moiety of the present CD-13-based chimeric protein or chimeric protein complex is a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; a Microbody; a peptide aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; affimers, an alphabody, a bicyclic peptide, a DuoBody, a Fv, a Fab, a Fab', a $F(ab')_2$, a peptide mimetic molecule, or a synthetic molecule, as described in U.S. Pat. Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-June; 3(3): 310-317.

In one embodiment, the CD13 targeting moiety comprises a single-domain antibody, such as VHH from, for example, an organism that produces VHH antibody such as a camelid, a shark, or a designed VHH. VHHs are antibody-derived therapeutic proteins that contain the unique structural and functional properties of naturally occurring heavy-chain antibodies. VHH technology is based on fully functional antibodies from camelids that lack light chains. These heavy-chain antibodies contain a single variable domain (VHH) and two constant domains ($C_{H2}$ and CH3).

In an embodiment, the CD13 targeting moiety comprises a VHH. In some embodiments, the VHH is a humanized VHH or camelized VHH.

In some embodiments, the VHH comprises a fully human VH domain, e.g. a HUMABODY (Crescendo Biologics, Cambridge, UK). In some embodiments, fully human VH domain, e.g. a HUMABODY is monovalent, bivalent, or trivalent. In some embodiments, the fully human VH domain, e.g. a HUMABODY is mono- or multi-specific such as monospecific, bispecific, or trispecific. Illustrative fully human VH domains, e.g. HUMABODIES are described in, for example, WO2016/113555 and WO2016/113557, the entire disclosure of which is incorporated by reference. In various embodiments, the CD13 targeting moiety's target (e.g. antigen, receptor) is found on one or more immune cells, which can include, without limitation, T cells, cytotoxic T lymphocytes, T helper cells, natural killer (NK) cells, natural killer T (NKT) cells, anti-tumor macrophages (e.g. M1 macrophages), B cells, dendritic cells, or subsets thereof. In some embodiments, the recognition domains specifically bind to a target (e.g. antigen, receptor) of interest and effectively, directly or indirectly, recruit one of more immune cells. In some embodiments, the target (e.g. antigen, receptor) of interest can be found on one or more endothelial cells of tumor neovasculature and/or tumor cells. In some embodiments, the target (e.g. antigen, receptor) of interest can be found on tumor vasculature, e.g., on epithelial cells of the tumor vasculature. In some embodiments, the disclosed chimeric proteins or chimeric protein complexes may directly or indirectly recruit an immune cell, e.g., in some embodiments, to a therapeutic site (e.g. a locus with one or more disease cell or cell to be modulated for a therapeutic effect). In some embodiments, the present CD13-targeted chimeric proteins or chimeric protein complexes may directly or indirectly recruit an immune cell, e.g. an immune cell that can kill and/or suppress a tumor cell, to a site of action (such as, by way of non-limiting example, the tumor microenvironment).

In various embodiments, the CD13 targeting moieties can directly or indirectly recruit cells, such as disease cells and/or effector cells. In some embodiments, the present CD13-targeted chimeric proteins or chimeric protein complexes are capable of, or find use in methods involving, shifting the balance of immune cells in favor of immune attack of a tumor. For instance, the present CD13-targeted chimeric proteins or chimeric protein complexes can shift the ratio of immune cells at a site of clinical importance in favor of cells that can kill and/or suppress a tumor (e.g. T cells, cytotoxic T lymphocytes, T helper cells, natural killer (NK) cells, natural killer T (NKT) cells, anti-tumor macrophages (e.g. M1 macrophages), B cells, dendritic cells, or subsets thereof) and in opposition to cells that protect tumors (e.g. myeloid-derived suppressor cells (MDSCs), regulatory T cells (Tregs); tumor associated neutrophils (TANs), M2 macrophages, tumor associated macrophages (TAMs), or subsets thereof). In some embodiments, the present CD13-targeted chimeric protein or chimeric protein complex is capable of increasing a ratio of effector T cells to regulatory T cells.

TNF Signaling Agents

In various embodiments, the present CD13-targeted chimeric proteins or chimeric protein complexes comprise a tumor necrosis factor (TNF) signaling agent. In some embodiments, the TNF signaling agent comprises a modified TNF as a signaling agent. In some embodiments, the modified TNF is a modified wild type TNF. In some embodiments, the modified TNF signaling agent is modified to have attenuated activity.

The TNF superfamily consists of pro-inflammatory cytokines with crucial functions in the immune system by regulating cell death, proliferation and differentiation. In addition, members of the family were described to exert functions on bone metabolism, the nervous system, on neo-vasculature and carcinogenesis. Although most TNF superfamily ligands are synthesized as membrane-bound proteins, soluble forms can be generated by proteolytic cleavage. All of them bind to one or more molecules from the TNF receptor superfamily through their C-terminal TNF homology domain, which exhibits ~20-30% sequence homology between family members.

Twenty nine (29) TNF superfamily receptors have been identified in humans. These are primarily type I (extracellular N terminus, intracellular C terminus) transmembrane glycoproteins with a cystein-rich motif in the ligand-binding extracellular domain. However, there are some exceptions like TRAIL-R3 that is attached to the membrane by a covalently linked C-terminal glycolipid. Soluble receptors can be generated by proteolytic cleavage (e.g. TNF-R1 and TNF-R2) or by alternative splicing of the exon encoding the transmembrane domain. The receptors of this superfamily can be divided in 3 groups based on their signaling properties: receptors with a cytoplasmic death domain that induce apoptosis; receptors with a TRAF-interacting motif that induce several signaling pathways such as NF-KB, JNK, p38, ERK and PI3K; and the decoy receptors that lack intracellular signaling domains. TNF induces apoptosis through interaction with TNF-R1 (p55), while binding to TNF-R2 (p75, primarily expressed on immune cells) promotes proliferation. TRAIL signaling is more complex as it can bind to two death receptors (TRAIL-R1 (DR4) and TRAIL-R2 (DR5)), to two decoy receptors (TRAIL-R3 (DCR1) and TRAIL-R4 (DCR2)) and to the soluble osteoprotegerin (OPG). Binding to one of the latter three receptors inhibits TRAIL-mediated apoptosis as it tethers TRAIL away from the death receptors (Gaur and Aggarwal, 2003; Hehlgans and Pfeffer, 2005; Huang and Sheikh, 2007).

The death-inducing TNF superfamily members TNF, CD95L (FasL) and TRAIL are potential therapeutics for cancers that express their respective receptor TNF-R1, CD95, TRAIL-R1 and TRAI L-R2. In fact, TNF was originally discovered more than 25 years ago as a factor with extraordinary antitumor activity, by causing hemorrhagic necrosis of certain tumors in vivo. Later it became clear that the selective damage attributed by TNF to tumor neovasculature also defines its anti-tumor potential (Lejeune et al., 2006; van Horssen et al., 2006). Unfortunately, systemic use of TNF in cancer treatment is still hampered by its shock-inducing properties. It is currently only clinically used in the setting of isolated limb perfusion in combination with chemotherapy to treat soft tissue sarcomas and in-transit melanoma (Roberts et al., 2011). Also, CD95L is toxic when administered systemically as it causes lethal hepatotoxicity due to massive hepatocyte apoptosis (Galle et al., 1995). TRAIL, however, has been shown to induce apoptosis in cancer cells with little or no cytotoxicity against non-transformed cells, and clinical trials in various advanced cancers report stable disease in many cases. Still, to obtain sufficient overall therapeutic activity combined treatment is required, which implies possible side effects due to sensitization of normal cells to TRAIL-induced apoptosis (Ashkenazi and Herbst, 2008; Falschlehner et al., 2009). Different approaches have been undertaken to minimize the toxicity upon systemic administration of death-inducing TNF superfamily members, such as mutant TNF with lower toxicity and higher efficiency (Li et al., 2012), delivery of TNF or TRAIL, normally as a single chain construct, by tumor-specific moieties (de Bruyn et al., 2013; Gregorc et al., 2009; Liu et al., 2006; Siegemund et al., 2012; Wang et al., 2006), chimeric soluble CD95L (Daburon et al., 2013) or agonistic TRAIL-R1-, TRAIL-R2 or CD95-specific antibodies (Johnstone et al., 2008; Ogasawara et al., 1993; Fox et al., 2010). Some of them can increase the therapeutic index but never to such an extent that it dramatically improves clinical outcome.

In some embodiments, the TNF signaling agent is TNF-α. TNF-α is a pleiotropic cytokine with many diverse functions, including regulation of cell growth, differentiation, apoptosis, tumorigenesis, viral replication, autoimmunity, immune cell functions and trafficking, inflammation, and septic shock. It binds to two distinct membrane receptors on target cells: TNFR1 (p55) and TNFR2 (p75). TNFR1 exhibits a very broad expression pattern whereas TNFR2 is expressed preferentially on certain populations of lymphocytes, Tregs, endothelial cells, certain neurons, microglia, cardiac myocytes and mesenchymal stem cells. Very distinct biological pathways are activated in response to receptor activation, although there is also some overlap. As a general rule, without wishing to be bound by theory, TNFR1 signaling is associated with induction of apoptosis (cell death) and TNFR2 signaling is associated with activation of cell survival signals (e.g. activation of NFκB pathway). Administration of TNF is systemically toxic, and this is largely due to TNFR1 engagement. However, it should be noted that activation of TNFR2 is also associated with a broad range of activities and, as with TNFR1, in the context of developing TNF-α based therapeutics, control over TNF-α targeting and activity is important.

In some embodiments, the TNF-α signaling agent is a modified TNF-α signaling agent. In some embodiments, the modified TNF-α signaling agent has reduced affinity and/or activity for TNFR1 and/or TNFR2. In some embodiments, the modified TNF-α signaling agent has substantially reduced or ablated affinity and/or activity for TNFR1 and/or TNFR2. TNFR1 is expressed in most tissues, and is involved in cell death signaling while, by contrast, TNFR2 is involved in cell survival signaling. Accordingly, in embodiments directed to methods of treating cancer, the modified TNF-α signaling agent has reduced affinity and/or activity for TNFR1 and/or substantially reduced or ablated affinity and/or activity for TNFR2. In these embodiments, the CD13-targeted chimeric proteins or chimeric protein complexes may be targeted to a cell for which apoptosis is desired, e.g. a tumor cell or a tumor vasculature endothelial cell. In embodiments directed to methods of promoting cell survival, for example, in neurogenesis for the treatment of neurodegenerative disorders, the modified TNF-α signaling agent has reduced affinity and/or activity for TNFR2 and/or substantially reduced or ablated affinity and/or activity for TNFR1. Stated another way, the present CD13-targeted chimeric proteins or chimeric protein complexes, in some embodiments, comprise modified TNF-α agent that allows of favoring either death or survival signals.

In some embodiments, the modified TNF-α signaling agent has reduced affinity and/or activity for TNFR1 and/or substantially reduced or ablated affinity and/or activity for TNFR2. Such a CD13-targeted chimeric protein or chimeric protein complex, in some embodiments, is a more potent inducer of apoptosis as compared to a wild type TNF and/or a chimera bearing only mutation(s) causing reduced affinity and/or activity for TNFR1. Such a CD13-targeted chimeric protein or chimeric protein complex, in some embodiments, finds use in inducing tumor cell death or a tumor vasculature endothelial cell death (e.g. in the treatment of cancers). Also, in some embodiments, these CD13-targeted chimeric proteins or chimeric protein complexes avoid or reduce activation of $Tr_{eg}$ cells via TNFR2, for example, thus further supporting TNFR1-mediated antitumor activity in vivo.

In some embodiments, the modified TNF-α signaling agent has reduced affinity and/or activity for TNFR2 and/or substantially reduced or ablated affinity and/or activity for TNFR1. Such a CD13-targeted chimeric protein or chimeric protein complex, in some embodiments, is a more potent activator of cell survival in some cell types, which may be a specific therapeutic objective in various disease settings, including without limitation, stimulation of neurogenesis. In addition, such a TNFR2-favoring chimeras also are useful in the treatment of autoimmune diseases (e.g. Crohn's, diabetes, MS, colitis, Sjogren's syndrome, multiple sclerosis, ankylosing spondylitis, and rheumatoid arthritis). In some embodiments, the CD13-targeted chimeric protein or chimeric protein complex is targeted to auto-reactive T cells. In some embodiments, the CD13-targeted chimeric protein or chimeric protein complex promotes $Tr_{eg}$ cell activation and indirect suppression of cytotoxic T cells.

In some embodiments, the CD13-targeted chimeric protein or chimeric protein complex causes the death of auto-reactive T cells, e.g. by activation of TNFR2 and/or avoidance TNFR1 (e.g. a modified TNF-α signaling agent having reduced affinity and/or activity for TNFR2 and/or substantially reduced or ablated affinity and/or activity for TNFR1). Without wishing to be bound by theory these auto-reactive T cells, have their apoptosis/survival signals altered e.g. by NFκB pathway activity/signaling alterations. In some embodiments, the CD13-targeted chimeric protein or chimeric protein complex causes the death of autoreactive T cells having lesions or modifications in the NFκB pathway, which underlie an imbalance of their cell death (apoptosis)/survival signaling properties and, optionally, altered susceptibility to certain death-inducing signals (e.g., TNFR2 activation).

In some embodiments, a TNFR-2 targeted TNF-α signaling agent has additional therapeutic applications in diseases, including autoimmune disease, various heart disease, demyelinating and neurodegenerative disorders, and infectious disease, among others.

In an embodiment, the wild type TNF-α has the amino acid sequence of:

(SEQ ID NO: 2)
VRSSSRTPSDKPVAHVVANPQAEGQLQWLNRRANALLANGVELRDNQLV

VSEGLYLIYSQVLFKGQGCPSTHVLLTHTISRIAVSYQTKVNLLSAIKS

PCQRETPEGAEAKPWYEPIYLGGVFQLEKGDRLSAEINRPDYLDFAESG

QVYFGIIAL.

In such embodiments, the modified TNF-α agent has mutations at one or more amino acid positions 29, 31, 32, 84, 85, 86, 87, 88, 89, 145, 146 and 147 which produces a modified TNF-α with reduced receptor binding affinity. See, for example, U.S. Pat. No. 7,993,636, the entire contents of which are hereby incorporated by reference.

In some embodiments, the modified human TNF-α signaling agent has mutations at one or more amino acid positions R32, N34, Q67, H73, L75, T77, S86, Y87, V91, I97, T105, P106, A109, P113, Y115, E127, N137, D143, A145, and E146 as described, for example, in WO/2015/007903, the entire contents of which is hereby incorporated by reference (numbering according to the human TNF sequence, Genbank accession number BAG70306, version BAG70306.1 GI: 197692685). In some embodiments, the modified human TNF-α moiety has substitution mutations selected from L29S, R32G, R32W, N34G, Q67G, H73G, L75G, L75A, L75S, T77A, S86G, S86T, Y87Q, Y87L, Y87A, Y87F, Y87H, V91G, V91A, I97A, I97Q, I97S, T105G, P106G, A109Y, P113G, Y115G, Y115A, E127G, N137G, D143N, A145G, A145R, A145T, E146D, E146K, and S147D. In some embodiments, the human TNF-α signaling agent has a mutation selected from Y87Q, Y87L, Y87A, Y87F, and Y87H. In another embodiment, the human TNF-α signaling agent has a mutation selected from I97A, I97Q, and I97S. In a further embodiment, the human TNF-α signaling agent has a mutation selected from Y115A and Y115G. In some embodiments, the human TNF-α signaling agent has an E146K mutation. In some embodiments, the human TNF-α signaling agent has an Y87H and an E146K mutation. In some embodiments, the human TNF-α signaling agent has an Y87H and an A145R mutation. In some embodiments, the human TNF-α signaling agent has a R32W and a S86T mutation. In some embodiments, the human TNF-α signaling agent has a R32W and an E146K mutation. In some embodiments, the human TNF-α signaling agent has a L29S and a R32W mutation. In some embodiments, the human TNF-α signaling agent has a D143N and an A145R mutation. In some embodiments, the human TNF-α signaling agent has a D143N and an A145R mutation. In some embodiments, the human TNF-α signaling agent has an A145T, an E146D, and a S147D mutation. In some embodiments, the human TNF-α signaling agent has an A145T and a S147D mutation.

In some embodiments, the modified TNF-α signaling agent has one or more mutations selected from N39Y, S147Y, and Y87H, as described in WO2008/124086, the entire contents of which is hereby incorporated by reference.

In some embodiments, the modified human TNF-α signaling agent has mutations that provide receptor selectivity as described in PCT/IB2016/001668, the entire contents of which are hereby incorporated by reference. In some embodiments, the mutations to TNF-α are TNF-R1 selective. In some embodiments, the mutations to TNF-α which are TNF-R1 selective are at one or more of positions R32, S86, and E146. In some embodiments, the mutations to TNF-α which are TNF-R1 selective are one or more of R32W, S86T, and E146K. In some embodiments, the mutations to TNF-α which are TNF-R1 selective are one or more of R32W, R32W/S86T, R32W/E146K and E146K. In some embodiments, the mutations to TNF-α are TNF-R2 selective. In some embodiments, the mutations to TNF-α which are TNF-R2 selective are at one or more of positions A145, E146, and S147. In some embodiments, the mutations to TNF-α which are TNF-R2 selective are one or more of A145T, A145R, E146D, and S147D. In some embodiments, the mutations to TNF-α which are TNF-R2 selective are one or more of A145R, A145T/S147D, and A145T/E146D/S147D.

In some embodiments, the TNF signaling agent is TNF-β. TNF-β can form a homotrimer or a heterotrimer with LT-β (LT-α1β2). In some embodiments, the TNF-β signaling agent is a modified TNF-β signaling agent. In some embodiments, the modified TNF-β signaling agent has substantially reduced or ablated affinity and/or activity for TNFR1 and/or TNFR2 and/or herpes virus entry mediator (HEVM) and/or LT-βR.

In an embodiment, the wild type TNF-β has the amino acid sequence of:

(SEQ ID NO: 3)
LPGVGLTPSAAQTARQHPKMHLAHSNLKPAAHLIGDPSKQNSLLWRANT

DRAFLQDGFSLSNNSLLVPTSGIYFVYSQVVFSGKAYSPKATSSPLYLA

HEVQLFSSQYPFHVPLLSSQKMVYPGLQEPWLHSMYHGAAFQLTQGDQL

STHTDGIPHLVLSPSTVFFGAFAL.

In such embodiments, the modified TNF-β signaling agent may comprise mutations at one or more amino acids at positions 106-113, which produce a modified TNF-β signaling agent with reduced receptor binding affinity to TNFR2. In an embodiment, the modified TNF-β signaling agent has one or more substitution mutations at amino acid positions 106-113. In illustrative embodiments, the substitution mutations are selected from Q107E, Q107D, S106E, S106D, Q107R, Q107N, Q107E/S106E, Q107E/S106D, Q107D/S106E, and Q107D/S106D. In another embodiment, the modified TNF-β signaling agent has an insertion of about 1 to about 3 amino acids at positions 106-113.

In some embodiments, the modified TNF signaling agent is a TNF family member (e.g. TNF-alpha, TNF-beta) which can be a single chain trimeric version as described in WO 2015/007903 and PCT/IB2016/001668, the entire contents of which are incorporated by reference.

In some embodiments, the modified TNF signaling agent is a TNF family member (e.g. TNF-alpha, TNF-beta) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TNFR1. In these embodiments, the modified TNF signaling agent is a TNF family member (e.g. TNF-alpha, TNF-beta) which also, optionally, has substantially reduced or ablated affinity and/or activity for TNFR2. In some embodiments, the modified TNF signaling agent is a TNF family member (e.g. TNF-alpha, TNF-beta) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TNFR2. In these embodiments, the modified TNF signaling agent is a TNF family member (e.g. TNF-alpha, TNF-beta) which also, optionally, has substantially reduced or ablated affinity and/or activity for TNFR1. The constructs of such embodiments find use in, for example, methods of dampening TNF response in a cell specific manner. In some embodiments, the antagonistic TNF family member (e.g. TNF-alpha, TNF-beta) is a single chain trimeric version as described in WO 2015/007903.

In some embodiments, the TNF signaling agent is TNF-related apoptosis-inducing ligand (TRAIL). In some embodiments, the TRAIL is a modified TRAIL agent. In some embodiments, the modified TRAIL agent has reduced affinity and/or activity for DR4 (TRAIL-RI) and/or DR5 (TRAIL-RII) and/or DcR1 and/or DcR2. In some embodiments, the modified TRAIL agent has substantially reduced or ablated affinity and/or activity for DR4 (TRAIL-RI) and/or DR5 (TRAIL-RII) and/or DcR1 and/or DcR2.

In an embodiment, the wild type TRAIL has the amino acid sequence of:

```
                                          (SEQ ID NO: 4)
MAMMEVQGGPSLGQTCVLIVIFTVLLQSLCVAVTYVYFTNELKQMQDKY

SKSGIACFLKEDDSYWDPNDEESMNSPCWQVKWQLRQLVRKMILRTSEE

TISTVQEKQQNISPLVRERGPQRVAAHITGTRGRSNTLSSPNSKNEKAL

GRKINSWESSRSGHSFLSNLHLRNGELVIHEKGFYYIYSQTYFRFQEEI

KENTKNDKQMVQYIYKYTSYPDPILLMKSARNSCWSKDAEYGLYSIYQG

GIFELKENDRIFVSVTNEHLIDMDHEASFFGAFLVG.
```

In such embodiments, the modified TRAIL agent may comprise a mutation at amino acid positions T127-R132, E144-R149, E155-H161, Y189-Y209, T214-1220, K224-A226, W231, E236-L239, E249-K251, T261-H264 and H270-E271 (Numbering based on the human sequence, Genbank accession number NP_003801, version 10 NP_003801.1, GI: 4507593; see above).

In some embodiments, the modified TRAIL agent may comprise one or more mutations that sustantially reduce its affinity and/or activity for TRAIL-R1. In such embodiments, the modified TRAIL agent may specifically bind to TRIL-R2. Illustrative mutations include mutations at one or more amino acid positions Y189, R191, Q193, H264, 1266, and D267. For example, the mutations may be one or more of Y189Q, R191K, Q193R, H264R, I266L and D267Q. In an embodiment, the modified TRAIL agent comprises the mutations Y189Q, R191K, Q193R, H264R, I266L and D267Q.

In some embodiments, the modified TRAIL agent may comprise one or more mutations that substantially reduce its affinity and/or activity for TRAIL-R2. In such embodiments, the modified TRAIL agent may specifically bind to TRIL-R1. Illustrative mutations include mutations at one or more amino acid positions G131, R149, S159, N199, K201, and S215. For example, the mutations may be one or more of G131R, R149I, S159R, N199R, K201H, and S215D. In an embodiment, the modified TRAIL agent comprises the mutations G131R, R149I, S159R, N199R, K201H, and S215D. Additional TRAIL mutations are described in, for example, Trebing et al., (2014) Cell Death and Disease, 5:e1035, the entire disclosure of which is hereby incorporated by reference.

IFN Signaling Agents

In some aspects, the present technology relates to therapeutic uses of CD13-targeted chimeric proteins or chimeric protein complexes having at least one targeting moiety that specifically binds to CD13 and at least one signaling agent that is an interferon (IFN) or a modified form thereof. In various embodiments, the IFN signaling agent may be modified to attenuate activity. In one embodiment, the interferon is IFN-γ or a modified form thereof. In some embodiments, the present invention includes the use of CD13 targeted chimeric proteins or chimeric protein complexes having at least one signaling moiety that is an IFN or a modified form thereof as the sole therapeutic agent. In other embodiments, the present invention includes the use of CD13 targeted chimeric protein or chimeric protein complexes having at least one signaling moiety that is an IFN or a modified form thereof for use in combination therapy as described herein. Various embodiments of the IFN or a modified form thereof that may be used in the present invention are described below. In one embodiment, the present invention includes the use of CD13 targeted chimeric protein or chimeric protein complexes having at least one IFN-γ signaling moiety or a modified form thereof for use in combination therapy. In another embodiment, the present invention includes the use of CD13 targeted chimeric protein or chimeric protein complexes having at least one IFN-γ signaling moiety or a modified form thereof for use as a sole therapeutic agent.

CD13-Targeted Chimeric Proteins

Linkers

In some embodiments, the present CD13-targeted chimeric protein or chimeric protein complex optionally comprises one or more linkers. In some embodiments, the present CD13-targeted chimeric protein or chimeric protein complex comprises a linker connecting the CD13 targeting moiety and the TNF signaling agent (e.g., modified TNF signaling agent). In some embodiments, the present CD13-targeted chimeric protein or chimeric protein complex comprises a linker connecting the CD13 targeting moiety and the Interferon signaling agent (e.g., modified IFN signaling agent). In some embodiments, the present CD13-targeted chimeric protein or chimeric protein complex comprises a linker within the TNF signaling agent (e.g., modified TNF signaling agent). In some embodiments, the present CD13-targeted chimeric protein or chimeric protein complex comprises a linker within the IFN signaling agent (e.g., modified IFN signaling agent). In some embodiments, the linker may be utilized to link various functional groups, residues, or moieties as described herein to the chimeric protein or chimeric protein complex. In some embodiments, the linker is a single amino acid or a plurality of amino acids that does not affect or reduce the stability, orientation, binding, neutralization, and/or clearance characteristics of the binding regions and the binding protein. In various embodiments, the linker is selected from a peptide, a protein, a sugar, or a nucleic acid.

In some embodiments, vectors encoding the present CD13-targeted chimeric proteins or chimeric protein complexes linked as a single nucleotide sequence to any of the linkers described herein are provided and may be used to prepare such chimeric proteins or chimeric protein complexes.

In some embodiments, the linker length allows for efficient binding of a CD13 targeting moiety and the TNF signaling agent (e.g., modified TNF signaling agent) to their receptors. For instance, in some embodiments, the linker length allows for efficient binding of one of the CD13 targeting moieties and the TNF signaling agent or the IFN signaling agent to receptors on the same cell.

In some embodiments, the linker length is at least equal to the minimum distance between the binding sites of one of the CD13 targeting moieties and the TNF signaling agent or the IFN signaling agent to receptors on the same cell. In some embodiments the linker length is at least twice, or three times, or four times, or five times, or ten times, or twenty times, or 25 times, or 50 times, or one hundred times, or more the minimum distance between the binding sites of one of the CD13 targeting moieties and the TNF signaling agent or the IFN signaling agent to receptors on the same cell.

As described herein, the linker length allows for efficient binding of one of the CD13 targeting moieties and the TNF signaling agent or the IFN signaling agent to receptors on the same cell, the binding being sequential, e.g. CD13 targeting moiety/receptor binding preceding TNF signaling agent/receptor binding or CD13 targeting moiety/receptor binding preceding IFN signaling agent/receptor binding.

In some embodiments, there are two linkers in a single chimera, each connecting the TNF signaling agent or the IFN signaling agent to a CD13 targeting moiety. In various embodiments, the linkers have lengths that allow for the formation of a site that has a disease cell and an effector cell without steric hindrance that would prevent modulation of the either cell.

The invention contemplates the use of a variety of linker sequences. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et al., (2000), Protein Eng. 13(5):309-312, the entire contents of which are hereby incorporated by reference. In various embodiments, the linker may be functional. For example, without limitation, the linker may function to improve the folding and/or stability, improve the expression, improve the pharmacokinetics, and/or improve the bioactivity of the present chimeric protein or chimeric protein complex.

In some embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is a polypeptide. In some embodiments, the linker is greater than about 100 amino acids long. For example, the linker may be greater than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid.

In some embodiments directed to CD13 targeted chimeric proteins or chimeric protein complexes having two or more CD13 targeting moieties, a linker connects the two CD13 targeting moieties to each other and this linker has a short length and a linker connects a CD13 targeting moiety and a TNF signaling agent this linker is longer than the linker connecting the two CD13 targeting moieties. For example, the difference in amino acid length between the linker connecting the two targeting moieties and the linker connecting a targeting moiety and a signaling agent may be about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids.

In various embodiments, the linker is substantially comprised of glycine and serine residues (e.g. about 30%, or about 40%, or about 50%, or about 60%, or about 70%, or about 80%, or about 90%, or about 95%, or about 97% glycines and serines). For example, in some embodiments, the linker is $(Gly_4Ser)_n$, where n is from about 1 to about 8, e.g. 1, 2, 3, 4, 5, 6, 7, or 8 (SEQ ID NOs: 5-12, respectively). In an embodiment, the linker sequence is GGSGGSGGGGSGGGGS (SEQ ID NO: 13). Additional illustrative linkers include, but are not limited to, linkers having the sequence LE, GGGGS (SEQ ID NO: 5), $(GGGGS)_n$ (n=1-4) (SEQ ID NOs: 5-8), $(Gly)_8$ (SEQ ID NO: 14), $(Gly)_6$ (SEQ ID NO: 15), $(EAAAK)_n$ (n=1-3) (SEQ ID NOs: 16-18), $A(EAAAK)_nA$ (n=2-5) (SEQ ID NOs: 19-22), AEAAAKEAAAKA (SEQ ID NO: 23), $A(EAAAK)_4$ $ALEA(EAAAK)_4A$ (SEQ ID NO: 24), PAPAP (SEQ ID NO: 25), KESGSVSSEQLAQFRSLD (SEQ ID NO: 26), EGKSSGSGSESKST (SEQ ID NO: 27), GSAGSAAGSGEF (SEQ ID NO: 28), and $(XP)_n$, with X designating any amino acid, e.g., Ala, Lys, or Glu. In various embodiments, the linker is $(GGS)_n$ (n=1-20) (SEQ ID NOs: 29-48). In some embodiments, the linker is G. In some embodiments, the linker is AAA. In some embodiments, the linker is $(GGGGS)_n$ (n=5-20) (SEQ ID NOs: 9-12 and 49-60).

In some embodiments, the linker is one or more of GGGSE (SEQ ID NO: 61), GSESG (SEQ ID NO: 62), GSEGS (SEQ ID NO: 63), GEGGSGEGSS-GEGSSSEGGGSEGGGSEGGGSEGGS (SEQ ID NO: 64), and a linker of randomly placed G, S, and E every 4 amino acid intervals.

In some embodiments, the linker is a synthetic linker such as PEG.

In various embodiments, the linker may be functional. For example, without limitation, the linker may function to improve the folding and/or stability, improve the expression, improve the pharmacokinetics, and/or improve the bioactivity of the present chimeric protein or chimeric protein complex. In another example, the linker may function to target the chimeric protein or chimeric protein complex to a particular cell type or location.

Multiple TNF Signaling Agents

Figure 6A:
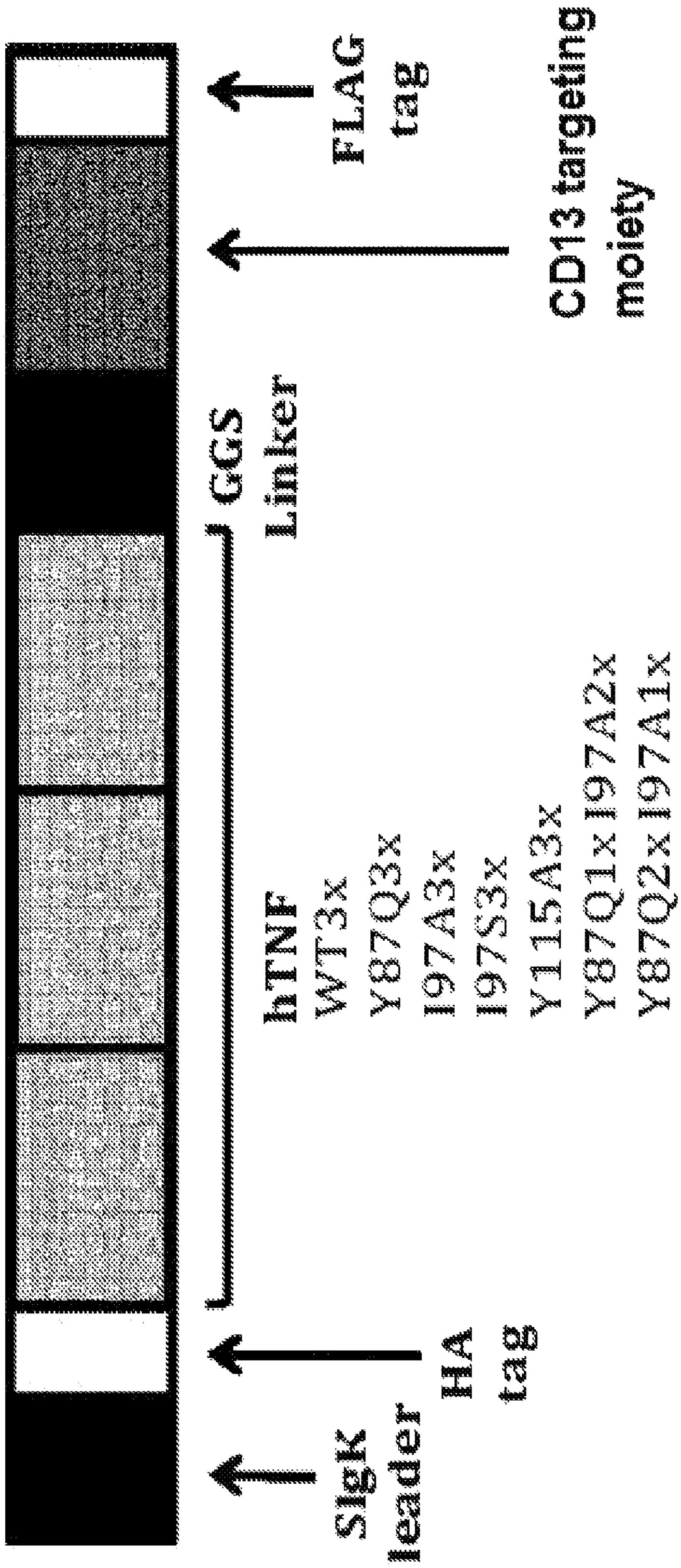
FIGS. 6A-B are exemplary, non-limiting embodiments of CD13-targeted chimeric proteins (hTNF=human tumor necrosis factor).
Figure 6B:
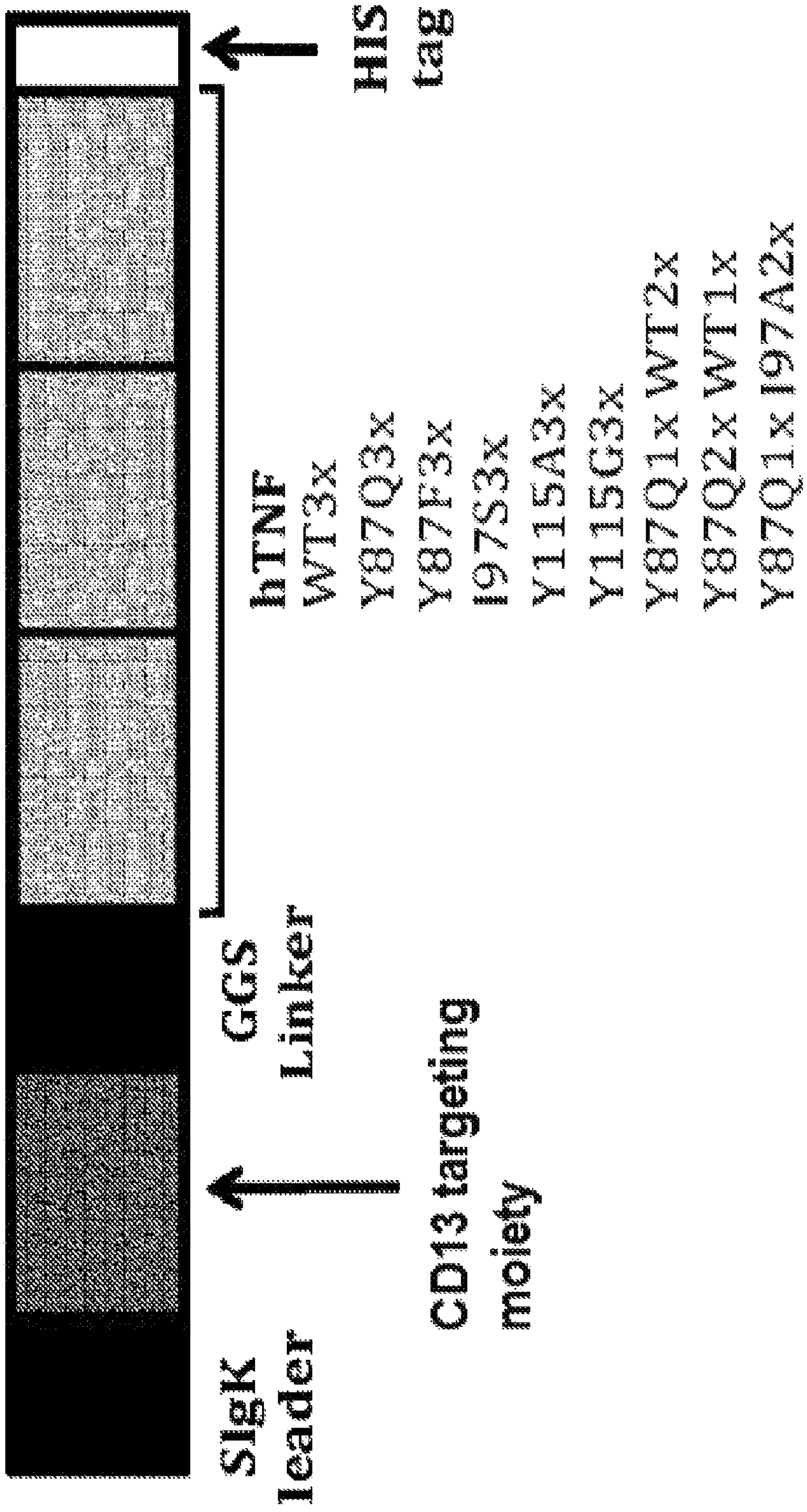

In some embodiments, the CD13-targeted chimeric protein or chimeric protein complex comprises 2 or more TNF signaling agents. In some embodiments, the CD13-targeted chimeric protein or chimeric protein complex comprises at least one wild type TNF signaling agent and at least one modified TNF signaling agent disclosed above. FIGS. 6A-B shows exemplary, non-limiting embodiments of a CD13-targeted chimeric protein or chimeric protein complex having 3 TNF signaling agents.

In some embodiments, the CD13-targeted chimeric protein or chimeric protein complex comprises 2 or more modified TNF signaling agents disclosed above. In some embodiments, the CD13-targeted chimeric protein or chimeric protein complex comprises 3 modified TNF signaling agents disclosed above.

In some embodiments, the 2 or more modified TNF signaling agents are members of the same TNF family, e.g., all are modified TNF-α signaling agents. In some embodiments, the 2 or more modified TNF signaling agents are members of the same TNF family and have identical modifications, e.g., all are modified human TNF-α signaling agents having a Y87Q modification. In some embodiments, the 2 or more modified TNF signaling agents are members of the same TNF family and each have different modifications, e.g., two modified human TNF-α signaling agents, one having a Y87Q modification and the other having a I97A modification or one having a I97S modification and the other having a I97A modification. In an exemplary embodiment, the CD13-targeted chimeric protein or chimeric protein complex comprises 3 copies of the same modified TNF signaling agent having the same mutation.

In some embodiments, the 2 or more modified TNF signaling agents are members of different TNF families, e.g., one modified TNF-α signaling agent and one modified TNF-β signaling agent.

In some embodiments, the CD13-targeted chimeric protein or chimeric protein complex comprises 3 or more modified TNF signaling agents, wherein the modified TNF signaling agents are members of the same TNF family and at least two have the same modification, e.g., two modified human TNF-α signaling agents having a Y87Q modification and a third modified human TNF-α signaling agent having a I97A modification.

In some embodiments, the CD13-targeted chimeric protein or chimeric protein complex comprises 3 or more modified TNF signaling agents, wherein at least two modified TNF signaling agents are members of the same TNF family.

In some embodiments, the CD13-targeted chimeric protein or chimeric protein complex comprises 2 or more modified TNF signaling agents, wherein the modified TNF signaling agents are consecutive monomers within a single chain polypeptide (see, e.g., FIGS. 6A-B). In an exemplary embodiment, the CD13-targeted chimeric protein or chimeric protein complex comprises 3 copies of the same modified TNF signaling agent having the same mutation in a single polypeptide chain.

Multiple IFN Signaling Agents

In some embodiments, the CD13-targeted chimeric protein or chimeric protein complex comprises 2 or more IFN signaling agents. In some embodiments, the CD13-targeted chimeric protein or chimeric protein complex comprises at least one wild type IFN signaling agent and at least one modified IFN signaling agent disclosed below. In some embodiments, the CD13-targeted chimeric protein or chimeric protein complex comprises 2 or more modified IFN signaling agents disclosed below. In some embodiments, the CD13-targeted chimeric protein or chimeric protein complex comprises 3 modified IFN signaling agents disclosed below. In some embodiments, the 2 or more modified IFN signaling agents are the same or different. In some embodiments, the 2 or more modified IFN signaling agents have identical modifications. In some embodiments, the 2 or more modified IFN signaling agents have different modifications. In some embodiments, the CD13-targeted chimeric protein or chimeric protein complex comprises 3 or more modified IFN signaling agents.

Use of CD13-Targeted Chimeric Proteins in Combination Therapy

In some embodiments, the present technology relates to use of CD13-targeted chimeric proteins or chimeric protein complexes in combination therapy. In some embodiments, the present CD13-targeted chimeric protein or chimeric protein complex is co-administered with at least one additional therapeutic agent. In some embodiments, the additional therapeutic agent is a CD8-targeted chimeric protein or chimeric protein complex. In some embodiments, the additional therapeutic agent is a CD13-targeted chimeric protein or chimeric protein complex. In some embodiments, the additional therapeutic agent is a chimeric protein or chimeric protein complex where the targeting moiety is directed to CD13 and the signaling agent is an interferon or a modified form thereof. In some embodiments, the signaling agent is IFN-γ or a modified form thereof. In some embodiments, the additional therapeutic agent is one or more agents selected from a phosphoinositide-3-kinase 9 (PI3K) inhibitor, anthracycline, and SMAC mimetic. In some embodiments, the anthracycline is a liposomal anthracycline.

CD8-Targeted or CD13-Targeted Chimeric Proteins

In some embodiments, the additional therapeutic agent is a CD8-targeted chimeric protein or chimeric protein complex having at least one targeting moiety that specifically binds to CD8 and at least one signaling agent that is an interferon (IFN) or a modified form thereof. In some embodiments, the additional therapeutic agent is a CD13-targeted chimeric protein or chimeric protein complex having at least one targeting moiety that specifically binds to CD13, as described herein, and at least one signaling agent that is an interferon (IFN) or a modified form thereof. In various embodiments, the IFN signaling agent is modified to have attenuate activity.

CD8 Targeting Moieties

In some embodiments, the additional therapeutic agent—that is used in the combination therapy described herein—is a CD8-targeted chimeric protein or chimeric protein complex having at least one targeting moiety that specifically binds to CD8 and at least one signaling agent that is an interferon (IFN) or a modified form thereof. In various embodiments, the CD8-targeted chimeric protein or chimeric protein complex comprises a CD8 targeting moiety that is a protein-based agent capable of specific binding to CD8. In various embodiments, the CD8 targeting moiety is a protein-based agent capable of specific binding to CD8 without functionally modulating (e.g. partial or complete neutralization) CD8.

CD8 is a heterodimeric type I transmembrane glycoprotein, whose α and β chains are both comprised of an immunoglobulin (Ig)-like extracellular domain connected by an extended O-glycosylated stalk to a single-pass transmembrane domain and a short cytoplasmic tail (Li et al., 2013). The cytoplasmic region of the CD8 α-chain contains two cysteine motifs that serve as a docking site for src tyrosine kinase p56Ick (Lck). In contrast, this Lck binding domain appears to be absent from the CD8 β chain, suggesting that the 6 chain is not involved in downstream signaling (Artyomov et al., 2010). CD8 functions as a co-receptor for the T-cell receptor with its principle role being the recruitment of Lck to the TCR-pMHC complex following co-receptor binding to MHC (Turner et al., 1990, Veillette et al., 1988). The increase in the local concentration of this kinase activates a signaling cascade that recruits and activates ζ-chain-associated protein kinase 70 (ZAP-70), subsequently leading to the amplification of T-cell activation signals (Purbhoo et al., 2001, Laugel et al., 2007a).

In some embodiments, the CD8 targeting moiety comprises an antigen recognition domain that recognizes an epitope present on the CD8 α and/or β chains. In an embodiment, the antigen-recognition domain recognizes one or more linear epitopes on the CD8 α and/or β chains. In some embodiment, a linear epitope refers to any continuous sequence of amino acids present on the CD8 α and/or β chains. In another embodiment, the antigen-recognition domain recognizes one or more conformational epitopes present on the CD8 α and/or β chains. As used herein, a conformation epitope refers to one or more sections of amino acids (which may be discontinuous) which form a three-dimensional surface with features and/or shapes and/or tertiary structures capable of being recognized by an antigen recognition domain.

In various embodiments, the CD8 targeting moiety may bind to the full-length and/or mature forms and/or isoforms and/or splice variants and/or fragments and/or any other naturally occurring or synthetic analogs, variants, or mutants of human CD8 α and/or β chains. In various embodiments, the CD8 targeting moiety may bind to any forms of the human CD8 α and/or β chains, including monomeric, dimeric, heterodimeric, multimeric and associated forms. In an embodiment, the CD8 binding agent binds to the monomeric form of CD8 α chain or CD8 chain. In another embodiment, the CD8 targeting moiety binds to a homodimeric form comprised of two CD8 α chains or two CD8 β chains. In a further embodiment, the CD8 binding agent binds to a heterodimeric form comprised of one CD8 α chain and one CD8 β chain.

In an embodiment, the CD8 targeting moiety comprises an antigen recognition domain that recognizes one or more epitopes present on the human CD8 α chain. In an embodiment, the human CD8 α chain comprises the amino acid sequence of:

Isoform 1

```
                                        (SEQ ID NO: 66)
MALPVTALLLPLALLLHAARPSQFRVSPLDRTWNLGETVELKCQVLLSN
PTSGCSWLFQPRGAAASPTFLLYLSQNKPKAAEGLDTQRFSGKRLGDTF
VLTLSDFRRENEGYYFCSALSNSIMYFSHFVPVFLPAKPTTTPAPRPPT
PAPTIASQPLSLRPEACRPAAGGAVHTRGLDFACDIYIWAPLAGTCGVL
LLSLVITLYCNHRNRRRVCKCPRPVVKSGDKPSLSARYV.
```

In an embodiment, the human CD8 α chain comprises the amino acid sequence of:

Isoform 2

```
                                        (SEQ ID NO: 67)
MALPVTALLLPLALLLHAARPSQFRVSPLDRTWNLGETVELKCQVLLSN
PTSGCSWLFQPRGAAASPTFLLYLSQNKPKAAEGLDTQRFSGKRLGDTF
```

-continued

```
VLTLSDFRRENEGYYFCSALSNSIMYFSHFVPVFLPAKPTTTPAPRPPT
PAPTIASQPLSLRPEACRPAAGGAGNRRRVCKCPRPWKSGDKPSLSARY
V.
```

In an embodiment, the human CD8 α chain comprises the amino acid sequence of:

Isoform 3

```
                                        (SEQ ID NO: 68)
MRNQAPGRPKGATFPPRRPTGSRAPPLAPELRAKQRPGERVMALPVTAL
LLPLALLLHAARPSQFRVSPLDRTWNLGETVELKCQVLLSNPTSGCSWL
FQPRGAAASPTFLLYLSQNKPKAAEGLDTQRFSGKRLGDTFVLTLSDFR
RENEGYYFCSALSNSIMYFSHFVPVFLPAKPTTTPAPRPPTPAPTIASQ
PLSLRPEACRPAAGGAVHTRGLDFACDIYIWAPLAGTCGVLLLSLVITL
YCNHRNRRRVCKCPRPVVKSGDKPSLSARYV.
```

In an embodiment, the CD8 targeting moiety comprises an antigen recognition domain that recognizes one or more epitopes present on the human CD8 β chain. In an embodiment, the human CD8 β chain comprises the amino acid sequence of:

Isoform 1

```
                                        (SEQ ID NO: 69)
MRPRLWLLLAAQLTVLHGNSVLQQTPAYIKVQTNKMVMLSCEAKISLSN
MRIYWLRQRQAPSSDSHHEFLALWDSAKGTIHGEEVEQEKIAVFRDASR
FILNLTSVKPEDSGIYFCMIVGSPELTFGKGTQLSVVDFLPTTAQPTKK
STLKKRVCRLPRPETQKGPLCSPITLGLLVAGVLVLLVSLGVAIHLCCR
RRRARLRFMKQFYK.
```

In an embodiment, the human CD8 β chain comprises the amino acid sequence of:

Isoform 2

```
                                        (SEQ ID NO: 70)
MRPRLWLLLAAQLTVLHGNSVLQQTPAYIKVQTNKMVMLSCEAKISLSN
MRIYWLRQRQAPSSDSHHEFLALWDSAKGTIHGEEVEQEKIAVFRDASR
FILNLTSVKPEDSGIYFCMIVGSPELTFGKGTQLSVVDFLPTTAQPTKK
STLKKRVCRLPRPETQKGPLCSPITLGLLVAGVLVLLVSLGVAIHLCCR
RRRARLRFMKQLRLHPLEKCSRMDY.
```

In an embodiment, the human CD8 β chain comprises the amino acid sequence of:

Isoform 3

```
                                        (SEQ ID NO: 71)
MRPRLWLLLAAQLTVLHGNSVLQQTPAYIKVQTNKMVMLSCEAKISLSN
MRIYWLRQRQAPSSDSHHEFLALWDSAKGTIHGEEVEQEKIAVFRDASR
FILNLTSVKPEDSGIYFCMIVGSPELTFGKGTQLSVVDFLPTTAQPTKK
STLKKRVCRLPRPETQKGRRRRARLRFMKQPQGEGISGTFVPQCLHGYY
SNTTTSQKLLNPWILKT.
```

In an embodiment, the human CD8 β chain comprises the amino acid sequence of:

Isoform 4

(SEQ ID NO: 72)

MRPRLWLLLAAQLTVLHGNSVLQQTPAYIKVQTNKMVMLSCEAKISLSN

MRIYWLRQRQAPSSDSHHEFLALWDSAKGTIHGEEVEQEKIAVFRDASR

FILNLTSVKPEDSGIYFCMIVGSPELTFGKGTQLSVVDFLPTTAQPTKK

STLKKRVCRLPRPETQKGPLCSPITLGLLVAGVLVLLVSLGVAIHLCCR

RRRARLRFMKQKFNIVCLKISGFTTCCCFQILQISREYGFGVLLQKDIG

Q.

In an embodiment, the human CD8 β chain comprises the amino acid sequence of:

Isoform 5

(SEQ ID NO: 73)

MRPRLWLLLAAQLTVLHGNSVLQQTPAYIKVQTNKMVMLSCEAKISLSNM

RIYWLRQRQAPSSDSHHEFLALWDSAKGTIHGEEVEQEKIAVFRDASRFI

LNLTSVKPEDSGIYFCMIVGSPELTFGKGTQLSVVDFLPTTAQPTKKSTL

KKRVCRLPRPETQKGPLCSPITLGLLVAGVLVLLVSLGVAIHLCCRRRRA

RLRFMKQPQGEGISGTFVPQCLHGYYSNTTTSQKLLNPWILKT.

In an embodiment, the human CD8 β chain comprises the amino acid sequence of:

Isoform 6

(SEQ ID NO: 74)

MRPRLWLLLAAQLTVLHGNSVLQQTPAYIKVQTNKMVMLSCEAKISLSNM

RIYWLRQRQAPSSDSHHEFLALWDSAKGTIHGEEVEQEKIAVFRDASRFI

LNLTSVKPEDSGIYFCMIVGSPELTFGKGTQLSVVDFLPTTAQPTKKSTL

KKRVCRLPRPETQKGRRRRARLRFMKQFYK.

In an embodiment, the human CD8 β chain comprises the amino acid sequence of:

Isoform 7

(SEQ ID NO: 75)

MRPRLWLLLAAQLTVLHGNSVLQQTPAYIKVQTNKMVMLSCEAKISLSNM

RIYWLRQRQAPSSDSHHEFLALWDSAKGTIHGEEVEQEKIAVFRDASRFI

LNLTSVKPEDSGIYFCMIVGSPELTFGKGTQLSVVDFLPTTAQPTKKSTL

KKRVCRLPRPETQKDFTNKQRIGFWCPATKRHRSVMSTMWKNERRDTFNP

GEFNGC.

In an embodiment, the human CD8 β chain comprises the amino acid sequence of:

Isoform 8

(SEQ ID NO: 76)

MRPRLWLLLAAQLTVLHGNSVLQQTPAYIKVQTNKMVMLSCEAKISLSNM

RIYWLRQRQAPSSDSHHEFLALWDSAKGTIHGEEVEQEKIAVFRDASRFI

LNLTSVKPEDSGIYFCMIVGSPELTFGKGTQLSVVDFLPTTAQPTKKSTL

KKRVCRLPRPETQKGLKGKVYQEPLSPNACMDTTAILQPHRSCLTHGS.

In some embodiments, the CD8 targeting moiety is capable of specific binding. In various embodiments, the CD8 targeting moiety comprises an antigen recognition domain such as an antibody or derivatives thereof. In an embodiment, the CD8 targeting moiety comprises an antibody. In various embodiments, the antibody is a full-length multimeric protein that includes two heavy chains and two light chains. Each heavy chain includes one variable region (e.g., $V_H$) and at least three constant regions (e.g., $CH_1$, $CH_2$ and $CH_3$), and each light chain includes one variable region ($V_L$) and one constant region ($C_L$). The variable regions determine the specificity of the antibody. Each variable region comprises three hypervariable regions also known as complementarity-determining regions (CDRs) flanked by four relatively conserved framework regions (FRs). The three CDRs, referred to as CDR1, CDR2, and CDR3, contribute to the antibody binding specificity. In some embodiments, the antibody is a chimeric antibody. In some embodiments, the antibody is a humanized antibody.

In some embodiments, the CD8 targeting moiety comprise an antibody derivative or format. In some embodiments, the CD8 targeting moiety comprises a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; an Affimer; an alphabody; a bicyclic peptide; a Microbody; an aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; a DuoBody, a Fv, a Fab, a Fab', a $F(ab')_2$, a peptide mimetic molecule, or a synthetic molecule, as described in U.S. Pat. Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. No. 7,838,629, 7,186,524, 6,004,746, 5,475,096, US 2004/146938, US 2004/157209, U.S. Pat. No. 6,994,982, 6,794,144, US 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-June; 3(3): 310-317.

In some embodiments, the CD8 targeting moiety comprises a single-domain antibody, such as a VHH. The VHH may be derived from, for example, an organism that produces VHH antibody such as a camelid, a shark, or the VHH may be a designed VHH. VHHs are antibody-derived therapeutic proteins that contain the unique structural and functional properties of naturally occurring heavy-chain antibodies. VHH technology is based on fully functional antibodies from camelids that lack light chains. These heavy-chain antibodies contain a single variable domain ($V_H$H) and two constant domains ($C_{H2}$ and CH3).

In an embodiment, the CD8 targeting moiety comprises a VHH. In some embodiments, the VHH is a humanized VHH or camelized VHH.

In some embodiments, the VHH comprises a fully human VH domain, e.g. a HUMABODY (Crescendo Biologics, Cambridge, UK). In some embodiments, fully human VH domain, e.g. a HUMABODY is monovalent, bivalent, or trivalent. In some embodiments, the fully human VH domain, e.g. a HUMABODY is mono- or multi-specific such as monospecific, bispecific, or trispecific. Illustrative fully human VH domains, e.g. a HUMABODIES are described in, for example, WO2016/113555 and WO2016/113557, the entire disclosure of which is incorporated by reference.

In some embodiments, the CD8 targeting moiety comprises a VHH comprising a single amino acid chain having four "framework regions" or FRs and three "complementary determining regions" or CDRs. As used herein, "framework region" or "FR" refers to a region in the variable domain, which is located between the CDRs. As used herein, "complementary determining region" or "CDR" refers to variable regions in VHHs that contains the amino acid sequences capable of specifically binding to antigenic targets.

In various embodiments, the CD8 targeting moiety comprises a VHH having a variable domain comprising at least one CDR1, CDR2, and/or CDR3 sequences.

In some embodiments, the CD8 CDR1 sequence is selected from:

(SEQ ID NO: 77)
GFTFDDYAMS;

(SEQ ID NO: 78)
GFTFDDYAIG;

(SEQ ID NO: 79)
GRSFSSYTLA;

(SEQ ID NO: 80)
GRTFSSYTMG;

(SEQ ID NO: 81)
GRTFSSYIMG;

(SEQ ID NO: 82)
GRTFSSYTMG;

(SEQ ID NO: 83)
GRTSGRTFSSYTMG;

(SEQ ID NO: 84)
GRTFSSYAMG;

(SEQ ID NO: 85)
GLTFSNYIMG;

(SEQ ID NO: 86)
GRTFSSYTMG;

(SEQ ID NO: 87)
GRTFSSDTMG;

(SEQ ID NO: 88)
GLTFSNYIMG;

(SEQ ID NO: 89)
GFTLDYYGIG;

(SEQ ID NO: 90)
GHTFSSYTMG;

(SEQ ID NO: 91)
GRTFSSYVIG;

(SEQ ID NO: 92)
GFAFDGYAIG;

(SEQ ID NO: 93)
GFAFGFFDMT;

(SEQ ID NO: 94)
GRTFSNYVIG;

(SEQ ID NO: 95)
GSIFSINVMG;

-continued (SEQ ID NO: 96)
GRTFSNYNVG;

(SEQ ID NO: 97)
GHTFSSYTMG;

(SEQ ID NO: 98)
GRTFSTYPVG;

(SEQ ID NO: 99)
GRTFSNYAMG;

(SEQ ID NO: 100)
GRTFSDYRMG;

(SEQ ID NO: 101)
GLTFSNYIMA;

(SEQ ID NO: 102)
GRTFSNSVMG;

(SEQ ID NO: 103)
GRTFSSYIIG;

(SEQ ID NO: 104)
GRTFSSYVMG;

(SEQ ID NO: 105)
GGTFSNYVMG;

(SEQ ID NO: 106)
GRTFSNYGIG;

(SEQ ID NO: 107)
GFTFDDYAIA;

(SEQ ID NO: 108)
GRTFSSYTVA;

(SEQ ID NO: 109)
GFPFDDYAIA;

(SEQ ID NO: 110)
GRTFSSYVMG;

(SEQ ID NO: 111)
GRTLSSNPMA;

(SEQ ID NO: 112)
GFTFDNYAIG;

(SEQ ID NO: 113)
GRAFSSYFMG;

(SEQ ID NO: 114)
TPTFSSYNMG;

(SEQ ID NO: 115)
GFTFDDYAIA;

(SEQ ID NO: 116)
GGTFSGYIMG;

(SEQ ID NO: 117)
GRSFSSYTIA;

(SEQ ID NO: 118)
GFSSDDYTIG;

(SEQ ID NO: 119)
GFTFDDYTIG;

(SEQ ID NO: 120)
GFSSDDYTIG;

(SEQ ID NO: 121)
GFTFDQYTIA;

(SEQ ID NO: 122)
GRTFSSYAMA;

-continued (SEQ ID NO: 123)
GFAFDGYAIG;

(SEQ ID NO: 124)
GFSSDDYTIA;

(SEQ ID NO: 125)
GFSSDDYTIG;

(SEQ ID NO: 126)
GFTFDDYTIG;

(SEQ ID NO: 127)
GFSSDDYTIG;

(SEQ ID NO: 128)
GFSSDDYTIG;

(SEQ ID NO: 129)
GFSFDDYAIA;

(SEQ ID NO: 130)
GFSSDDYTIG;

(SEQ ID NO: 131)
GFTGNDLAIG;

(SEQ ID NO: 132)
GFSSDDYTIA;

(SEQ ID NO: 133)
EGTLSSYGIG;

(SEQ ID NO: 134)
GFSSDDYTIA;

(SEQ ID NO: 135)
GFTFDDYAIA;

(SEQ ID NO: 136)
GLSSDDYTIG;

(SEQ ID NO: 137)
GLSSDDYTIG;

(SEQ ID NO: 138)
GFSSDDYTIG;

(SEQ ID NO: 139)
GFSFDDYTIG;

(SEQ ID NO: 140)
GFTFDDYAIA;

(SEQ ID NO: 141)
GFTFDDYAIG;

(SEQ ID NO: 142)
GFTFGDYTIG;

(SEQ ID NO: 143)
EGTFSSYGIG;

(SEQ ID NO: 144)
GFSSDDYTIG;

(SEQ ID NO: 145)
GVSIGDYNIG;

(SEQ ID NO: 146)
GFTFDDYTIA;
or (SEQ ID NO: 147)
GFTFDDYTIA.

In some embodiments, the CD8 CDR2 sequence is selected from:

(SEQ ID NO: 148)
TINWNGGSAEYAEPVKG;

(SEQ ID NO: 149)
CIRVSDGSTYYADPVKG;

(SEQ ID NO: 150)
ASITWGGGNTY;

(SEQ ID NO: 151)
AATVWTGAGTV;

(SEQ ID NO: 152)
AAIGWSADITV;

(SEQ ID NO: 153)
AFIDWSGGGTY;

(SEQ ID NO: 154)
ATITWGGGSTY;

(SEQ ID NO: 155)
AAISWSGGPTV;

(SEQ ID NO: 156)
AAITWGGGSTV;

(SEQ ID NO: 157)
AAITWSGVSTV;

(SEQ ID NO: 158)
GAIMWSGAFTH;

(SEQ ID NO: 159)
AAITWGGGSTV;

(SEQ ID NO: 160)
SCISSSDRNTY;

(SEQ ID NO: 161)
AFIDWSGGGTY;

(SEQ ID NO: 162)
AVITWSGDSTY;

(SEQ ID NO: 163)
ACISSKDGSTY;

(SEQ ID NO: 164)
SGINSIGGSTT;

(SEQ ID NO: 165)
AVVTWSGDSTY;

(SEQ ID NO: 166)
AKITNFGITS;

(SEQ ID NO: 167)
SFISWISDITY;

(SEQ ID NO: 168)
AFIDWSGGGTY;

(SEQ ID NO: 169)
AVILWSGVSTY;

(SEQ ID NO: 170)
AAIVWSGGSTY;

(SEQ ID NO: 171)
AAISSSGYHTY;

(SEQ ID NO: 172)
SCISSPDGSTY;

(SEQ ID NO: 173)
AAVLWSGVSTA;

-continued (SEQ ID NO: 174) VAITWDGSATT;

(SEQ ID NO: 175) AAIGWNGGITY;

(SEQ ID NO: 176) GFITWSGASTY;

(SEQ ID NO: 177) AGINWSGESAD;

(SEQ ID NO: 178) SCIERSDGSTY;

(SEQ ID NO: 179) SCISNTDSSTY;

(SEQ ID NO: 180) SCISNTDSSTY;

(SEQ ID NO: 181) AQISWSAGSIY;

(SEQ ID NO: 182) AGMSWNPGPAV;

(SEQ ID NO: 183) SCISRSDGSTY;

(SEQ ID NO: 184) ANIGWTGDMTY;

(SEQ ID NO: 185) AAIIWSGSMTY;

(SEQ ID NO: 186) SCISNTDSSTY;

(SEQ ID NO: 187) AANTWSGGPTY;

(SEQ ID NO: 188) SCISSDGSTG;

(SEQ ID NO: 189) SCYSSSDGSTG;

(SEQ ID NO: 190) SCISSDGSTG;

(SEQ ID NO: 191) GCIKSSDGTTG;

(SEQ ID NO: 192) SCISNTDSSTY;

(SEQ ID NO: 193) AAIAWSAGSTY;

(SEQ ID NO: 194) SCISSKEGSTY;

(SEQ ID NO: 195) SCISSSDGSTG;

(SEQ ID NO: 196) SCYSSRDGTTG;

(SEQ ID NO: 197) SCISSDGSTG;

(SEQ ID NO: 198) SCYSSSDGSTG;

(SEQ ID NO: 199) SCFSSSDGSTG;

(SEQ ID NO: 200) SCISNTDSSTF;

-continued (SEQ ID NO: 201) SCYSSSDGSTG;

(SEQ ID NO: 202) SCISNTDSSTY;

(SEQ ID NO: 203) SCISSSDGSTG;

(SEQ ID NO: 204) GGINWSGDSTD;

(SEQ ID NO: 205) SCFSSSDGSAG;

(SEQ ID NO: 206) SCISNTDSSTY;

(SEQ ID NO: 207) SCFSTRDGNAG;

(SEQ ID NO: 208) SCFSSRDGSTG;

(SEQ ID NO: 209) SCFSSRDGSTG;

(SEQ ID NO: 210) SCISSDGSTG;

(SEQ ID NO: 211) SCISNTDSSTY;

(SEQ ID NO: 212) SCISSPDGSTY;

(SEQ ID NO: 213) SCYSSSDGNTG;

(SEQ ID NO: 214) GGINWSGDSTD;

(SEQ ID NO: 215) SCFSSSDGSTG;

(SEQ ID NO: 216) SCISSGDGTTY;

(SEQ ID NO: 217) SCISSDGSTG; or (SEQ ID NO: 218) SCISSDGSTG.

In some embodiments, the CD8 CDR3 sequence is selected from:

(SEQ ID NO: 219) KDADLVWYNLS;

(SEQ ID NO: 220) KDADLVWYNLR;

(SEQ ID NO: 221) AGSLYTCVQSIVVVPARPYYDMDY;

(SEQ ID NO: 222) AKGLRNSDWDLRRGYEYDY;

(SEQ ID NO: 223) ADQASVPPPYGSERYDIASPSEYDY;

(SEQ ID NO: 224) ANSRAYYSSSYDLGRLASYDY;

(SEQ ID NO: 225) AAQRLGSVTDYTKYDY;

-continued (SEQ ID NO: 226)
ASVKVVAGSGIDISGSRNYDY;

(SEQ ID NO: 227)
AKRLDYSATDKGVDLSDEYDY;

(SEQ ID NO: 228)
AAGGSGRLRDLKVGQNYDY;

(SEQ ID NO: 229)
ADSPPRTYSSGSVNLEDGSEYDY;

(SEQ ID NO: 230)
VIPGRGSALPIDVGKSDEYEY;

(SEQ ID NO: 231)
AAGASGRLRDLKVGQNYDY;

(SEQ ID NO: 232)
ADGNVWSPPICGSAGPPPGGMDY;

(SEQ ID NO: 233)
AAQRLGSVTDYTKYDY;

(SEQ ID NO: 234)
AIPPRAYSGGSYSLKDQSKYEY;

(SEQ ID NO: 235)
ADGNVWSPPICSSAGPPPGGMDY;

(SEQ ID NO: 236)
KSRSSYSNN;

(SEQ ID NO: 237)
AMPPRAYTGRSVSLKDQSKYEY;

(SEQ ID NO: 238)
LDTTGWGPPPYQY;

(SEQ ID NO: 239)
AHPPDPSRGGEWRLQTPSEYDY;

(SEQ ID NO: 240)
AAQRLGSVTDYTKYDY;

(SEQ ID NO: 241)
VPRSHFTTAQDMGQDMGAPSWYEY;

(SEQ ID NO: 242)
AVLIRYYSGGYQGLSDANEYDY;

(SEQ ID NO: 243)
VVKYLSGSYSYAGQYNF;

(SEQ ID NO: 244)
ADFNVWSPPICGSVGPPPGGMDY;

(SEQ ID NO: 245)
AHESTYYSGTYYLTDPRRYVY;

(SEQ ID NO: 246)
AVPARGLTMDLENSDIYDH;

(SEQ ID NO: 247)
AATLQVTGSYYLDLSTVDIYDN;

(SEQ ID NO: 248)
ATLFRSNGPKDLSSGYEYDY;

(SEQ ID NO: 249)
AGESGVWVGGLDY;

(SEQ ID NO: 250)
VGSANSGEFRFGWVLKPDLYNY;

(SEQ ID NO: 251)
ADGNVWSPPICGSAGPPPGGMDY;

(SEQ ID NO: 252)
ADGNVWSPPICGSAGPPPGGMDY;

-continued (SEQ ID NO: 253)
ERGYAYCSDDGCQRTQDYDY;

(SEQ ID NO: 254)
GAARAWWSGSYDYTRMNNYDY;

(SEQ ID NO: 255)
AETSADSGEFRFGWVLKPSLYDY;

(SEQ ID NO: 256)
AAGSAYSGSYWNITMAANYDY;

(SEQ ID NO: 257)
AQRIFGAQPMDLSGDYEY;

(SEQ ID NO: 258)
ADGNVWSPPICGSAGPPPGGMDY;

(SEQ ID NO: 259)
ARDYRGIKDLDLKGDYDY;

(SEQ ID NO: 260)
ADFNVWSPPICGSIWYGPPPRGMDY;

(SEQ ID NO: 261)
ADSNVWSPPICGSRWYGPPPGGMAY;

(SEQ ID NO: 262)
ADFNVWSPPICGSNWYGPPPGGMDY;

(SEQ ID NO: 263)
ADFNVWSPPICGSIWYGPPPGGMDY;

(SEQ ID NO: 264)
ADGNVWSPPICGSAGPPPGGMDY;

(SEQ ID NO: 265)
ARIITVATMRLDSDYDY;

(SEQ ID NO: 266)
ADGNVWSPPICGSAGPPPGGMDY;

(SEQ ID NO: 267)
ADSNVWSPPICGRTWYGPPPGGMDY;

(SEQ ID NO: 268)
ADFNVWSPPICGSIWYGPPPGGMAY;

(SEQ ID NO: 269)
ADFNVWSPPICGSNWYGPPPGGMDY;

(SEQ ID NO: 270)
ADFNVWSPPICGSSWYGPPPGGMDY;

(SEQ ID NO: 271)
ADFNVWSPPICGSRWYGPPPGGMEY;

(SEQ ID NO: 272)
ADGNVWSPPICGSAGPPPGGMDY;

(SEQ ID NO: 273)
ADFNVWSPPICGSRWYGPPPGGMAY;

(SEQ ID NO: 274)
ADGNVWSPPICGSAGPPPGGMDY;

(SEQ ID NO: 275)
ADSNVWSPPICGKTWYGPPPGGMDY;

(SEQ ID NO: 276)
AGESGVWVGGLDY;

(SEQ ID NO: 277)
ADSNVWSPPICGSTWYGPPPGGMAY;

(SEQ ID NO: 278)
ADGNVWSPPICGSAGPPPGGMDY;

(SEQ ID NO: 279)
ADFNVWSPPICGSRWYGPPPGGMDY;

-continued (SEQ ID NO: 280)
ADFNVWSPPICGSRWYGPPPGGMDY;

(SEQ ID NO: 281)
ADFNVWSPPICGSRWYGPPPGGMDY;

(SEQ ID NO: 282)
ADFNVWSPPICGSIWYGPPPGGMDY;

(SEQ ID NO: 283)
ADGNVWSPPICGSAGPPPGGMDY;

(SEQ ID NO: 284)
ADFNVWSPPICGSVGPPPGGMDY;

(SEQ ID NO: 285)
ADFNVWSPPICGSSWYGPPPGGMAY;

(SEQ ID NO: 286)
AGESGVWVGGLDY;

(SEQ ID NO: 287)
ADFNVWSPPICGSSWYGPPPGGMEY;

(SEQ ID NO: 288)
ADGNVWSPPICGSAGPPPGGMDY;

(SEQ ID NO: 289)
ADFNVWSPPICSSNWYGPPPRGMDY;
or (SEQ ID NO: 290)
ADFNVWSPPICGSIWYGPPPRGMDY.

In various embodiments, the CD8 targeting moiety comprises SEQ ID NO: 77, SEQ ID NO: 148, and SEQ ID NO: 219.

In various embodiments, the CD8 targeting moiety comprises SEQ ID NO: 77, SEQ ID NO: 148, and SEQ ID NO: 220.

In various embodiments, the CD8 targeting moiety comprises SEQ ID NO: 77, SEQ ID NO: 148, and SEQ ID NO: 221.

In various embodiments, the CD8 targeting moiety comprises SEQ ID NO: 77, SEQ ID NO: 149, and SEQ ID NO: 219.

In various embodiments, the CD8 targeting moiety comprises SEQ ID NO: 77, SEQ ID NO: 149, and SEQ ID NO: 220.

In various embodiments, the CD8 targeting moiety comprises SEQ ID NO: 77, SEQ ID NO: 149, and SEQ ID NO: 221.

In various embodiments, the CD8 targeting moiety comprises SEQ ID NO: 78, SEQ ID NO: 148, and SEQ ID NO: 219.

In various embodiments, the CD8 targeting moiety comprises SEQ ID NO: 78, SEQ ID NO: 148, and SEQ ID NO: 220.

In various embodiments, the CD8 targeting moiety comprises SEQ ID NO: 78, SEQ ID NO: 148, and SEQ ID NO: 221.

In various embodiments, the CD8 targeting moiety comprises SEQ ID NO: 78, SEQ ID NO: 149, and SEQ ID NO: 219.

In various embodiments, the CD8 targeting moiety comprises SEQ ID NO: 78, SEQ ID NO: 149, and SEQ ID NO: 220.

In various embodiments, the CD8 targeting moiety comprises SEQ ID NO: 78, SEQ ID NO: 149, and SEQ ID NO: 221.

By way of example, in some embodiments, the CD8 targeting moiety comprises an amino acid sequence selected from the following sequences:

R3HCD27
(SEQ ID NO: 291)
QVQLQESGGGSVQPGGSLRLSCAASGFTFDDYAMSWVRQVPGKGLEWV
STINWNGGSAEYAEPVKGRFTISRDNAKNTVYLQMNSLKLEDTAVYYCAK
DADLVWYNLSTGQGTQVTVSSAAAYPYDVPDYGS;

R3HCD129
(SEQ ID NO: 292)
QVQLQESGGGLVQPGGSLRLSCAASGFTFDDYAMSWVRQVPGKGLEWV
STINWNGGSAEYAEPVKGRFTISRDNAKNTVYLQMNSLKLEDTAVYYCAK
DADLVWYNLRTGQGTQVTVSSAAAYPYDVPDYGS;
or

R2HCD26
(SEQ ID NO: 293)
QVQLQESGGGLVQAGGSLRLSCAASGFTFDDYAIGWFRQAPGKEREGVS
CIRVSDGSTYYADPVKGRFTISSDNAKNTVYLQMNSLKPEDAAVYYCAAG
SLYTCVQSIVVVPARPYYDMDYWGKGTQVTVSSAAAYPYDVPDYGS.

In various embodiments, the CD8 targeting moiety comprises an amino acid sequence selected from the following sequences:

1CDA 7
(SEQ ID NO: 294)
QVQLQESGGGLVQAGGSLRLSCAASGRSFSSYTLAWFRQAPGKEREFVASITWGGGNTYYPDSVKGRFTISRD

DAKNTVYLQMNSLKPEDTAVYYCAAKGLRNSDWDLRRGYEYDYWGQGTQVTVSSAAAYPYDVPDYGSHHHHH

H;

1CDA 12
(SEQ ID NO: 295)
QVQLQESGGGLVQDGGSLRLSCAFSGRTFSSYTMGWFRQGPGKEREFVAATVWTGAGTVYADSVKGRFTISR

DNAKNTVYLQMNSLRPEDTAVYYCAADQASVPPPYGSERYDIASPSEYDYWGQGTQVTVSSAAAYPYDVPDYG

SHHHHHH;

1CDA 14
(SEQ ID NO: 296)
QVQLQESGGGLVQAGASLRLSCAASGRTFSSYIMGWFRQAPGKEREFVAAIGWSADITVYADSVKGRFTISRDN

AENMVYLQMNSLNPEDTAVYYCAANSRAYYSSSYDLGRLASYDYWGQGTQVTVSSAAAYPYDVPDYGSHHHH

HH;

-continued

1CDA 15

(SEQ ID NO: 297)
QVQLQESGGGLVQAGGSLRLSCAASGRTFSSYTMGWFRQAPGKEREFVAFIDWSGGGTYYDDSVKGRFTISR
DNAENTVYLQMNNLEPEDTAVYYCAAAQRLGSVTDYTKYDYWGQGTQVTVSSAAAYPYDVPDYGSHHHHHH;

1CDA 17

(SEQ ID NO: 298)
QVQLQESGGGLVQAGGSLRLSCAASGRTSGRTFSSYTMGWFRQAPGKEREFVATITWGGGSTYYADSVKGRF
TISRDNANNTVYLQMNSLKPEDTAVYYCAASVKWAGSGIDISGSRNYDYWGQGTQVTVSSAAAYPYDVPDYGS
HHHHHH;

1CDA 18

(SEQ ID NO: 299)
QVQLQESGGGLVQPGGSLRLSCLASGRTFSSYAMGWFRQAPGKEREFVAAISWSGGPTVYADHVKGRFTISRD
NAKNTVYLQVNSLKPEDTADYYCAAKRLDYSATDKGVDLSDEYDYWGQGTQVTVSSAAAYPYDVPDYGSHHHH
HH;

1CDA 19

(SEQ ID NO: 300)
QVQLQESGGGLVQAGDSLRLSCAASGLTFSNYIMGWFRQAPGKEREFVAAITWGGGSTVYADSVEGRFTISRD
GTKNTVSLQMNSLLPEDTAVYYCAAAGGSGRLRDLKVGQNYDYWGQGTQVTVSSAAAYPYDVPDYGSHHHHH
H;

1CDA 24

(SEQ ID NO: 301)
QVQLQESGGGLVQAGGSLRLSCAASGRTFSSYTMGWFRQAPGREREFVAAITWSGVSTVYTDSVKGRFTVSR
DNAKNTVYLQMNSLKPEDTAVYYCAADSPPRTYSSGSVNLEDGSEYDYWGQGTQVTVSSAAAYPYDVPDYGS
HHHHHH;

1CDA 26

(SEQ ID NO: 302)
QVQLQESGGGLVQAGGSLRLSCAASGRTFSSDTMGWFRQAPGKEREFVGAIMWSGAFTHYADSVKGRFTISR
DNAKNTVYLQMNALKPEDTAVYYCAVIPGRGSALPIDVGKSDEYEYWGQGTQVTVSSAAAYPYDVPDYGSHHH
HHH;

1CDA 28

(SEQ ID NO: 303)
QVQLQESGGGLVQAGDSLRLSCAASGLTFSNYIMGWFRQAPGKEREFVAAITWGGGSTVYADSVEGRFTISRD
GTKNTVSLQMNSLQPEDTAVYYCAAAGASGRLRDLKVGQNYDYWGQGTQVTVSSAAAYPYDVPDYGSHHHHH
H;

1CDA 37

(SEQ ID NO: 304)
QVQLQESGGGLVQAGGSLRLSCAGSGFTLDYYGIGWFRQAPGKEREGVSCISSSDRNTYYADSVKGRFTISGD
NAKNTVYLQMNNLKPEDTAVYYCAADGNVWSPPICGSAGPPPGGMDYWGKGTQVTVSSAAAYPYDVPDYGSH
HHHHH;

1CDA 43

(SEQ ID NO: 305)
QVQLQESGGGLVQAGGSLRLSCVASGHTFSSYTMGWFRQAPGKEREFVAFIDWSGGGTYYANSVKGRFTISR
DNAENTVYLQMNNLKPEDTAVYYCAAAQRLGSVTDYTKYDYWGQGTQVTVSSAAAYPYDVPDYGSHHHHHH;

1CDA 45

(SEQ ID NO: 306)
QVQLQESGGGLVQAGGSLRLSCAASGRTFSSYVIGWFRQAPGKEREFVAVITWSGDSTYSSDSLKGRFTISRDN
AKNTVYLQMNALNPEDTAVYYCAAIPPRAYSGGSYSLKDQSKYEYWGQGTQVTVSSAAAYPYDVPDYGSHHHH
HH;

1CDA 47

(SEQ ID NO: 307)
QVQLQESGGGLVQAEGSLKLSCISGFAFDGYAIGWFRQAPGKEREGVACISSKDGSTYYADSVKGRFTMSVDK
TKNTVYLQMSSLKPEDTAVYYCAADGNVWSPPICSSAGPPPGGMDYWGKGTQVTVSSAAAYPYDVPDYGSHH

-continued

HHHH;

1CDA 48

(SEQ ID NO: 308)
QVQLQESGGGLVQPGGSLTLSCAASGFAFGFFDMTWVRQAPGKGLEWVSGINSIGGSTTYADSVKGRFTISRD

NAKNELYLQMNSLKPDDTAVYYCAKSRSSYSNNWRPPGQGTQVTVSSAAAYPYDVPDYGSHHHHHH;

1CDA 58

(SEQ ID NO: 309)
QVQLQESGGGLVQARGSLTLSCAASGRTFSNYVIGWFRQAPGEEREFVAVVTWSGDSTYSSDSLKGRFTISRD

NAKNTVYLQMNNLNPEDTAVYYCAAMPPRAYTGRSVSLKDQSKYEYWGQGTQVTVSSAAAYPYDVPDYGSHH

HHHH;

1CDA 65

(SEQ ID NO: 310)
QVQLQESGGGLVQPGGSLRLSCAASGSIFSINVMGWYRQTPGKERELVAKITNFGITSYADSAQGRFTISRGNAK

NTVYLQMNSLKPEDTAVYYCNLDTTGWGPPPYQYWGQGTQVTVSSAAAYPYDVPDYGSHHHHHH;

1CDA 68

(SEQ ID NO: 311)
QVQLQESGGGLVQAGASLRLSCAASGRTFSNYNVGWFRQAPGKEREFVSFISWISDITYYSDSVKGRFIISRDNA

KNMVYLQMNSLKPEDTAVYYCAAHPPDPSRGGEWRLQTPSEYDYWGQGTQVTVSSAAAYPYDVPDYGSHHH

HHH;

1CDA 73

(SEQ ID NO: 312)
QVQLQESGGGLVQAGGSLRLSCAASGHTFSSYTMGWFRQAPGKEREFVAFIDWSGGGTYYADSVKGRFTISR

DNAENTVYLQMNNLKPEDTAVYYCAAAQRLGSVTDYTKYDYWGQGTQVTVSSAAAYPYDVPDYGSHHHHHH;

1CDA 75

(SEQ ID NO: 313)
QVQLQESGGGLVQAGGSLRLSCAASGRTFSTYPVGWFRQAPGKEREFVAVILWSGVSTYYADSVKGRFTISRD

NAQNTVYLQMDSLKPEDTAVYYCAVPRSHFTTAQDMGQDMGAPSWYEYWGQGTQVTVSSAAAYPYDVPDYG

SHHHHHH;

1CDA 86

(SEQ ID NO: 314)
QVQLQESGGGLVQAGGSLRLSCAASGRTFSNYAMGWFRQAPGKEREFVAAIVWSGGSTYYADSVKGRFTISR

DNAKNTVYLQMNSLKPEDTAVYYCAAVLIRYYSGGYQGLSDANEYDYWGQGTQVTVSSAAAYPYDVPDYGSHH

HHHH;

1CDA 87

(SEQ ID NO: 315)
QVQLQESGGGLVQAGASLRLSCSASGRTFSDYRMGWFRQAPGKEREWVAAISSSGYHTYYADSVKGRFTISR

DNAKNTGYLQMSSLKPEDTAVYYCAVVKYLSGSYSYAGQYNFWGQGTQVTVSSAAAYPYDVPDYGSHHHHHH;

1CDA 88

(SEQ ID NO: 316)
QVQLQESGGGLVQAGDSLKLSCAASGLTFSNYIMAWFRQAPGKEREGVSCISSPDGSTYYADSVKGRFTISSDN

AKNTVYLQMNSLKPEDTAVYYCAADFNVWSPPICGSVGPPPGGMDYWGKGTQVTVSSAAAYPYDVPDYGSHH

HHHH;

1CDA 89

(SEQ ID NO: 317)
QVQLQESGGGLVQAGGSLRLSCAASGRTFSNSVMGWFRQPPGKEREFVAAVLWSGVSTAYADSVKGRFTISR

DNAKNTVYLQMNNLKPDDTAVYYCAAHESTYYSGTYYLTDPRRYVYWGQGTQVTVSSAAAYPYDVPDYGSHH

HHHH;

1CDA 92

(SEQ ID NO: 318)
QVQLQESGGGLVQAGGSLRLSCVGDGRTFSSYIIGWFRQAPGNEREFVVAITWDGSATTYADSVKGRFTVSRD

SAKNTAYLQMNSLKPEDTAVYYCAAVPARGLTMDLENSDIYDHWGRGTQVTVSSAAAYPYDVPDYGSHHHHHH;

-continued

1CDA 93

(SEQ ID NO: 319)
QVQLQESGGGLVQAGGSLRLSCAASGRTFSSYVMGWFRQALGKEREFVAAIGWNGGITYYADSVKGRFAISRD

NAKNTVYLQMNSLKPEDTAVYYCAAATLQVTGSYYLDLSTVDIYDNWGQGTQVTVSSAAAYPYDVPDYGSHHH

HHH;

2CDA 1

(SEQ ID NO: 320)
QVQLQESGGGLVQAGGSLRLSCAASGGTFSNYVMGWFRQAPGKEREFVGFITWSGASTYYADSVKGRFTISR

DNAENTVYLQMNSLKPEDTAVYYCAATLFRSNGPKDLSSGYEYDYWGQGTQVTVSSAAAYPYDVPDYGSHHH

HHH;

2CDA 5

(SEQ ID NO: 321)
QVQLQESGGGLVQAGDSLRLTCTASGRTFSNYGIGWFRQAPGKEREFVAGINWSGESADYADSVKGRFTISRD

NAKNTVYLQMNSLKPEDTAVYYCAAGESGVWVGGLDYWXQGTQVTVSSAAAYPYDVPDYGSHHHHHH;

2CDA 22

(SEQ ID NO: 322)
QVQLQESGGGLVQAGGSLRLSCAASGFTFDDYAIAWFRQAPGKEREGVSCIERSDGSTYYADSVKGRFTISSDN

AKNTVYLQMNSLKPEDTAVYYCAVGSANSGEFRFGWVLKPDLYNYWGQGTQVTVSSAAAYPYDVPDYGSHHH

HHH;

2CDA 28

(SEQ ID NO: 323)
QVQLQESGGGLVQAGGSLRLSCTASGRTFSSYTVAWFRQSPGKEREGISCISNTDSSTYYADSVKGRFTISSDN

AKSTVHLQMSSLKPEDTAVYYCAADGNVWSPPICGSAGPPPGGMDYWGKGTQVTVSSAAAYPYDVPDYGSHH

HHHH;

2CDA 62

(SEQ ID NO: 324)
QVQLQESGGGLVQPGGSLRLSCATFGFPFDDYAIAWFRQAPGKEREGVSCISNTDSSTYYADSVKGRFTISSDN

AKNTVHLQMSSLKPEDTAVYYCAADGNVWSPPICGSAGPPPGGMDYWGKGTQVTVSSAAAYPYDVPDYGSHH

HHHH;

2CDA 68

(SEQ ID NO: 325)
QVQLQESGGGLVQAGGSLRLSCAASGRTFSSYVMGWFRQAPGKEREFVAQISWSAGSIYYADSVKGRFTISND

NAKRTVYLQMNSLKPEDTAVYYCAERGYAYCSDDGCQRTQDYDYWGQGTQVTVSSAAAYPYDVPDYGSHHH

HHH;

2CDA 73

(SEQ ID NO: 326)
QVQLQESGGGLVQAGGSLRLSCAASGRTLSSNPMAWFRQAAGKEREFVAGMSWNPGPAVYADSVKGRFTISR

DSAENTVYLQMNSLKPEDTAVYYCAGAARAWWSGSYDYTRMNNYDYWGPGTQVTVSSAAAYPYDVPDYGSH

HHHHH;

2CDA 74

(SEQ ID NO: 327)
QVQLQESGGGLVQAGGSLRLSCAVSGFTFDNYAIGWFRQAPGKEREGVSCISRSDGSTYYADSVRGRFTISSD

NAKNTVYLQMNSLKPEDTAVYYCAAETSADSGEFRFGWVLKPSLYDYWGQGTQVTVSSAAAYPYDVPDYGSH

HHHHH;

2CDA 75

(SEQ ID NO: 328)
QVQLQESGGGLVQAGGSLRLSCAASGRAFSSYFMGWFRQTPGKEREFVANIGWTGDMTYYADSVKGRFTISR

DNAKNTVYLQMNSLKPEDTAVYYCAAAGSAYSGSYWNITMAANYDYWGQGTQVTVSSAAAYPYDVPDYGSHH

HHHH;

-continued

2CDA 77

(SEQ ID NO: 329)

QVQLQESGGGLVQAGGSLRLSCAASTPTFSSYNMGWFRQAPGKEREFVAAIIWSGSMTYYADSMKGRFTVSID

NAKNTVYLQMNSLKPEDTAVYYCAAQRIFGAQPMDLSGDYEYWGQGTQVTVSSAAAYPYDVPDYGSHHHHHH;

2CDA 81

(SEQ ID NO: 330)

QVQLQESGGGLVQAGGSLRLSCATFGFTFDDYAIAWFRQAPGKEREGISCISNTDSSTYYADSVKGRFTISSDSA

KNTVHLQMSSLKPEDTAVYYCAADGNVWSPPICGSAGPPPGGMDYWGKGTQVTVSSAAAYPYDVPDYGSHHH

HHH;

2CDA 87

(SEQ ID NO: 331)

QVQLQESGGGLVQAGGSLRLSCKASGGTFSGYIMGWFRQAPGKEREFVAANTWSGGPTYYSDSVKGRFTISR

DNAKNTVYLQMNTLKPEDTAVYQCAARDYRGIKDLDLKGDYDYWGQGTQVTVSSAAAYPYDVPDYGSHHHHH

H;

2CDA 88

(SEQ ID NO: 332)

QVQLQESGGGLVQAGDSLKLSCATSGRSFSSYTIAWFRQAPGKEREGISCISSDGSTGYADSVRGRFTISSDNA

KNTVYLQMNSLKPEDTAVYYCAADFNVWSPPICGSIWYGPPPRGMDYWGKGTQVTVSSAAAYPYDVPDYGSH

HHHHH;

2CDA 89

(SEQ ID NO: 333)

QVQLQESGGGLVQAGGYLRLSCAASGFSSDDYTIGWFRQAPGKEREGISCYSSSDGSTGFADSVKGRFTISSD

NAKNTVYLQMNNLRPEDTAVYYCAADSNVWSPPICGSRWYGPPPGGMAYWGKGTQVTVSSAAAYPYDVPDY

GSHHHHHH;

2CDA 91

(SEQ ID NO: 334)

QVQLQESGGGLAQVGGSLRLSCTASGFTFDDYTIGWFRQAPGKEREGISCISSDGSTGYADSVKGRFTISSDNA

KNTVYLQMNSLKPEDTAVYYCAADFNVWSPPICGSNWYGPPPGGMDYWGKGTQVTVSSAAAYPYDVPDYGSH

HHHHH;

2CDA 92

(SEQ ID NO: 335)

QVQLQESGGGLVQAGGSLRLSCAASGFSSDDYTIGWFRQAPGKEREGIGCIKSSDGTTGYADSVKGRFTISSDN

AKNTVYLQMNSLKPEDTAVYYCAADFNVWSPPICGSIWYGPPPGGMDYWGKGTQVTVSSAAAYPYDVPDYGS

HHHHHH;

2CDA 93

(SEQ ID NO: 336)

QVQLQESGGGLAQAGGSLRLSCAASGFTFDQYTIAWFRQAPGKEREGVSCISNTDSSTYYADSVKGRFTISSDN

AKNTVYLQMSSLKPEDTAVYYCAADGNVWSPPICGSAGPPPGGMDYWGKGTQVTVSSAAAYPYDVPDYGSHH

HHHH;

2CDA 94

(SEQ ID NO: 337)

QVQLQESGGGLVQAGGSLRLSCAASGRTFSSYAMAWFRQAPGKEREFVAAIAWSAGSTYYADSVKGRFAISRD

NAENTVYLQMNSLKPEDTAVYYCAARIITVATMRLDSDYDYWGQGTQVTVSSAAAYPYDVPDYGSHHHHHH;

2CDA 95

(SEQ ID NO: 338)

QVQLQESGGGLVQAGGSLRLSCAASGFAFDGYAIGWFRQAPGKEREGVSCISSKEGSTYYADSVKGRFTISSD

NAKNTVYLQMSSLKPEDTAVYYCAADGNVWSPPICGSAGPPPGGMDYWGKGTQVTVSSAAAYPYDVPDYGSH

HHHHH;

-continued

3CDA 3

(SEQ ID NO: 339)
QVQLQESGGGLVQAGGSLRLSCAASGFSSDDYTIAWFRRAPGKEREGISCISSSDGSTGYADSVKGRFTITSDS

AKNTVYLQMNSLKPEDTAVYYCAADSNVWSPPICGRTWYGPPPGGMDYWGKGTQVTVSSAAAYPYDVPDYGS

HHHHHH;

3CDA 8

(SEQ ID NO: 340)
QVQLQESGGGLVQPGGSLRLSCAASGFSSDDYTIGWFRQAPGKEREGISCYSSRDGTTGYADSVKGRFTISSD

NAKNTVYLQMNSLKPEDTAVYYCAADFNVWSPPICGSIWYGPPPGGMAYWGQGTQVTVSSAAAYPYDVPDYG

SHHHHHH;

3CDA 11

(SEQ ID NO: 341)
QVQLQESGGGLVQAGGSLRLSCAASGFTFDDYTIGWFRQAPGKEREGISCISSDGSTGYADSVKGRFTISSDNA

KNTVYLQMNSLKPEDTAVYYCAADFNVWSPPICGSNWYGPPPGGMDYWGKGTQVTVSSAAAYPYDVPDYGSH

HHHHH;

3CDA 18

(SEQ ID NO: 342)
QVQLQESGGGLVQAGGSLRLSCAASGFSSDDYTIGWFRQAPGKEREGISCYSSSDGSTGYADSVKGRFTISSD

NAKNTVYLQMNSLKPEDTAVYYCAADFNVWSPPICGSSWYGPPPGGMDYWGKGTQVTVSSAAAYPYDVPDYG

SHHHHHH;

3CDA 19

(SEQ ID NO: 343)
QVQLQESGGGLVQAGGSLRLSCAASGFSSDDYTIGWFRQAPGKEREGISCFSSSDGSTGFADSVKGRFTISSD

NATNTVYLEMNSLKPEDTAVYYCAADFNVWSPPICGSRWYGPPPGGMEYWGKGTQVTVSSAAAYPYDVPDYG

SHHHHHH;

3CDA 21

(SEQ ID NO: 344)
QVQLQESGGGLVQAGGSLRLSCATFGFSFDDYAIAWFRQAPGKEREGISCISNTDSSTFYADSVKGRFTISSDNA

KNTVHLQMSSLKPEDTAVYYCAADGNVWSPPICGSAGPPPGGMDYWGKGTQVTVSSAAAYPYDVPDYGSHHH

HHH;

3CDA 24

(SEQ ID NO: 345)
QVQLQESGGGLVQAGGSLRLSCAASGFSSDDYTIGWFRQAPGKEREGISCYSSSDGSTGFADSVKGRFTISSD

NAKNTVYLQMNSLRPEDTAVYYCAADFNVWSPPICGSRWYGPPPGGMAYWGKGTQVTVSSAAAYPYDVPDYG

SHHHHHH;

3CDA 28

(SEQ ID NO: 346)
QVQLQESGGGLVQVGGSLRLSCTISGFTGNDLAIGWFRQAPGKDQREGISCISNTDSSTYYADSVKGRFTISSDN

AKNTVHLQMSSLKPEDTAVYYCAADGNVWSPPICGSAGPPPGGMDYWGKGTQVTVSSAAAYPYDVPDYGSHH

HHHH;

3CDA 29

(SEQ ID NO: 347)
QVQLQESGGGLVQAGGSLRLSCAASGFSSDDYTIAWFRRAPGKEREGISCISSSDGSTGYADSVKGRFTISSDN

AKNTVYLQMTSLKPEDTAVYYCAADSNVWSPPICGKTWYGPPPGGMDYWGKGTQVTVSSAAAYPYDVPDYGS

HHHHHH;

3CDA 31

(SEQ ID NO: 348)
QVQLQESGGGLVQAGDSLRLSCAGSEGTLSSYGIGWFRQAPGKEREFVGGINWSGDSTDYADSVKGRFTISRD

SAKNTVYLQMNSLKPEDTAVYYCAAGESGVWVGGLDYWGQGTQVTVSSAAAYPYDVPDYGSHHHHHH;

-continued

3CDA 32
(SEQ ID NO: 349)
QVQLQESGGGLVQAGGSLRLSCAASGFSSDDYTIAWFRRAPGKEREGISCFSSSDGSAGYADSVKGRFTVSSD
NAKNTVYLQMNSLKPEDTAVYYCAADSNVWSPPICGSTWYGPPPGGMAYWGKGTQVTVSSAAAYPYDVPDYG
SHHHHHH;

3CDA 33
(SEQ ID NO: 350)
QVQLQESGGGLVQAGGSLRLSCATSGFTFDDYAIAWFRQAPGKEREGVSCISNTDSSTYYADSVKGRFTISSDN
AKNTVYLQMSSLKPEDTAVYYCAADGNVWSPPICGSAGPPPGGMDYWGKGTQVTVSSAAAYPYDVPDYGSHH
HHHH;

3CDA 37
(SEQ ID NO: 351)
QVQLQESGGGLVQAGGSLRLSCEVSGLSSDDYTIGWFRQAPGKEREGFSCFSTRDGNAGYADSVKGRFTISSD
NAKNTVYLQMNNLKPEDTAVYYCAADFNVWSPPICGSRWYGPPPGGMDYWGKGTQVTVSSAAAYPYDVPDYG
SHHHHHH;

3CDA 40
(SEQ ID NO: 352)
QVQLQESGGGLVQAGGSLRLSCEVSGLSSDDYTIGWFRQAPGKKREGFSCFSSRDGSTGYADSVKGRFTISSD
NAKNTVYLQMNSLKPEDTAVYYCAADFNVWSPPICGSRWYGPPPGGMDYWGKGTQVTVSSAAAYPYDVPDYG
SHHHHHH;

3CDA 41
(SEQ ID NO: 353)
QVQLQESGGGLVQAGGSLRLSCAASGFSSDDYTIGWFRQAPGKEREGFSCFSSRDGSTGYADSVKGRFTISSD
NAKNTVYLQMNSLKPEDTAVYYCAADFNVWSPPICGSRWYGPPPGGMDYWGKGTQVTVSSAAAYPYDVPDYG
SHHHHHH;

3CDA 48
(SEQ ID NO: 354)
QVQLQESGGGLVQAGGSLRLSCAASGFSFDDYTIGWFRQVPGKEREGISCISSDGSTGYADSVKGRFTISSDNA
KNTVYLQINSLKPEDTAVYYCAADFNVWSPPICGSIWYGPPPGGMDYWGKGTQVTVSSAAAYPYDVPDYGSHH
HHHH;

3CDA 57
(SEQ ID NO: 355)
QVQLQESGGGLVQAGGSLRLSCATFGFTFDDYAIAWFRQAPGKEREGISCISNTDSSTYYADSVKGRFTISSDNA
KNTVHLQMSSLKPEDTAVYYCAADGNVWSPPICGSAGPPPGGMDYWGKGTQVTVSSAAAYPYDVPDYGSHHH
HHH;

3CDA 65
(SEQ ID NO: 356)
QVQLQESGGGLVQAGGSLXLSCAASGFTFDDYAIGWFRQAPGKEREGVSCISSPDGSTYYADSVKGRFTISSDN
AKNTVYLQMNSLKPEDTAVYYCAADFNVWSPPICGSVGPPPGGMDYWGKGTQVTVSSAAAYPYDVPDYGSHH
HHHH;

3CDA 70
(SEQ ID NO: 357)
QVQLQESGGGLVQAGASLRLSCKASGFTFGDYTIGWFRQAPGKEREGISCYSSSDGNTGYADSVKGRFTISSD
NAKNTVYLQMNSLRPEDTAVYYCAADFNVWSPPICGSSWYGPPPGGMAYWGKGTQVTVSSAAAYPYDVPDYG
SHHHHHH;

3CDA 73
(SEQ ID NO: 358)
QVQLQESGGGLVQAGDSLRLSCAGSEGTFSSYGIGWFRQAPGKEREFVGGINWSGDSTDYADSVKGRFTISRD
NAKNTVYLQMNSLKPEDTAVYYCAAGESGVWVGGLDYWGQGTQVTVSSAAAYPYDVPDYGSHHHHHH;

-continued

3CDA 83
(SEQ ID NO: 359)
QVQLQESGGGLVQAGGSLRLSCAASGFSSDDYTIGWFRQAPGKEREGISCFSSSDGSTGFADSVKGRFTISSD

NATNTVYLQMNSLKPEDTAVYYCAADFNVWSPPICGSSWYGPPPGGMEYWGKGTQVTVSSAAAYPYDVPDYG

SHHHHHH;

3CDA 86
(SEQ ID NO: 360)
QVQLQESGGGLVQAGDSLRLSCTASGVSIGDYNIGWFRQAPGKEREGVSCISSGDGTTYYTDSVKGRFTISTDN

AKNTVYLQMNSLKPEDTAVYYCAADGNVWSPPICGSAGPPPGGMDYWGKGTQVTVSSAAAYPYDVPDYGSHH

HHHH;

3CDA 88
(SEQ ID NO: 361)
QVQLQESGGGLVQAGGSLRLSCAASGFTFDDYTIAWFRQAPGGKEREGISCISSDGSTGYADSVKGRFTISSDN

AKNMVYLQMNSLKPEDTALYYCAADFNVWSPPICSSNWYGPPPRGMDYWGKGTQVTVSSAAAYPYDVPDYGS

HHHHHH;
or

3CDA 90
(SEQ ID NO: 362)
QVQLQESGGGLVQAGGSLRLSCAASGFTFDDYTIAWFRQAPGKEREGISCISSDGSTGYADSVRGRFTISSDNA

KNTVYLQMNSLKPEDTAVYYCAADFNVWSPPICGSIWYGPPPRGMDYWGKGTQVTVSSAAAYPYDVPDYGSH

HHHHH.

In some embodiments, the CD8 targeting moiety comprises an amino acid sequence selected from SEQ ID NOs: 294-362 (provided above) without the terminal histidine tag sequence (i.e., HHHHHH; SEQ ID NO: 363).

In some embodiments, the CD8 targeting moiety comprises an amino acid sequence selected from SEQ ID NOs: 294-362 (provided above) without the HA tag (i.e., YPYDVPDYGS; SEQ ID NO: 364).

In some embodiments, the CD8 targeting moiety comprises an amino acid sequence selected from SEQ ID NOs: 294-362 (provided above) without the MA linker (i.e., MA).

In some embodiments, the CD8 targeting moiety comprises an amino acid sequence selected from SEQ ID NOs: 294-362 (provided above) without the MA linker and HA tag.

In some embodiments, the CD8 targeting moiety comprises an amino acid sequence selected from SEQ ID NOs: 294-362 (provided above) without the AM linker, HA tag, and terminal histidine tag sequence (i.e., AAAYPYDVPDYGSHHHHHH; SEQ ID NO: 365).

In some embodiments, the CD8 targeting moiety comprises an amino acid sequence described in US Patent Publication No. 2014/0271462, the entire contents of which are incorporated by reference. In various embodiments, the CD8 binding agent comprises an amino acid sequence described in Table 0.1, Table 0.2, Table 0.3, and/or FIGS. 1A-12I of US Patent Publication No. 2014/0271462, the entire contents of which are incorporated by reference. In various embodiments, the CD8 binding agent comprises a HCDR1 of a HCDR1 of SEQ ID NO: 366 or 367 and/or a HCDR2 of HCDR2 of SEQ ID NO: 366 or 367 and/or a HCDR3 of HCDR3 of SEQ ID NO: 366 or 367 and/or a LCDR1 of LCDR1 of SEQ ID NO: 368 and/or a LCDR2 of LCDR2 of SEQ ID NO: 368 and/or a LCDR3 of LCDR3 of SEQ ID NO: 368.

SEQ ID NO: 366:
Glu Val Gln Leu Val Glu Ser Gly Gly Gly Leu Val
Gln Pro Gly Gly Ser Leu Arg Leu Ser Cys Ala Ala
Ser Gly Phe Asn Ile Lys Asp Thr Tyr Ile His Trp
Val Arg Gln Ala Pro Gly Lys Gly Leu Glu Trp Val
Ala Arg Ile Asp Pro Ala Asn Asp Asn Thr Leu Tyr
Ala Ser Lys Phe Gln Gly Arg Ala Thr Ile Ser Ala
Asp Thr Ser Lys Asn Thr Ala Tyr Leu Gln Met Asn
Ser Leu Arg Ala Glu Asp Thr Ala Val Tyr Tyr Cys
Gly Arg Gly Tyr Gly Tyr Tyr Val Phe Asp His Trp
Gly Gln Gly Thr Leu Val Thr Val Ser Ser.

SEQ ID NO: 367:
Gln Val Gln Leu Val Gln Ser Gly Ala Glu Val Lys
Lys Pro Gly Ala Thr Val Lys Ile Ser Cys Lys Val
Ser Gly Phe Asn Ile Lys Asp Thr Tyr Ile His Trp
Val Gln Gln Ala Pro Gly Lys Gly Leu Glu Trp Met
Gly Arg Ile Asp Pro Ala Asn Asp Asn Thr Leu Tyr
Ala Ser Lys Phe Gln Gly Arg Val Thr Ile Thr Ala
Asp Thr Ser Thr Asp Thr Ala Tyr Met Glu Leu Ser
Ser Leu Arg Ser Glu Asp Thr Ala Val Tyr Tyr Cys
Ala Arg Gly Tyr Gly Tyr Tyr Val Phe Asp His Trp
Gly Gln Gly Thr Leu Val Thr Val Ser Ser.

-continued

SEQ ID NO: 368:
Asp Val Gln Ile Thr Gln Ser Pro Ser Ser Leu Ser

Ala Ser Val Gly Asp Arg Val Thr Ile Thr Cys Arg

Thr Ser Arg Ser Ile Ser Gln Tyr Leu Ala Trp Tyr

Gln Gln Lys Pro Gly Lys Val Pro Lys Leu Leu Ile

Tyr Ser Gly Ser Thr Leu Gln Ser Gly Val Pro Ser

Arg Phe Ser Gly Ser Gly Ser Gly Thr Asp Phe Thr

Leu Thr Ile Ser Ser Leu Gln Pro Glu Asp Val Ala

Thr Tyr Tyr Cys Gln Gln His Asn Glu Asn Pro Leu

Thr Phe Gly Gly Gly Thr Lys Val Glu Ile Lys.

In some embodiments, the present technology contemplates the use of any natural or synthetic analogs, mutants, variants, alleles, homologs and orthologs (herein collectively referred to as "analogs") of the CD8 targeting moiety described herein. In some embodiments, the amino acid sequence of the CD8 targeting moiety further includes an amino acid analog, an amino acid derivative, or other non-classical amino acids.

In some embodiments, the CD8 targeting moiety comprises a targeting moiety comprising a sequence that is at least 60% identical to any one of the CD8 sequences disclosed herein. For example, the CD8 targeting moiety may comprise a targeting moiety comprising a sequence that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to any one of the CD8 sequences disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity to any one of the CD8 sequences disclosed herein).

In various embodiments, the CD8 targeting moiety comprises an amino acid sequence having one or more amino acid mutations with respect to any one of the CD8 sequences disclosed herein. In various embodiments, the CD8 binding agent comprises a targeting moiety comprising an amino acid sequence having one, or two, or three, or four, or five, or six, or seen, or eight, or nine, or ten, or fifteen, or twenty amino acid mutations with respect to any one of the CD8 sequences disclosed herein. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids (e.g. selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

In various embodiments, the amino acid mutation may be in the CDRs of the targeting moiety (e.g., the CDR1, CDR2 or CDR3 regions). In another embodiment, amino acid alteration may be in the framework regions (FRs) of the targeting moiety (e.g., the FR1, FR2, FR3, or FR4 regions).

Modification of the amino acid sequences may be achieved using any known technique in the art e.g., site-directed mutagenesis or PCR based mutagenesis. Such techniques are described, for example, in Sambrook et al., Molecular Cloning: A Laboratory Manual, Cold Spring Harbor Press, Plainview, N.Y., 1989 and Ausubel et al., Current Protocols in Molecular Biology, John Wiley & Sons, New York, N.Y., 1989.

In various embodiments, the mutations do not substantially reduce the CD8 targeting moiety's capability to specifically bind to CD8. In various embodiments, the mutations do not substantially reduce the CD8 targeting moiety's capability to specifically bind to CD8 without functionally modulating CD8.

In various embodiments, the binding affinity of the CD8 targeting moiety for the full-length and/or mature forms and/or isoforms and/or splice variants and/or fragments and/or any other naturally occurring or synthetic analogs, variants, or mutants (including monomeric, dimeric, heterodimeric, multimeric and/or associated forms) of human CD8 α and/or β chains may be described by the equilibrium dissociation constant ($K_D$). In various embodiments, the CD8 targeting moiety binds to the full-length and/or mature forms and/or isoforms and/or splice variants and/or fragments and/or any other naturally occurring or synthetic analogs, variants, or mutants (including monomeric, dimeric, heterodimeric, multimeric and/or associated forms) of human CD8 α and/or β chains with a $K_D$ of less than about 1 μM, about 900 nM, about 800 nM, about 700 nM, about 600 nM, about 500 nM, about 400 nM, about 300 nM, about 200 nM, about 100 nM, about 90 nM, about 80 nM, about 70 nM, about 60 nM, about 50 nM, about 40 nM, about 30 nM, about 20 nM, about 10 nM, or about 5 nM, or about 1 nM.

In various embodiments, the CD8 targeting moiety binds but does not functionally modulate the antigen of interest, i.e., CD8. For instance, in various embodiments, the CD8 targeting moiety simply targets the antigen but does not substantially functionally modulate the antigen, e.g.it does not substantially inhibit, reduce or neutralize a biological effect that the antigen has. In various embodiments, the CD8 targeting moiety binds an epitope that is physically separate from an antigen site that is important for its biological activity (e.g. an antigen's active site).

Such non-functionally modulating (e.g. non-neutralizing) binding finds use in various embodiments of the present invention, including methods in which the CD8 targeting moiety is used to directly or indirectly recruit active immune cells to a site of need via an effector antigen. For example, in various embodiments, the CD8 targeting moiety may be used to directly or indirectly recruit cytotoxic T cells via CD8 to a tumor cell in a method of reducing or eliminating a tumor (e.g. the CD8 binding agent may comprise a targeting moiety having an anti-CD8 antigen recognition domain and a targeting moiety having a recognition domain (e.g. an antigen recognition domain) directed against a tumor antigen or receptor). In such embodiments, it is desirable to directly or indirectly recruit CD8-expressing cytotoxic T cells but not to neutralize the CD8 activity. In these embodiments, CD8 signaling is an important piece of the tumor reducing or eliminating effect.

CD13 Targeting Moieties

In some embodiments, the additional therapeutic agent—that is used in the combination therapy described herein—is a CD13-targeted chimeric protein or chimeric protein complex having at least one targeting moiety that specifically binds to CD13 and at least one signaling agent that is an interferon (IFN) or a modified form thereof. Various CD13 targeting moieties are described above and may be used as a component of the additional therapeutic agent. For example, the additional therapeutic agent—that is used in combination therapy—is a CD13 targeted chimeric protein or chimeric protein complex, which includes a targeting moiety that specifically binds to CD13 and at least one signaling agent that is an interferon or a modified form thereof. In some embodiments, the interferon is IFN-γ. In some embodiments, the modified form of IFN is a modified form IFN-γ.

Interferon Signaling Agent

In various embodiments, the CD8-targeted chimeric proteins or chimeric protein complexes or the CD13-targeted chimeric proteins or chimeric protein complexes comprise an interferon (IFN) signaling agent. In some embodiments, the IFN signaling agent comprises a modified IFN as a signaling agent.

In some embodiments, the IFN signaling agent is an interferon or a modified version of an interferon such as interferon types I, II, and III. Illustrative interferons, including for example, interferon-α-1, 2, 4, 5, 6, 7, 8, 10, 13, 14, 16, 17, and 21, interferon-β and interferon-γ, interferon κ, interferon ε, interferon τ, and interferon $\overline{\omega}$.

In some embodiments, the modified IFN signaling agent is interferon α. In such embodiments, the modified IFN-α agent has reduced affinity and/or activity for the IFN-α/β receptor (IFNAR), i.e., IFNAR1 and/or IFNAR2 chains. In some embodiments, the modified IFN-α agent has substantially reduced or ablated affinity and/or activity for the IFN-α/β receptor (IFNAR), i.e., IFNAR1 and/or IFNAR2 chains.

Mutant forms of interferon α are known to the person skilled in the art. In an illustrative embodiment, the modified signaling agent is the allelic form IFN-α2a having the amino acid sequence of:

IFN-α2a:

(SEQ ID NO: 369)

```
CDLPQTHSLGSRRTLMLLAQMRKISLFSCLKDRHDFGFPQEEFGNQFQK

AETIPVLHEMIQQIFNLFSTKDSSAAWDETLLDKFYTELYQQLNDLEAC

VIQGVGVTETPLMKEDSILAVRKYFQRITLYLKEKKYSPCAWEVVRAEI

MRSFSLSTNLQESLRSKE.
```

In an illustrative embodiment, the modified IFN signaling agent is the allelic form IFN-α2b having the amino acid sequence of (which differs from IFN-α2a at amino acid position 23):

IFN-α2b:

(SEQ ID NO: 370)

```
CDLPQTHSLGSRRTLMLLAQMRRISLFSCLKDRHDFGFPQEEFGNQFQK

AETIPVLHEMIQQIFNLFSTKDSSAAWDETLLDKFYTELYQQLNDLEAC

VIQGVGVTETPLMKEDSILAVRKYFQRITLYLKEKKYSPCAWEVVRAEI

MRSFSLSTNLQESLRSKE.
```

In some embodiments, said IFN-α2 mutant (IFN-α2a or IFN-α2b) is mutated at one or more amino acids at positions 144-154, such as amino acid positions 148, 149 and/or 153. In some embodiments, the IFN-α2 mutant comprises one or more mutations selected from L153A, R149A, and M148A. Such mutants are described, for example, in WO2013/107791 and Piehler et al., (2000) J. Biol. Chem, 275:40425-33, the entire contents of all of which are hereby incorporated by reference.

In some embodiments, the IFN-α2 mutants have reduced affinity and/or activity for IFNAR1. In some embodiments, the IFN-α2 mutant comprises one or more mutations selected from F64A, N65A, T69A, L80A, Y85A, and Y89A, as described in WO2010/030671, the entire contents of which is hereby incorporated by reference.

In some embodiments, the IFN-α2 mutant comprises one or more mutations selected from K133A, R144A, R149A, and L153A as described in WO2008/124086, the entire contents of which is hereby incorporated by reference.

In some embodiments, the IFN-α2 mutant comprises one or more mutations selected from R120E and R120E/K121E, as described in WO2015/007520 and WO2010/030671, the entire contents of which are hereby incorporated by reference. In such embodiments, said IFN-α2 mutant antagonizes wildtype IFN-α2 activity. In such embodiments, said mutant IFN-α2 has reduced affinity and/or activity for IFNAR1 while affinity and/or activity of IFNR2 is retained.

In some embodiments, the human IFN-α2 mutant comprises (1) one or more mutations selected from R120E and R120E/K121E, which, without wishing to be bound by theory, create an antagonistic effect and (2) one or more mutations selected from K133A, R144A, R149A, and L153A, which, without wishing to be bound by theory, allow for an attenuated effect at, for example, IFNAR2. In an embodiment, the human IFN-α2 mutant comprises R120E and L153A.

In some embodiments, the human IFN-α2 mutant comprises one or more mutations selected from, L15A, A19W, R22A, R23A, L26A, F27A, L30A, L30V, K31A, D32A, R33K, R33A, R33Q, H34A, D35A, Q40A, D114R, L117A, R120A, R125A, K134A, R144A, A145G, A145M, M148A, R149A, S152A, L153A, and N156A as disclosed in WO 2013/059885, the entire disclosures of which are hereby incorporated by reference. In some embodiments, the human IFN-α2 mutant comprises the mutations H57Y, E58N, Q61S, and/or L30A as disclosed in WO 2013/059885. In some embodiments, the human IFN-α2 mutant comprises the mutations H57Y, E58N, Q61S, and/or R33A as disclosed in WO 2013/059885. In some embodiments, the human IFN-α2 mutant comprises the mutations H57Y, E58N, Q61S, and/or M148A as disclosed in WO 2013/059885. In some embodiments, the human IFN-α2 mutant comprises the mutations H57Y, E58N, Q61S, and/or L153A as disclosed in WO 2013/059885. In some embodiments, the human IFN-α2 mutant comprises the mutations N65A, L80A, Y85A, and/or Y89A as disclosed in WO 2013/059885. In some embodiments, the human IFN-α2 mutant comprises the mutations N65A, L80A, Y85A, Y89A, and/or D114A as disclosed in WO 2013/059885. In some embodiments, the human IFN-α2 mutant comprises one or more mutations selected from R144X$_1$, A145X$_2$, and R33A, wherein X$_1$ is selected from A, S, T, Y, L, and I, and wherein X2 is selected from G, H, Y, K, and D.

In some embodiments, the human IFN-α2 mutant comprises one or more mutations selected from L15A, R22A, R23A, S25A, L26A, F27A, L30A, L30V, K31A, D32A, R33A, R33K, R33Q, H34A, Q40A, D113R, L116A, R119A, R119E, R124A, R124E, K130A, E131A, K132A, K133A, M147A, R148A, S149A, L152A, N155A, (L30A, H57Y, E58N and Q61S), (M147A, H57Y, E58N and Q61S), (L152A, H57Y, E58N and Q61S), (R143A, H57Y, E58N and Q61S), (N65A, L80A, Y85A and Y89A,) (N65A, L80A, Y85A, Y89A and D113A), (N65A, L80A, Y85A, Y89A and L116A), (N65A, L80A, Y85A, Y89A and RI 190A), (Y85A, Y89A and D113A), (D113A and RI119A), (L116A and R119A), (L116A, R119A and K120A), (R119A and K120A), (R119E and K120E), replacement of R at position 143 with A, D, E, G, H, I, K, L, N, Q, S, T, V or Y, replacement of A at position 144 with D, E, G, H, I, K, L, M, N, Q, S, T, V or Y, and deletion of residues L160 to E164.

In some embodiments, the human IFN-α2 mutant comprises a mutation which does not permit O-linked glycosylation at a position when, e.g., produced in mammalian cell culture. In some embodiments, the human IFN-α2 mutant comprises a mutation at T106. In some embodiments, T106 is substituted with A, C, D, E, F, G, H, I, K, L, M, N, P, Q, R, S, V, W, or Y.

In some embodiments, the human IFN-α2 mutant is a mutant of the IFN-α2-1b variant. Mutations in the IFN-α2-1b variant are disclosed in WO 2015/168474, the entire disclosures of which are hereby incorporated by reference. By way of example, in some embodiments IFN-α2-1b comprises one or more of the following mutations: H58A, E59A, R145A, M149A, and R150A.

In some embodiments, the modified IFN signaling agent is interferon R. In such embodiments, the modified interferon β agent has reduced affinity and/or activity for the IFN-α/β receptor (IFNAR), i.e., IFNAR1 and/or IFNAR2 chains. In some embodiments, the modified interferon β agent has substantially reduced or ablated affinity and/or activity for the IFN-α/β receptor (IFNAR), i.e., IFNAR1 and/or IFNAR2 chains.

In an illustrative embodiment, the modified IFN signaling agent is IFN-β. In various embodiments, the IFN-β encompasses functional derivatives, analogs, precursors, isoforms, splice variants, or fragments of IFN-β. In various embodiments, the IFN-β encompasses IFN-β derived from any species. In an embodiment, the chimeric protein or chimeric protein complex comprises a modified version of mouse IFN-6. In another embodiment, the chimeric protein or chimeric protein complex comprises a modified version of human IFN-6. Human IFN-β is a polypeptide with a molecular weight of about 22 kDa comprising 166 amino acid residues. The amino acid sequence of human IFN-β is:

(SEQ ID NO: 371)

```
MSYNLLGFLQRSSNFQCQKLLWQLNGRLEYCLKDRMNFDIPEEIKQLQQ
FQKEDAALTIYEMLQNIFAIFRQDSSSTGWNETIVENLLANVYHQINHL
KTVLEEKLEKEDFTRGKLMSSLHLKRYYGRILHYLKAKEYSHCAWTIVR
VEILRNFYFINRLTGYLRN.
```

In some embodiments, the human IFN-β is IFN-β-1a which is a glycosylated form of human IFN-β. In some embodiments, the human IFN-β is IFN-β-1b which is a non-glycosylated form of human IFN-β that has a Met-1 deletion and a Cys-17 to Ser mutation.

In various embodiments, the modified IFN-β has one or more mutations that reduce its binding to or its affinity for the IFNAR1 subunit of IFNAR. In one embodiment, the modified IFN-β has reduced affinity and/or activity at IFNAR1. In various embodiments, the modified IFN-β is human IFN-β and has one or more mutations at positions F67, R71, L88, Y92,195, N96, K123, and R124. In some embodiments, the one or more mutations are substitutions selected from F67G, F67S, R71A, L88G, L88S, Y92G, Y92S, 195A, N96G, K123G, and R124G. In an embodiment, the modified IFN-β comprises the F67G mutation. In an embodiment, the modified IFN-β comprises the K123G mutation. In an embodiment, the modified IFN-β comprises the F67G and R71A mutations. In an embodiment, the modified IFN-β comprises the L88G and Y92G mutations. In an embodiment, the modified IFN-β comprises the Y92G, 195A, and N96G mutations. In an embodiment, the modified IFN-β comprises the K123G and R124G mutations. In an embodiment, the modified IFN-β comprises the F67G, L88G, and Y92G mutations. In an embodiment, the modified IFN-β comprises the F67S, L88S, and Y92S mutations.

In some embodiments, the modified IFN-β has one or more mutations that reduce its binding to or its affinity for the IFNAR2 subunit of IFNAR. In one embodiment, the modified IFN-β has reduced affinity and/or activity at IFNAR2. In various embodiments, the modified IFN-β is human IFN-β and has one or more mutations at positions W22, R27, L32, R35, V148, L151, R152, and Y155. In some embodiments, the one or more mutations are substitutions selected from W22G, R27G, L32A, L32G, R35A, R35G, V148G, L151G, R152A, R152G, and Y155G. In an embodiment, the modified IFN-β comprises the W22G mutation. In an embodiment, the modified IFN-β comprises the L32A mutation. In an embodiment, the modified IFN-β comprises the L32G mutation. In an embodiment, the modified IFN-β comprises the R35A mutation. In an embodiment, the modified IFN-β comprises the R35G mutation. In an embodiment, the modified IFN-β comprises the V148G mutation. In an embodiment, the modified IFN-β comprises the R152A mutation. In an embodiment, the modified IFN-β comprises the R152G mutation. In an embodiment, the modified IFN-β comprises the Y155G mutation. In an embodiment, the modified IFN-β comprises the W22G and R27G mutations. In an embodiment, the modified IFN-β comprises the L32A and R35A mutation. In an embodiment, the modified IFN-β comprises the L151G and R152A mutations. In an embodiment, the modified IFN-β comprises the V148G and R152A mutations.

In some embodiments, the modified IFN-β has one or more of the following mutations: R35A, E42K, M62I, G78S, A141Y, A142T, E149K, and R152H. In some embodiments, the modified IFN-β has one or more of the following mutations: R35A, R35T, E42K, M62I, G78S, A141Y, A142T. E149K, and R152H in combination with C178 or C17A.

In some embodiments, the modified IFN-β has one or more of the following mutations: R35A, R35T, E42K, M62I, G788, A141Y, A142T, E149K, and R152H in combination with any of the other IFN-β mutations described herein.

The crystal structure of human IFN-β is known and is described in Karpusas et al., (1998) PNAS, 94(22): 11813-11818. Specifically, the structure of human IFN-β has been shown to include five α-helices (i.e., A, B, C, D, and E) and four loop regions that connect these helices (i.e., AB, BC, CD, and DE loops). In various embodiments, the modified IFN-β has one or more mutations in the A, B, C, D, E helices and/or the AB, BC, CD, and DE loops which reduce its binding affinity or activity at a therapeutic receptor such as IFNAR. Illustrative mutations are described in WO 2000/023114 and US 20150011732, the entire contents of which are hereby incorporated by reference. In an illustrative embodiment, the modified IFN-β is human IFN-β comprising alanine substitutions at amino acid positions 15, 16, 18, 19, 22, and/or 23. In an illustrative embodiment, the modified IFN-β is human IFN-β comprising alanine substitutions at amino acid positions 28-30, 32, and 33. In an illustrative embodiment, the modified IFN-β is human IFN-β comprising alanine substitutions at amino acid positions 36, 37, 39, and 42. In an illustrative embodiment, the modified IFN-β is human IFN-β comprising alanine substitutions at amino acid positions 64 and 67 and a serine substitution at position 68. In an illustrative embodiment, the modified IFN-β is human IFN-β comprising alanine substitutions at amino acid positions 71-73. In an illustrative embodiment, the modified IFN-β is human IFN-β comprising alanine substitutions at amino acid positions 92, 96, 99, and 100. In an illustrative embodiment, the modified IFN-β is human IFN-β comprising alanine substitutions at amino acid positions 128, 130, 131, and 134. In an illustrative embodiment, the modified IFN-β is human IFN-β comprising alanine substitutions at amino acid positions 149, 153, 156, and 159. In some embodiments, the mutant IFNβ comprises SEQ ID NO:

371 and a mutation at W22, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at R27, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at W22, the mutation being an aliphatic hydrophobic residue selected from glycine (G), alanine (A), leucine (L), isoleucine (I), methionine (M), and valine (V) and a mutation at R27, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at L32, the mutation being an aliphatic hydrophobic residue selected from glycine (G), alanine (A), isoleucine (I), methionine (M), and valine (V).

In some embodiments, the mutant IFNβ comprises SEQ ID NO: 371 and a mutation at R35, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at L32, the mutation being an aliphatic hydrophobic residue selected from glycine (G), alanine (A), isoleucine (I), methionine (M), and valine (V) and a mutation at R35, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at F67, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at R71, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at F67, the mutation being an aliphatic hydrophobic residue selected from glycine (G), alanine (A), leucine (L), isoleucine (I), methionine (M), and valine (V) and a mutation at R71, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at L88, the mutation being an aliphatic hydrophobic residue selected from glycine (G), alanine (A), isoleucine (I), methionine (M), and valine (V).

In some embodiments, the mutant IFNβ comprises SEQ ID NO: 371 and a mutation at Y92, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at F67, the mutation being an aliphatic hydrophobic residue selected from glycine (G), alanine (A), leucine (L), isoleucine (I), methionine (M), and valine (V) and a mutation at L88, the mutation being an aliphatic hydrophobic residue selected from glycine (G), alanine (A), isoleucine (I), methionine (M), and valine (V) and a mutation at Y92, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at L88, the mutation being an aliphatic hydrophobic residue selected from glycine (G), alanine (A), isoleucine (I), methionine (M), and valine (V) and a mutation at Y92, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at 195, the mutation being an aliphatic hydrophobic residue selected from glycine (G), alanine (A), leucine (L), methionine (M), and valine (V) and a mutation at Y92, the mutation being an aliphatic hydrophobic residue selected from glycine (G), alanine (A), leucine (L), isoleucine (1), methionine (M), and valine (V).

In some embodiments, the mutant IFNβ comprises SEQ ID NO: 371 and a mutation at N96, the mutation being an aliphatic hydrophobic residue selected from glycine (G), alanine (A), leucine (L), isoleucine (1), methionine (M), and valine (V) and a mutation at Y92, the mutation being an aliphatic hydrophobic residue selected from glycine (G), alanine (A), leucine (L), isoleucine (1), methionine (M), and valine (V).

In some embodiments, the mutant IFNβ comprises SEQ ID NO: 371 and a mutation at Y92, the mutation being an aliphatic hydrophobic residue selected from glycine (G), alanine (A), leucine (L), isoleucine (1), methionine (M), and valine (V) and a mutation at 195, the mutation being an aliphatic hydrophobic residue selected from glycine (G), alanine (A), leucine (L), methionine (M), and valine (V) and a mutation at N96, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at K123, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at R124, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at K123, the mutation being an aliphatic hydrophobic residue selected from glycine (G), alanine (A), leucine (L), isoleucine (I), methionine (M), and valine (V) and a mutation at R124, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at L151, the mutation being an aliphatic hydrophobic residue selected from glycine (G), alanine (A), isoleucine (I), methionine (M), and valine (V).

In some embodiments, the mutant IFNβ comprises SEQ ID NO: 371 and a mutation at R152, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at L151, the mutation being an aliphatic hydrophobic residue selected from glycine (G), alanine (A), isoleucine (I), methionine (M), and valine (V) and a mutation at R152, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at V148, the mutation being an aliphatic hydrophobic residue selected from glycine (G), alanine (A), leucine (L), isoleucine (I), and methionine (M).

In some embodiments, the mutant IFNβ comprises SEQ ID NO: 371 and a mutation at V148, the mutation being an aliphatic hydrophobic residue selected from glycine (G), alanine (A), leucine (L), isoleucine (I), methionine (M), and valine (V) and a mutation at R152, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 371 and a mutation at Y155, the mutation being an aliphatic hydrophobic residue selected from glycine (G), alanine (A), leucine (L), isoleucine (I), methionine (M), and valine (V).

In an embodiment, the CD-8-targeted chimeric protein or chimeric protein complex comprising: (a) a modified IFN-β, having the amino acid sequence of SEQ ID NO: 371 and a mutation at position W22, wherein the mutation is an aliphatic hydrophobic residue and a CD8 targeting moiety disclosed herein. In various embodiments the mutation at position W22 is aliphatic hydrophobic residue is selected from G, A, L, I, M, and V. In various embodiments the mutation at position W22 is G.

Additional illustrative IFNβ mutants are provided in PCT/EP2017/061544, the entire disclosure of which is incorporated by reference herein.

In some embodiments, the modified IFN signaling agent is interferon γ. In such embodiments, the modified interferon γ agent has reduced affinity and/or activity for the interferon-gamma receptor (IFNGR), i.e., IFNGR1 and IFNGR2 chains. In some embodiments, the modified interferon γ agent has substantially reduced or ablated affinity and/or activity for the interferon-gamma receptor (IFNGR), i.e., IFNGR1 and/or IFNGR2 chains.

Among the various interferons, IFN-γ is the only member of the type II class of interferons. IFN-γ is produced predominantly by natural killer (NK) and natural killer T (NKT) cells as part of the innate immune response. IFN-γ is also produced by CD4 Th1 and CD8 cytotoxic T lymphocyte (CTL) effector T cells, macrophages, dendritic cells, and B cells. Activated IFN-γ forms a dimer which acts through a heterodimeric receptor (i.e., IFN-γ receptor or IFN-γR) composed of IFN-γ receptor 1 and IFN-γ receptor 2 subunits. IFN-γ receptor 1 is the major ligand-binding subunit, while IFN-γ receptor 2 is necessary for signal transduction and also increases the affinity of IFN-γ receptor 1 for its ligand. Binding of the IFN-γ dimer to the receptor activates the JAK-STAT signaling pathway to elicit various biological effects.

In various embodiments, the chimeric protein or chimeric protein complex of the invention comprises a modified version of IFN-γ as a signaling agent. In various embodiments, the IFN-γ encompasses functional derivatives, analogs, precursors, isoforms, splice variants, or fragments of IFN-γ. In various embodiments, the IFN-γ encompasses IFN-γ derived from any species. In an embodiment, the chimeric protein or chimeric protein complex comprises a modified version of mouse IFN-γ. In another embodiment, the chimeric protein or chimeric protein complex comprises a modified version of human IFN-γ.

Human IFN-γ is a polypeptide comprising 166 amino acid residues. In an embodiment, the human IFN-γ has the amino acid sequence of SEQ ID NO: 380, in which the signal peptide comprises the first 23 amino acids and is underlined.

(SEQ ID NO: 380)

<u>MKYTSYILAFQLCIVLGSLGCYC</u>QDPYVKEAENLKKYFNAGHSDVADNG

TLFLGILKNWKEESDRKIMQSQIVSFYFKLFKNFKDDQSIQKSVETIKE

DMNVKFFNSNKKKRDDFEKLTNYSVTDLNVQRKAIHELIQVMAELSPAA

KTGKRKRSQMLFRGRRASQ

As used herein, human IFN-γ may also refer to mature human IFN-γ without the N-terminal signal peptide. In this embodiment, the mature human IFN-γ comprises 143 amino acids and has the amino acid sequence of SEQ ID NO: 381.

```
                                    (SEQ ID NO: 381)
QDPYVKEAENLKKYFNAGHSDVADNGTLFLGILKNWKEESDRKIMQSQI

VSFYFKLFKNFKDDQSIQKSVETIKEDMNVKFFNSNKKKRDDFEKLTNY

SVTDLNVQRKAIHELIQVMAELSPAAKTGKRKRSQMLFRGRRASQ
```

In some embodiments, the human IFN-γ is a glycosylated form of human IFN-γ. In some embodiments, the human IFN-γ is a non-glycosylated form of human IFN-γ.

In various embodiments, the IFN-γ is modified to have one or more mutations. In some embodiments, the mutations allow for the modified IFN-γ to have one or more of attenuated activity such as one or more of reduced binding affinity, reduced endogenous activity, and reduced specific bioactivity relative to unmutated, e.g., the wild type form of IFN-γ. For instance, the one or more of attenuated activity such as reduced binding affinity, reduced endogenous activity, and reduced specific bioactivity relative to unmutated, e.g., the wild type form of IFN-γ may be at a therapeutic receptor such as the IFN-γ receptor. Consequentially, in various embodiments, the mutations allow for the modified soluble agent to have reduced systemic toxicity, reduced side effects, and reduced off-target effects relative to unmutated, e.g., the wild type form of IFN-γ.

In various embodiments, the IFN-γ is modified to have a mutation that reduces its binding affinity and/or activity at a therapeutic receptor such as the IFN-γ receptor comprising the IFN-γ receptor 1 and IFN-γ receptor 2 subunits. In some embodiments, the activity provided by the wild type IFN-γ is agonism at the therapeutic receptor (e.g., activation of a cellular effect at a site of therapy). For example, the wild type IFN-γ may activate the therapeutic receptor. In such embodiments, the mutation results in the modified IFN-γ to have reduced activating activity at the therapeutic receptor.

In some embodiments, the reduced affinity and/or activity at the therapeutic receptor (e.g., IFN-γ receptor) is restorable by attachment with a targeting moiety. In other embodiments, the reduced affinity and/or activity at the therapeutic receptor is not substantially restorable by attachment with the targeting moiety. In various embodiments, the therapeutic chimeric proteins or chimeric protein complexes of the present invention reduce off-target effects because the IFN-γ has mutations that weaken binding affinity and/or activity at a therapeutic receptor. In various embodiments, this reduces side effects observed with, for example, the wild type IFN-γ. In various embodiments, the modified IFN-γ is substantially inactive en route to the site of therapeutic activity and has its effect substantially on specifically targeted cell types, which greatly reduces undesired side effects.

In various embodiments, the modified IFN-γ has one or more mutations that cause the IFN-γ to have attenuated or reduced affinity and/or actvity, e.g., binding (e.g., $K_D$) and/or activation (measurable as, for example, $K_A$ and/or $EC_{50}$) for one or more therapeutic receptors (e.g., IFN-γ receptor). In various embodiments, the reduced affinity and/or actvity at the therapeutic receptor allows for attenuation of activity and/or signaling from the therapeutic receptor.

In various embodiments, the modified IFN-γ has one or more mutations that reduce its binding to or its affinityfor and/or biological activity for the IFN-γ receptor 1 subunit. In one embodiment, the modified IFN-γ has reduced affinity and/or activity at the IFN-γ receptor 1 subunit. In various embodiments, the modified IFN-γ is human IFN-γ that has one or more mutations at amino acid residues involved with binding to the IFN-γ receptor 1 subunit. In some embodiments, the modified IFN-γ is human IFN-γ that has one or more mutations at amino acids located at the interface with the IFN-γ receptor 1 subunit. In various embodiments, the one or more mutations are at amino acids selected from, but not limited to Q1, V5, E9, K12, H19, S20, V22, A23, D24, N25, G26, T27, L30, K108, H111, E112, I114, Q115, A118, E119, and K125 (each with respect SEQ ID NO: 381, which is a wild type human IFN-γ and which lacks its N-terminal signal sequence). In some embodiments, the one or more mutations are substitutions selected from V5E, S20E, V22A, A23G, A23F, D24G, G26Q, H111A, H111D, 1114A, Q115A, and A118G (each with respect SEQ ID NO: 381). In embodiments, the one or more mutations are substitutions selected from V22A, A23G, D24G, H111A, H111D, 1114A, Q115A, and A118G. In an embodiment, the modified IFN-γ comprises the mutations A23G and D24G. In another embodiment, the modified IFN-γ comprises the mutations 1114A and A118G. In a further embodiment, the modified IFN-γ comprises the mutations V5E, S20E, A23F, and G26Q.

In various embodiments, the modified IFN-γ has one or more of the following mutations: deletion of residue A23, deletion of residue D24, an S201 substitution, an A23V substitution, a D21K substitution and a D24A substitution.

In some embodiments, the modified IFN-γ has one or more mutations that reduce its binding to or its affinity and/or biological activity for the IFN-γ receptor 2 subunit.

In some embodiments, the modified IFN-γ has one or more mutations that reduce its binding to or its affinity and/or biological activity for both IFN-γ receptor 1 and IFN-γ receptor 2 subunits.

In some embodiments, the modified IFN-γ has one or more mutations that reduce its binding to or its affinity and/or biological activity for IFN-γ receptor 1 and one or more mutations that substantially reduce or ablate binding to or its affinity and/or biological activity for IFN-γ receptor 2. In some embodiments, chimeric proteins or chimeric protein complexes with such modified IFN-γ can provide target-selective IFN-γ receptor 1 activity (e.g., IFN-γ receptor 1 activity is restorable via targeting through the targeting moiety).

In some embodiments, the modified IFN-γ has one or more mutations that reduce its binding to or its affinity and/or biological activity for IFN-γ receptor 1 and one or more mutations that reduce its binding to or its affinity and/or biological activity for IFN-γ receptor 1. In some embodiments, chimeric proteins or chimeric protein complexes with such modified IFN-γ can provide target-selective IFN-γ receptor 1 and/or IFN-γ receptor 1 activity (e.g., IFN-γ receptor 1 and IFN-γ receptor 2 activities are restorable via targeting through the targeting moiety).

In various embodiments, the modified IFN-γ is truncated at the C-terminus. In some embodiments, the modified IFN-γ is mature IFN-γ comprising the amino acid sequence of SEQ ID NO: 381 with deletions of the C-terminal terminus. In such embodiments, the mature IFN-γ may comprise a C-terminal truncation of at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, or about 25 amino acid residues. In an embodiment, the modified IFN-γ is mature IFN-γ comprising the amino acid sequence of SEQ ID NO: 381 with C-terminal deletions of 5 amino acids. In an embodiment, the modified IFN-γ is mature IFN-γ with C-terminal deletions of 7 amino acids. In an embodiment, the modified IFN-γ is mature IFN-γ comprising the amino acid sequence of SEQ ID NO: 381 with C-terminal deletions of 14 amino acids. In an embodiment, the modified IFN-γ is mature IFN-γ comprising the amino acid sequence of SEQ ID NO: 381 with C-terminal deletions of 15 amino acids. In an embodiment, the modified IFN-γ is mature IFN-γ comprising the amino acid sequence of SEQ ID NO: 381 with C-terminal deletions of 16 amino acids. Additional modified IFN-γ with C-terminal truncations that may be utilized in the present invention is described in Haelewyn et al., *Biochem. J.* (1997), 324:591-595 and Lundell et al., *Protein Eng.* (1991) 4:335-341, the entire contents are hereby incorporated by reference In various embodiments, the modified IFN-γ is a single chain IFN-γ as described, for example, in Randal et al. (2001) *Structure* 9:155-163 and Randal et al. (1998) *Protein Sci.* 7:1057-1060, the entire contents are hereby incorporated by reference. In some embodiments, the single chain IFN-γ comprises a first IFN-γ chain linked at its C-terminus to the N-terminus of a second IFN-γ chain. In various embodiments, the first and second IFN-γ chains are linked by a linker, as described elsewhere herein.

In some embodiments, the first IFN-γ chain comprises a C-terminal truncation of at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, or about 25 amino acid residues. In an embodiment, the first IFN-γ chain comprises a C-terminal truncation of about 24 amino acid residues. In some embodiments, the second IFN-γ chain comprises an N-terminal truncation of at least about 1, about 2, about 3, about 4, or about 5 amino acid residues. In an embodiment, the second IFN-γ chain comprises an N-terminal truncation of about 3 amino acid residues. In some embodiments, the second IFN-γ chain comprises a C-terminal truncation of at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, or about 25 amino acid residues. In various embodiments, the first and/or second IFN-γ chains comprise one or more amino acid mutations at Q1, V5, E9, K12, H19, S20, V22, A23, D24, N25, G26, T27, L30, K108, H111, E112, 1114, Q115, A118, E119, and K125, as described elsewhere herein. In various embodiments, the first and/or second IFN-γ chains comprise one or more substitutions selected from VSE, S20E, V22A, A23G, A23F, D24G, G26Q, H111A, H111D, 1114A, Q115A, and A118G. In various embodiments, the first and/or second IFN-γ chains comprise one or more substitutions selected from V22A, A23G, D24G, H111A, H111D, I114A, Q115A, and A118G. In various embodiments, the first and/or second IFN-γ chains comprise the A23G and the D24G substitution. In various embodiments, the first and/or second IFN-γ chains comprise the I114A and the A118G substitution. In another embodiment, the mutations are VSE, S20E, A23F, and G26Q.

In various embodiments, a first and/or second IFN-γ chain comprises one or more substitutions as disclosed herein and the first and/or second IFN-γ chain comprises a C-terminal truncation as disclosed herein.

In various embodiments, a first and/or second IFN-γ chain comprises one or more substitutions as disclosed herein and a C-terminal truncation as disclosed herein.

The crystal structure of human IFN-γ is known and is described in, for example, Ealick et al., (1991) Science, 252: 698-702. Specifically, the structure of human IFN-γ has been shown to include a core of six α-helices and an extended unfolded sequence in the C-terminal region. In various embodiments, the modified IFN-γ has one or more mutations in the one or more helices which reduce its binding affinity and/or biological activity at a therapeutic receptor (e.g., IFN-γ receptor).

In various embodiments, the modified IFN-γ has about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, or about 10%-20%, about 20%-40%, about 50%, about 40%-60%, about 60%-80%, about 80%-100% of the affinity and/or biological activity for the therapeutic receptor (e.g., IFN-γ receptor or any one of its IFN-γ receptor 1 and IFN-γ receptor 2 subunits) relative to the wild type IFN-γ. In some embodiments, the binding affinity and/or biological activity is at least about 2-fold lower, about 3-fold lower, about 4-fold lower, about 5-fold lower, about 6-fold lower, about 7-fold lower, about 8-fold lower, about 9-fold lower, at least about 10-fold lower, at least about 15-fold lower, at least about 20-fold lower, at least about 25-fold lower, at least about 30-fold lower, at least about 35-fold lower, at least about 40-fold lower, at least about 45-fold lower, at least about 50-fold lower, at least about 100-fold lower, at least about 150-fold lower, or about 10-50-fold lower, about 50-100-fold lower, about 100-150-fold lower, about 150-200-fold lower, or more than 200-fold lower relative to the wild type IFN-γ.

In various embodiments, the modified IFN-γ comprises one or more mutations that reduce the endogenous activity of the IFN-γ to about 75%, or about 70%, or about 60%, or about 50%, or about 40%, or about 30%, or about 25%, or about 20%, or about 10%, or about 5%, or about 3%, or about 1%, e.g., relative to the wild type IFN-γ.

In some embodiments, the modified IFN-γ comprises one or more mutations that cause the modified IFN-γ to have reduced affinity and/or biological activity for a receptor. In some embodiments, the modified IFN-γ's binding affinity and/or biological activity for a receptor is lower than the binding affinity and/or biological activity of the targeting moiety for its receptor. In some embodiments, this binding affinity and/or biological activity differential is between the modified IFN-γ/receptor and targeting moiety/receptor on the same cell. In some embodiments, this binding affinity and/or biological activity, differential allows for the modified IFN-γ to have localized, on-target effects and to minimize off-target effects that underlie side effects that are observed with wild type IFN-γ. In some embodiments, this binding affinity and/or biological activity is at least about 2-fold, or at least about 5-fold, or at least about 10-fold, or at least about 15-fold lower, or at least about 25-fold, or at least about 50-fold lower, or at least about 100-fold, or at least about 150-fold less.

Receptor binding activity may be measured using methods known in the art. For example, affinity and/or binding activity may be assessed by Scatchard plot analysis and computer-fitting of binding data (e.g., Scatchard, 1949) or by reflectometric interference spectroscopy under flow through conditions, as described by Brecht et al. (1993), the entire contents of all of which are hereby incorporated by reference.

In various embodiments, the attenuated activity at the therapeutic receptor, the weakened affinity and/or biological activity at the therapeutic receptor is restorable by attachment with a targeting moiety, having high affinity for an antigen at the site of therapeutic activity (e.g., an antibody or antibody format described herein). The targeting is realized by linking the modified IFN-γ to a targeting moiety. In an embodiment, the modified IFN-γ is linked to a targeting moiety through its amino-terminus. In another embodiment, the modified IFN-γ is linked to a targeting moiety through its carboxy-terminus. In this way, the present chimeric proteins or chimeric protein complexes provide, in some embodiments, localized, on-target, and controlled therapeutic action at the therapeutic receptor In various embodiments, a chimeric protein or chimeric protein complex of the present invention comprises an IFN-γ comprising one or more substitutions as disclosed herein and/or a C-terminal truncation as disclosed herein.

In some embodiments, the modified IFN signaling agent is a consensus interferon. The consensus interferon is generated by scanning the sequences of several human non-allelic IFN-α subtypes and assigning the most frequently observed amino acid in each corresponding position. The consensus interferon differs from IFN-α2b at 20 out of 166 amino acids (88% homology), and comparison with IFN-β shows identity at over 30% of the amino acid positions. In various embodiments, the consensus interferon comprises the following amino acid sequence:

(SEQ ID NO: 372)
MCDLPQTHSLGNRRALILLAQMRRISPFSCLKDRHDFGFPQEEFDGNQF

QKAQAISVLHEMIQQTFNLFSTKDSSAAWDESLLEKFYTELYQQLNDLE

ACVIQEVGVEETPLMNVDSILAVKKYFQRITLYLTEKKYSPCAWEWRAE

IMRSFSLSTNLQERLRRKE.

In some embodiments, the consensus interferon comprises the amino acid sequence of SEQ ID NO: 373, which differs from the amino acid sequence of SEQ ID NO: 372 by one amino acid, i.e., SEQ ID NO: 373 lacks the initial methionine residue of SEQ ID NO: 372:

(SEQ ID NO: 373)
CDLPQTHSLGNRRALILLAQMRRISPFSCLKDRHDFGFPQEEFDGNQFQ

KAQAISVLHEMIQQTFNLFSTKDSSAAWDESLLEKFYTELYQQLNDLEA

CVIQEVGVEETPLMNVDSILAVKKYFQRITLYLTEKKYSPCAWEVVRAE

IMRSFSLSTNLQERLRRKE.

In various embodiments, the consensus interferon comprises a modified version of the consensus interferon, i.e., a consensus interferon variant, as a signaling agent. In various embodiments, the consensus interferon variant encompasses functional derivatives, analogs, precursors, isoforms, splice variants, or fragments of the consensus interferon.

In an embodiment, the consensus interferon variants are selected form the consensus interferon variants disclosed in U.S. Pat. Nos. 4,695,623, 4,897,471, 5,541,293, and 8,496,921, the entire contents of all of which are hereby incorporated by reference. For example, the consensus interferon variant may comprise the amino acid sequence of IFN-$CON_2$ or IFN-$CON_3$ as disclosed in U.S. Pat. Nos. 4,695,623, 4,897,471, and 5,541,293. In an embodiment, the consensus interferon variant comprises the amino acid sequence of IFN-$CON_2$:

(SEQ ID NO: 374)
CDLPQTHSLGNRRTLMLLAQMRRISPFSCLKDRHDFGFPQEEFDGNQFQ

KAQAISVLHEMIQQTFNLFSTKDSSAAWDESLLEKFYTELYQQLNDLEA

CVIQEVGVEETPLMNVDSILAVKKYFQRITLYLTEKKYSPCAWEVVRAE

IMRSFSLSTNLQERLRRKE.

In an embodiment, the consensus interferon variant comprises the amino acid sequence of IFN-$CON_3$:

(SEQ ID NO: 375)
CDLPQTHSLGNRRALILLAQMRRISPFSCLKDRHDFGFPQEEFDGNQFQ

KAQAISVLHEMIQQTFNLFSTKDSSAAWDESLLEKFYTELYQQLNDLEA

CVIQEVGVEETPLMNEDSILAVRKYFQRITLYLTEKKYSPCAWEVVRAE

IMRSFSLSTNLQERLRRKE.

In an embodiment, the consensus interferon variant comprises the amino acid sequence of any one of the variants disclosed in U.S. Pat. No. 8,496,921. For example, the consensus variant may comprise the amino acid sequence of:

(SEQ ID NO: 376)
MCDLPQTHSLGNRRALILLAQMRRISPFSCLKDRHDFGFPQEEFDGNQF

QKAQAISVLHEMIQQTFNLFSTKDSSAAWDESLLEKFYTELYQQLNDLE

ACVIQEVGVEETPLMNEDSILAVRKYFQRITLYLTEKKYSPCAWEVVRA

EIMRSFSLSTNLQERLRRKE.

In another embodiment, the consensus interferon variant may comprise the amino acid sequence of:

(SEQ ID NO: 377)
MCDLPQTHSLGNRRALILLAQMRRISPFSCLKDRHDFGFPQEEFDGNQF

QKAQAISVLHEMIQQTFNLFSTKDSSAAWDESLLEKFYTELYQQLNDLE

ACVIQEVGVEETPLMNEDSILAVRKYFQRITLYLTEKKYSPCAWEVVRA

EIMRSFSLCTNLQERLRRKE.

In some embodiments, the consensus interferon variant may be PEGylated, i.e., comprises a PEG moiety. In an embodiment, the consensus interferon variant may comprise a PEG moiety attached at the S156C position of SEQ ID NO: 377.

In some embodiments, the engineered interferon is a variant of human IFN-α2a, with an insertion of Asp at approximately position 41 in the sequence Glu-Glu-Phe-Gly-Asn-Gln (SEQ ID NO: 378) to yield Glu-Glu-Phe-Asp-Gly-Asn-Gln (SEQ ID NO: 379) (which resulted in a renumbering of the sequence relative to IFN-α2a sequence) and the following mutations of Arg23Lys, Leu26Pro, Glu53Gln, Thr54Ala, Pro56Ser, Asp86Glu, Ile104Thr, Gly106Glu, Thr110Glu, Lys117Asn, Arg125Lys, and Lys136Thr. All embodiments herein that describe consensus interferons apply equally to this engineered interferon.

In various embodiments, the consensus interferon variant comprises an amino acid sequence having one or more amino acid mutations. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

In various embodiments, the substitutions may also include non-classical amino acids (e.g. selenocysteine, pyrrolysine, N-formylmethionine β-alanine, GABA and 5-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, 6-alanine, fluoro-amino acids, designer amino acids such as β methyl amino acids, C α-methyl amino acids, N α-methyl amino acids, and amino acid analogs in general).

In various embodiments, the consensus interferon is modified to have one or more mutations. In some embodiments, the mutations allow for the consensus interferon variant to have one or more of attenuated activity such as one or more of reduced binding affinity, reduced endogenous activity, and reduced specific bioactivity relative to unmutated, e.g., the wild type form of the consensus interferon (e.g., the consensus interferon having an amino acid sequence of SEQ ID NO: 372 or 373). For instance, the one or more of attenuated activity such as reduced binding affinity, reduced endogenous activity, and reduced specific bioactivity relative to unmutated, e.g. the wild type form of the consensus interferon, may be at a therapeutic receptor such as IFNAR. Consequentially, in various embodiments, the mutations allow for the consensus interferon variant to have reduced systemic toxicity, reduced side effects, and reduced off-target effects relative to unmutated, e.g. the wild type form of the consensus interferon.

In various embodiments, the consensus interferon is modified to have a mutation that reduces its binding affinity or activity at a therapeutic receptor such as IFNAR. In some embodiments, the activity provided by the consensus interferon is agonism at the therapeutic receptor (e.g. activation of a cellular effect at a site of therapy). For example, the consensus interferon may activate the therapeutic receptor. In such embodiments, the mutation results in the consensus interferon variant to have reduced activating activity at the therapeutic receptor.

In some embodiments, the reduced affinity or activity at the therapeutic receptor is restorable by attachment with a targeting moiety. In other embodiments, the reduced affinity or activity at the therapeutic receptor is not substantially restorable by attachment with the targeting moiety. In various embodiments, the therapeutic chimeric proteins or chimeric protein complexes of the present invention reduce off-target effects because the consensus interferon variant has mutations that weaken binding affinity or activity at a therapeutic receptor. In various embodiments, this reduces side effects observed with, for example, the wild type consensus interferon. In various embodiments, the consensus interferon variant is substantially inactive en route to the site of therapeutic activity and has its effect substantially on specifically targeted cell types, which greatly reduces undesired side effects.

In various embodiments, the consensus interferon variant has one or more mutations that cause the consensus interferon variant to have attenuated or reduced affinity, e.g. binding (e.g. $K_D$) and/or activation (measurable as, for example, $K_A$ and/or $EC_{50}$) for one or more therapeutic receptors. In various embodiments, the reduced affinity at the therapeutic receptor allows for attenuation of activity and/or signaling from the therapeutic receptor.

In various embodiments, the consensus interferon variant has one or more mutations that reduce its binding to or its affinity for the IFNAR1 subunit of IFNAR. In one embodiment, the consensus interferon variant has reduced affinity and/or activity at IFNAR1. In some embodiments, the consensus interferon variant has one or more mutations that reduce its binding to or its affinity for the IFNAR2 subunit of IFNAR. In some embodiments, the consensus interferon variant has one or more mutations that reduce its binding to or its affinity for both IFNAR1 and IFNAR2 subunits.

In some embodiments, the consensus interferon variant has one or more mutations that reduce its binding to or its affinity for IFNAR1 and one or more mutations that substantially reduce or ablate binding to or its affinity for IFNAR2. In some embodiments, chimeric proteins or chimeric protein complexes with such consensus interferon variant can provide target-selective IFNAR1 activity (e.g. IFNAR1 activity is restorable via targeting through the CD8 targeting moiety).

In some embodiments, the consensus interferon variant has one or more mutations that reduce its binding to or its affinity for IFNAR2 and one or more mutations that substantially reduce or ablate binding to or its affinity for IFNAR1. In some embodiments, chimeric proteins or chimeric protein complexes with such consensus interferon variant can provide target-selective IFNAR2 activity (e.g. IFNAR2 activity is restorable via targeting through the CD8 targeting moiety).

In some embodiments, the consensus interferon variant has one or more mutations that reduce its binding to or its affinity for IFNAR1 and one or more mutations that reduce its binding to or its affinity for IFNAR2. In some embodiments, chimeric proteins or chimeric protein complexes with such consensus interferon variant can provide target-selective IFNAR1 and/or IFNAR2 activity (e.g. IFNAR1 and/IFNAR2 activity is restorable via targeting through the CD8 targeting moiety).

In some embodiments, the consensus interferon is modified to have a mutation at one or more amino acids at positions 145-155, such as amino acid positions 149, 150 and/or 154, with reference to SEQ ID NO: 373, the substitutions optionally being hydrophobic and selected from alanine, valine, leucine, and isoleucine. In some embodiments, the consensus interferon mutant comprises one or more mutations selected from M149A, R150A, and L154A, and, with reference to SEQ ID NO: 373.

In an embodiment, the consensus interferon is modified to have a mutation at amino acid position 121 (i.e., K121), with reference to SEQ ID NO: 373. In an embodiment, the consensus interferon comprises a K121E mutation, with reference to SEQ ID 373.

Linkers in CD8-Targeted Chimeric Proteins

In some embodiments, the CD8-targeted chimeric protein or chimeric protein complex optionally comprises one or more linkers. In some embodiments, the present CD8-targeted chimeric protein or chimeric protein complex comprises a linker connecting the CD8 targeting moiety and the IFN signaling agent (e.g., modified IFN signaling agent). In some embodiments, the CD8-targeted chimeric protein or chimeric protein complex comprises a linker within the IFN signaling agent (e.g., modified IFN signaling agent). In some embodiments, the linker may be utilized to link various functional groups, residues, or moieties as described herein to the chimeric protein or chimeric protein complex. In some embodiments, the linker is a single amino acid or a plurality of amino acids that does not affect or reduce the stability, orientation, binding, neutralization, and/or clearance characteristics of the binding regions and the binding protein. In various embodiments, the linker is selected from a peptide, a protein, a sugar, or a nucleic acid.

In some embodiments, vectors encoding the CD8-targeted chimeric proteins or chimeric protein complexes linked as a single nucleotide sequence to any of the linkers described herein are provided and may be used to prepare such chimeric proteins or chimeric protein complexes.

In some embodiments, the linker length allows for efficient binding of a CD8 targeting moiety and the IFN signaling agent (e.g., modified IFN signaling agent) to their receptors. For instance, in some embodiments, the linker length allows for efficient binding of one of the CD8 targeting moieties and the IFN signaling agent to receptors on the same cell.

In some embodiments, the linker length is at least equal to the minimum distance between the binding sites of one of the CD8 targeting moieties and the IFN signaling agent to receptors on the same cell. In some embodiments the linker length is at least twice, or three times, or four times, or five times, or ten times, or twenty times, or 25 times, or 50 times, or one hundred times, or more the minimum distance between the binding sites of one of the CD8 targeting moieties and the IFN signaling agent to receptors on the same cell.

As described herein, the linker length allows for efficient binding of one of the CD8 targeting moieties and the IFN signaling agent to receptors on the same cell, the binding being sequential, e.g. CD8 targeting moiety/receptor binding preceding IFN signaling agent/receptor binding.

In some embodiments, there are two linkers in a single chimera, each connecting the IFN signaling agent to a CD8 targeting moiety. In various embodiments, the linkers have lengths that allow for the formation of a site that has a disease cell and an effector cell without steric hindrance that would prevent modulation of the either cell.

The use of a variety of linker sequences may be used to link the CD8 targeting moieties and the IFN signaling agent. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et al., (2000), Protein Eng. 13(5):309-312, the entire contents of which are hereby incorporated by reference. In various embodiments, the linker may be functional. For example, without limitation, the linker may function to improve the folding and/or stability, improve the expression, improve the pharmacokinetics, and/or improve the bioactivity of the CD8-targeted chimeric protein or chimeric protein complex.

In some embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is a polypeptide. In some embodiments, the linker is greater than about 100 amino acids long. For example, the linker may be greater than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid.

In embodiments directed to CD8 targeted chimeric proteins or chimeric protein complexes having two or more CD8 targeting moieties, a linker connects the two CD8 targeting moieties to each other and this linker has a short length and a linker connects a CD8 targeting moiety and an IFN signaling agent this linker is longer than the linker connecting the two CD8 targeting moieties. For example, the difference in amino acid length between the linker connecting the two targeting moieties and the linker connecting a targeting moiety and a signaling agent may be about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids.

In various embodiments, the linker is substantially comprised of glycine and serine residues (e.g. about 30%, or about 40%, or about 50%, or about 60%, or about 70%, or about 80%, or about 90%, or about 95%, or about 97% glycines and serines). For example, in some embodiments, the linker is $(Gly_4Ser)_n$, where n is from about 1 to about 8, e.g. 1, 2, 3, 4, 5, 6, 7, or 8 (SEQ ID NOs: 5-12, respectively). In an embodiment, the linker sequence is GGSGGSGGGGSGGGGS (SEQ ID NO: 13). Additional illustrative linkers include, but are not limited to, linkers having the sequence LE, GGGGS (SEQ ID NO: 5), $(GGGGS)_n$ (n=1-4) (SEQ ID NOs: 5-8), $(Gly)_8$ (SEQ ID NO: 14), $(Gly)_6$ (SEQ ID NO: 15), $(EAAAK)_n$ (n=1-3) (SEQ ID NOs: 16-18), $A(EAAAK)_nA$ (n=2-5) (SEQ ID NOs: 19-22), AEAAAKEAAAKA (SEQ ID NO: 23), $A(EAAAK)_4ALEA(EAAAK)_4A$ (SEQ ID NO: 24), PAPAP (SEQ ID NO: 25), KESGSVSSEQLAQFRSLD (SEQ ID NO: 26), EGKSSGSGSESKST (SEQ ID NO: 27), GSAGSAAGSGEF (SEQ ID NO: 28), and $(XP)_n$, with X designating any amino acid, e.g., Ala, Lys, or Glu. In various embodiments, the linker is $(GGS)_n$ (n=1-20) (SEQ ID NOs: 29-48). In some embodiments, the linker is G. In some embodiments, the linker is AAA. In some embodiments, the linker is $(GGGGS)_n$ (n=5-20) (SEQ ID NOs: 9-12 and 49-60). In some embodiments, the linker is one or more of GGGSE (SEQ ID NO: 61), GSESG (SEQ ID NO: 62), GSEGS (SEQ ID NO: 63), GEGGSGEGSSGEGSSSEGGGSEGGGSEGGGSEGGS (SEQ ID NO: 64), and a linker of randomly placed G, S, and E every 4 amino acid intervals.

In some embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). In various embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2.

According to crystallographic studies, the immunoglobulin hinge region can be further subdivided functionally into three regions: the upper hinge region, the core region, and the lower hinge region. See Shin et al., 1992 *Immunological Reviews* 130:87. The upper hinge region includes amino acids from the carboxyl end of $C_{H1}$ to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the $C_{H2}$ domain and includes residues in $C_{H2}$. Id. The core hinge region of wild-type human IgG1 contains the sequence Cys-Pro-Pro-Cys (SEQ ID NO: 65), which when dimerized by disulfide bond formation, results in a cyclic octapeptide believed to act as a pivot, thus conferring flexibility. In various embodiments, the present linker comprises, one, or two, or three of the upper hinge region, the core region, and the lower hinge region of any antibody (e.g., of IgG, IgA, IgD, and IgE, inclusive of subclasses (e.g. IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In various embodiments, the linker of the present invention comprises one or more glycosylation sites. In various embodiments, the linker is a hinge-$C_{H2}$-CH3 domain of a human IgG4 antibody.

In some embodiments, the linker is a synthetic linker such as PEG.

In various embodiments, the linker may be functional. For example, without limitation, the linker may function to improve the folding and/or stability, improve the expression, improve the pharmacokinetics, and/or improve the bioactivity of the present chimeric protein or chimeric protein complex. In another example, the linker may function to target the CD8-targeted chimeric protein or chimeric protein complex to a particular cell type or location.

Other Therapeutic Agents

In some embodiments, the additional therapeutic agent is one or more agents selected from a phosphoinositide-3-kinase 9 (PI3K) inhibitor, anthracycline, and SMAC mimetic.

By way of example, in some embodiments the PI3K inhibitor is selected from: Wortmannin, PX-866, demethoxyviridin, LY294002, idelalisib, umbralisib, duvelisib, copanlisib, buparlisib, pilaralisib, pictilisib, alpelisib, taselisib, NCP-BEZ235, LY3023414, GSK2126458, perifosine, dactolisib, CUDC-907, voxtalisib, ME-401, IPI-549, SF1126, RP6530, INK1117, XL147 (a/k/a SAR245408), palomid 529, GSK1059615, ZSTK474, PWT33597, IC87114, TG-100-115, CAL263, RP6503, PI-103, GNE-477, and AEZS-136.

By way of example, in some embodiments the anthracycline is selected from: doxorubicin, daunorubicin, epirubicin, mitoxantrone, idarubicin, aldoxorubicin, annamycin, plicamycin, pirarubicin, aclarubicin, zorubicin, sabarubicin, zoptarelin doxorubicin, GPX-150, SP10490, and valrubicin. In some embodiments, the anthracycline is encapsulated by a liposome (e.g., liposomal doxorubicin). In some embodiments, the liposomal anthracycline is pegylated (e.g., pegylated liposomal doxorubicin).

By way of example, in some embodiments the SMAC mimetic is selected from: birinapant (TL32711), LCL161 (Novartis), GDC-0917 (Genentech), HGS1029 (Human Genome Sciences), TPI 1237-22, AT-406/Debio1143, and GT13402.

Chimeric Protein Complexes with Fc Domains

In some embodiments, the present invention relates to chimeric protein complexes where the complexes include one or more fragment crystallizable domain (Fc domain). In some embodiments, the Fc domain has one or more mutations that reduces or eliminates one or more effector functions of the Fc domain, promotes Fc chain pairing in the Fc domain, and/or stabilizes a hinge region in the Fc domain.

In various embodiments, the present invention includes chimeric protein complexes comprising one or more targeting agents, one or more signaling agents and one or more Fc domains. In one embodiment, the chimeric protein complex includes at least one targeting moiety that specifically binds to CD13, at least one signaling agent that is a tumor necrosis factor (TNF), and at least one Fc domain. In various embodiments, the TNF signaling agent may be modified to attenuate activity. In some embodiments, the CD13-targeted chimeric protein complex may directly or indirectly recruit an immune cell to a site of action (such as, by way of non-limiting example, the tumor microenvironment).

In some embodiments, the present invention relates to a CD13-targeted chimeric protein complex having at least one targeting moiety that specifically binds to CD13, at least one signaling agent that is an interferon (IFN) or a modified form thereof and at least one Fc domain. In various embodiments, the IFN signaling agent may be modified to attenuate activity. In one embodiment, the interferon is IFN-γ or a modified form thereof.

The fragment crystallizable domain (Fc domain) is the tail region of an antibody that interacts with Fc receptors located on the cell surface of cells that are involved in the immune system, e.g., B lymphocytes, dendritic cells, natural killer cells, macrophages, neutrophils, eosinophils, basophils, and mast cells. In IgG, IgA and IgD antibody isotypes, the Fc domain is composed of two identical protein fragments, derived from the second and third constant domains of the antibody's two heavy chains. In IgM and IgE antibody isotypes, the Fc domain contains three heavy chain constant domains (CH domains 2-4) in each polypeptide chain.

In some embodiments, the Fc-based chimeric protein of complex the present technology includes a Fc domain. In some embodiments, the Fc domains are from selected from IgG, IgA, IgD, IgM or IgE. In some embodiments, the Fc domains are from selected from IgG1, IgG2, IgG3, or IgG4.

In some embodiments, the Fc domains are from selected from human IgG, IgA, IgD, IgM or IgE. In some embodiments, the Fc domains are from selected from human IgG1, IgG2, IgG3, or IgG4.

In some embodiments, the Fc domains of the Fc-based chimeric protein complex comprise the CH2 and CH3 regions of IgG. In some embodiments, the IgG is human IgG. In some embodiments, the human IgG is selected from IgG1, IgG2, IgG3, or IgG4.

In some embodiments, the Fc domains comprise one or more mutations. In some embodiments, the mutation(s) to the Fc domains reduces or eliminates the effector function the Fc domains. In some embodiments, the mutated Fc domain has reduced affinity or binding to a target receptor. By way of example, in some embodiments, the mutation to the Fc domains reduces or eliminates the binding of the Fc domains to FcγR. In some embodiments, the FcγR is selected from FcγRI; FcγRIIa, 131 R/R; FcγRIIa, 131 H/H, FcγRIIb; and FcγRIII. In some embodiments, the mutation to the Fc domains reduces or eliminated binding to complement proteins, such as, e.g., C1q. In some embodiments, the mutation to the Fc domains reduces or eliminated binding to both FcγR and complement proteins, such as, e.g., C1q.

In some embodiments, the Fc domains comprise the LALA mutation to reduce or eliminate the effector function of the Fc domains. By way of example, in some embodiments, the LALA mutation comprises L234A and L235A substitutions in human IgG (e.g., IgG1) (wherein the numbering is based on the commonly used numbering of the CH2 residues for human IgG1 according to EU convention (Edelman et al., PNAS, 1969; 63 (1) 78-85)).

In some embodiments, the Fc domains of human IgG comprise a mutation at 46. to reduce or eliminate the effector function of the Fc domains. By way of example, in some embodiments, the mutations are selected from L234A, L234F, L235A, L235E, L235Q, K322A, K322Q, D265A, P329G, P329A, P331G, and P331S.

In some embodiments, the Fc domains comprise the FALA mutation to reduce or eliminate the effector function of the Fc domains. By way of example, in some embodiments, the FALA mutation comprises F234A and L235A substitutions in human IgG4.

In some embodiments, the Fc domains of human IgG4 comprise a mutation at one or more of F234, L235, K322, D265, and P329 to reduce or eliminate the effector function of the Fc domains. By way of example, in some embodiments, the mutations are selected from F234A, L235A, L235E, L235Q, K322A, K322Q, D265A, P329G, and P329A.

In some embodiments, the mutation(s) to the Fc domain stabilize a hinge region in the Fc domain. By way of example, in some embodiments, the Fc domain comprises a mutation at S228 of human IgG to stabilize a hinge region. In some embodiments, the mutation is S228P.

In some embodiments, the mutation(s) to the Fc domain promote chain pairing in the Fc domain. In some embodiments, chain pairing is promoted by ionic pairing (a/k/a charged pairs, ionic bond, or charged residue pair).

In some embodiments, the Fc domain comprises a mutation at one more of the following amino acid residues of IgG to promote of ionic pairing: D356, E357, L368, K370, K392, D399, and K409.

By way of example, in some embodiments, the human IgG Fc domain comprise one of the mutation combinations in Table 1 to promote of ionic pairing.

TABLE 1

| Substitution(s) on one Fc Chain | Substitution(s) on other Fc Chain |
|---|---|
| D356K D399K | K392D K409D |
| E357R L368R | K370D K409D |
| E357R L368K | K370D K409D |
| E357R D399K | K370D K409D |
| E357R | K370D |
| L368R D399K | K392D K409D |
| L368K D399K | K392D K409D |
| L368R D399K | K409D |
| L368K D399K | K409D |
| L368R | K409D |
| L368K | K409D |
| K370D K409D | E357R D399K |
| K370D K409D | E357R L368R |
| K370D K409D | E357R L368K |
| K370D K409D | E357R D399K |
| K370D K409D | E357R L368R |
| K370D K409D | E357R L368K |
| K370D | E357R |
| K370D | E357R |
| K392D K409D | D356K D399K |
| K392D K409D | L368R D399K |
| K392D K409D | L368K D399K |
| K392D K409D | D399K |
| D399K | K392D K409D |
| D399K | K409D |
| K409D | L368R |
| K409D | L368K |
| K409D | L368R D399K |
| K409D | L368K D399K |
| K409D | L368R |
| K409D | L368K |
| K409D | L368R D399K |
| K409D | L368K D399K |
| K409D | D399K |

In some embodiments, chain pairing is promoted by a knob-in-hole mutations. In some embodiments, the Fc domain comprises one or more mutations to allow for a knob-in-hole interaction in the Fc domain. In some embodiments, a first Fc chain is engineered to express the "knob" and a second Fc chain is engineered to express the complementary "hole." By way of example, in some embodiments, human IgG Fc domain comprises the mutations of Table 2 to allow for a knob-in-hole interaction.

TABLE 2

| Substitution(s) on one Fc Chain | Substitution(s) on other Fc Chain |
|---|---|
| T366Y | Y407T |
| T366Y/F405A | T394W/Y407T |
| T366W | Y407A |
| T366W | Y407V |
| T366Y | Y407A |
| T366Y | Y407V |
| T366Y | Y407T |

In some embodiments, the Fc domains in the Fc-based chimeric protein complexes of the present technology comprise any combination of the above-disclosed mutations. By way of example, in some embodiments, the Fc domain comprises mutations that promote ionic pairing and/or a knob-in-hole interaction. By way of example, in some embodiments, the Fc domain comprises mutations that have one or more of the following properties: promote ionic pairing, induce a knob-in-hole interaction, reduce or eliminate the effector function of the Fc domain, and cause Fc stabilization (e.g. at hinge).

By way of example, in some embodiments, a human IgG Fc domains comprise mutations disclosed in Table 3, which promote ionic pairing and/or promote a knob-in-hole interaction in the Fc domain.

TABLE 3

| Substitution(s) on one Fc Chain | Substitution(s) on other Fc Chain |
|---|---|
| T366W K370D | E357R Y407A |
| T366W K370D | E357R Y407V |
| T366W K409D | L368R Y407A |
| T366W K409D | L368R Y407V |
| T366W K409D | L368K Y407A |
| T366W K409D | L368K Y407V |
| T366W K409D | L368R D399K Y407A |
| T366W K409D | L368R D399K Y407V |
| T366W K409D | L368K D399K Y407A |
| T366W K409D | L368K D399K Y407V |
| T366W K409D | D399K Y407A |
| T366W K409D | D399K Y407V |
| T366W K392D K409D | D399K Y407A |
| T366W K392D K409D | D399K Y407V |
| T366W K392D K409D | D356K D399K Y407A |
| T366W K392D K409D | D356K D399K Y407V |
| T366W K370D K409D | E357R D399K Y407A |
| T366W K370D K409D | E357R D399K Y407V |
| T366W K370D K409D | E357R L368R Y407A |
| T366W K370D K409D | E357R L368R Y407V |
| T366W K370D K409D | E357R L368K Y407A |
| T366W K370D K409D | E357R L368K Y407V |
| T366W K392D K409D | L368R D399K Y407A |
| T366W K392D K409D | L368R D399K Y407V |
| T366W K392D K409D | L368K D399K Y407A |

TABLE 3-continued

| Substitution(s) on one Fc Chain | Substitution(s) on other Fc Chain |
|---|---|
| T366W K392D K409D | L368K D399K Y407V |
| E357R T366W | K370D Y407A |
| E357R T366W | K370D Y407V |
| T366W L368R | Y407A K409D |
| T366W L368R | Y407V K409D |
| T366W L368K | Y407A K409D |
| T366W L368K | Y407V K409D |
| T366W L368R D399K | Y407A K409D |
| T366W L368R D399K | Y407V K409D |
| T366W L368K D399K | Y407A K409D |
| T366W L368K D399K | Y407V K409D |
| T366W D399K | Y407A K409D |
| T366W D399K | Y407V K409D |
| 1366W D399K | K392D Y407A K409D |
| T366W D399K | K392D Y407V K409D |
| T366W D356K D399K | K392D Y407A K409D |
| T366W D356K D399K | K392D Y407V K409D |
| E357R T366W D399K | K370D Y407A K409D |
| E357R T366W D399K | K370D Y407V K409D |
| E357R T366W L368R | K370D Y407A K409D |
| E357R T366W L368R | K370D Y407V K409D |
| E357R T366W L368K | K370D Y407A K409D |
| E357R T366W L368K | K370D Y407V K409D |
| T366W L368R D399K | K392D Y407A K409D |
| T366W L368R D399K | K392D Y407V K409D |
| T366W L368K D399K | K392D Y407A K409D |

By way of example, in some embodiments, a human IgG Fc domains comprise mutations disclosed in Table 4, which promote ionic pairing, promote a knob-in-hole interaction, or a combination thereof in the Fc domain. In embodiments, the "Chain 1" and "Chain 2" of Table 4 can be interchanged (e.g. Chain 1 can have Y407T and Chain 2 can have T366Y).

TABLE 4

| Chain 1 mutation | Chain 2 mutation | Reference | IgG |
|---|---|---|---|
| T366Y | Y407T | Ridgway et al., 1996 Protein Engineering, Design and Selection, Volume 9, Issue 7, 1 Jul. 1996, Pages 617-62 | IgG1 |
| T366Y/F405A | T394W/Y407T | Ridgway et al., 1996 Protein Engineering, Design and Selection, Volume 9, Issue 7, 1 Jul. 1996, Pages 617-62 | IgG1 |
| T366W | Y407A | Atwell et al., 1997 JMB Volume 270, Issue 1, 4 Jul. 1997, Pages 26-35 | IgG1 |
| T366W | T366S/L368V/Y407A | Atwell et al., 1997 JMB Volume 270, Issue 1, 4 Jul. 1997, Pages 26-35 | IgG1 |
| T366W | L368A/Y407A | Atwell et al., 1997 JMB Volume 270, Issue 1, 4 Jul. 1997, Pages 26-35 | IgG1 |
| T366W | T366S/L368A/Y407A | Atwell et al., 1997 JMB Volume 270, Issue 1, 4 Jul. 1997, Pages 26-35 | IgG1 |
| T366W | T366S/L368G/Y407V | Atwell et al., 1997 JMB Volume 270, Issue 1, 4 Jul. 1997, Pages 26-35 | IgG1 |
| T366W/D399C | T366S/L368A/K392C/Y407V | Merchant et al., 1998 Nature Biotechnology volume 16, pages 677-681 (1998) | IgG1 |
| T366W/K392C | T366S/L368A/D399C/Y407V | Merchant et al., 1998 Nature Biotechnology volume 16, pages 677-681 (1998) | IgG1 |
| S354C/T366W | Y349C/T3665/L368A/Y407V | Merchant et al., 1998 Nature Biotechnology volume 16, pages 677-681 (1998) | IgG1 |
| Y349C/T366W | S354C/T366S/L368A/Y407V | Merchant et al., 1998 Nature Biotechnology volume 16, pages 677-681 (1998) | IgG1 |

TABLE 4-continued

| Chain 1 mutation | Chain 2 mutation | Reference | IgG |
|---|---|---|---|
| E356C/T366W | Y349C/T366S/L368A/Y407V | Merchant et al., 1998 Nature Biotechnology volume 16, pages 677-681 (1998) | IgG1 |
| Y349C/T366W | E356C/T366S/L368A/Y407V | Merchant et al., 1998 Nature Biotechnology volume 16, pages 677-681 (1998) | IgG1 |
| E357C/T366W | Y349C/T366S/L368A/Y407V | Merchant et al., 1998 Nature Biotechnology volume 16, pages 677-681 (1998) | IgG1 |
| Y349C/T366W | E357C/T366S/L368A/Y407V | Merchant et al., 1998 Nature Biotechnology volume 16, pages 677-681 (1998) | IgG1 |
| D339R | K409E | Gunasekaran et al., 2010 The Journal of Biological Chemistry 285, 19637-19646. | IgG1 |
| D339K | K409E | Gunasekaran et al., 2010 The Journal of Biological Chemistry 285, 19637-19646. | IgG1 |
| D339R | K409D | Gunasekaran et al., 2010 The Journal of Biological Chemistry 285, 19637-19646. | IgG1 |
| D339K | K409D | Gunasekaran et al., 2010 The Journal of Biological Chemistry 285, 19637-19646. | IgG1 |
| D339K | K360D/K409E | Gunasekaran et al., 2010 The Journal of Biological Chemistry 285, 19637-19646. | IgG1 |
| D339K | K392D/K409E | Gunasekaran et al., 2010 The Journal of Biological Chemistry 285, 19637-19646. | IgG1 |
| D339K/E356K | K392D/K409E | Gunasekaran et al., 2010 The Journal of Biological Chemistry 285, 19637-19646. | IgG1 |
| D339K/E357K | K392D/K409E | Gunasekaran et al., 2010 The Journal of Biological Chemistry 285, 19637-19646. | IgG1 |
| D339K/E356K | K409E/K439D | Gunasekaran et al., 2010 The Journal of Biological Chemistry 285, 19637-19646. | IgG1 |
| D339K/E357K | K370D/K409E | Gunasekaran et al., 2010 The Journal of Biological Chemistry 285, 19637-19646. | IgG1 |
| D339K/E356K/E357K | K370D/K392D/K409E | Gunasekaran et al., 2010 The Journal of Biological Chemistry 285, 19637-19646. | IgG1 |
| S364H/F405A | Y349T/T394F | Moore et al., 2011 mAbs, 3:6, 546-557 | IgG1 |
| S364H/T394F | Y349T/F405A | Moore et al., 2011 mAbs, 3:6, 546-557 | IgG1 |
| D221R/P228R/K409R | D221E/P228E/L368E | Strop et al., 2012 JMB Volume 420, Issue 3, 13 July 2012, Pages 204-219 | IgG1 |
| C223R/E225R/P228R/K409R | C223E/P228E/L368E | Strop et al., 2012 JMB Volume 420, Issue 3, 13 July 2012, Pages 204-219 | IgG2 |
| F405L | K409R | Labrijn et al. 2013 PNAS Mar. 26, 2013. 110 (13) 5145-5150 | IgG1 |
| F405A/Y407V | T394W | Von Kreudenstein et al., 2013 mAbs Volume 5, 2013-Issue 5, pp. 644-654 | IgG1 |
| F405A/Y407V | T366I/T394W | Von Kreudenstein et al., 2013 mAbs Volume 5, 2013-Issue 5, pp. 644-654 | IgG1 |
| F405A/Y407V | T366L/T394W | Von Kreudenstein et al., 2013 mAbs Volume 5, 2013-Issue 5, pp. 644-654 | IgG1 |
| F405A/Y407V | T366L/K392M/T394W | Von Kreudenstein et al., 2013 mAbs Volume 5, 2013-Issue 5, pp. 644-654 | IgG1 |
| L351Y/F405A/Y407V | T366L/K392M/T394W | Von Kreudenstein et al., 2013 mAbs Volume 5, 2013-Issue 5, pp. 644-654 | IgG1 |
| T350V/L351Y/F405A/Y407V | T350V/T366L/K392M/T394W | Von Kreudenstein et al., 2013 mAbs Volume 5, 2013-Issue 5, pp. 644-654 | IgG1 |
| T350V/L351Y/F405A/Y407V | T350V/T366L/K392L/T394W | Von Kreudenstein et al., 2013 mAbs Volume 5, 2013-Issue 5, pp. 644-654 | IgG1 |
| K409W | D339V/F405T | Choi et al., 2013 PNAS Jan. 2, 2013. 110 (1) 270-275 | IgG1 |
| K360E | Q347R | Choi et al., 2013 PNAS Jan. 2, 2013. 110 (1) 270-275 | IgG1 |
| K360E/K409W | D339V/Q347R/F405T | Choi et al., 2013 PNAS Jan. 2, 2013. 110 (1) 270-275 | IgG1 |
| Y3490/K360E/K409W | D339V/Q347R/S3540/F405T | Choi et al., 2013 PNAS Jan. 2, 2013. 110 (1) 270-275 | IgG1 |
| K392A/K409D | E356K/D399K | Leaver-Fey et al., 2016 Structure Volume 24, Issue 4, 5 Apr. 2016, Pages 641-651 | IgG1 |
| T366W | T3665/L358A/Y407A | Leaver-Fey et al., 2016 Structure Volume 24, Issue 4, 5 Apr. 2016, Pages 641-651 | IgG1 |
| D339M/Y407A | T336V/K409V | Leaver-Fey et al., 2016 Structure Volume 24, Issue 4, 5 Apr. 2016, Pages 641-651 | IgG1 |
| D339M/K360D/Y407A | T336V/E345R/Q347R/K409V | Leaver-Fey et al., 2016 Structure Volume 24, Issue 4, 5 Apr. 2016, Pages 641-651 | IgG1 |

TABLE 4-continued

| Chain 1 mutation | Chain 2 mutation | Reference | IgG |
|---|---|---|---|
| Y3495/T366V/K370Y/K409V | E357D/S364Q/Y407A | Leaver-Fey et al., 2016 Structure Volume 24, Issue 4, 5 Apr. 2016, Pages 641-651 | IgG1 |
| Y3495/T366M/K370Y/K409V | E356G/E357D/S364Q/Y407A | Leaver-Fey et al., 2016 Structure Volume 24, Issue 4, 5 Apr. 2016, Pages 641-651 | IgG1 |
| Y3495/T366M/K370Y/K409V | E357D/S364R/Y407A | Leaver-Fey et al., 2016 Structure Volume 24, Issue 4, 5 Apr. 2016, Pages 641-651 | IgG1 |

And any combination as described in Tables 1-3 of US20150284475A1

By way of example, in some embodiments, a human IgG Fc domains comprise mutations disclosed in Table 5, which reduce or eliminate FcγR and/or complement binding in the Fc domain. In embodiments, the Table 5 mutations are in both chains.

TABLE 5

| Chain 1 mutation | Reference | IgG |
|---|---|---|
| L234A/L235A | Alegre et al., 1994 Transplantation 57:1537-1543 | IgG1 |
| F234A/L235A | Alegre et al., 1994 Transplantation 57:1537-1543 | IgG4 |
| L235E | Morgan et al., 1995 Immunology. 1995 October; 86(2): 319-324. | IgG1 |
| L235E | Morgan et al., 1995 Immunology. 1995 October; 86(2): 319-324. | IgG4 |
| L235A | Morgan et al., 1995 Immunology. 1995 October; 86(2): 319-324. | IgG1 |
| G237A | Morgan et al., 1995 Immunology. 1995 October; 86(2): 319-324. | IgG1 |
| N297H | Tao and Morrison, J. Immunol. 1989; 143:2595-2601 | IgG1 |
| N297Q | Tao and Morrison, J. Immunol. 1989; 143:2595-2601 | IgG1 |
| N297K | Tao and Morrison, J. Immunol. 1989; 143:2595-2601 | IgG3 |
| N297Q | Tao and Morrison, J. Immunol. 1989; 143:2595-2601 | IgG3 |
| D265A | Idusogie et al., 2000 J Immunol Apr. 15, 2000, 164 (8) 4178-4184 | IgG1 |
| D270A, V, K | Idusogie et al., 2000 J Immunol Apr. 15, 2000, 164 (8) 4178-4184 | IgG1 |
| K322A, L, M, D, E | Idusogie et al., 2000 J Immunol Apr. 15, 2000, 164 (8) 4178-4184 | IgG1 |
| P329A, X | Idusogie et al., 2000 J Immunol Apr. 15, 2000, 164 (8) 4178-4184 | IgG1 |
| P331A, S, G, X | Idusogie et al., 2000 J Immunol Apr. 15, 2000, 164 (8) 4178-4184 | IgG1 |
| D265A | Idusogie et al., 2000 J Immunol Apr. 15, 2000, 164 (8) 4178-4184 | IgG1 |
| L234A | Hezareh et al., 2001 J. Virol. December 2001 vol. 75 no. 24 12161-12168 | IgG1 |
| L234A/L235A | Hezareh et al., 2001 J. Virol. December 2001 vol. 75 no. 24 12161-12168 | IgG1 |
| L234F/L235E/P331S | Oganesyan et al., 2008 Acta Cryst. (2008). D64, 700-704 | IgG1 |
| H268Q/V309L/A330S/P331S | An et al., 2009 mAbs Volume 1, 2009-Issue 6, pp. 572-579 | IgG1 |
| G236R/L328R | Moore et al., 2011 mAbs Volume 3, 2011-Issue 6, pp. 546-557 | IgG1 |
| N297G | Couch et al., 2013 Sci. Transl. Med., 5 (2013) 183ra57, 1-12 | IgG1 |
| N297G/D265A | Couch et al., 2013 Sci. Transl. Med., 5 (2013) 183ra57, 1-12 | IgG1 |

TABLE 5-continued

| Chain 1 mutation | Reference | IgG |
|---|---|---|
| V234A/G237A/P328S/H268A/V309L/A330S/P331S | Vafa et al., 2014 Methods Volume 65, Issue 1, 1 Jan. 2014, Pages 114-126 | IgG2 |
| L234A/L235A/P329G | Lo et al., 2016 The Journal of Biological Chemistry 292, 3900-3908 | IgG1 |
| N297D | Schlothauer et al., 2016 Protein Engineering, Design and Selection, Volume 29, Issue 10, 1 Oct. 2016, Pages 457-466 | IgG1 |
| S228P/L235E | Schlothauer et al., 2016 Protein Engineering, Design and Selection, Volume 29, Issue 10, 1 Oct. 2016, Pages 457-466 | IgG4 |
| S228P/L235E/P329G | Schlothauer et al., 2016 Protein Engineering, Design and Selection, Volume 29, Issue 10, 1 Oct. 2016, Pages 457-466 | IgG4 |
| L234F/L235A/K322Q | Borrok et al., 2017 J Pharm Sci April 2017 Volume 106, Issue 4, Pages 1008-1017 | IgG1 |
| L234F/L235Q/P331G | Borrok et al., 2017 J Pharm Sci April 2017 Volume 106, Issue 4, Pages 1008-1017 | IgG1 |
| L234F/L235Q/K322Q | Borrok et al., 2017 J Pharm Sci April 2017 Volume 106, Issue 4, Pages 1008-1017 | IgG1 |
| L234A/L235A/G237A/P3285/H268A/A330S/P331S | Tam et al., 2017 Open Access Antibodies 2017, 6(3), 12; doi:10.3390/antib6030012 | IgG1 |
| S228P/F234A/L235A | Tam et al., 2017 Open Access Antibodies 2017, 6(3), 12; doi:10.3390/antib6030012 | IgG4 |
| S228P/F234A/L235A/G237A/P238S | Tam et al., 2017 Open Access Antibodies 2017, 6(3), 12; doi:10.3390/antib6030012 | IgG4 |
| S228P/F234A/L235A/G236□/G237A/P238S | Tam et al., 2017 Open Access Antibodies 2017, 6(3), 12; doi:10.3390/antib6030012 | IgG4 |

In some embodiments, the Fc domains in the Fc-based chimeric protein complexes of the present technology are homodimeric, i.e., the Fc region in the chimeric protein complex comprises two identical protein fragments.

In some embodiments, the Fc domains in the Fc-based chimeric protein complexes of the present technology are heterodimeric, i.e., the Fc domain comprises two non-identical protein fragments.

In some embodiments, heterodimeric Fc domains are engineered using ionic pairing and/or knob-in-hole mutations described herein. In some embodiments, the heterodimeric Fc-based chimeric protein complexes have a trans orientation/configuration. In a trans orientation/configuration, the targeting moiety and signaling agent are, in embodiments, not found on the same polypeptide chain in the present Fc-based chimeric protein complexes.

In some embodiments, the Fc domains includes or starts with the core hinge region of wild-type human IgG1, which contains the sequence Cys-Pro-Pro-Cys. In some embodiments, the Fc domains also include the upper hinge, or parts thereof (e.g., DKTHTCPPC; see WO 2009053368), EPKSCDKTHTCPPC, or EPKSSDKTHTCPPC; see Lo et al., Protein Engineering vol.11 no.6 pp.495-500, 1998)).

Fc-based Chimeric Protein Complexes

The Fc-based chimeric protein complexes of the present technology comprise at least one Fc domain disclosed herein, at least one signaling agent and at least one targeting moiety (TM) disclosed herein.

It is understood that, the present Fc-based chimeric protein complexes may encompass a complex of two fusion proteins, each comprising an Fc domain.

In some embodiments, the Fc-based chimeric protein complex is heterodimeric. In some embodiments, the heterodimeric Fc-based chimeric protein complex has a trans orientation/configuration. In some embodiments, the heterodimeric Fc-based chimeric protein complex has a cis orientation/configuration.

In some embodiments, heterodimeric Fc domains are engineered using ionic pairing and/or knob-in-hole mutations described herein. In some embodiments, the heterodimeric Fc-based chimeric protein complexes have a trans orientation.

In a trans orientation, the targeting moiety and signaling agent are, in embodiments, not found on the same polypeptide chain in the present Fc-based chimeric protein complexes. In a trans orientation, the targeting moiety and signaling agent are, in embodiments, found on separate polypeptide chains in the Fc-based chimeric protein complexes. In a cis orientation, the targeting moiety and signaling agent are, in embodiments, found on the same polypeptide chain in the Fc-based chimeric protein complexes.

In some embodiments, where more than one targeting moiety is present in the heterodimeric protein complexes described herein, one targeting moiety may be in trans orientation (relative to the signaling agent), whereas another targeting moiety may be in cis orientation (relative to the signaling agent). In some embodiments, the signaling agent and target moiety are on the same ends/sides (N-terminal or C-terminal ends) of an Fc domain. In some embodiments, the signaling agent and targeting moiety are on different sides/ends of a Fc domain (N-terminal and C-terminal ends).

In some embodiments, where more than one targeting moiety is present in the heterodimeric protein complexes described herein, the targeting moieties may be found on the same Fc chain or on two different Fc chains in the heterodimeric protein complex (in the latter case the targeting moieties would be in trans relative to each other, as they are on different Fc chains). In some embodiments, where more than one targeting moiety is present on the same Fc chain, the targeting moieties may be on the same or different sides/ends of a Fc chain (N-terminal or/and C-terminal ends).

In some embodiments, where more than one signaling agent is present in the heterodimeric protein complexes described herein, the signaling agents may be found on the same Fc chain or on two different Fc chains in the heterodimeric protein complex (in the latter case the signaling agents would be in trans relative to each other, as they are on different Fc chains). In some embodiments, where more than one signaling agent is present on the same Fc chain, the signaling agents may be on the same or different sides/ends of a Fc chain (N-terminal or/and C-terminal ends).

In some embodiments, where more than one signaling agent is present in the heterodimeric protein complexes described herein, one signaling agent may be in trans orientation (as relates to the targeting moiety), whereas another signaling agent may be in cis orientation (as relates to the targeting moiety).

In some embodiments, the heterodimeric Fc-based chimeric protein complex does not comprise the signaling agent and targeting moiety on a single polypeptide.

In some embodiments, the Fc-based chimeric protein has an improved in vivo half-life relative to a chimeric protein lacking an Fc or a chimeric protein, which is not a heterodimeric complex. In some embodiments, the Fc-based chimeric protein has an improved solubility, stability and other pharmacological properties relative to a chimeric protein lacking an Fc or a chimeric protein, which is not a heterodimeric complex.

Heterodimeric Fc-based chimeric protein complexes are composed of two different polypeptides. In embodiments described herein, the targeting domain is on a different polypeptide than the signaling agent and accordingly, proteins that contain only one targeting domain copy, and also only one signaling agent. Further, in embodiments, one targeting domain (e.g. VHH) only can avoid cross-linking of the antigen on the cell surface (which could elicit undesired effects in some cases). Further, in embodiments, one signaling agent may alleviate molecular "crowding" and potential interference with avidity mediated restoration of effector function in dependence of the targeting domain. Further, in embodiments, heterodimeric Fc-based chimeric protein complexes can have two targeting moieties and these can be placed on the two different polypeptides. For instance, in embodiments, the C-terminus of both targeting moieties (e.g. VHHs) can be masked to avoid potential autoantibodies or pre-existing antibodies (e.g. VHH autoantibodies or pre-existing antibodies). Further, in embodiments, heterodimeric Fc-based chimeric protein complexes, e.g. with the targeting domain on a different polypeptide than the signaling agent may favor "cross-linking" of two cell types (e.g. a tumor cell and an immune cell). Further, in embodiments, heterodimeric Fc-based chimeric protein complexes can have two signaling agent, each on different polypeptides to allow more complex effector responses.

Further, in embodiments, heterodimeric Fc-based chimeric protein complexes, e.g. with the targeting domain on a different polypeptide than the signaling agent combinatorial diversity of targeting moiety and signaling agent. For instance, in embodiments, polypeptides with any of the targeting moieties described herein can be combined "off the shelf" with polypeptides with any of the signaling agents described herein to allow rapid generation of various combinations of targeting moieties and signaling agents in single Fc-based chimeric protein complexes.

In some embodiments, the Fc-based chimeric protein complex comprises one or more linkers. In some embodiments, the Fc-based chimeric protein complex includes a linker that connects the Fc domain, signaling agent and targeting moiety(ies). In some embodiments, the Fc-based chimeric protein complex includes a linker that connects each signaling agent and targeting moiety (or, if more than one targeting moiety, a signaling agent). In some embodiments, the Fc-based chimeric protein complex includes a linker that connects each signaling agent to the Fc domain. In some embodiments, the Fc-based chimeric protein complex includes a linker that connects each targeting moiety to the Fc domain. In some embodiments, the Fc-based chimeric protein complex includes a linker that connects a targeting moiety to another targeting moiety. In some embodiments, the Fc-based chimeric protein complex includes a linker that connects a signaling agent to another signaling agent.

In some embodiments, a Fc-based chimeric protein complex comprises two or more targeting moieties. In such embodiments, the targeting moieties can be the same targeting moiety or they can be different targeting moieties.

In some embodiments, a Fc-based chimeric protein complex comprises two or more signaling agents. In such embodiments, the signaling agents can be the same targeting moiety or they can be different targeting moieties.

By way of example, in some embodiments, the Fc-based chimeric protein complex comprise a Fc domain, at least two signaling agents (SA), and at least two targeting moieties (TM), wherein the Fc domain, signaling agents, and targeting moieties are selected from any of the Fc domains, signaling agents, and targeting moieties disclosed herein. In some embodiments, the Fc domain is homodimeric.

In various embodiments, the Fc-based chimeric protein complex takes the form of any of the schematics of FIGS. 13A-F.

In various embodiments, the Fc-based chimeric protein complex takes the form of any of the schematics of FIGS. 14A-H.

In various embodiments, the Fc-based chimeric protein complex takes the form of any of the schematics of FIGS. 15A-H.

In various embodiments, the Fc-based chimeric protein complex takes the form of any of the schematics of FIGS. 16A-D.

In various embodiments, the Fc-based chimeric protein complex takes the form of any of the schematics of FIGS. 17A-F.

In various embodiments, the Fc-based chimeric protein complex takes the form of any of the schematics of FIGS. 18A-J.

In various embodiments, the Fc-based chimeric protein complex takes the form of any of the schematics of FIGS. 19A-D.

In various embodiments, the Fc-based chimeric protein complex takes the form of any of the schematics of FIGS. 20A-F.

In various embodiments, the Fc-based chimeric protein complex takes the form of any of the schematics of FIGS. 21A-J.

In various embodiments, the Fc-based chimeric protein complex takes the form of any of the schematics of FIGS. 22A-F.

In various embodiments, the Fc-based chimeric protein complex takes the form of any of the schematics of FIGS. 23A-L.

In various embodiments, the Fc-based chimeric protein complex takes the form of any of the schematics of FIGS. 24A-L.

In various embodiments, the Fc-based chimeric protein complex takes the form of any of the schematics of FIGS. 25A-F.

In various embodiments, the Fc-based chimeric protein complex takes the form of any of the schematics of FIGS. 26A-L.

In various embodiments, the Fc-based chimeric protein complex takes the form of any of the schematics of FIGS. 27A-L.

In various embodiments, the Fc-based chimeric protein complex takes the form of any of the schematics of FIGS. 28A-J.

In various embodiments, the Fc-based chimeric protein complex takes the form of any of the schematics of FIGS. 29A-J.

In various embodiments, the Fc-based chimeric protein complex takes the form of any of the schematics of FIGS. 30A-F.

In various embodiments, the Fc-based chimeric protein complex takes the form of any of the schematics of FIGS. 31A-F.

In some embodiments, the signaling agents are linked to the targeting moieties and the targeting moieties are linked to the Fc domain on the same terminus (see FIGS. 13A-F). In some embodiments, the Fc domain is homodimeric.

In some embodiments, the signaling agents and targeting moieties are linked to the Fc domain, wherein the targeting moieties and signaling agents are linked on the same terminus (see FIGS. 13A-F). In some embodiments, the Fc domain is homodimeric.

In some embodiments, the targeting moieties are linked to signaling agents and the signaling agents are linked to the Fc domain on the same terminus (see FIGS. 13A-F). In some embodiments, the Fc domain is homodimeric.

In some embodiments, the homodimeric Fc-based chimeric protein complex has two or more targeting moieties. In some embodiments, there are four targeting moieties and two signaling agents, the targeting moieties are linked to the Fc domain and the signaling agents are linked to targeting moieties on the same terminus (see FIGS. 14A-H). In some embodiments, the Fc domain is homodimeric. In some embodiments, where there are four targeting moieties and two signaling agents, two targeting moieties are linked to the Fc domain and two targeting moieties are linked to the signaling agents, which are linked to the Fc domain on the same terminus (see FIGS. 14A-H). In some embodiments, the Fc domain is homodimeric. In some embodiments, where there are four targeting moieties and two signaling agents, two targeting moieties are linked to each other and one of the targeting moieties of from each pair is linked to the Fc domain on the same terminus and the signaling agents are linked to the Fc domain on the same terminus (see FIGS. 14A-H). In some embodiments, the Fc domain is homodimeric. In some embodiments, where there are four targeting moieties and two signaling agents, two targeting moieties are linked to each other, wherein one of the targeting moieties of from each pair is linked to a signaling agent and the other targeting moiety of the pair is linked the Fc domain, wherein the targeting moieties linked to the Fc domain are linked on the same terminus (see FIGS. 14A-H). In some embodiments, the Fc domain is homodimeric.

In some embodiments, the homodimeric Fc-based chimeric protein complex has two or more signaling agents. In some embodiments, where there are four signaling agents and two targeting moieties, two signaling agents are linked to each other and one of the signaling agents of from pair is linked to the Fc domain on the same terminus and the targeting moieties are linked to the Fc domain on the same terminus (see FIGS. 15A-H). In some embodiments, the Fc domain is homodimeric. In some embodiments, where there are four signaling agents and two targeting moieties, two signaling agents are linked to the Fc domain one the same terminus and two of the signaling agents are each linked to a targeting moiety, wherein the targeting moieties are linked to the Fc domain at the same terminus (see FIGS. 15A-H). In some embodiments, the Fc domain is homodimeric. In some embodiments, where there are four signaling agents and two targeting moieties, two signaling agents are linked to each other and one of the signaling agents of from pair is linked to a targeting moiety and the targeting moieties are linked to the Fc domain on the same terminus (see FIGS. 15A-H). In some embodiments, the Fc domain is homodimeric.

By way of example, in some embodiments, the Fc-based chimeric protein complex comprise a Fc domain, wherein the Fc domain comprises ionic pairing mutation(s) and/or knob-in-hole mutation(s), at least one signaling agent and at least one targeting moiety, wherein the ionic pairing motif and/or a knob-in-hole motif, signaling agent and targeting moiety are selected from any of the ionic pairing motif and/or a knob-in-hole motif, signaling agents, and targeting moieties disclosed herein. In some embodiments, the Fc domain is heterodimeric. In some embodiments, the Fc domain comprises a mutation that reduces or eliminates its effector function.

In some embodiments, the signaling agent is linked to the targeting moiety, which is linked to the Fc domain (see FIGS. 22A-F and 25A-F). In some embodiments, the targeting moiety is linked to the signaling agent, which is linked to the Fc domain (see FIGS. 22A-F and 25A-F). In some embodiments, the Fc domain is heterodimeric. In some embodiments, the Fc domain comprises a mutation that reduces or eliminates its effector function.

In some embodiments, the signaling agent and targeting moiety are linked to the Fc domain (see FIGS. 16A-D, 17A-D, 22A-F, and 25A-F). In some embodiments, the targeting moiety and the signaling agent are linked to different Fc chains on the same terminus (see FIGS. 16A-D and 19A-D). In some embodiments, the targeting moiety and the signaling agent are linked to different Fc chains on different termini (see FIGS. 16A-D and 19A-D). In some embodiments, the targeting moiety and the signaling agent are linked to the same Fc chain (see FIGS. 22A-F and 25A-F). In some embodiments, the Fc domain is heterodimeric. In some embodiments, the Fc domain comprises a mutation that reduces or eliminates its effector function.

In some embodiments, where there are one signaling agent and two targeting moieties, the signaling agent is linked to the Fc domain and two targeting moieties can be: 1) linked to each other with one of the targeting moieties linked to the Fc domain; or 2) each linked to the Fc domain (see FIGS. 17A-F, 20A-F, 23A-L, 26A-L, 28A-J, and 29A-J). In some embodiments, the targeting moieties are linked on one Fc chain and the signaling agent is on the other Fc chain (see FIGS. 17A-F and 20A-F). In some embodiments, the paired targeting moieties and the signaling agent are linked to the same Fc chain (see FIGS. 23A-L and 26A-L). In some embodiments, a targeting moiety is linked to the Fc domain and the other targeting moiety is linked to the signaling agent and the paired targeting moiety is linked to the Fc domain (see FIGS. 23A-L, 26A-L, 28A-J, and 29A-J). In some embodiments, the unpaired targeting moiety and paired targeting moiety are linked to the same Fc chain (see FIGS. 23A-L and 26A-L). In some embodiments, the unpaired targeting moiety and paired targeting moiety are linked to different Fc chains (see FIGS. 28A-J and 29A-J). In some embodiments, the unpaired targeting moiety and paired targeting moiety are linked on the same terminus (see FIGS. 28A-J and 29A-J). In some embodiments, the Fc domain is heterodimeric. In some embodiments, the Fc domain comprises a mutation that reduces or eliminates its effector function.

In some embodiments, where there are one signaling agent and two targeting moieties, a targeting moiety is linked to the signaling agent which is linked to the Fc domain, and the unpaired targeting moiety is linked the Fc domain (see FIGS. 23A-L, 26A-L, 28A-J, and 29A-J). In some embodiments, the paired signaling agent and unpaired targeting moiety are linked to the same Fc chain (see FIGS. 23A-L and 26A-L). In some embodiments, the paired signaling agent and unpaired targeting moiety are linked to different Fc chains (see FIGS. 28A-J and 29A-J). In some embodiments, the paired signaling agent and unpaired targeting moiety are linked on the same terminus (see FIGS. 28A-J and 29A-J). In some embodiments, the Fc domain is heterodimeric. In some embodiments, the Fc domain comprises a mutation that reduces or eliminates its effector function.

In some embodiments, where there are one signaling agent and two targeting moieties, the targeting moieties are linked together and the signaling agent is linked to one of the paired targeting moieties, wherein the targeting moiety not linked to the signaling agent is linked to the Fc domain (see FIGS. 23A-L and 26A-L). In some embodiments, the Fc domain is heterodimeric. In some embodiments, the Fc domain comprises a mutation that reduces or eliminates its effector function.

In some embodiments, where there are one signaling agent and two targeting moieties, the targeting moieties are linked together and the signaling agent is linked to one of the paired targeting moieties, wherein the signaling agent is linked to the Fc domain (see FIGS. 23A-L and 26A-L). In some embodiments, the Fc domain is heterodimeric. In some embodiments, the Fc domain comprises a mutation that reduces or eliminates its effector function.

In some embodiments, where there are one signaling agent and two targeting moieties, the targeting moieties are both linked to the signaling agent wherein one of the targeting moieties is linked to the Fc domain (see FIGS. 23A-L and 26A-L). In some embodiments, the Fc domain is heterodimeric. In some embodiments, the Fc domain comprises a mutation that reduces or eliminates its effector function.

In some embodiments, where there are one signaling agent and two targeting moieties, the targeting moieties and the signaling agent are linked to the Fc domain (see FIGS. 28A-J and 29A-J). In some embodiments, the targeting moieties are linked on the terminus (see FIGS. 28A-J and 29A-J). In some embodiments, the Fc domain is heterodimeric. In some embodiments, the Fc domain comprises a mutation that reduces or eliminates its effector function.

In some embodiments, where there are two signaling agents and one targeting moiety, the signaling agents are linked to the Fc domain on the same terminus and the targeting moiety is linked to the Fc domain (see FIGS. 18A-J and 21A-J). In some embodiments, the signaling agents are linked to the Fc domain on the same Fc chain and the targeting moiety is linked on the other Fc chain (see FIGS. 30A-F and 31A-F). In some embodiments, the Fc domain is heterodimeric. In some embodiments, the Fc domain comprises a mutation that reduces or eliminates its effector function.

In some embodiments, where there are two signaling agents and one targeting moiety, a signaling agent is linked to the targeting moiety, which is linked to the Fc domain and the other signaling agent is linked to the Fc domain (see FIGS. 18A-J, 19A-J, 24A-L, and 27A-L). In some embodiments, the targeting moiety and the unpaired signaling agent are linked to different Fc chains (see FIGS. 18A-J and 21A-J). In some embodiments, the targeting moiety and the unpaired signaling agent are linked to different Fc chains on the same terminus (see FIGS. 18A-J and 21A-J). In some embodiments, the targeting moiety and the unpaired signaling agent are linked to different Fc chains on different termini (see FIGS. 18A-J and 21A-J). In some embodiments, the targeting moiety and the unpaired signaling agent are linked to the same Fc chains (see FIGS. 24A-L and 27A-L). In some embodiments, the Fc domain is heterodimeric. In some embodiments, the Fc domain comprises a mutation that reduces or eliminates its effector function.

In some embodiments, where there are two signaling agents and one targeting moiety, the targeting moiety is linked to a signaling agent which is linked to the Fc domain and the other signaling agent is linked to the Fc domain (see FIGS. 18A-J and 21A-J). In some embodiments, the paired signaling agent and the unpaired signaling agent are linked to different Fc chains (see FIGS. 18A-J and 21A-J). In some embodiments, the paired signaling agent and the unpaired signaling agent are linked to different Fc chains on the same terminus (see FIGS. 18A-J and 21A-J). In some embodiments, the paired signaling agent and the unpaired signaling agent are linked to different Fc chains on different termini (see FIGS. 18A-J and 21A-J). In some embodiments, the Fc domain is heterodimeric. In some embodiments, the Fc domain comprises a mutation that reduces or eliminates its effector function.

In some embodiments, where there are two signaling agents and one targeting moiety, the signaling agents are linked together and the targeting moiety is linked to one of the paired signaling agents, wherein the targeting moiety is linked to the Fc domain (see FIGS. 24A-L and 27A-L). In some embodiments, the Fc domain is heterodimeric. In some embodiments, the Fc domain comprises a mutation that reduces or eliminates its effector function.

In some embodiments, where there are two signaling agents and one targeting moiety, the signaling agents are linked together and one of the signaling agents is linked to the Fc domain and the targeting moiety is linked to the Fc domain (see FIGS. 24A-L, 27A-L, 30A-F, and 31A-F). In some embodiments, the paired signaling agents and targeting moiety are linked to the same Fc chain (see FIGS. 24A-L and 27A-L). In some embodiments, the paired signaling agents and targeting moiety are linked to different Fc chains (see FIGS. 30A-F and 31A-F). In some embodiments, the paired signaling agents and targeting moiety are linked to different Fc chains on the same terminus (see FIGS. 30A-F and 31A-F). In some embodiments, the Fc domain is heterodimeric. In some embodiments, the Fc domain comprises a mutation that reduces or eliminates its effector function.

In some embodiments, where there are two signaling agents and one targeting moiety, the signaling agents are both linked to the targeting moiety, wherein one of the signaling agents is linked to the Fc domain (see FIGS. 24A-L and 27A-L). In some embodiments, the Fc domain is heterodimeric. In some embodiments, the Fc domain comprises a mutation that reduces or eliminates its effector function.

In some embodiments, where there are two signaling agents and one targeting moiety, the signaling agents are linked together and one of the signaling agents is linked to the targeting moiety and the other signaling agent is linked to the Fc domain (see FIGS. 24A-L and 27A-L).

In some embodiments, where there are two signaling agents and one targeting moiety, each signaling agent is linked to the Fc domain and the targeting moiety is linked to one of the signaling agents (see FIGS. 24A-L and 27A-L). In some embodiments, the signaling agents are linked to the same Fc chain (see FIGS. 24A-L and 27A-L).

In some embodiments, a targeting moiety or signaling agent is linked to the Fc domain, comprising one or both of $C_H2$ and $C_H3$ domains, and optionally a hinge region. For example, vectors encoding the targeting moiety, signaling agent, or combination thereof, linked as a single nucleotide sequence to an Fc domain can be used to prepare such polypeptides.

Modifications and Production of Chimeric Proteins

In various embodiments, the CD13-targeted chimeric proteins or chimeric protein complexes and CD8-targeted chimeric proteins or chimeric protein complexes disclosed herein comprise a targeting moiety (e.g., CD13 and CD8) that is a VHH. In various embodiments, the VHH is not limited to a specific biological source or to a specific method of preparation. For example, the VHH can generally be obtained: (1) by isolating the $V_HH$ domain of a naturally occurring heavy chain antibody; (2) by expression of a nucleotide sequence encoding a naturally occurring $V_HH$ domain; (3) by "humanization" of a naturally occurring $V_HH$ domain or by expression of a nucleic acid encoding a such humanized $V_HH$ domain; (4) by "camelization" of a naturally occurring VH domain from any animal species, such as from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known in the art; (7) by preparing a nucleic acid encoding a VHH using techniques for nucleic acid synthesis known in the art, followed by expression of the nucleic acid thus obtained; and/or (8) by any combination of one or more of the foregoing.

In an embodiment, the CD13-targeted chimeric protein or chimeric protein complex and CD8-targeted chimeric protein or chimeric protein complex comprise a VHH that corresponds to the $V_HH$ domains of naturally occurring heavy chain antibodies directed against a target of interest. In some embodiments, such $V_HH$ sequences can generally be generated or obtained by suitably immunizing a species of Camelid with a molecule of based on the target of interest (e.g., CD13 and CD8) (i.e., so as to raise an immune response and/or heavy chain antibodies directed against the target of interest), by obtaining a suitable biological sample from the Camelid (such as a blood sample, or any sample of B-cells), and by generating $V_HH$ sequences directed against the target of interest, starting from the sample, using any suitable known techniques. In some embodiments, naturally occurring $V_HH$ domains against the target of interest can be obtained from naive libraries of Camelid $V_HH$ sequences, for example, by screening such a library using the target of interest or at least one part, fragment, antigenic determinant or epitope thereof using one or more screening techniques known in the art. Such libraries and techniques are, for example, described in WO 9937681, WO 0190190, WO 03025020 and WO 03035694, the entire contents of which are hereby incorporated by reference. In some embodiments, improved synthetic or semi-synthetic libraries derived from naive $V_HH$ libraries may be used, such as $V_HH$ libraries obtained from naive $V_HH$ libraries by techniques such as random mutagenesis and/or CDR shuffling, as for example, described in WO 0043507, the entire contents of which are hereby incorporated by reference. In some embodiments, another technique for obtaining $V_HH$ sequences directed against a target of interest involves suitably immunizing a transgenic mammal that is capable of expressing heavy chain antibodies (i.e., so as to raise an immune response and/or heavy chain antibodies directed against the target of interest), obtaining a suitable biological sample from the transgenic mammal (such as a blood sample, or any sample of B-cells), and then generating $V_HH$ sequences directed against XCR1 starting from the sample, using any suitable known techniques. For example, for this purpose, the heavy chain antibody-expressing mice and the further methods and techniques described in WO 02085945 and in WO 04049794 (the entire contents of which are hereby incorporated by reference) can be used.

In an embodiment, the CD13-targeted chimeric protein or chimeric protein complex and CD8-targeted chimeric protein or chimeric protein complex comprise a VHH that has been "humanized" i.e., by replacing one or more amino acid residues in the amino acid sequence of the naturally occurring $V_HH$ sequence (and in particular in the framework sequences) by one or more of the amino acid residues that occur at the corresponding position(s) in a VH domain from a conventional 4-chain antibody from a human being. This can be performed using humanization techniques known in the art. In some embodiments, possible humanizing substitutions or combinations of humanizing substitutions may be determined by methods known in the art, for example, by a comparison between the sequence of a VHH and the sequence of a naturally occurring human VH domain. In some embodiments, the humanizing substitutions are chosen such that the resulting humanized VHHs still retain advantageous functional properties. Generally, as a result of humanization, the VHHs of the invention may become more "human-like," while still retaining favorable properties such as a reduced immunogenicity, compared to the corresponding naturally occurring $V_HH$ domains. In various embodiments, the humanized VHHs of the invention can be obtained in any suitable manner known in the art and thus are not strictly limited to polypeptides that have been obtained using a polypeptide that comprises a naturally occurring $V_HH$ domain as a starting material.

In an embodiment, the CD13-targeted chimeric protein or chimeric protein complex and CD8-targeted chimeric protein or chimeric protein complex comprise a VHH that has been "camelized," i.e., by replacing one or more amino acid residues in the amino acid sequence of a naturally occurring VH domain from a conventional 4-chain antibody by one or more of the amino acid residues that occur at the corresponding position(s) in a $V_HH$ domain of a heavy chain antibody of a camelid. In some embodiments, such "camelizing" substitutions are inserted at amino acid positions that form and/or are present at the VH-VL interface, and/or at the so-called Camelidae hallmark residues (see, for example, WO 9404678, the entire contents of which are hereby incorporated by reference). In some embodiments, the VH sequence that is used as a starting material or starting point for generating or designing the camelized VHH is a VH sequence from a mammal, for example, the VH sequence of a human being, such as a VH3 sequence. In various embodiments, the camelized VHHs can be obtained in any suitable manner known in the art (i.e., as indicated under points (1)-(8) above) and thus are not strictly limited to polypeptides that have been obtained using a polypeptide that comprises a naturally occurring VH domain as a starting material.

In various embodiments, both "humanization" and "camelization" can be performed by providing a nucleotide sequence that encodes a naturally occurring $V_H$H domain or VH domain, respectively, and then changing, in a manner known in the art, one or more codons in the nucleotide sequence in such a way that the new nucleotide sequence encodes a "humanized" or "camelized" VHH, respectively. This nucleic acid can then be expressed in a manner known in the art, so as to provide the desired VHH of the invention. Alternatively, based on the amino acid sequence of a naturally occurring $V_H$H domain or VH domain, respectively, the amino acid sequence of the desired humanized or camelized VHH of the invention, respectively, can be designed and then synthesized de novo using techniques for peptide synthesis known in the art. Also, based on the amino acid sequence or nucleotide sequence of a naturally occurring $V_H$H domain or VH domain, respectively, a nucleotide sequence encoding the desired humanized or camelized VHH, respectively, can be designed and then synthesized de novo using techniques for nucleic acid synthesis known in the art, after which the nucleic acid thus obtained can be expressed in a manner known in the art, so as to provide the desired VHH of the invention. Other suitable methods and techniques for obtaining the VHHs of the invention and/or nucleic acids encoding the same, starting from naturally occurring VH sequences or $V_H$H sequences, are known in the art, and may, for example, comprise combining one or more parts of one or more naturally occurring VH sequences (such as one or more FR sequences and/or CDR sequences), one or more parts of one or more naturally occurring $V_H$H sequences (such as one or more FR sequences or CDR sequences), and/or one or more synthetic or semi-synthetic sequences, in a suitable manner, so as to provide a VHH of the invention or a nucleotide sequence or nucleic acid encoding the same.

Methods for producing the CD13-targeted chimeric protein or chimeric protein complex and CD8-targeted chimeric protein or chimeric protein complex are described herein. For example, DNA sequences encoding the CD13-targeted chimeric protein or chimeric protein complex and CD8-targeted chimeric protein or chimeric protein complex (e.g., DNA sequences encoding the signaling agent (e.g., TNF or IFN) and the targeting moiety (e.g., CD13 or CD8) and, optionally a linker) can be chemically synthesized using methods known in the art. Synthetic DNA sequences can be ligated to other appropriate nucleotide sequences, including, e.g., expression control sequences, to produce gene expression constructs encoding the desired chimeric proteins or chimeric protein complexes. Accordingly, in various embodiments, the present invention provides for isolated nucleic acids comprising a nucleotide sequence encoding the chimeric protein or chimeric protein complex of the invention.

Nucleic acids encoding the chimeric protein or chimeric protein complex of the invention can be incorporated (ligated) into expression vectors, which can be introduced into host cells through transfection, transformation, or transduction techniques. For example, nucleic acids encoding the chimeric protein or chimeric protein complex of the invention can be introduced into host cells by retroviral transduction. Illustrative host cells are E. coli cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells. Transformed host cells can be grown under conditions that permit the host cells to express the genes that encode the chimeric protein or chimeric protein complex of the invention. Accordingly, in various embodiments, the present invention provides expression vectors comprising nucleic acids that encode the chimeric protein or chimeric protein complex of the invention. In various embodiments, the present invention additional provides host cells comprising such expression vectors.

Specific expression and purification conditions will vary depending upon the expression system employed. For example, if a gene is to be expressed in E. coli, it is first cloned into an expression vector by positioning the engineered gene downstream from a suitable bacterial promoter, e.g., Trp or Tac, and a prokaryotic signal sequence. In another example, if the engineered gene is to be expressed in eukaryotic host cells, e.g., CHO cells, it is first inserted into an expression vector containing for example, a suitable eukaryotic promoter, a secretion signal, enhancers, and various introns. The gene construct can be introduced into the host cells using transfection, transformation, or transduction techniques.

The CD13-targeted chimeric protein or chimeric protein complex and CD8-targeted chimeric protein or chimeric protein complex can be produced by growing a host cell transfected with an expression vector encoding the chimeric protein or chimeric protein complex under conditions that permit expression of the protein. Following expression, the protein can be harvested and purified using techniques well known in the art, e.g., affinity tags such as glutathione-S-transferase (GST) and histidine tags or by chromatography. In an embodiment, the chimeric protein or chimeric protein complex comprises a His tag. In an embodiment, the chimeric protein or chimeric protein complex comprises a His tag and a proteolytic site to allow cleavage of the His tag.

Accordingly, in various embodiments, the present invention provides for a nucleic acid encoding a CD13-targeted chimeric protein or chimeric protein complex and CD8-targeted chimeric protein or chimeric protein complex. In various embodiments, the present invention provides for a host cell comprising a nucleic acid encoding a CD13-targeted chimeric protein or chimeric protein complex and CD8-targeted chimeric protein or chimeric protein complex.

In various embodiments, the CD13-targeted chimeric protein or chimeric protein complex or CD8-targeted chimeric protein or chimeric protein complex may be expressed in vivo, for instance, in a patient. For example, in various embodiments, the CD13-targeted chimeric protein or chimeric protein complex or CD8-targeted chimeric protein or chimeric protein complex is administered in the form of nucleic acid, which encodes the CD13-targeted chimeric protein or chimeric protein complex or CD8-targeted chimeric protein or chimeric protein complex. In various embodiments, the nucleic acid is DNA or RNA. In some embodiments, the CD13-targeted chimeric protein or chimeric protein complex or CD8-targeted chimeric protein or chimeric protein complex is encoded by a modified mRNA, i.e. an mRNA comprising one or more modified nucleotides. In some embodiments, the modified mRNA comprises one or modifications found in U.S. Pat. No. 8,278,036, the entire contents of which are hereby incorporated by reference. In some embodiments, the modified mRNA comprises one or more of m5C, m5U, m6A, s2U, ψ, and 2'-O-methyl-U. In some embodiments, the present invention relates to administering a modified mRNA encoding one or more of the present chimeric proteins or chimeric protein complexes. In some embodiments, the present invention relates to gene therapy vectors comprising the same. In some embodiments, the present invention relates to gene therapy methods comprising the same. In various embodiments, the nucleic acid is in the form of an oncolytic virus, e.g. an adenovirus, reovirus, measles, herpes simplex, Newcastle disease virus or vaccinia.

In some embodiments, the CD13-targeted chimeric protein or chimeric protein complex or CD8-targeted chimeric protein or chimeric protein complex described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc.

Functional Groups

In various embodiments, the CD13-targeted chimeric protein or chimeric protein complex or CD8-targeted chimeric protein or chimeric protein complex may include one or more functional groups, residues, or moieties. In various embodiments, the one or more functional groups, residues, or moieties are attached or genetically fused to any of the signaling agents or targeting moieties described herein. In some embodiments, such functional groups, residues or moieties confer one or more desired properties or functionalities to the chimeric protein or chimeric protein complex of the invention. Examples of such functional groups and of techniques for introducing them into the chimeric protein or chimeric protein complex are known in the art, for example, see *Remington's Pharmaceutical Sciences,* 16th ed., Mack Publishing Co., Easton, Pa. (1980).

In various embodiments, the CD13-targeted chimeric protein or chimeric protein complex or CD8-targeted chimeric protein or chimeric protein complex may by conjugated and/or fused with another agent to extend half-life or otherwise improve pharmacodynamic and pharmacokinetic properties. In some embodiments, the chimeric proteins or chimeric protein complexes may be fused or conjugated with one or more of PEG, XTEN (e.g., as rPEG), polysialic acid (POLYXEN), albumin (e.g., human serum albumin or HAS), elastin-like protein (ELP), PAS, HAP, GLK, CTP, transferrin, and the like. In some embodiments, the chimeric protein or chimeric protein complex may be fused or conjugated with an antibody or an antibody fragment such as an Fc fragment. For example, the CD13-targeted chimeric protein or chimeric protein complex or CD8-targeted chimeric protein or chimeric protein complex may be fused to either the N-terminus or the C-terminus of the Fc domain of human immunoglobulin (Ig) G. In various embodiments, each of the CD13-targeted chimeric protein or chimeric protein complex or CD8-targeted chimeric protein or chimeric protein complex is fused to one or more of the agents described in BioDrugs (2015) 29:215-239, the entire contents of which are hereby incorporated by reference.

In some embodiments, the functional groups, residues, or moieties comprise a suitable pharmacologically acceptable polymer, such as poly(ethyleneglycol) (PEG) or derivatives thereof (such as methoxypoly(ethyleneglycol) or mPEG). In some embodiments, attachment of the PEG moiety increases the half-life and/or reduces the immunogenecity of the CD13-targeted chimeric protein or chimeric protein complex or CD8-targeted chimeric protein or chimeric protein complex. Generally, any suitable form of pegylation can be used, such as the pegylation used in the art for antibodies and antibody fragments (including but not limited to single domain antibodies such as VHHs); see, for example, Chapman, Nat. Biotechnol., 54, 531-545 (2002); by Veronese and Harris, *Adv. Drug Deliv. Rev.* 54, 453-456 (2003), by Harris and Chess, *Nat. Rev. Drug. Discov.,* 2, (2003) and in WO 04060965, the entire contents of which are hereby incorporated by reference. Various reagents for pegylation of proteins are also commercially available, for example, from Nektar Therapeutics, USA. In some embodiments, site-directed pegylation is used, in particular via a cysteine-residue (see, for example, Yang et al., Protein Engineering, 16, 10, 761-770 (2003), the entire contents of which is hereby incorporated by reference). In some embodiments, the CD13-targeted chimeric protein or chimeric protein complex or CD8-targeted chimeric protein or chimeric protein complex is modified so as to suitably introduce one or more cysteine residues for attachment of PEG, or an amino acid sequence comprising one or more cysteine residues for attachment of PEG may be fused to the amino- and/or carboxy-terminus of the chimeric proteins or chimeric protein complexes, using techniques known in the art.

In some embodiments, the functional groups, residues, or moieties comprise N-linked or O-linked glycosylation. In some embodiments, the N-linked or O-linked glycosylation is introduced as part of a co-translational and/or post-translational modification.

In some embodiments, the functional groups, residues, or moieties comprise one or more detectable labels or other signal-generating groups or moieties. Suitable labels and techniques for attaching, using and detecting them are known in the art and, include, but are not limited to, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels include moieties that can be detected using NMR or ESR spectroscopy. Such labeled VH Hs and polypeptides of the invention may, for example, be used for in vitro, in vivo or in situ assays (including immunoassays known per se such as ELISA, RIA, EIA and other "sandwich assays," etc.) as well as in vivo diagnostic and imaging purposes, depending on the choice of the specific label.

In some embodiments, the functional groups, residues, or moieties comprise a tag that is attached or genetically fused to the CD13-targeted chimeric protein or chimeric protein complex or CD8-targeted chimeric protein or chimeric protein complex. In some embodiments, the CD13-targeted chimeric protein or chimeric protein complex or CD8-targeted chimeric protein or chimeric protein complex may include a single tag or multiple tags. The tag for example is a peptide, sugar, or DNA molecule that does not inhibit or prevent binding of the CD13-targeted chimeric protein or chimeric protein complex or CD8-targeted chimeric protein or chimeric protein complex to its target or any other antigen of interest such as tumor antigens. In various embodiments, the tag is at least about: three to five amino acids long, five to eight amino acids long, eight to twelve amino acids long, twelve to fifteen amino acids long, or fifteen to twenty amino acids long. Illustrative tags are described for example, in U.S. Patent Publication No. US2013/0058962. In some embodiment, the tag is an affinity tag such as glutathione-S-transferase (GST) and histidine (His) tag. In an embodiment, the CD13-targeted chimeric protein or chimeric protein complex or CD8-targeted chimeric protein or chimeric protein complex comprises a His tag.

In some embodiments, the functional groups, residues, or moieties comprise a chelating group, for example, to chelate one of the metals or metallic cations. Suitable chelating groups, for example, include, without limitation, diethylenetriaminepentaacetic acid (DTPA) or ethylenediaminetetraacetic acid (EDTA).

In some embodiments, the functional groups, residues, or moieties comprise a functional group that is one part of a specific binding pair, such as the biotin-(strept)avidin binding pair. Such a functional group may be used to link the chimeric protein or chimeric protein complex of the invention to another protein, polypeptide or chemical compound that is bound to the other half of the binding pair, i.e., through formation of the binding pair. For example, the CD13-targeted chimeric protein or chimeric protein complex or CD8-targeted chimeric protein or chimeric protein complex may be conjugated to biotin, and linked to another protein, polypeptide, compound or carrier conjugated to avidin or streptavidin. For example, such a conjugated CD13-targeted chimeric protein or chimeric protein complex or CD8-targeted chimeric protein or chimeric protein complex may be used as a reporter, for example, in a diagnostic system where a detectable signal-producing agent is conjugated to avidin or streptavidin. Such binding pairs may, for example, also be used to bind the CD13-targeted chimeric protein or chimeric protein complex or CD8-targeted chimeric protein or chimeric protein complex to a carrier, including carriers suitable for pharmaceutical purposes. One non-limiting example are the liposomal formulations described by Cao and Suresh, *Journal of Drug Targeting,* 8, 4, 257 (2000). Such binding pairs may also be used to link a therapeutically active agent to the CD13-targeted chimeric protein or chimeric protein complex or CD8-targeted chimeric protein or chimeric protein complex.

Pharmaceutically Acceptable Salts and Excipients

The CD13-targeted chimeric protein or chimeric protein complex and CD8-targeted chimeric protein or chimeric protein complex described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science,* 66, 2-19 (1977) and *The Handbook of Pharmaceutical Salts*; Properties, Selection, and Use. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the compositions of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N, N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like.

In some embodiments, the compositions described herein are in the form of a pharmaceutically acceptable salt.

Pharmaceutical Compositions and Formulations

In various embodiments, the present invention pertains to pharmaceutical compositions comprising the CD13-targeted chimeric protein or chimeric protein complex and CD8-targeted chimeric protein or chimeric protein complex described herein and a pharmaceutically acceptable carrier or excipient. In some embodiments, the present invention pertains to pharmaceutical compositions comprising the present chimeric protein or chimeric protein complex. In a further embodiment, the present invention pertains to pharmaceutical compositions comprising a combination of the present chimeric protein or chimeric protein complex and any other therapeutic agents described herein. Any pharmaceutical compositions described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

In various embodiments, pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents. Other examples of suitable pharmaceutical excipients are described in Remington's Pharmaceutical Sciences 1447-1676 (Alfonso R. Gennaro eds., 19th ed. 1995), incorporated herein by reference.

The present invention includes the described pharmaceutical compositions (and/or additional therapeutic agents) in various formulations. Any inventive pharmaceutical composition (and/or additional therapeutic agents) described herein can take the form of solutions, suspensions, emulsion, drops, tablets, pills, pellets, capsules, capsules containing liquids, gelatin capsules, powders, sustained-release formulations, suppositories, emulsions, aerosols, sprays, suspensions, lyophilized powder, frozen suspension, dessicated powder, or any other form suitable for use. In one embodiment, the composition is in the form of a capsule. In another embodiment, the composition is in the form of a tablet. In yet another embodiment, the pharmaceutical composition is formulated in the form of a soft-gel capsule. In a further embodiment, the pharmaceutical composition is formulated in the form of a gelatin capsule. In yet another embodiment, the pharmaceutical composition is formulated as a liquid.

Where necessary, the inventive pharmaceutical compositions (and/or additional agents) can also include a solubilizing agent. Also, the agents can be delivered with a suitable vehicle or delivery device as known in the art. Combination therapies outlined herein can be co-delivered in a single delivery vehicle or delivery device.

The formulations comprising the inventive pharmaceutical compositions (and/or additional agents) of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In various embodiments, any pharmaceutical compositions (and/or additional agents) described herein is formulated in accordance with routine procedures as a composition adapted for a mode of administration described herein.

Routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, or topically. Administration can be local or systemic. In some embodiments, the administering is effected orally. In another embodiment, the administration is by parenteral injection. The mode of administration can be left to the discretion of the practitioner, and depends in-part upon the site of the medical condition. In most instances, administration results in the release of any agent described herein into the bloodstream.

In one embodiment, the chimeric protein or chimeric protein complex described herein is formulated in accordance with routine procedures as a composition adapted for oral administration. Compositions for oral delivery can be in the form of tablets, lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving any chimeric proteins or chimeric protein complexes described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art. Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

The compositions provided herein, alone or in combination with other suitable components, can be made into aerosol formulations (i.e., "nebulized") to be administered via inhalation. Aerosol formulations can be placed into pressurized acceptable propellants, such as dichlorodifluoromethane, propane, nitrogen, and the like.

Any inventive pharmaceutical compositions (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled-or sustained-release of one or more active ingredients using, for example, hydropropyl cellulose, hydropropylmethyl cellulose, polyvinylpyrrolidone, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

Administration and Dosage

It will be appreciated that the actual dose of the CD13-targeted chimeric protein or chimeric protein complex and additional therapeutic agent(s) (e.g., CD8-targeted chimeric protein or chimeric protein complex, PI3K inhibitor, anthracycline, or SMAC mimetic) to be administered according to the present invention will vary according to the particular dosage form, and the mode of administration. Many factors that may modify the action of the CD13-targeted chimeric protein or chimeric protein complex and additional therapeutic agent(s) (e.g., body weight, gender, diet, time of administration, route of administration, rate of excretion, condition of the subject, drug combinations, genetic disposition and reaction sensitivities) can be taken into account by those skilled in the art.

Administration can be carried out continuously or in one or more discrete doses within the maximum tolerated dose. Optimal administration rates for a given set of conditions can be ascertained by those skilled in the art using conventional dosage administration tests.

In some embodiments, a suitable dosage of the CD13-targeted chimeric protein or chimeric protein complex and additional therapeutic agents is in a range of about 0.01 μg/kg to about 100 mg/kg of body weight of the subject, about 0.01 μg/kg to about 10 mg/kg of body weight of the subject, or about 0.01 μg/kg to about 1 mg/kg of body weight of the subject for example, about 0.01 μg/kg, about 0.02 μg/kg, about 0.03 μg/kg, about 0.04 μg/kg, about 0.05 μg/kg, about 0.06 μg/kg, about 0.07 μg/kg, about 0.08 μg/kg, about 0.09 μg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, or about 100 mg/kg body weight, inclusive of all values and ranges therebetween.

Individual doses of the CD13-targeted chimeric protein or chimeric protein complex and additional therapeutic agents can be administered in unit dosage forms (e.g., tablets, capsules, or liquid formulations) containing, for example, from about 1 μg to about 100 mg, from about 1 μg to about 90 mg, from about 1 μg to about 80 mg, from about 1 μg to about 70 mg, from about 1 μg to about 60 mg, from about 1 μg to about 50 mg, from about 1 μg to about 40 mg, from about 1 μg to about 30 mg, from about 1 μg to about 20 mg, from about 1 μg to about 10 mg, from about 1 μg to about 5 mg, from about 1 μg to about 3 mg, from about 1 μg to about 1 mg per unit dosage form, or from about 1 μg to about 50 μg per unit dosage form. For example, a unit dosage form can be about 1 μg, about 2 μg, about 3 μg, about 4 μg, about 5 μg, about 6 μg, about 7 μg, about 8 μg, about 9 μg, about 10 μg, about 11 μg, about 12 μg, about 13 μg, about 14 μg, about 15 μg, about 16 μg, about 17 μg, about 18 μg, about 19 μg, about 20 μg, about 21 μg, about 22 μg, about 23 μg, about 24 μg, about 25 μg, about 26 μg, about 27 μg, about 28 μg, about 29, about 30 μg, about 35 μg, about 40 μg, about 45 μg, about 50 μg, about 60 μg, about 70 μg, about 80 μg, about 90 μg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg, inclusive of all values and ranges therebetween. In an embodiment, the chimeric protein or chimeric protein complex is administered as a unit dosage form containing about 9 μg of the chimeric protein or chimeric protein complex. In another embodiment, the chimeric protein or chimeric protein complex is administered as a unit dosage form containing about 15 μg of the chimeric protein or chimeric protein complex.

In one embodiment, the CD13-targeted chimeric protein or chimeric protein complex and additional therapeutic agents are each administered at an amount of from about 1 μg to about 100 mg daily, from about 1 μg to about 90 mg daily, from about 1 μg to about 80 mg daily, from about 1 μg to about 70 mg daily, from about 1 μg to about 60 mg daily, from about 1 μg to about 50 mg daily, from about 1 μg to about 40 mg daily, from about 1 μg to about 30 mg daily, from about 1 μg to about 20 mg daily, from about 01 μg to about 10 mg daily, from about 1 μg to about 5 mg daily, from about 1 μg to about 3 mg daily, or from about 1 μg to about 1 mg daily. In various embodiments, the chimeric protein or chimeric protein complex is administered at a daily dose of about 1 μg, about 2 μg, about 3 μg, about 4 μg, about 5 μg, about 6 μg, about 7 μg, about 8 μg, about 9 μg, about 10 μg, about 11 μg, about 12 μg, about 13 μg, about 14 μg, about 15 μg, about 16 μg, about 17 μg, about 18 μg, about 19 μg, about 20 μg, about 21 μg, about 22 μg, about 23 μg, about 24 μg, about 25 μg, about 26 μg, about 27 μg, about 28 μg, about 29, about 30 μg, about 35 μg, about 40 μg, about 45 μg, about 50 μg, about 60 μg, about 70 μg, about 80 μg, about 90 μg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg, inclusive of all values and ranges therebetween.

In accordance with certain embodiments of the invention, a pharmaceutical composition comprising the CD13-targeted chimeric protein or chimeric protein complex is co-administered with at least one additional therapeutic agent, for example, more than once daily (e.g., about two times, about three times, about four times, about five times, about six times, about seven times, about eight times, about nine times, or about ten times daily), about once per day, about every other day, about every third day, about once a week, about once every two weeks, about once every month, about once every two months, about once every three months, about once every six months, or about once every year. In an embodiment, the pharmaceutical composition comprising the chimeric protein or chimeric protein complex is administered about three times a week.

In various embodiments, the CD13-targeted chimeric protein or chimeric protein complex and at least one additional therapeutic agent may be co-administered for a prolonged period. For example, the CD13-targeted chimeric protein or chimeric protein complex and at least one additional therapeutic agent may be co-administered as described herein for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. For example, the CD13-targeted chimeric protein or chimeric protein complex and at least one additional therapeutic agent may be co-administered for 12 weeks, 24 weeks, 36 weeks or 48 weeks. In some embodiments, the CD13-targeted chimeric protein or chimeric protein complex and at least one additional therapeutic agent may be co-administered for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In some embodiments, the CD13-targeted chimeric protein or chimeric protein complex and at least one additional therapeutic agent may be co-administered for at least about 1 year, at least about 2 years, at least about 3 years, at least about 4 years, or at least about 5 years.

In various embodiments, co-administration of the CD13-targeted chimeric protein or chimeric protein complex and at least one additional therapeutic agent can be simultaneous or sequential. For example, in one embodiment, the CD13-targeted chimeric protein or chimeric protein complex is administered alongwith the therapeutic agent(s). In another embodiment, the CD13-targeted chimeric protein or chimeric protein complex is administered before the therapeutic agent. In yet another embodiment, the CD13-targeted chimeric protein or chimeric protein complex is administered after the therapeutic agent.

In one embodiment, the additional therapeutic agent (e.g., CD13-targeted chimeric protein or chimeric protein complex, CD8-targeted chimeric protein or chimeric protein complex, PI3K inhibitor, anthracycline, or SMAC mimetic) and the CD13-targeted chimeric protein or chimeric protein complex of the present invention are administered to a subject simultaneously. The term "simultaneously" as used herein, means that the additional therapeutic agent and the CD13-targeted chimeric protein or chimeric protein complex are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the CD13-targeted chimeric protein or chimeric protein complex can be by simultaneous administration of a single formulation (e.g., a formulation comprising the additional therapeutic agent and the chimeric protein or chimeric protein complex) or of separate formulations (e.g., a first formulation including the additional therapeutic agent and a second formulation including the chimeric protein or chimeric protein complex).

Co-administration does not require the therapeutic agents to be administered simultaneously, if the timing of their administration is such that the pharmacological activities of the additional therapeutic agent and the chimeric protein or chimeric protein complex overlap in time, thereby exerting a combined therapeutic effect. For example, the additional therapeutic agent and the CD13-targeted chimeric protein or chimeric protein complex can be administered sequentially. The term "sequentially" as used herein means that the additional therapeutic agent and the CD13-targeted chimeric protein or chimeric protein complex are administered with a time separation of more than about 60 minutes. For example, the time between the sequential administration of the additional therapeutic agent and the CD13-targeted chimeric protein or chimeric protein complex can be more than about 60 minutes, more than about 2 hours, more than about 5 hours, more than about 10 hours, more than about 1 day, more than about 2 days, more than about 3 days, more than about 1 week apart, more than about 2 weeks apart, or more than about one month apart. The optimal administration times will depend on the rates of metabolism, excretion, and/or the pharmacodynamic activity of the additional therapeutic agent and the CD13-targeted chimeric protein or chimeric protein complex being administered. Either the additional therapeutic agent or the CD13-targeted chimeric protein or chimeric protein complex cell may be administered first.

Co-administration also does not require the therapeutic agents to be administered to the subject by the same route of administration. Rather, each therapeutic agent can be administered by any appropriate route, for example, parenterally or non-parenterally.

In some embodiments, the CD13-targeted chimeric protein or chimeric protein complex described herein acts synergistically when co-administered with another therapeutic agent (e.g., CD13-targeted chimeric protein or chimeric protein complex, CD8-targeted chimeric protein or chimeric protein complex, PI3K inhibitor, anthracycline, or SMAC mimetic). In such embodiments, the CD13-targeted chimeric protein or chimeric protein complex and the additional therapeutic agent may be administered at doses that are lower than the doses employed when the agents are used in the context of monotherapy.

Methods of Treatment

Methods and compositions described herein have application to treating cancer. In some embodiments, the present invention relates to the treatment of, or a patient having cancer. As used herein, cancer refers to any uncontrolled growth of cells that may interfere with the normal functioning of the bodily organs and systems and includes both primary and metastatic tumors. Primary tumors or cancers that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject. For example, cancers can include benign and malignant cancers, polyps, hyperplasia, as well as dormant tumors or micrometastases.

Illustrative cancers that may be treated include, but are not limited to, carcinomas, e.g. various subtypes, including, for example, adenocarcinoma, basal cell carcinoma, squamous cell carcinoma, and transitional cell carcinoma), sarcomas (including, for example, bone and soft tissue), leukemias (including, for example, acute myeloid, acute lymphoblastic, chronic myeloid, chronic lymphocytic, and hairy cell), lymphomas and myelomas (including, for example, Hodgkin and non-Hodgkin lymphomas, light chain, non-secretory, MGUS, and plasmacytomas), and central nervous system cancers (including, for example, brain (e.g. gliomas (e.g. astrocytoma, oligodendroglioma, and ependymoma), meningioma, pituitary adenoma, and neuromas, and spinal cord tumors (e.g. meningiomas and neurofibroma).

Illustrative cancers that may be treated include, but are not limited to, basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma (e.g., Kaposi's sarcoma); skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome. In an embodiment, the present invention relates to the treatment of leukemia including hairy cell leukemia. In another embodiment, the present invention relates to the treatment of melanoma including malignant melanoma. In a further embodiment, the present invention relates to the treatment of Kaposi's sarcoma including AIDS-related Kaposi's sarcoma.

Kits

The invention also provides kits for the administration of any agent described herein (e.g. the CD13-targeted chimeric protein or chimeric protein complex with or without various additional therapeutic agents). The kit is an assemblage of materials or components, including at least one of the inventive pharmaceutical compositions described herein. Thus, in some embodiments, the kit contains at least one of the pharmaceutical compositions described herein.

The exact nature of the components configured in the kit depends on its intended purpose. In one embodiment, the kit is configured for treating human subjects.

Instructions for use may be included in the kit. Instructions for use typically include a tangible expression describing the technique to be employed in using the components of the kit to effect a desired outcome, such as to treat cancer. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials and components assembled in the kit can be provided to the practitioner stored in any convenience and suitable ways that preserve their operability and utility. For example, the components can be provided at room, refrigerated or frozen temperatures. The components are typically contained in suitable packaging materials. In various embodiments, the packaging material is constructed by well-known methods, preferably to provide a sterile, contaminant-free environment. The packaging material may have an external label, which indicates the contents and/or purpose of the kit and/or its components.

Definitions

As used herein, "a," "an," or "the" can mean one or more than one.

Unless specifically stated or obvious from context, as used herein, the term "or" is understood to be inclusive and covers both "or" and "and".

Further, the term "about" when used in connection with a referenced numeric indication means the referenced numeric indication plus or minus up to 10% of that referenced numeric indication, e.g., within (plus or minus) 10%, 9%, 8%, 7%, 6%, 5%, 4%, 3%, 2%, 1%, 0.5%, 0.1%, 0.05%, or 0.01% of the stated value. For example, the language "about 50" covers the range of 45 to 55.

An "effective amount," when used in connection with medical uses is an amount that is effective for providing a measurable treatment, prevention, or reduction in the rate of pathogenesis of a disease of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the 1050 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein.

EXAMPLES

Example 1

Treatment of CD13-Targeted TNF in Mouse Tumor Model

Study shows that mCD13-AFR activates endothelial cells similarly to wild type mTNF, as evidenced by induction of the endothelial cell adhesion marker ICAM-1 and by induction of intravascular coagulation.

FIG. 1 shows immunohistochemical analysis of B16BI6 tumor after p.1. treatment with 5 μg wild-type sc mTNF or 50 μg of the AcTakine mCD13 VHH-sc mTNF Y114L. The upper panel was taken 4 hours after treatment and stained for mouse ICAM-1. The lower panel was taken 24 hours after treatment and shows aspecific fluorescence in blood clots. Sections were made transverse and pictures were taken close to the skin, near the site of injection.

Example 2

Co-Administration of CD13-Targeted TNF and CD8-Targeted IFN in Mouse Tumor Model These studies demonstrate synergistic antitumor effects of mCD13-AFR with mCD8-AcTaferon, revealing that concomitant activation of tumor endothelium an activation of cytotoxic T lymphocytes generates strong antitumor effects. Importantly, antitumor activity was observed with absence of overt toxicity (e.g., no change in body weight).

Figure 2B:
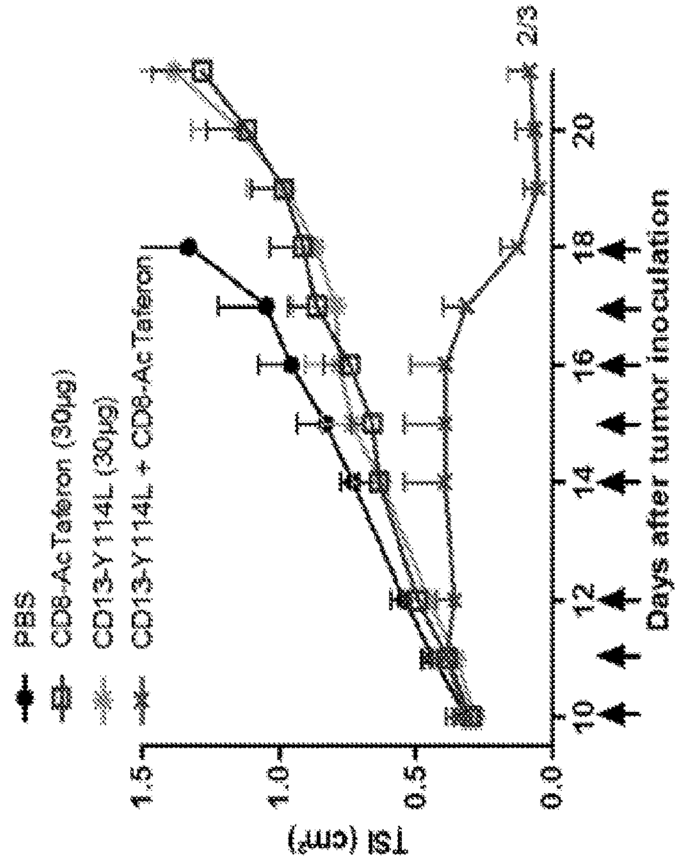
FIG. 2B is a graph showing the change in B16BI6 tumor size in B16 mice treated with PBS, CD8-targeted chimeric protein (CD8-Actaferon) alone, CD13 targeted mutated murine TNF (Y114L) alone, or CD8-targeted chimeric protein (CD8-Actaferon) and CD13 targeted mutated murine TNF (Y114L).
Figure 2A:
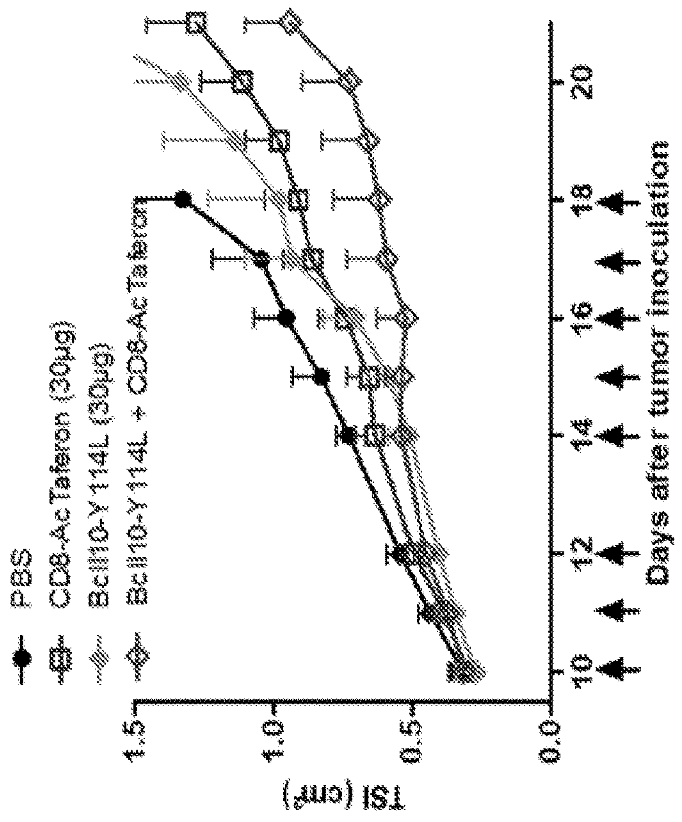
FIG. 2A is a graph showing the change in B16BI6 tumor size in B16 mice treated with PBS, CD8-targeted chimeric protein (CD8-Actaferon) alone, BcII10 targeted mutated murine TNF (Y114L) alone, or CD8-targeted chimeric protein (CD8-Actaferon) and BcII10 targeted mutated murine TNF (Y114L).

As shown in FIGS. 2A-B, treatment with: 1) CD8-targeted modified IFN (Q124R) (CD8-AcTaferon) alone; 2) BclI10-targeted modified TNF (Y114L) (negative control) alone; and 3) CD13-targeted modified TNF (Y114L) alone had moderate tumor growth. Additionally, FIG. 2A shows that combination treatment with BclI10-targeted modified TNF (Y114L) and CD8-AcTaferon had little effect on tumor growth.

FIG. 2B shows that combination treatment with CD13-targeted modified TNF (Y114L) and CD8-AcTaferon had a synergistic effect and greatly reduced tumor growth.

Figure 2C:
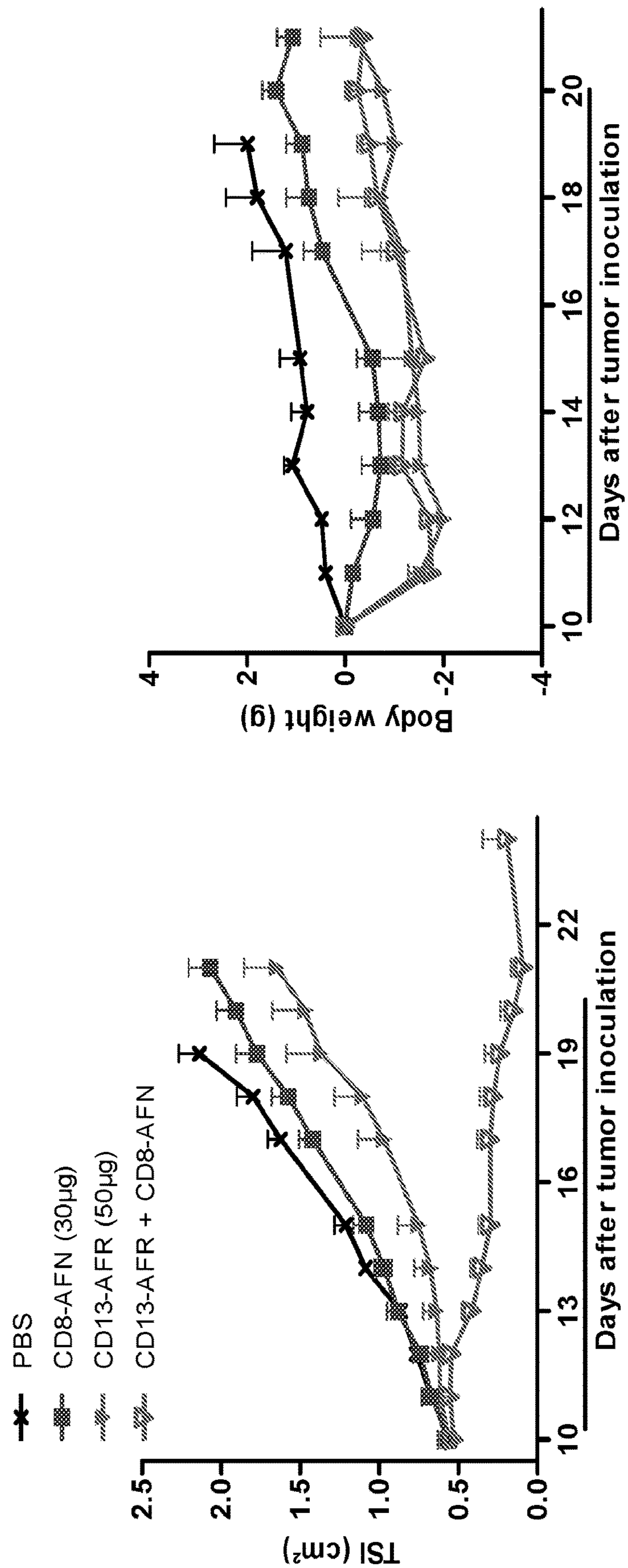
FIG. 2C shows B16BI6 tumor growth and body weight change after daily p.I. injection of 30 μg mCD8-AFN, 50 μg mCD13-AFR or combinations thereof. Tumor growth is shown as mean TSI+SEM (n=6 per group). The line under the graph represents the treatment period.
Figure 2D:
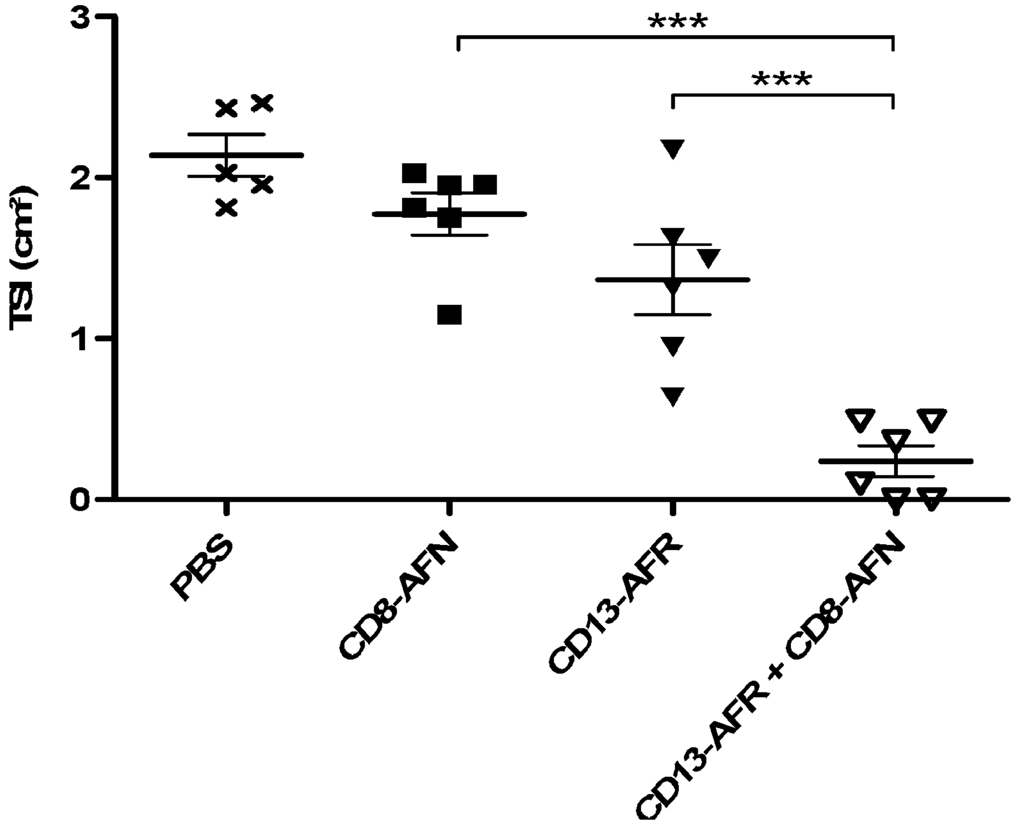
FIG. 2D shows TSI of individual tumors of the indicated treatment groups at day 19 after tumor inoculation. Error bars are SEM. ***, p<0.001 by one-way ANOVA with Bonferroni's multiple comparison test.

The combination of mCD13-AFR and mCD8α-targeted AcTaferon (mCD8-AFN) therapy was evaluated in the B16BI6 mouse melanoma model. mCD8-AFN therapy, which had no effect on itself, clearly synergized with mCD13-AFR, leading to extensive tumor regression (FIGS. 2C-D). Again, no toxic side effects were observed in all combinations tested, further underscoring the selectivity and safety of AcTakine therapy.

Example 3

Co-Administration of CD13-Targeted TNF and Wortmannin in Mouse Tumor Model

Examples 3, 4 and 5 are the studies that show that mCD13-AFR synergizes with various agents to induce potent antitumor activity (tumor regression), including PI3K inhibition (Wortmannin), chemotherapy (doxorubicin, which induces immunogenic tumor cell death), and IAP inhibition (Birinapant, a SMAC mimetic, which inhibits IAP apoptosis inhibitors).

Figure 3A:
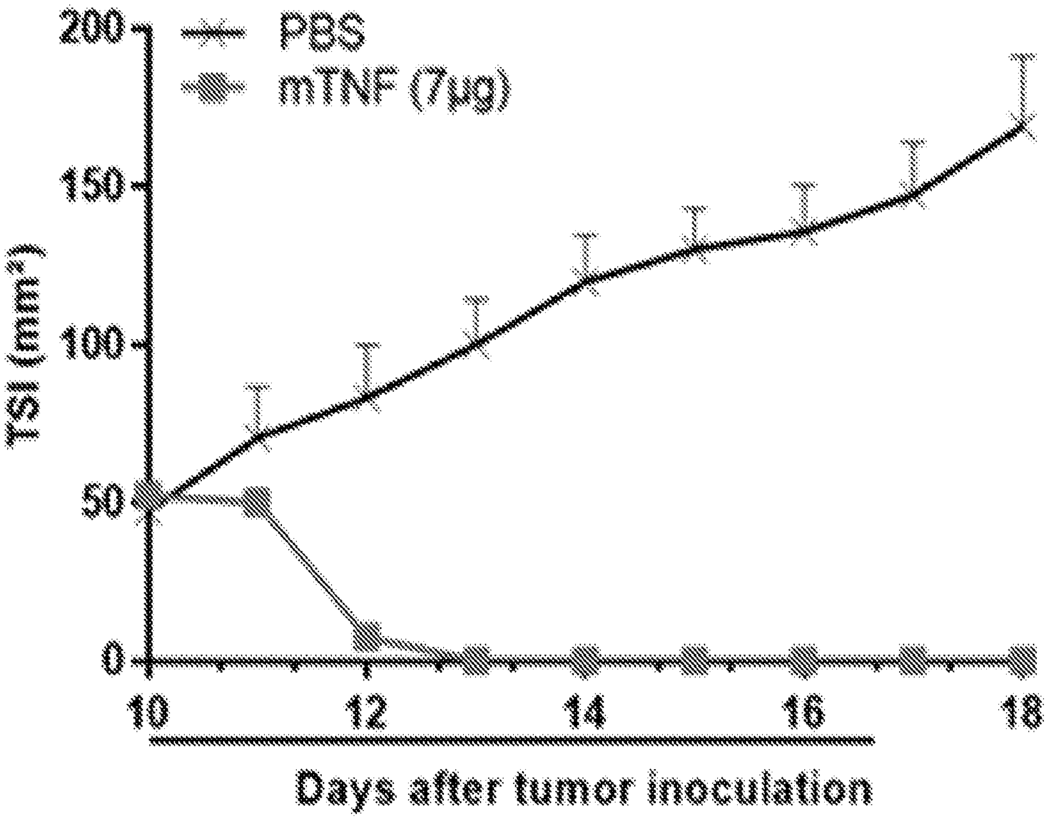
FIG. 3A is a graph showing the change in B16BI6 tumor size in B16 mice treated with PBS or mTNF.

FIG. 3A shows antitumor effects of wild type mouse TNF at 7 μg. This was associated with substantial toxicity (not shown: e.g., body weight loss and lethality), consistent with the pleiotropic activity of untargeted wild type TNF.

Figure 3B:
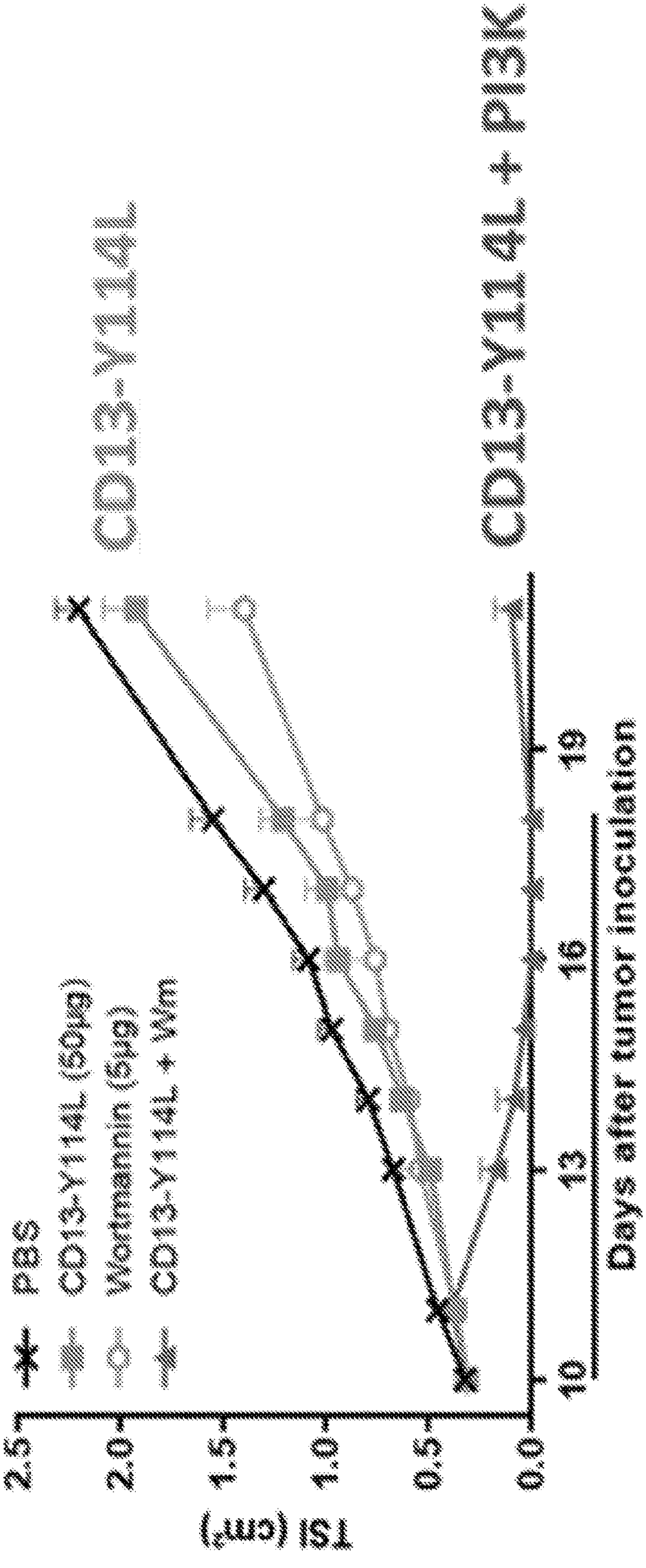
FIG. 3B is a graph showing the change in B16BI6 tumor size in B16 mice treated with PBS, CD13 targeted mutated murine TNF (Y114L) alone, Wortmannin alone, or CD13 targeted mutated murine TNF (Y114L) and Wortmannin.

As shown in FIG. 3B, treatment with Wortmannin alone and CD13-targeted modified TNF (Y114L) alone had very little effect on tumor growth. FIG. 3B also shows that combination treatment with CD13-targeted modified TNF (Y114L) and Wortmannin had a synergistic effect and greatly reduced tumor growth.

Example 4

Co-Administration of CD13-Targeted TNF and PEGylated Liposomal Doxorubicin in Mouse Tumor Model This study shows the synergistic antitumor activity of mCD13-AFR in combination with the chemotherapy agent doxorubicin, which promotes immunogenic tumor cell death.

Figure 4A:
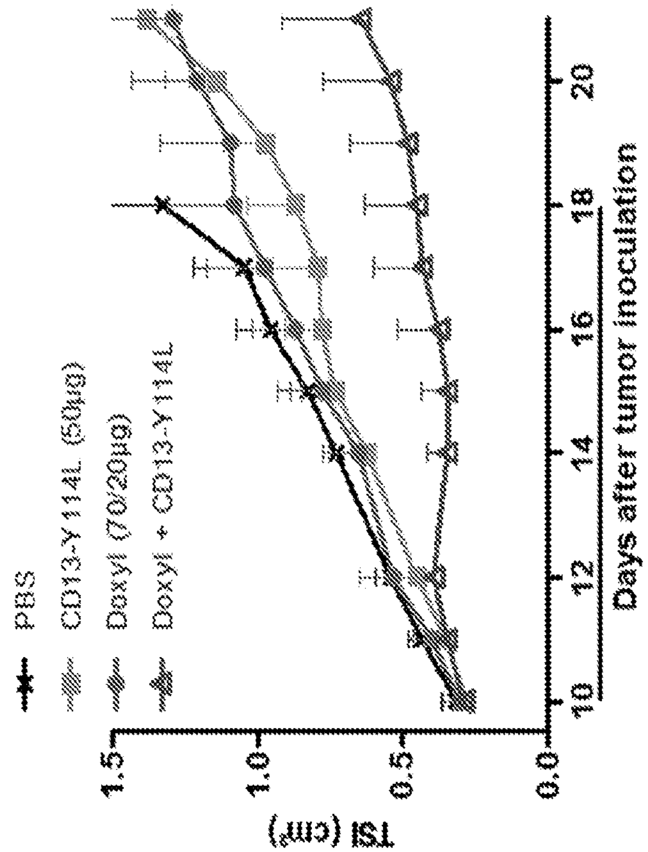
FIG. 4A-B are graphs showing the change in B16BI6 tumor size (FIG. 4A) and change in weight (FIG. 4B) in B16 mice treated with PBS, CD13 targeted mutated murine TNF (Y114L) alone, PEGylated liposomal doxorubicin alone, or CD13 targeted mutated murine TNF (Y114L) and PEGylated liposomal doxorubicin.

FIG. 4A shows that treatment with pegylated liposomal doxorubicin (Doxyl) alone and CD13-targeted modified TNF (Y114L) alone had very little effect on tumor growth. FIG. 4A also shows that combination treatment with CD13-targeted modified TNF (Y114L) and Doxyl had a synergistic effect and greatly reduced tumor growth.

Figure 4B:
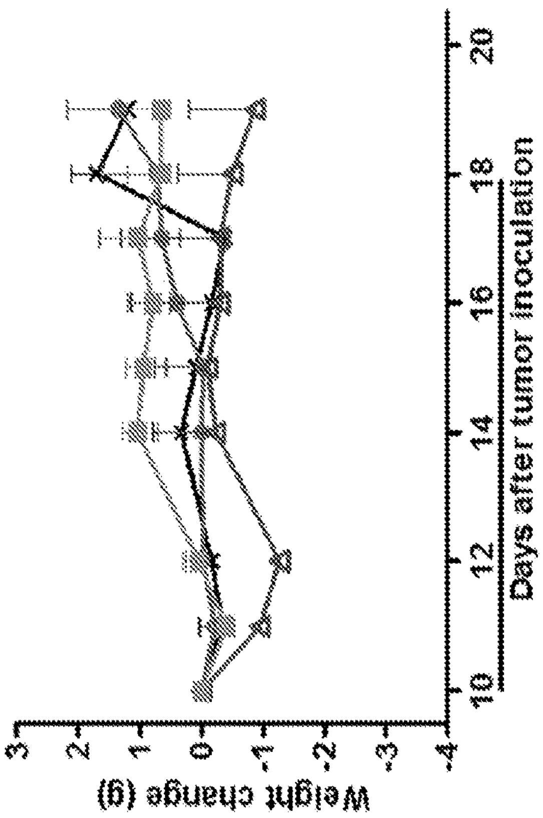

FIG. 4B shows that the combined treatment of CD13-targeted modified TNF (Y114L) and Doxyl had minimal adverse effect on body weight.

Example 5

Co-Administration of CD13-Targeted TNF and Birinapant in Mouse Tumor Model

This study shows the synergistic antitumor activity of mCD13-AFR in combination with Birinapant, an inhibitor of IAP apoptosis inhibitor proteins.

Figure 5B:
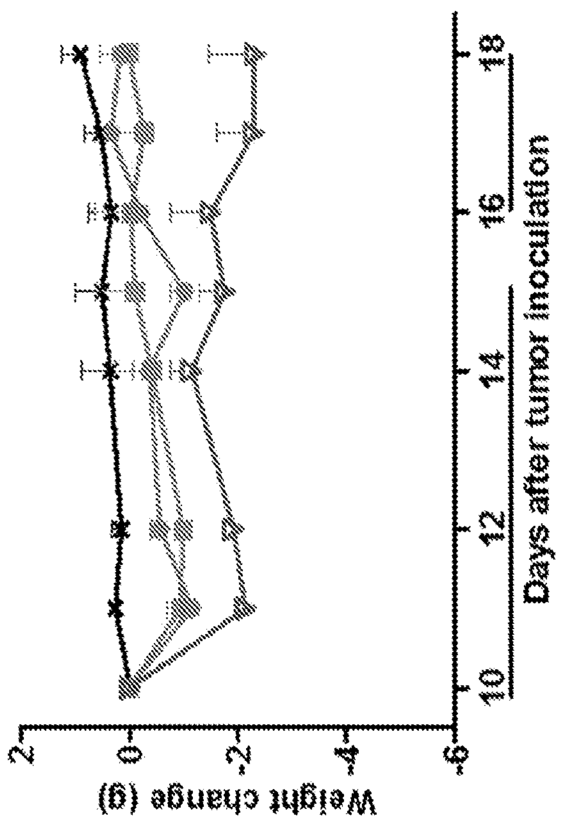
FIGS. 5A-B are graphs showing the change in B16BI6 tumor size (FIG. 5A) and change in weight (FIG. 5B) in B16 mice treated with PBS, CD13 targeted mutated murine TNF (Y114L) alone, birinapant alone, or CD13 targeted mutated murine TNF (Y114L) and birinapant.
Figure 5A:
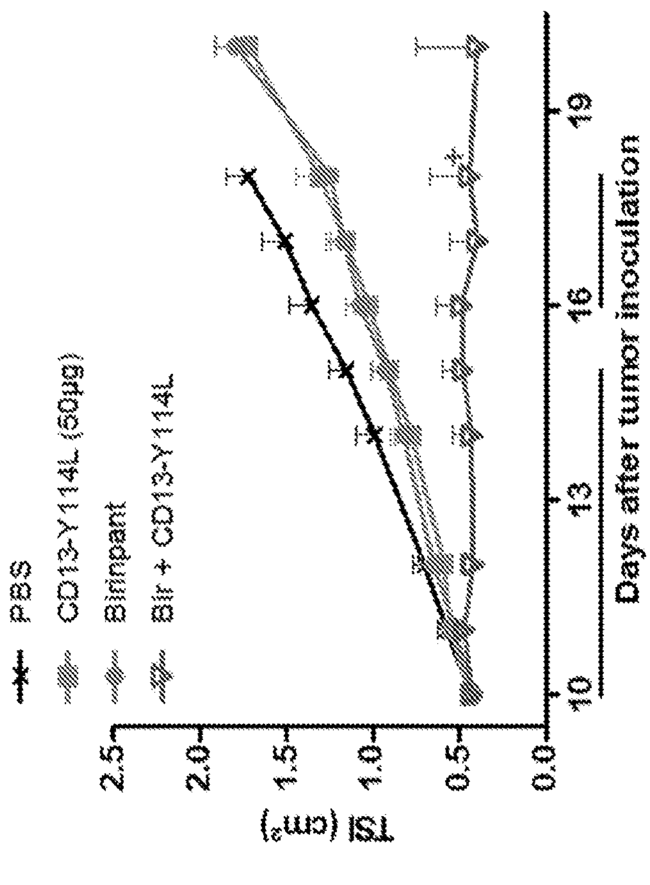

FIG. 5A shows that treatment with birinapant (Bir) alone and CD13-targeted modified TNF (Y114L) alone had very little effect on tumor growth. FIG. 5A also shows that combination treatment with CD13-targeted modified TNF (Y114L) and Bir had a synergistic effect and greatly reduced tumor growth.

FIG. 5B shows that the combined treatment of CD13-targeted modified TNF (Y114L) and Bir had minimal adverse effect on body weight.

Example 6

AFRs Combine Safety and Activity In Vivo

To evaluate in vivo toxicity, the i.v. shock model in naive C57BL/6 mice was used first. The BclI10-AFR was used to avoid target-specific effects. Injection of 10 μg scTNF, which is lethal when using wtTNF, only led to a moderate drop in body temperature (FIG. 7A), but induced significant levels of circulating IL-6, a sensitive marker for systemic TNF activity (FIG. 7B). 35 μg (1.75 mg/kg) of scTNF was an LD100 in this model and was characterized by a dramatic drop in body temperature and concomitant increase in circulating IL-6. For BclI10-AFR, 5 consecutive daily i.v. bolus injections of 200 μg (10 mg/kg) were completely non-toxic and did not induce any drop in body temperature or increase in circulating IL-6, confirming that untargeted AFRs are inactive.

Figure 7A:
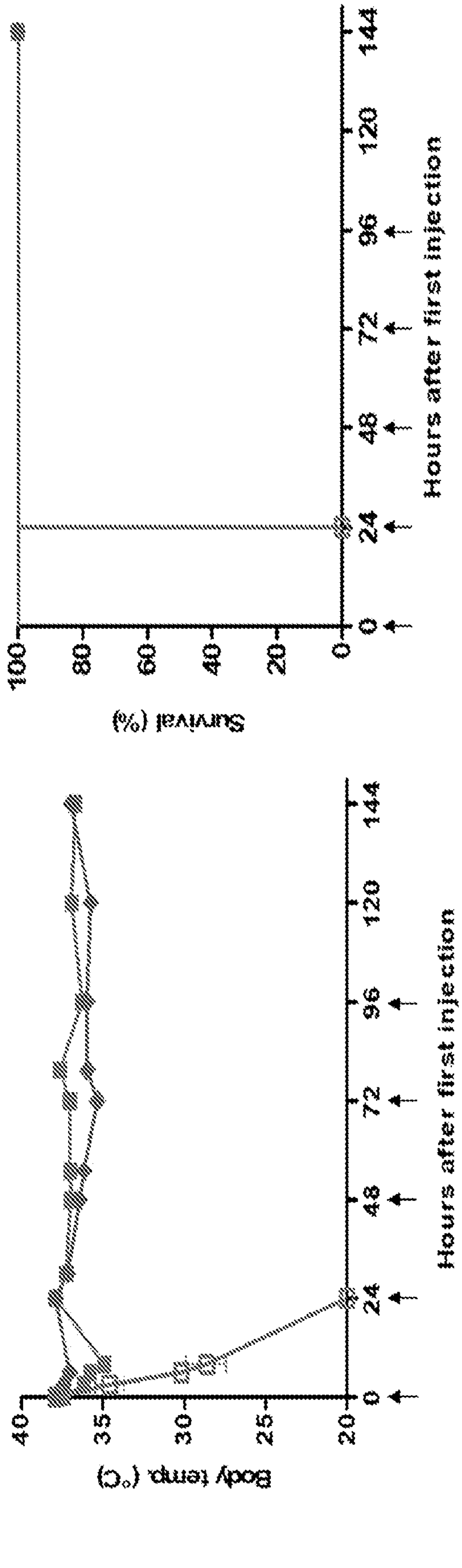
FIGS. 7A-E show that sc mTNF Y86F is non-toxic and mCD13-AFR is active in mice.
Figure 7B:
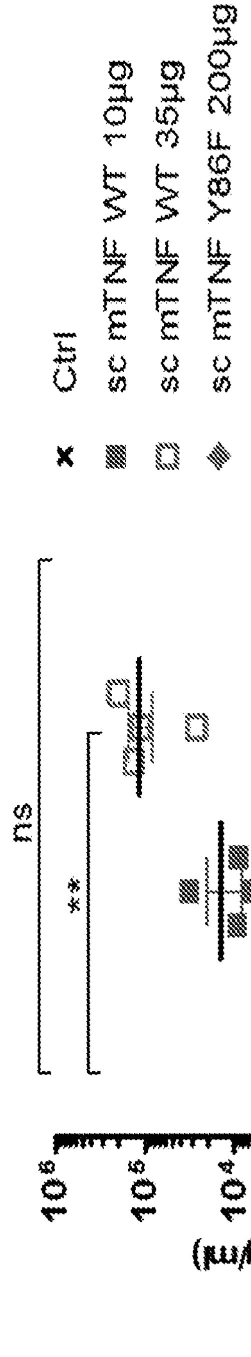
Figure 7C:
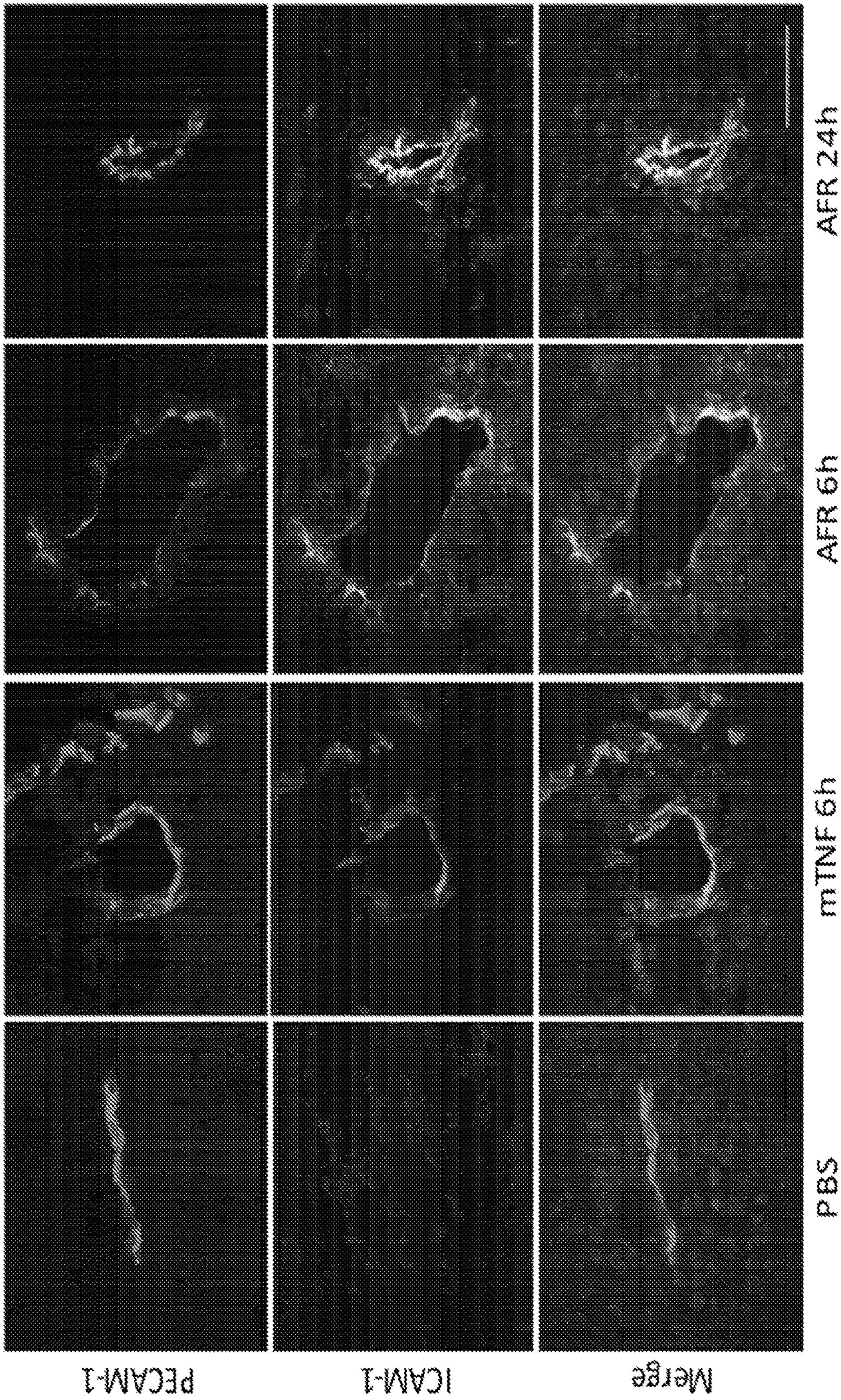
Figure 7D:
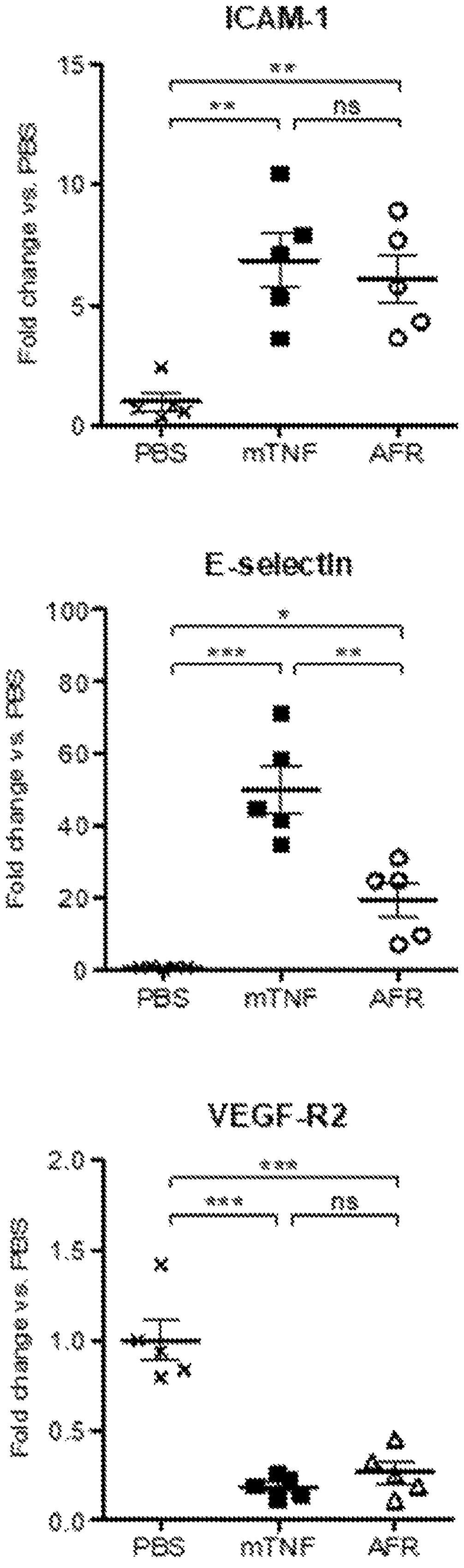
Figure 7E:
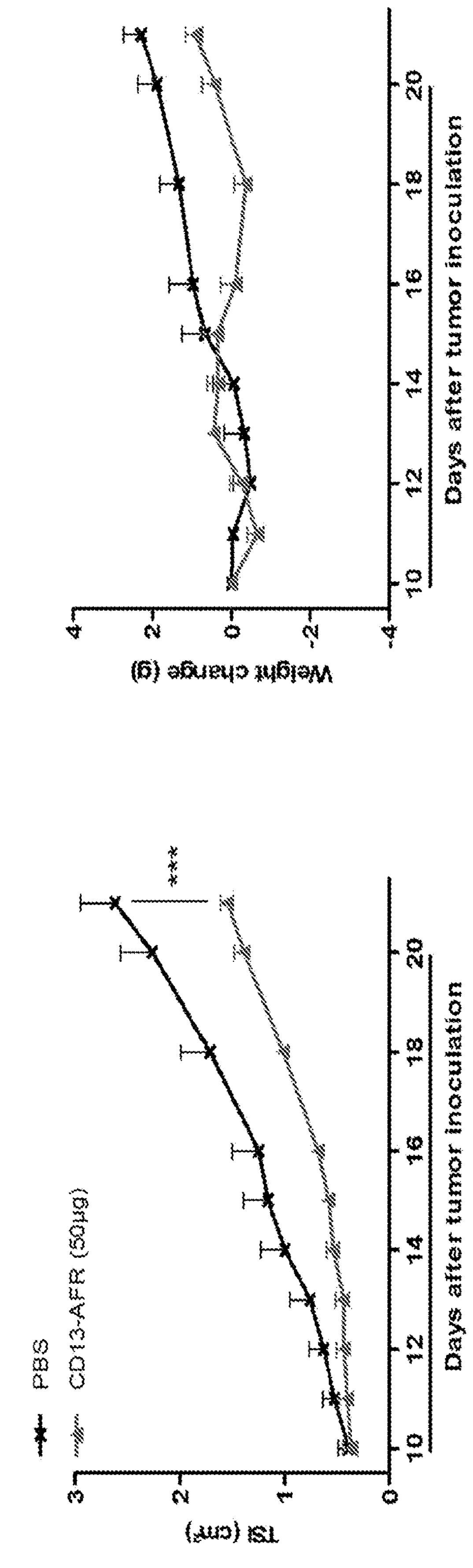

To target tumor vasculature, a VHH against mouse CD13 was generated (Pasqualini, R., et al., *Cancer Res,* 2000. 60(3): p. 722-7). This VHH was fused to wt scTNF or mutant Y86F. The immunocytokine mCD13-targeted wt scTNF was slightly more efficient in the B16B16 melanoma model than untargeted scTNF, confirming the targeting potential of this VHH (data not shown). To demonstrate the in vivo activity of tumor vasculature-targeted AFRs, immunohistochemical analysis of tumor sections after injection of wtTNF or mCD13-AFR (FIGS. 1 and 7C) was performed. Six hours after injection, clear induction of ICAM-1 on tumor vessels was observed, which was even more pronounced 24 hours after injection, indicating prolonged endothelial activation. Induction of ICAM-1 expression was confirmed via qPCR analysis on whole tumor RNA (FIG. 7D). Quite similar to wtTNF, mCD13-AFR induced expression of both ICAM-1 and E-selectin and repression of VEGF-R2 at 4 hours after injection. Since tumor-bearing mice tend to be sensitized towards TNF toxicity (Cauwels, A., et al., Cancer Res, 2018. 78(2): p. 463-474), mCD13-AFR in the B16B16 melanoma model was tested next. Daily treatment for 10 consecutive days with 2.5 mg/kg mCD13-AFR caused no significant weight loss or other apparent toxicity, confirming its safety, while also demonstrating moderate antitumor activity (FIG. 7E).

Example 7

IFN-γ Sensitizes Tumor Endothelial Cells for TNF Activity

Figure 8B:
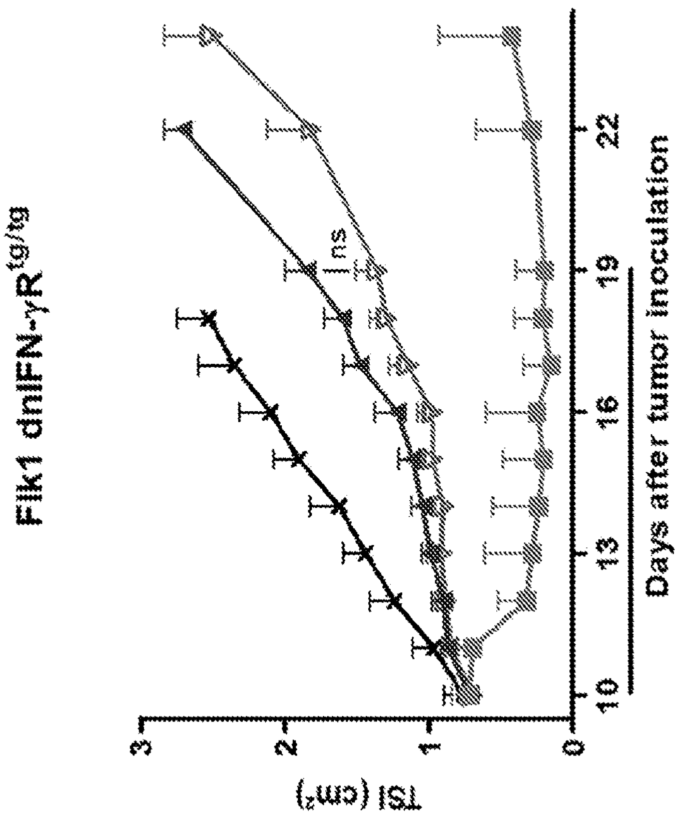
FIG. 8A-E show that IFN-γ sensitizes tumor endothelial cells for TNF.
Figure 8A:
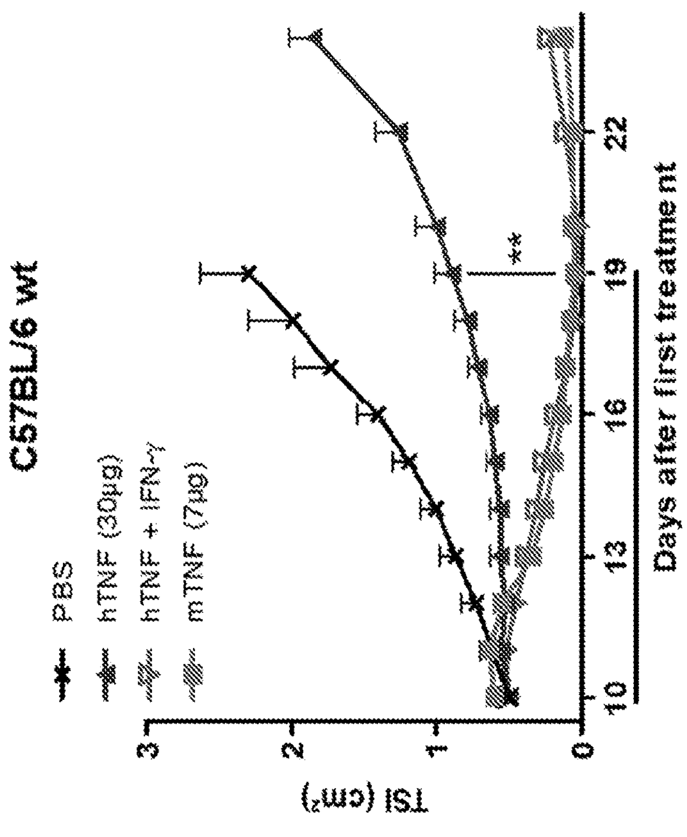

In the B16B16 model, synergism between IFN-γ and TNF is clear when mIFN-γ is combined with hTNF. Human TNF, which can be considered as a low-toxic, fast-cleared mTNF mutant in the mouse (Ameloot, P., et al., *Eur J Immunol,* 2002. 32(10): p. 2759-65), is unable to induce complete tumor regression in the B16B16 model, except when combined with mIFN-γ (FIG. 8A). To investigate whether the synergistic effect of TNF and IFN-γ depends on direct actions on tumor cells or on host cells, IFN-γ-insensitive B16BI6 tumor cells (B16-dnIFN-γR) were generated. When wt mice carrying a B16-dnIFN-γR tumor were treated with hTNF and mIFN-γ the synergistic antitumor effect was still present (FIG. 9A). By contrast, this synergy was completely absent in IFN-γR knockout mice carrying a parental B16BI6 tumor (FIG. 9B), pointing towards the important role of the host microenvironment. It was hypothesized that IFN-γ may also act on endothelial cells, sensitizing them for the effects of TNF. Therefore transgenic mice were generated in which the vasculature is selectively unresponsive to IFN-γ by endothelial-specific Flk1 promoter-driven expression of a truncated, dominant-negative IFN-γR (FIGS. 10A and 10B). As shown in FIG. 8B, treatment of these mice resulted in complete loss of the synergy between hTNF and mIFN-γ, confirming the critical role of IFN-γ signaling in endothelial cells.

Figure 8C:
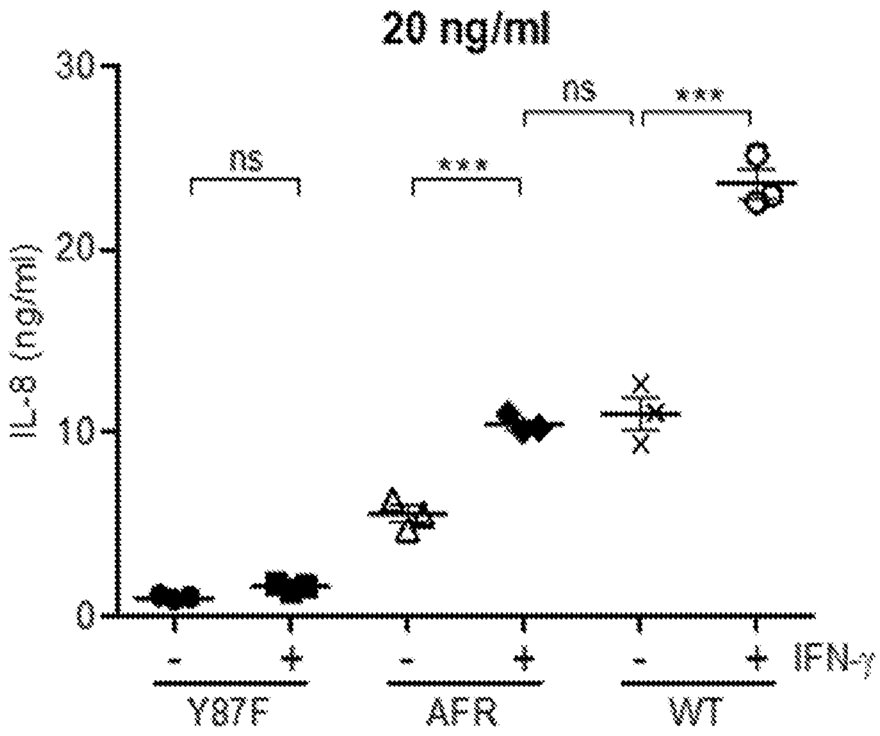
Figure 8C:
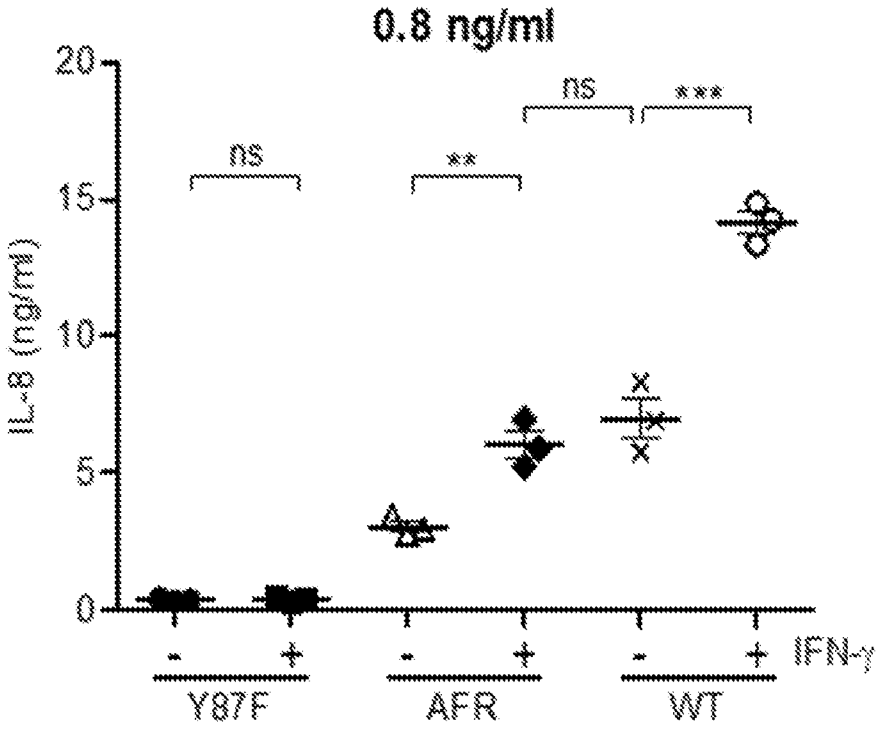
Figure 8D:
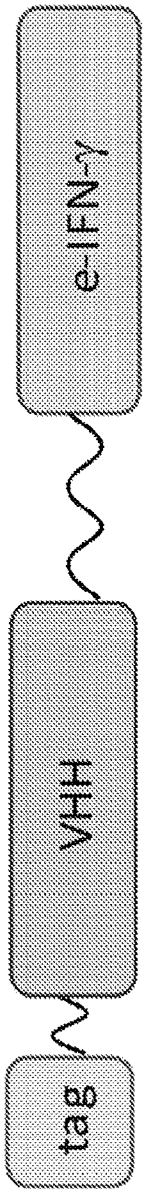

It was also tested whether IFN-γ could sensitize HUVECs to TNF, using either wtTNF or hCD13-AFR. Indeed, whilst IFN-γ treatment alone had no effect on IL-8 secretion by HUVECs, it sensitized for TNF signaling leading to a 2 to 3-fold increased IL-8 secretion when compared with wtTNF or hCD13-AFR alone (FIG. 8C). Of note, IL-8 secretion levels of hCD13-AFR plus hIFN-γ stimulated cells were equal to those after stimulation with wtTNF alone.

Example 8

Type II AcTaferon Synerqizes With CD13-AFR for Tumor Destruction

Figure 8E:
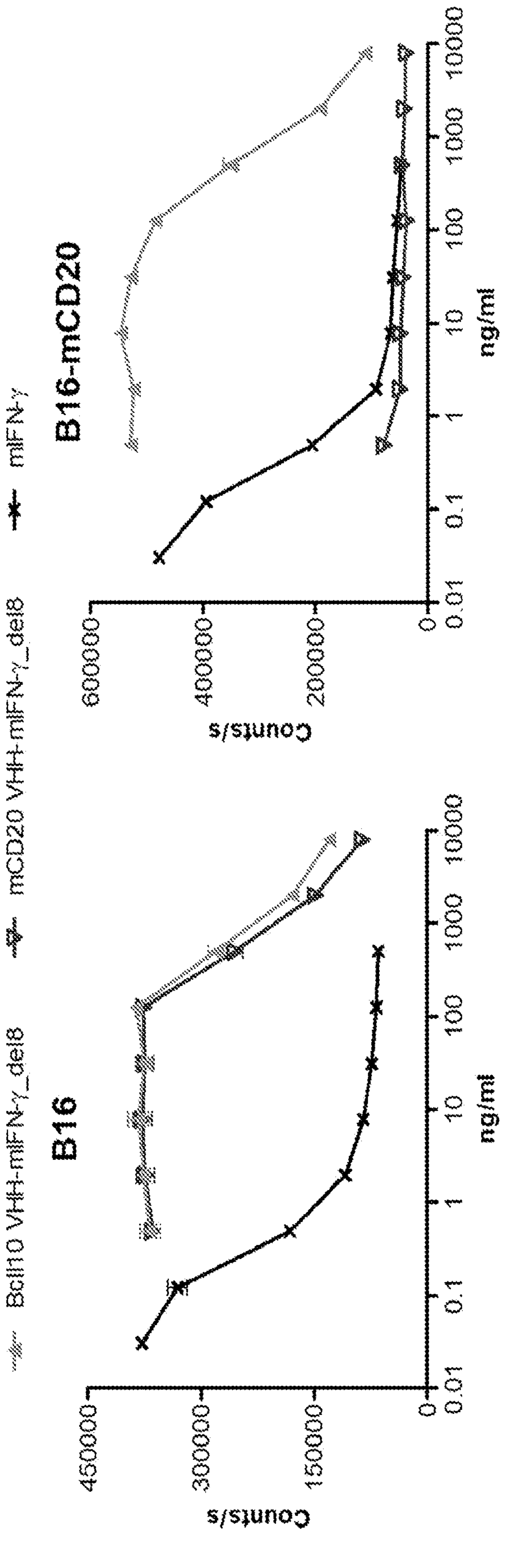
Figure 9:
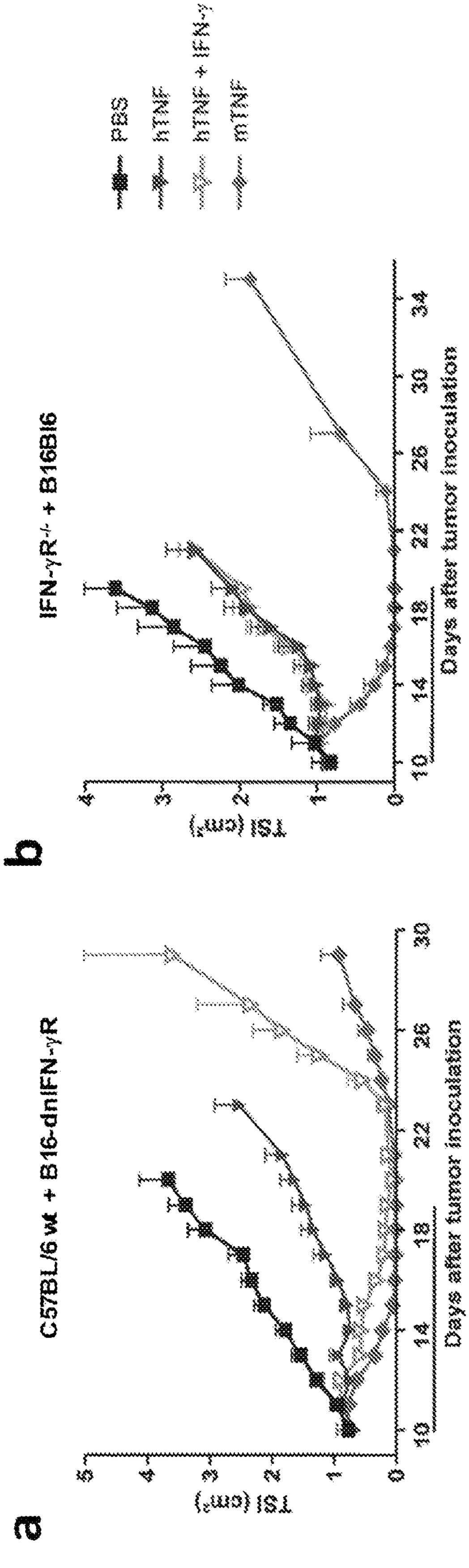
FIGS. 9A-B show the synergistic antitumor effect of TNF and IFN-γ depends on expression of IFN-γR on host cells but not on tumor cells.
Figure 10:
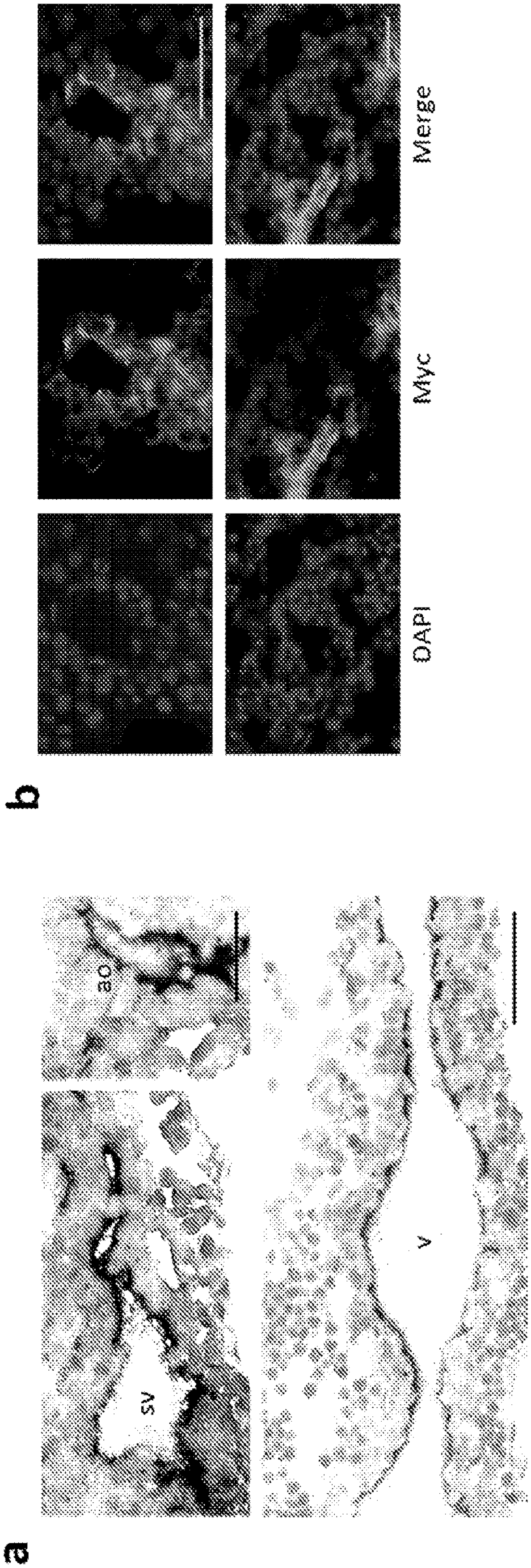
FIG. 10A-B show endothelial expression of the dnIFN-γR transgene in Flk1 dnIFN-γRtog mice.
Figure 11:
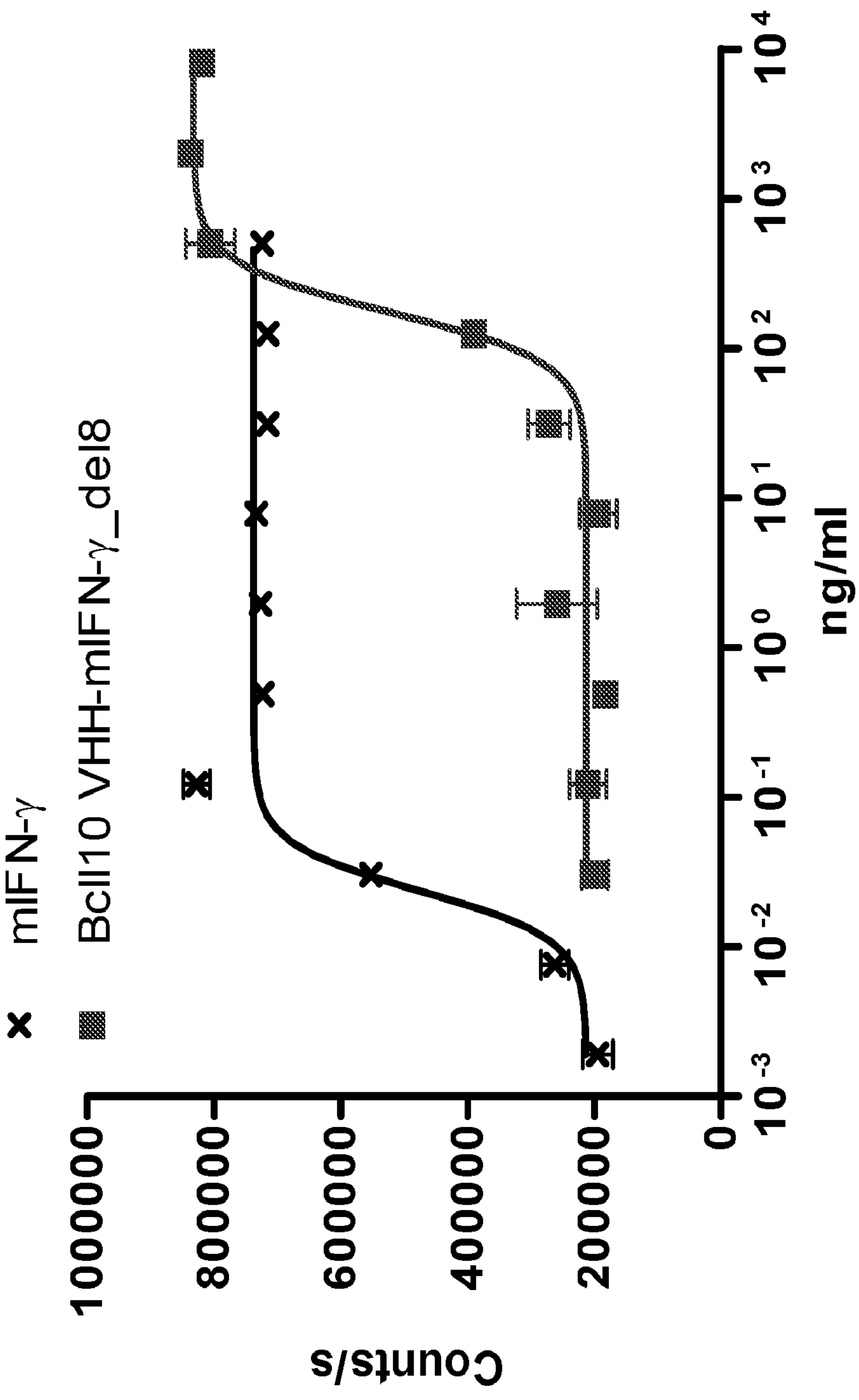
FIG. 11 shows the bioactivity of mIFN-γ de18 mutant in the EMCV cytopathic effect assay in L929 cells. L929 cells were stimulated for 24 h with wt mIFN-γ or de18 mutant before virus (~99% CPE) was added. One day later, cell viability was measured via an ATP luminescence assay.
Figure 12A:
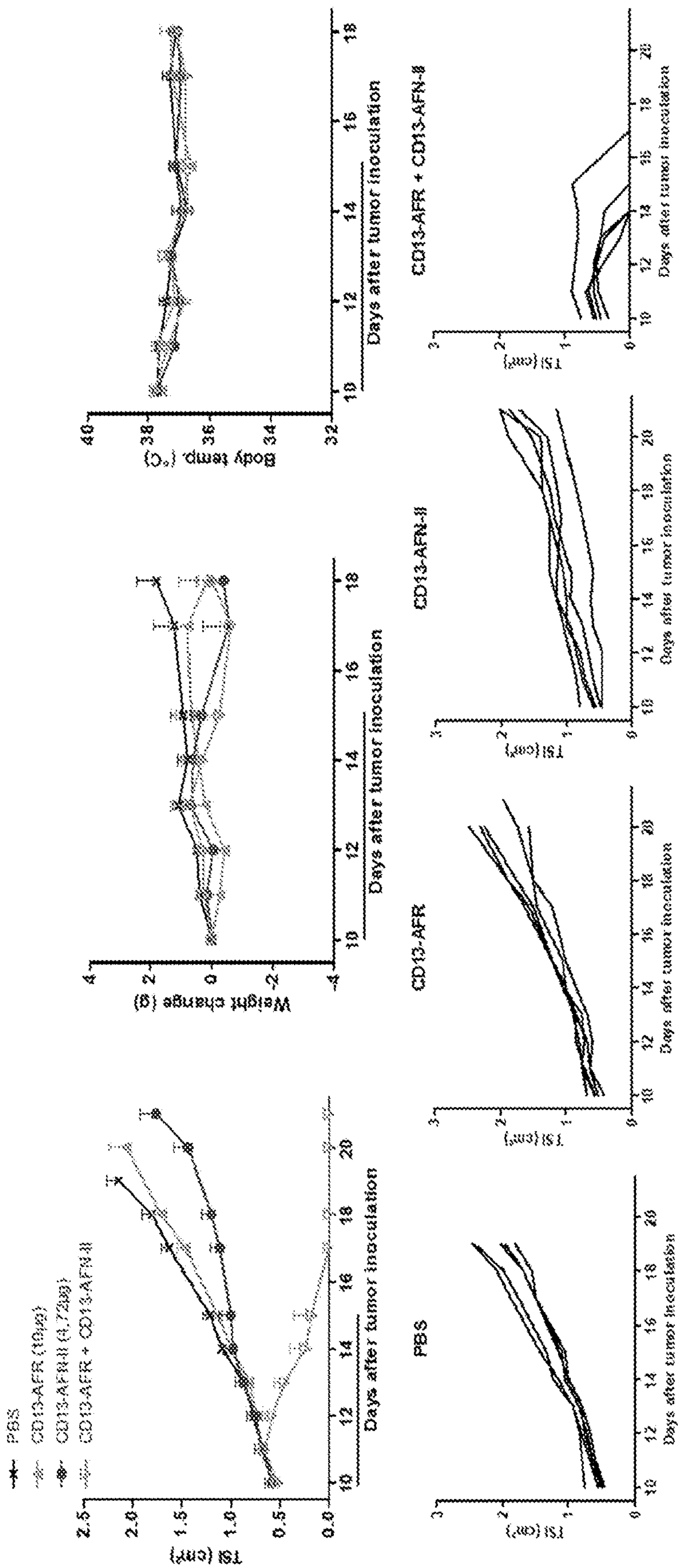
FIGS. 12A-C show that CD13-AFN-II synergizes with CD13-AFR for tumor destruction.
Figure 12B:
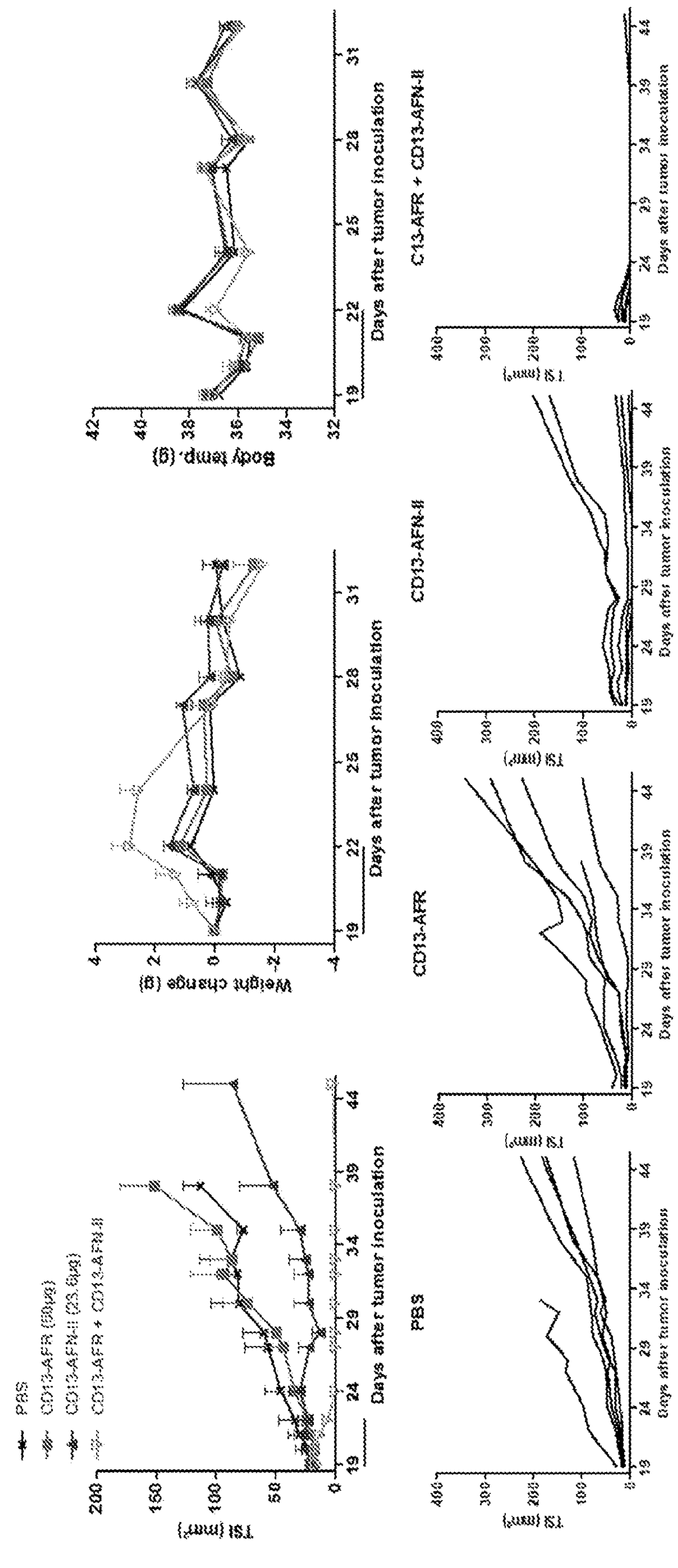
Figure 12C:
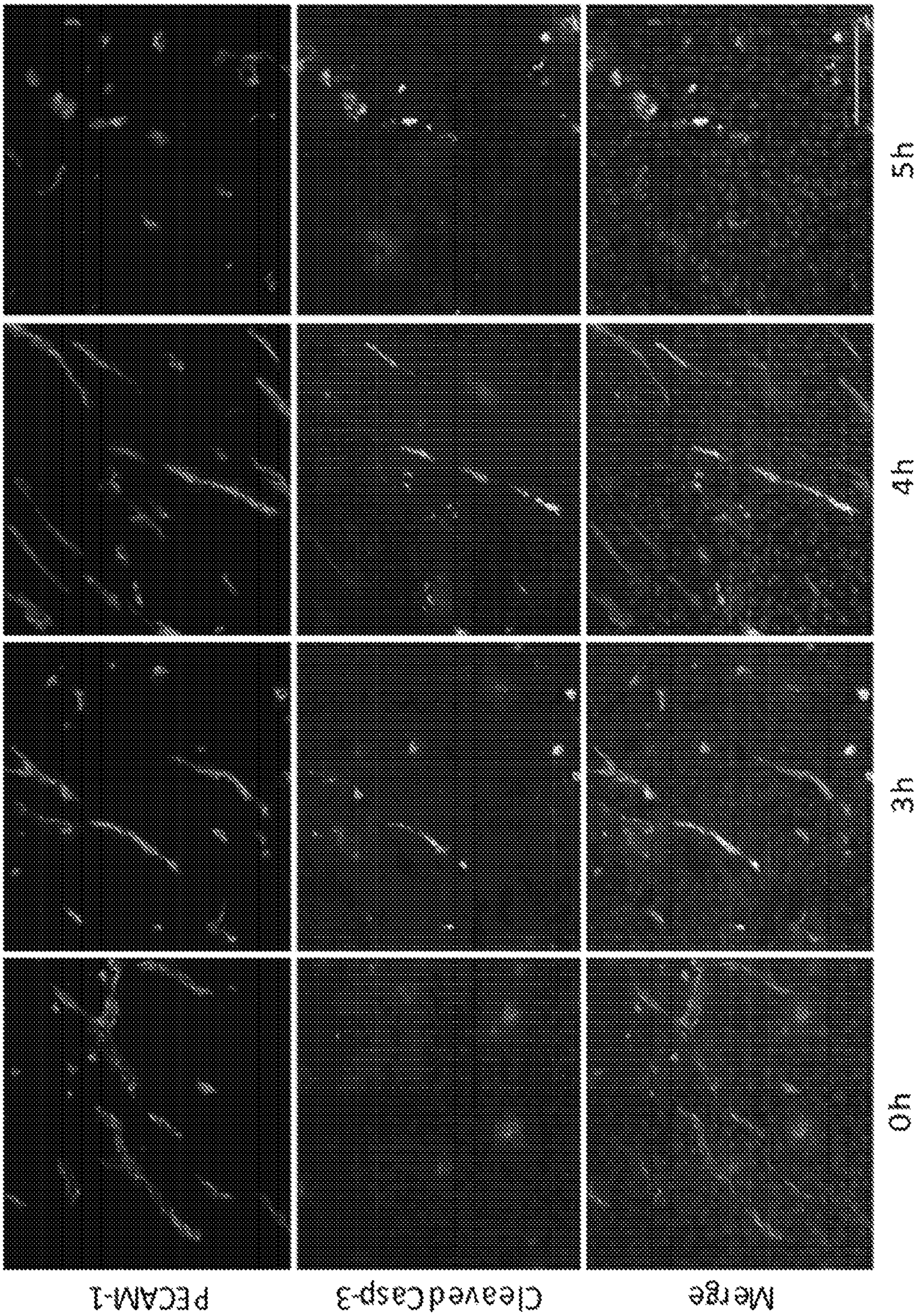
Figure 13A:
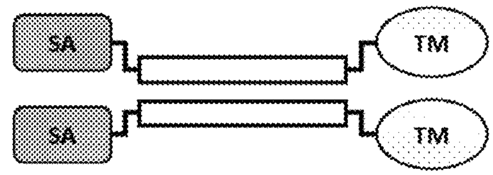
Figure 13B:
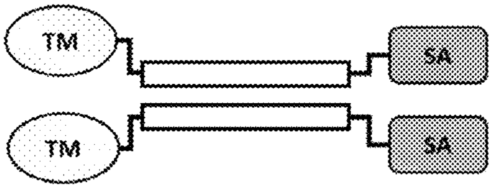
Figure 13C:
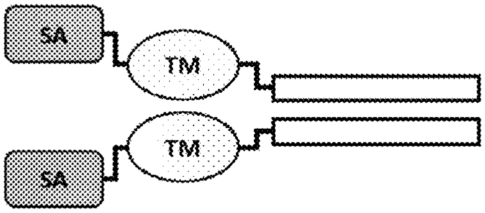
Figure 13D:
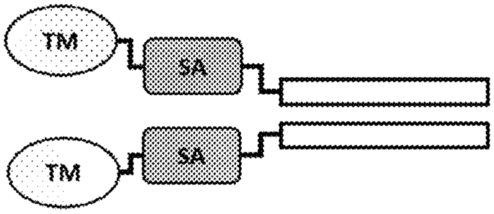
Figure 13E:
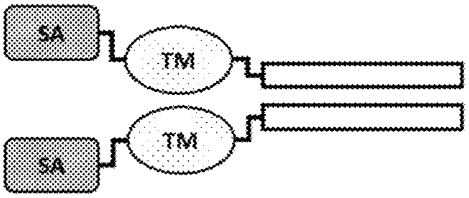
Figure 13F:
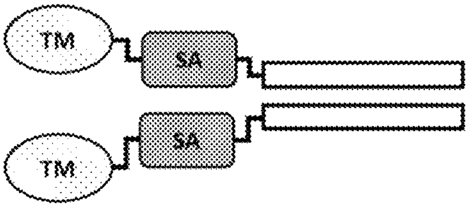
Figure 14A:
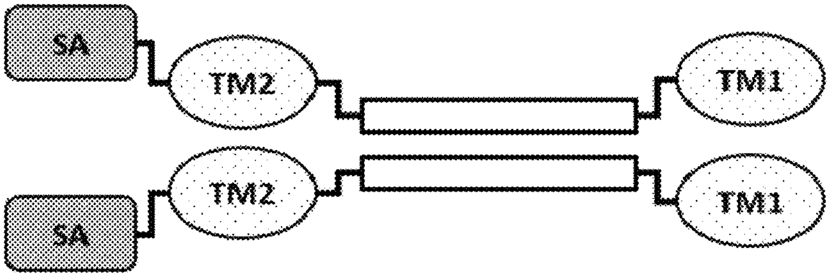
Figure 14B:
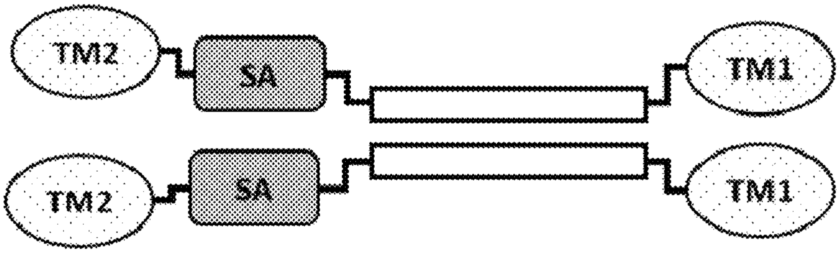
Figure 14C:
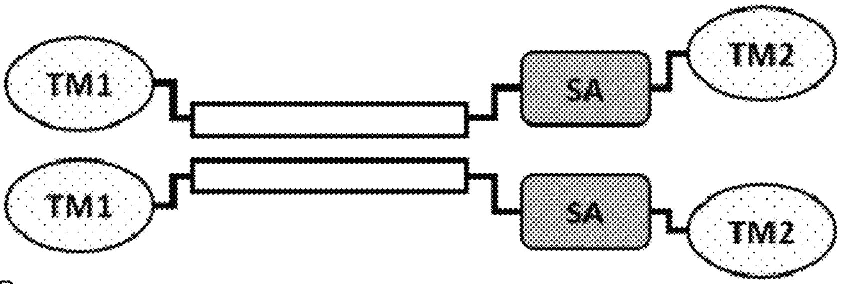
Figure 14D:
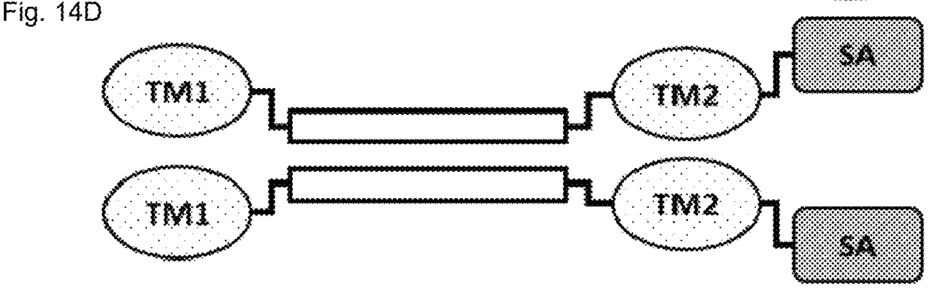
Figure 15A:
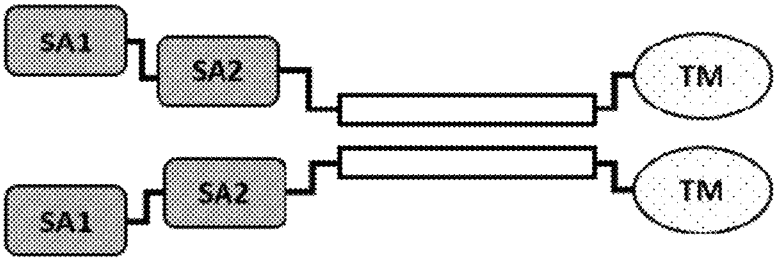
Figure 15B:
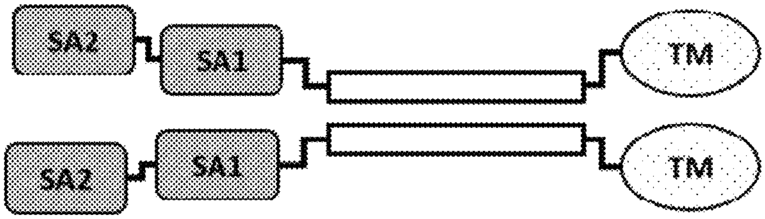
Figure 15C:
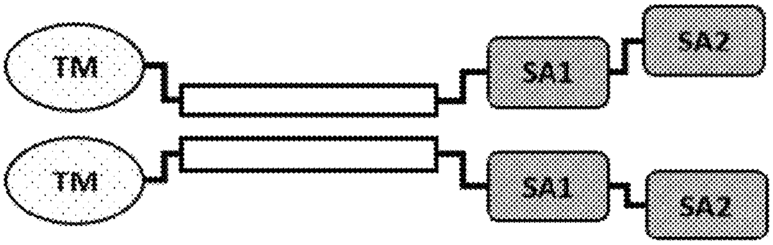
Figure 15D:
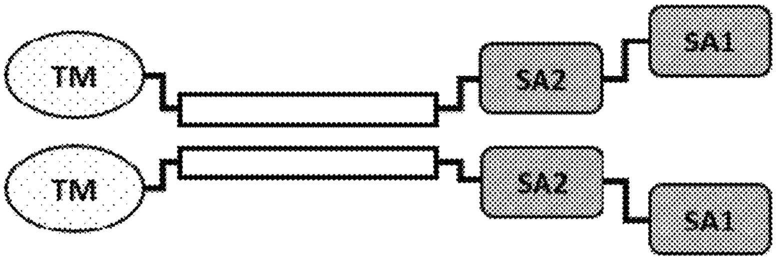
Figure 15E:
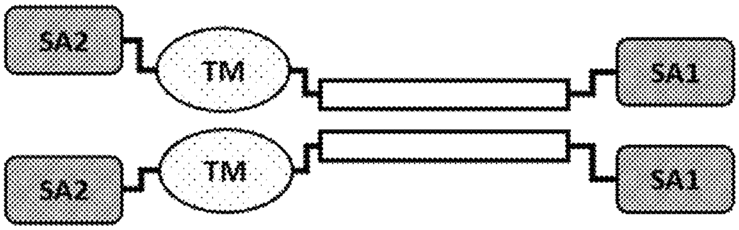
Figure 15F:
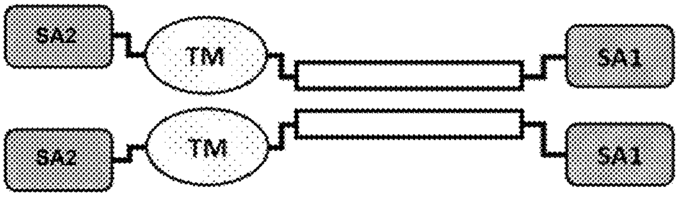
Figure 15G:
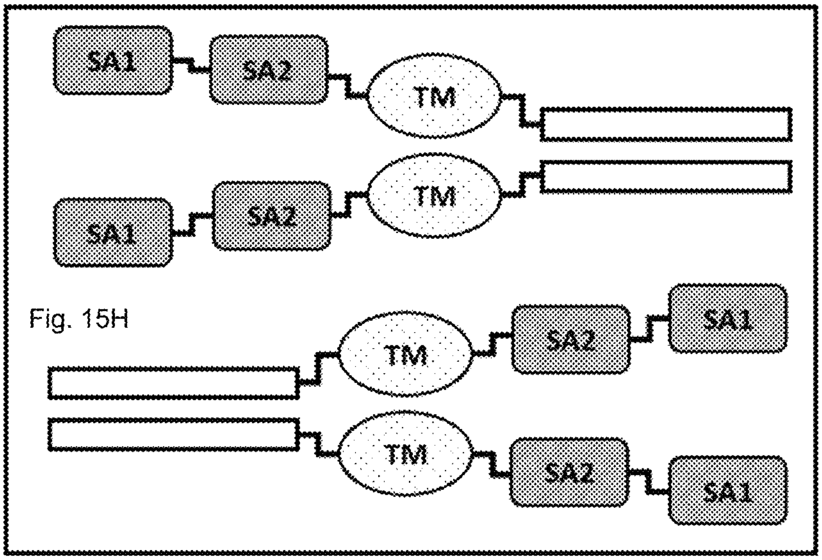
Figure 16A:
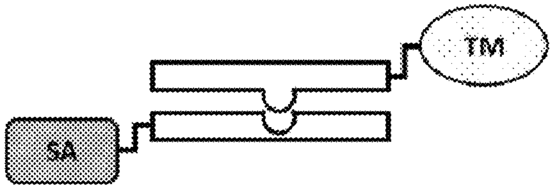
Figure 16B:
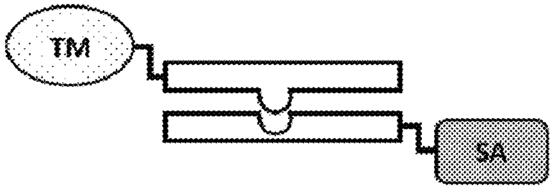
Figure 16C:
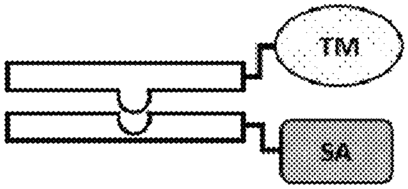
Figure 16D:
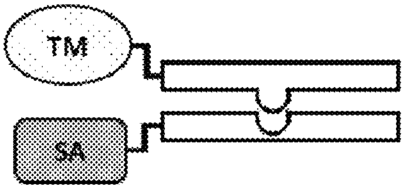
Figure 17A:
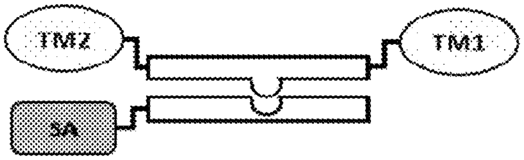
Figure 17B:
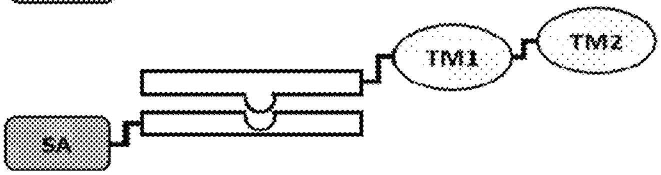
Figure 17C:
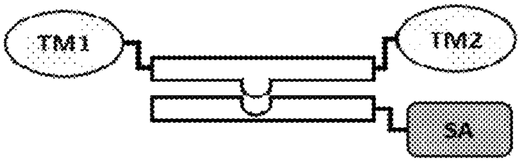
Figure 17D:
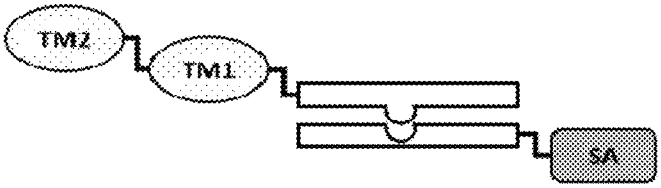
Figure 17E:
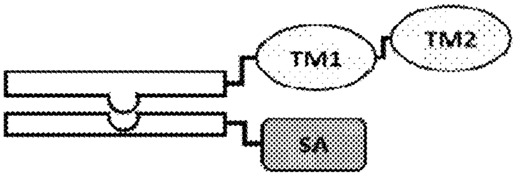
Figure 17F:
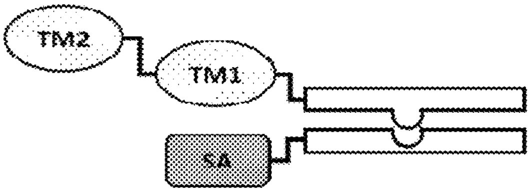
Figure 18A:
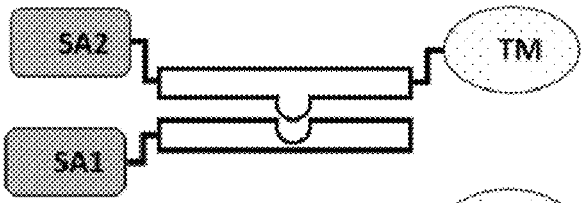
Figure 18B:
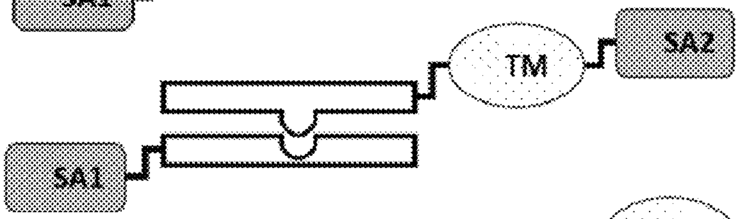
Figure 18C:
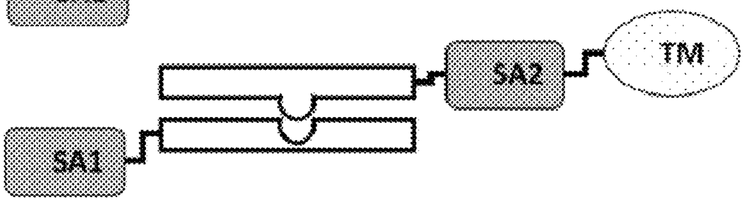
Figure 18D:
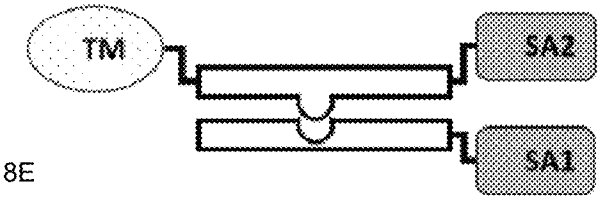
Figure 18E:
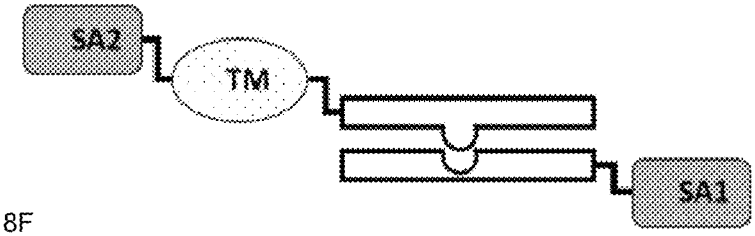
Figure 18F:
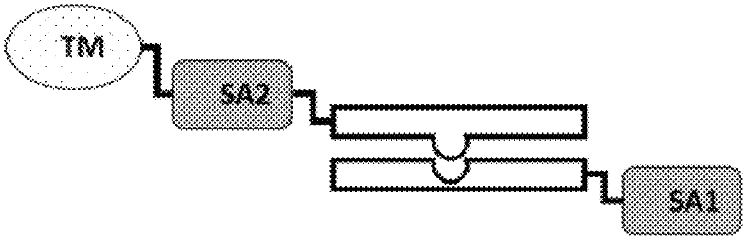
Figure 18G:
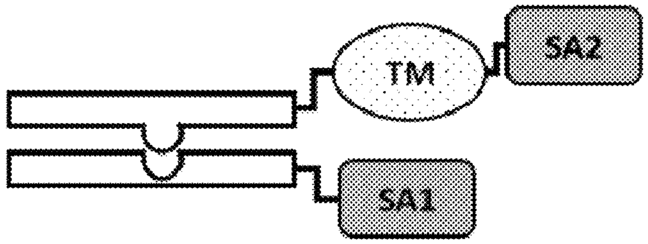
Figure 18H:
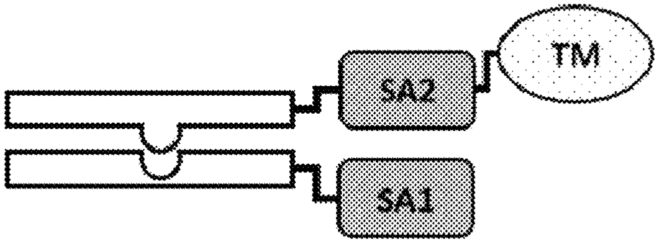
Figure 18I:
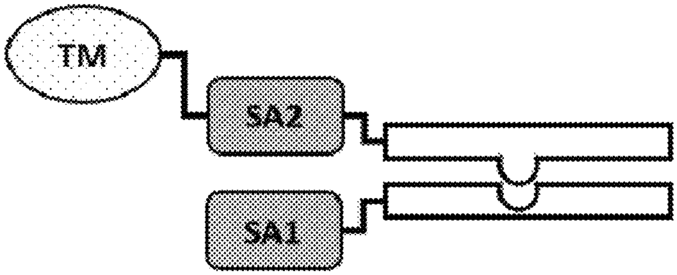
Figure 18J:
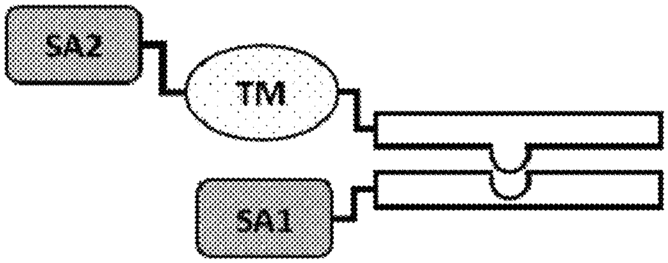
Figure 19A:
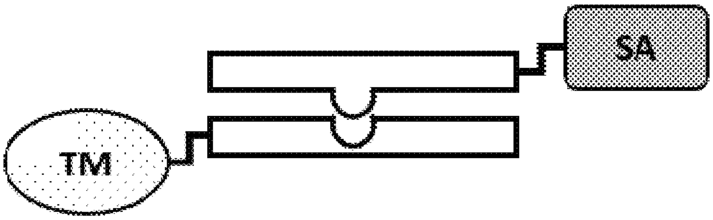
Figure 19B:
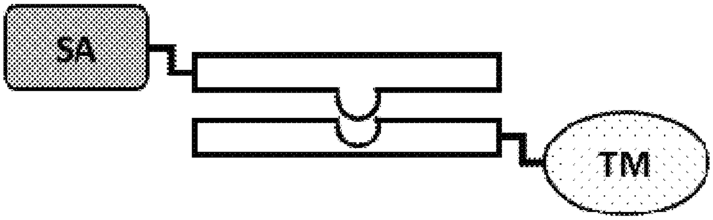
Figure 19C:
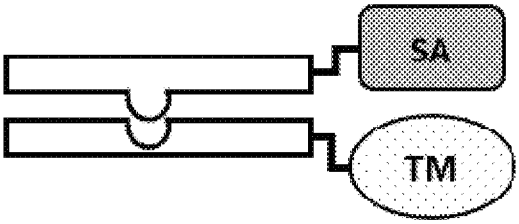
Figure 19D:
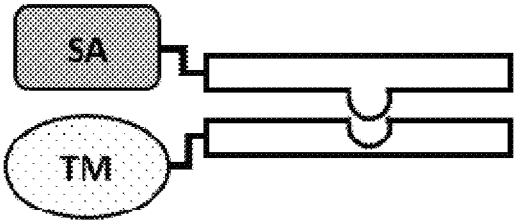
Figure 20A:
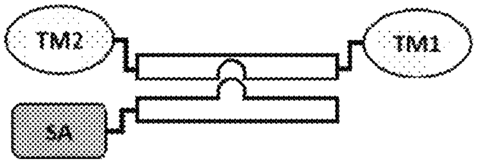
Figure 20B:
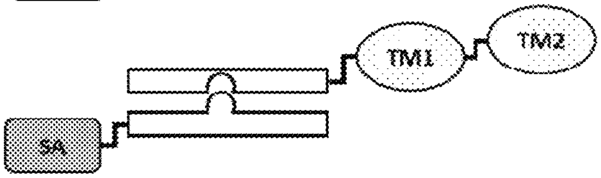
Figure 20C:
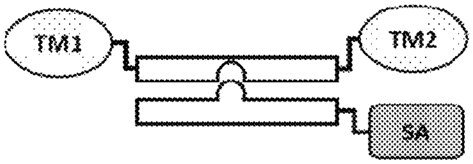
Figure 20D:
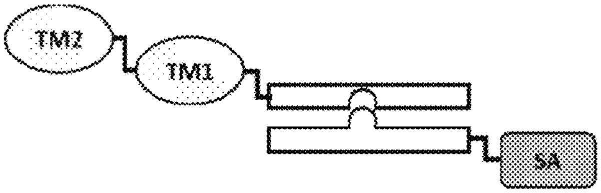
Figure 20E:
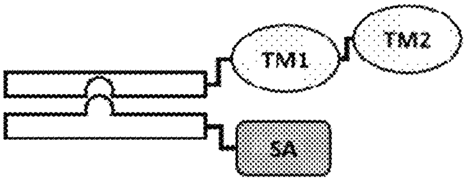
Figure 20F:
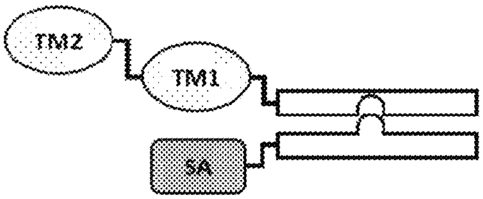
Figure 21A:
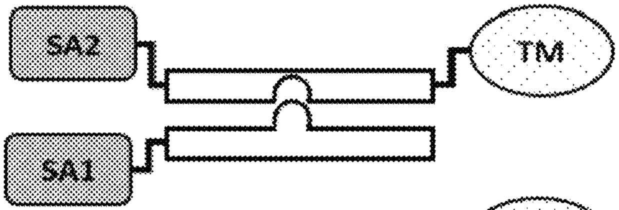
Figure 21B:
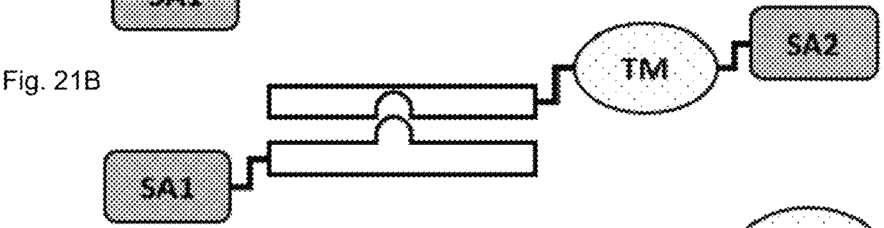
Figure 21C:
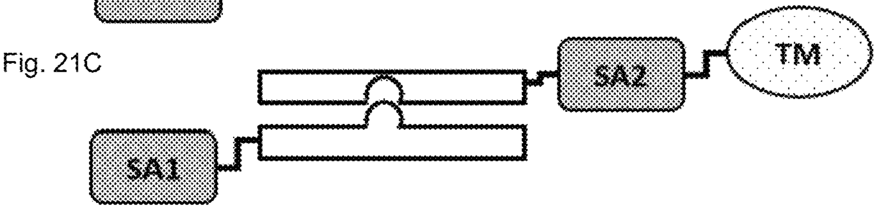
Figure 21D:
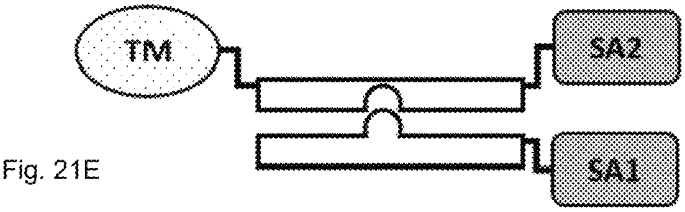
Figure 21E:
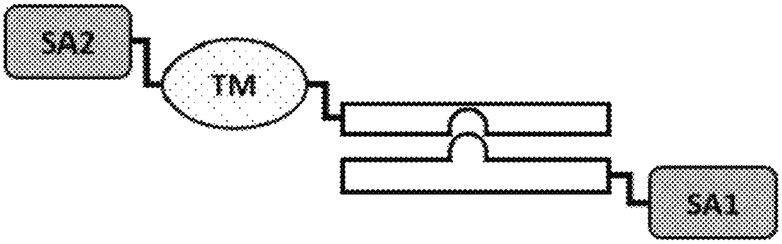
Figure 21F:
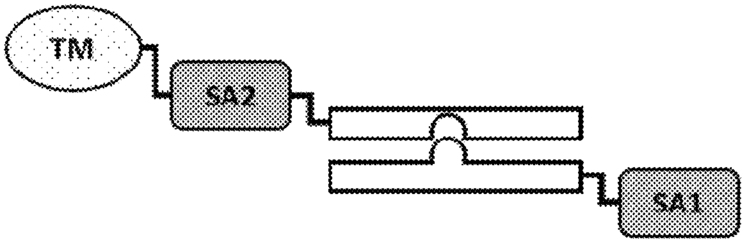
Figure 21G:
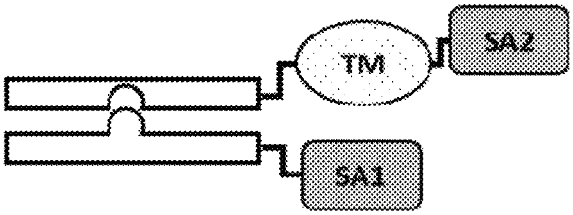
Figure 21H:
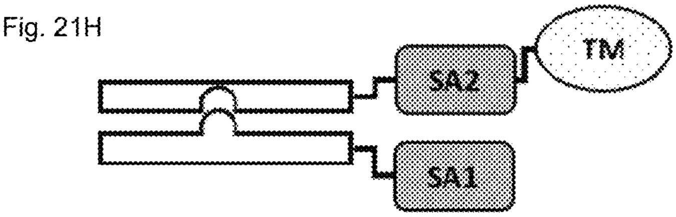
Figure 21I:
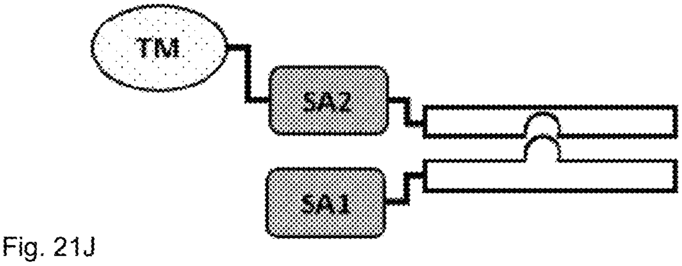
Figure 21J:
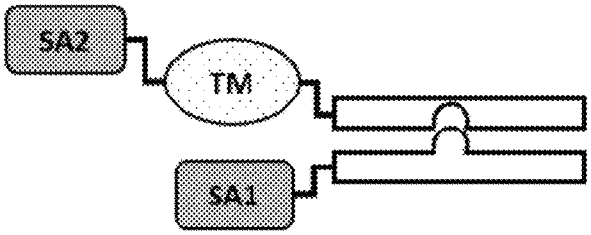
Figure 22A:
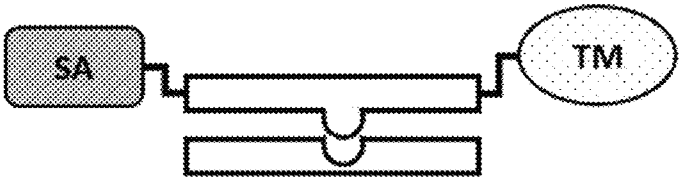
Figure 22B:
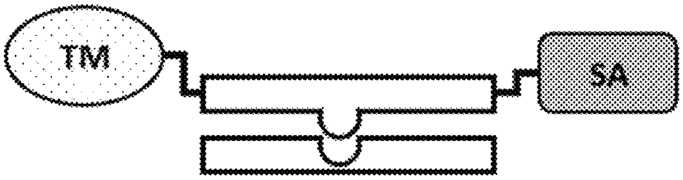
Figure 22C:
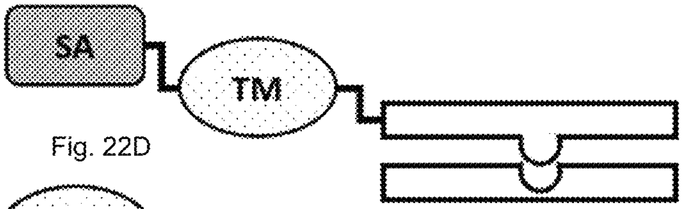
Figure 22D:
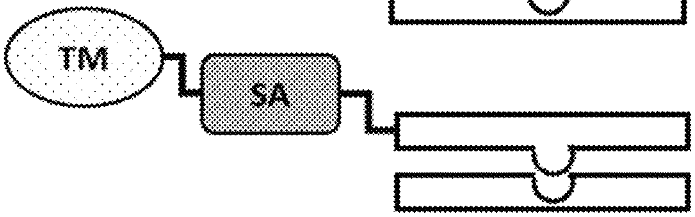
Figure 22E:
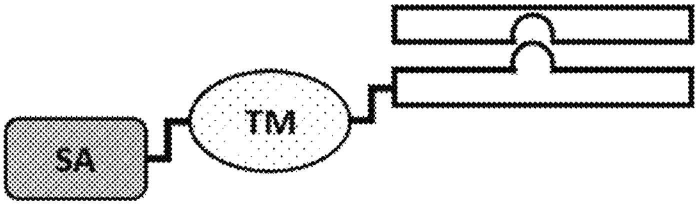
Figure 22F:
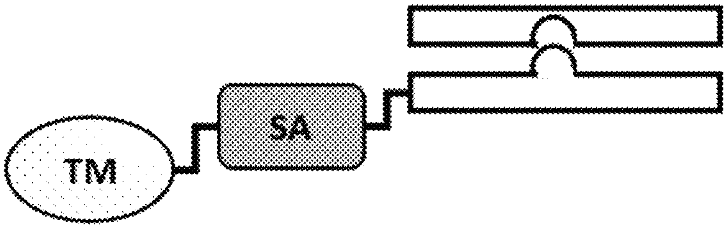
Figure 23A:
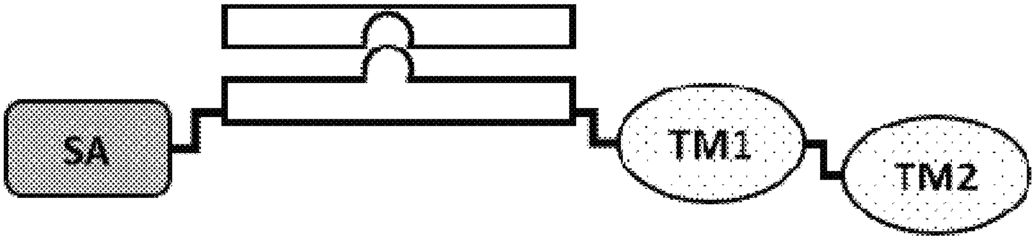
Figure 23B:
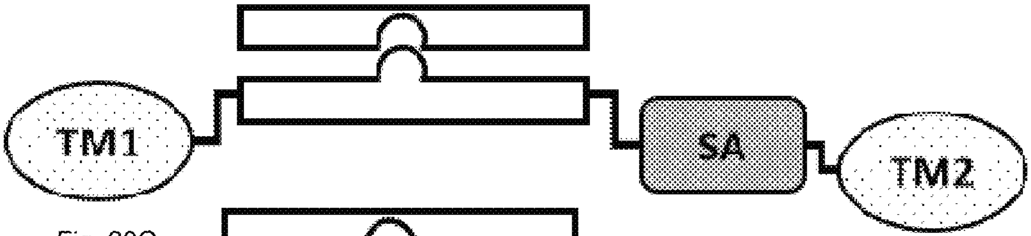
Figure 23C:
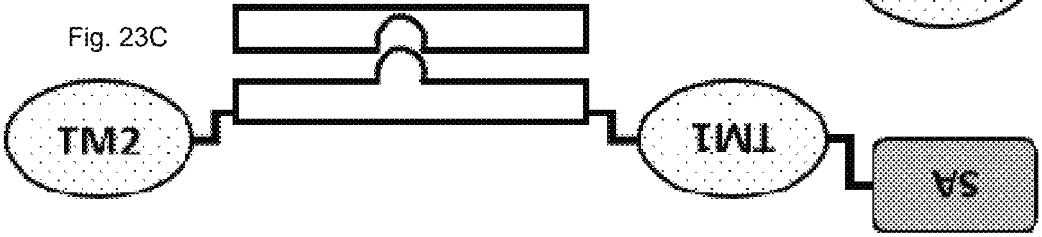
Figure 23D:
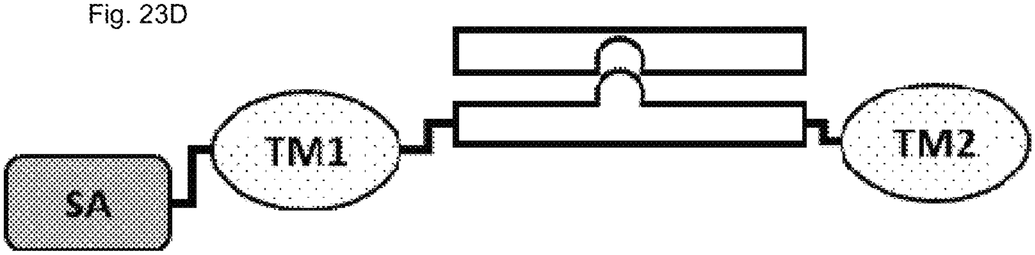
Figure 23E:
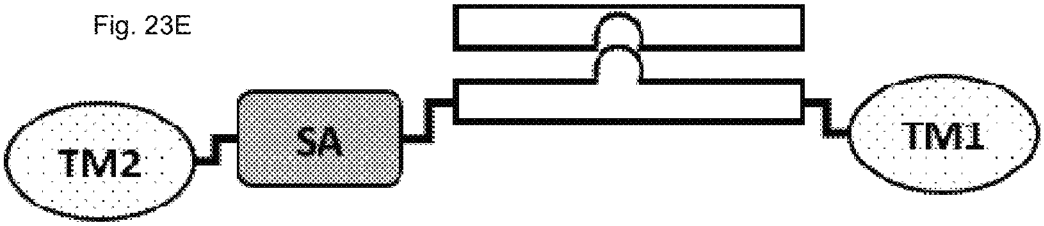
Figure 23F:
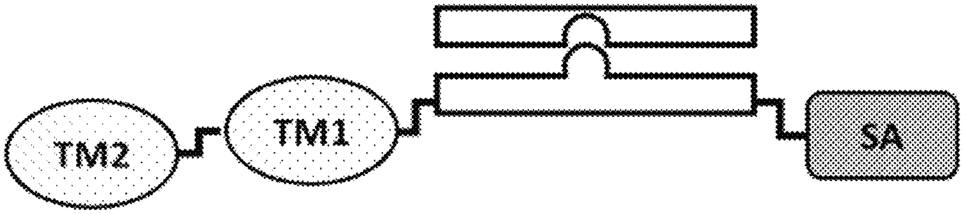
Figure 23G:
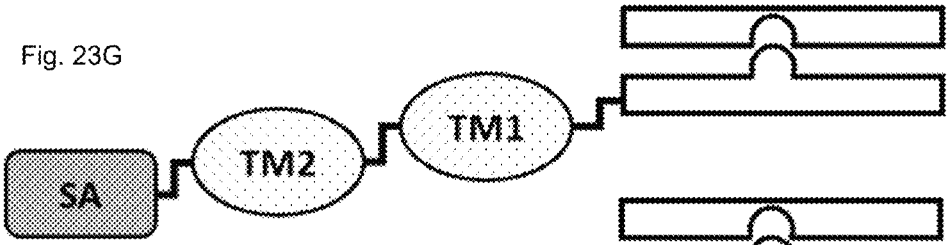
Figure 23H:
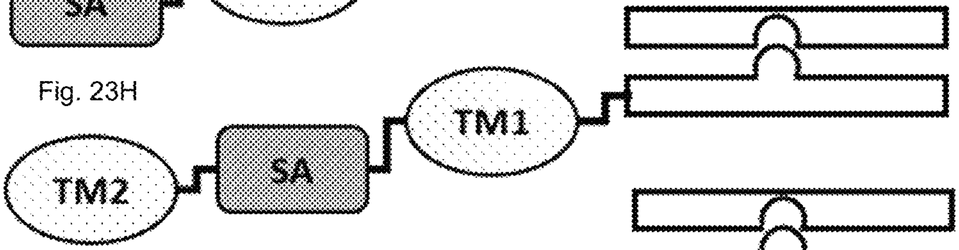
Figure 23I:
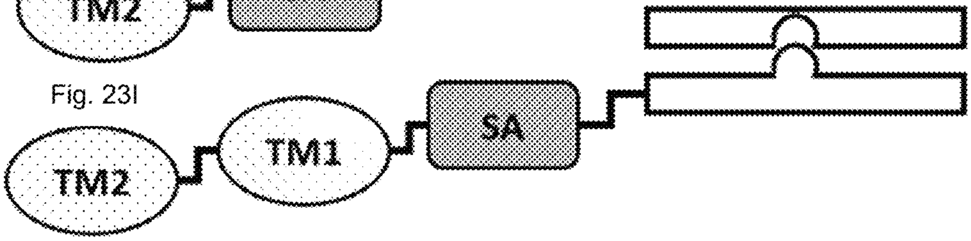
Figure 23J:
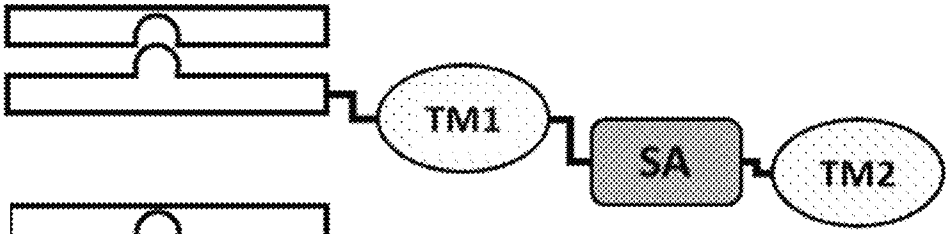
Figure 23K:
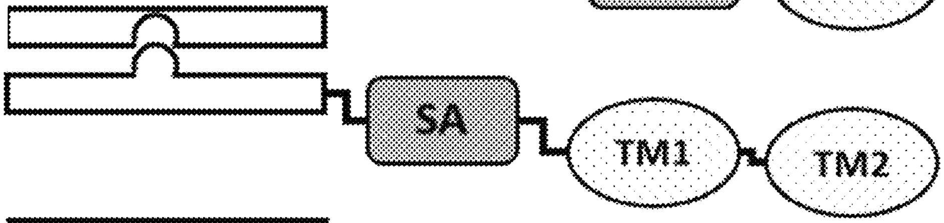
Figure 23L:
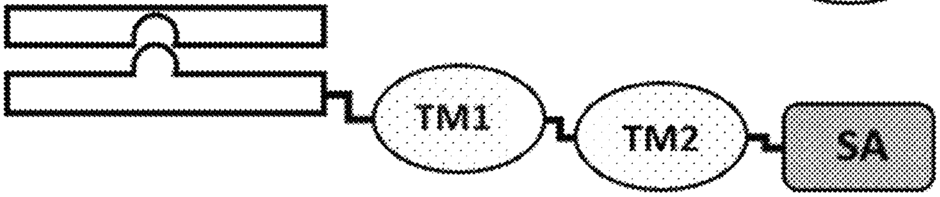
Figure 24A:
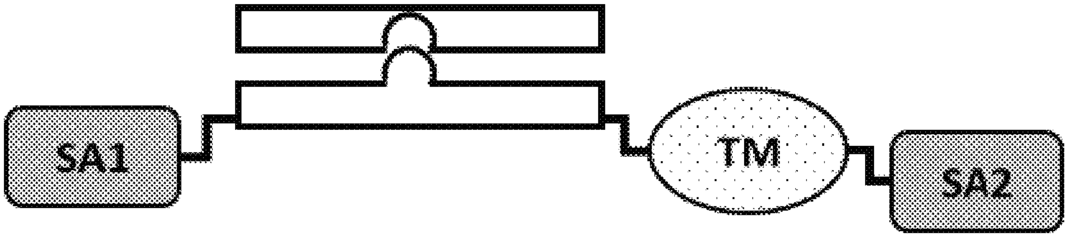
Figure 24B:
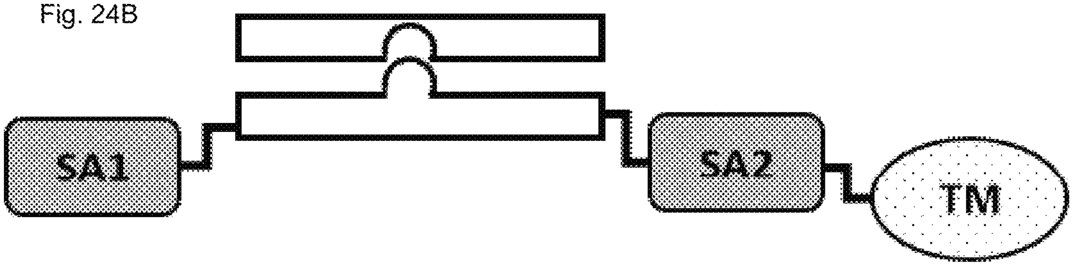
Figure 24C:
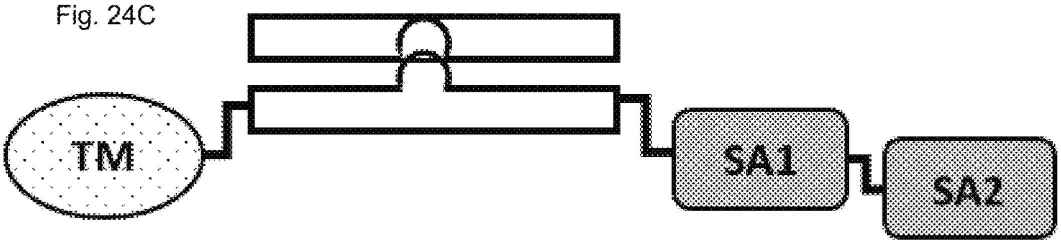
Figure 24D:
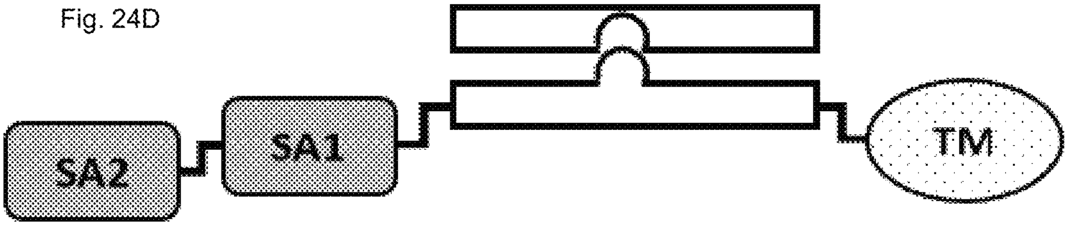
Figure 24E:
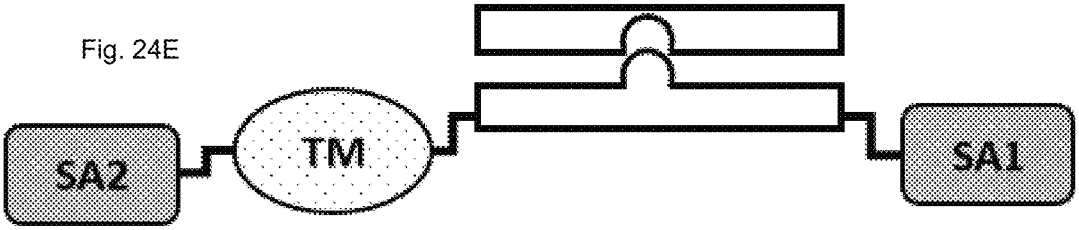
Figure 24F:
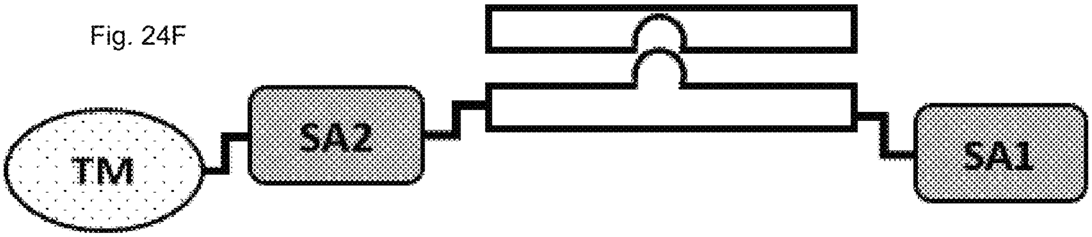
Figure 24G:
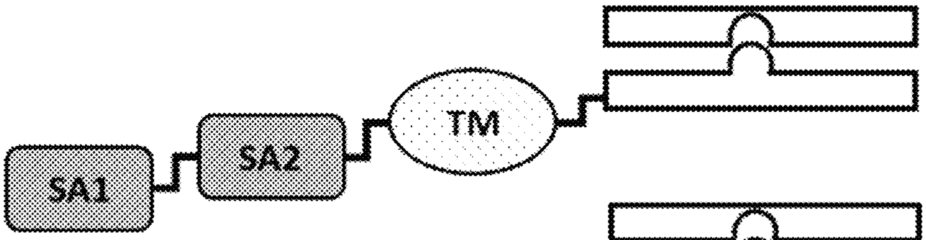
Figure 24H:
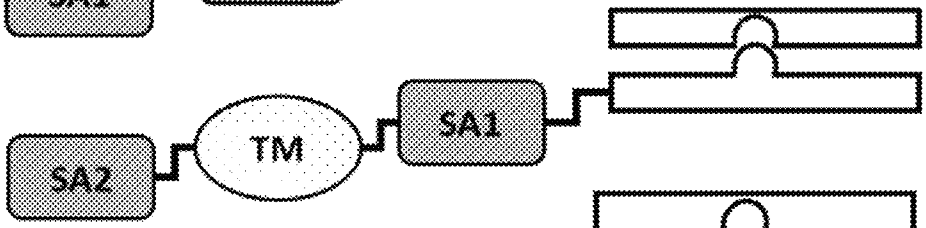
Figure 24I:
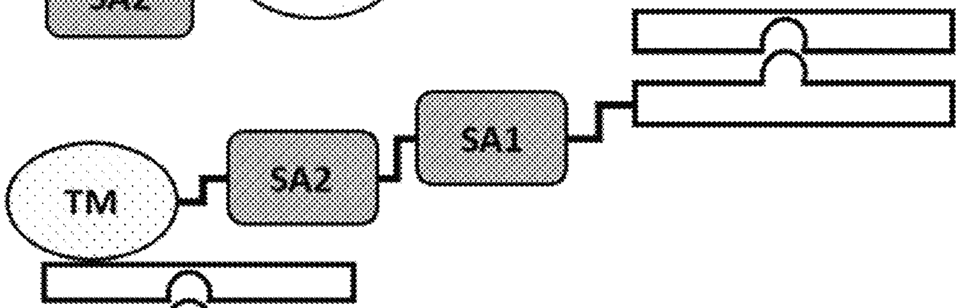
Figure 24J:
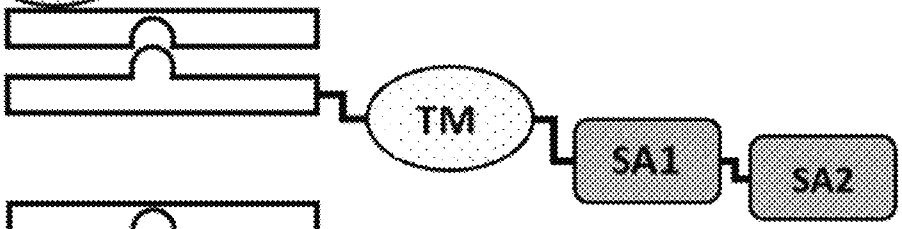
Figure 24K:
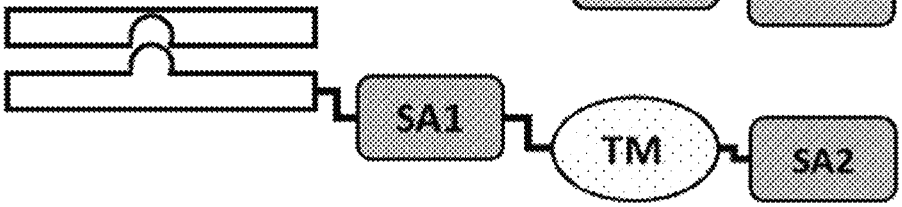
Figure 24L:
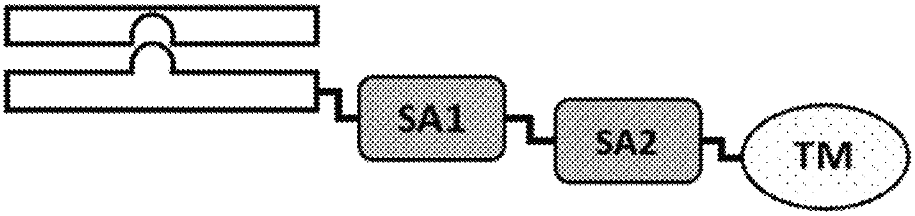
Figure 25A:
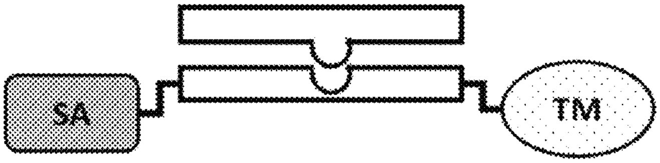
Figure 25B:
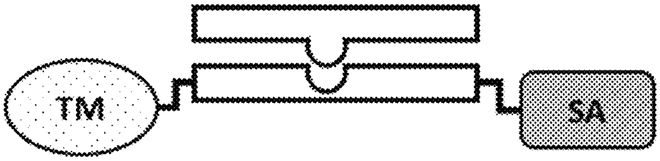
Figure 25C:
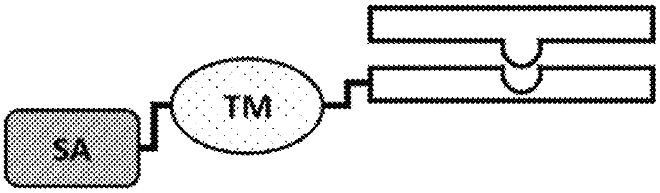
Figure 25D:
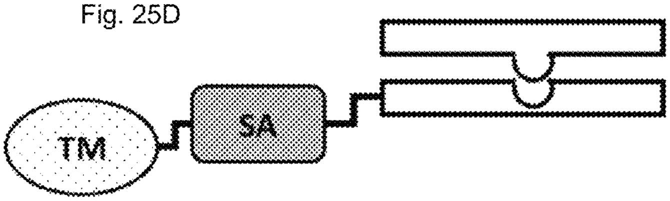
Figure 25E:
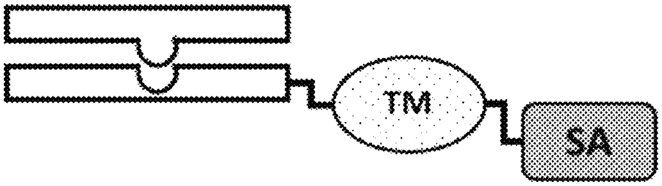
Figure 25F:
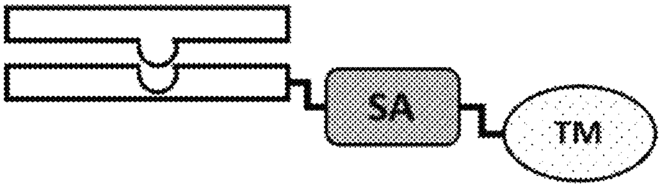
Figure 26A:
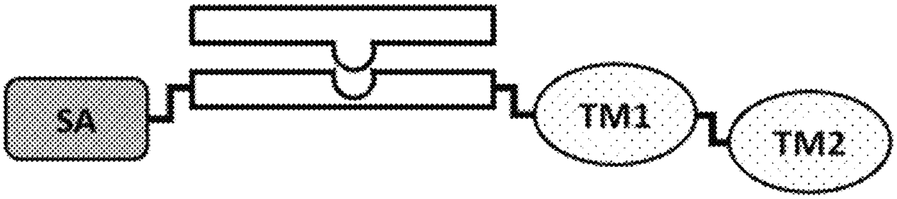
Figure 26B:
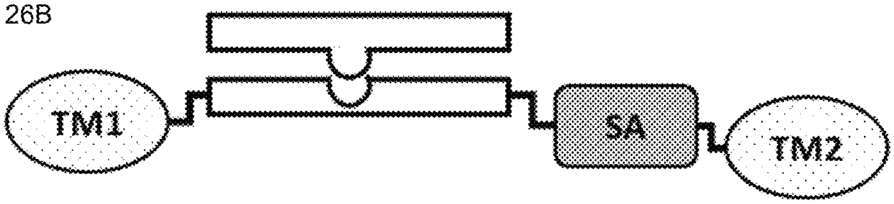
Figure 26C:
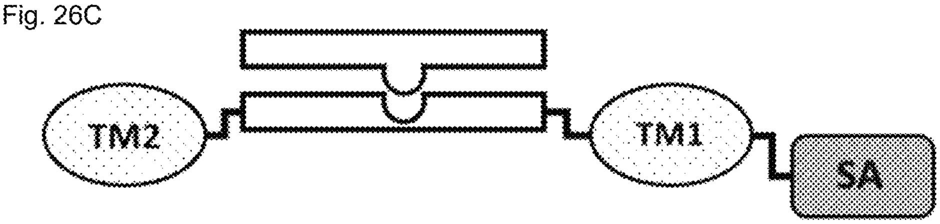
Figure 26D:
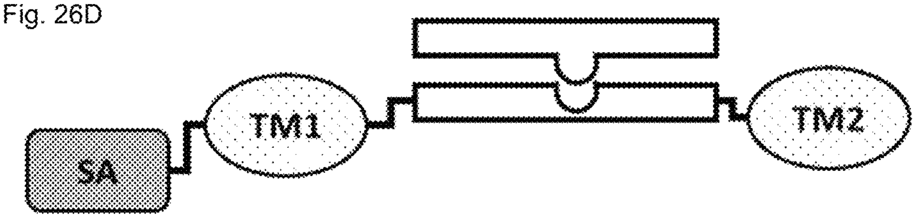
Figure 26E:
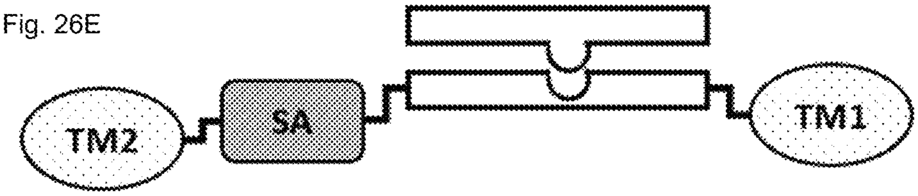
Figure 26F:
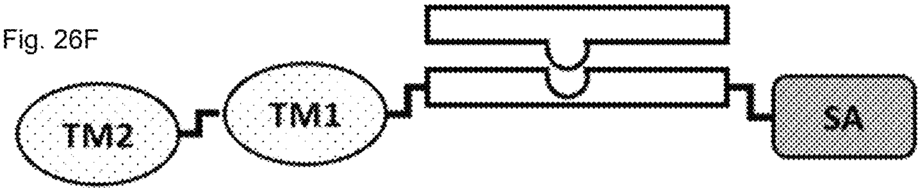
Figure 26G:
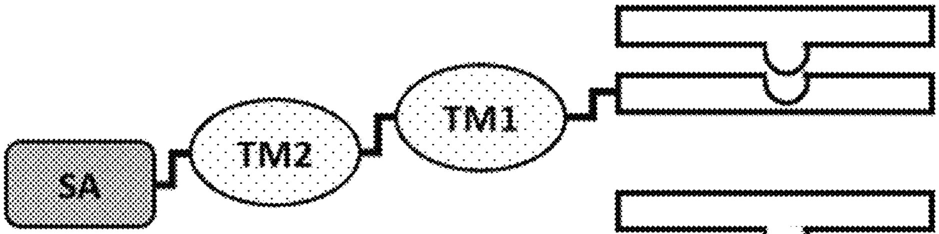
Figure 26H:
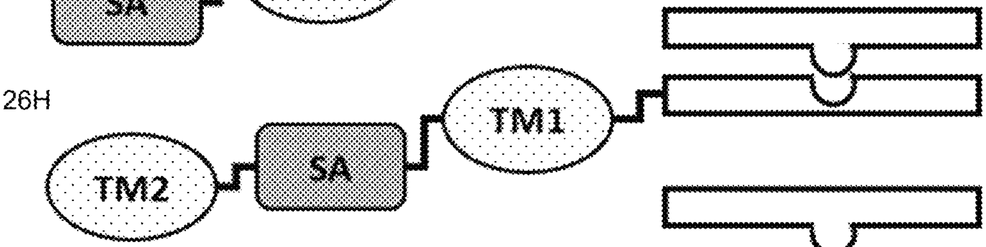
Figure 26I:
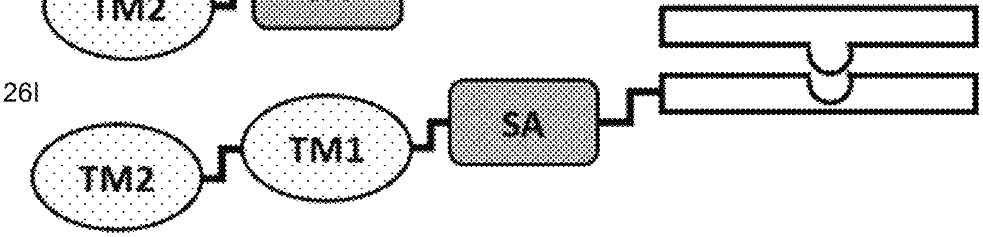
Figure 26J:
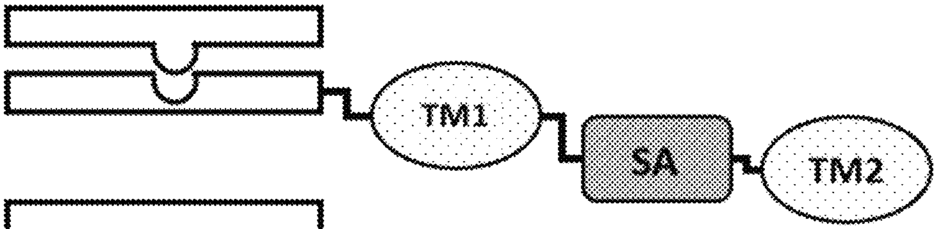
Figure 26K:
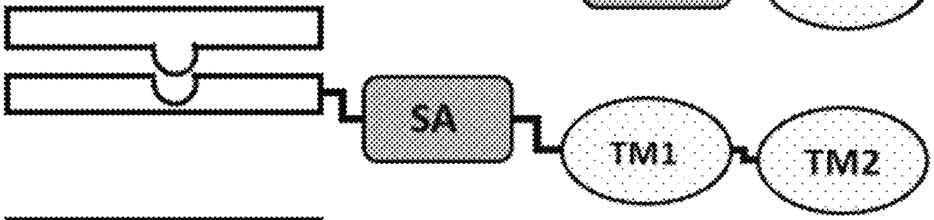
Figure 26L:
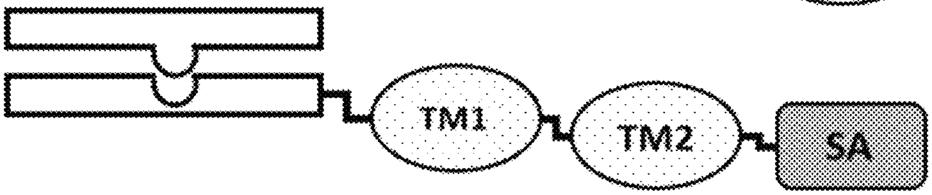
Figure 27A:
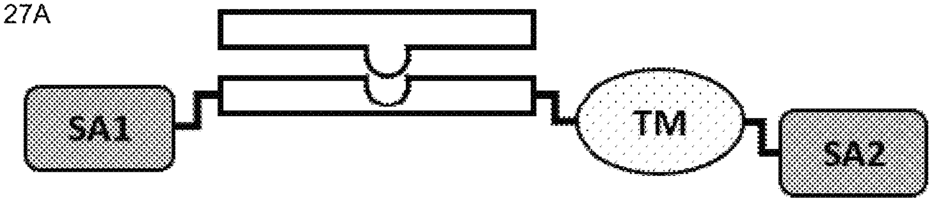
Figure 27B:
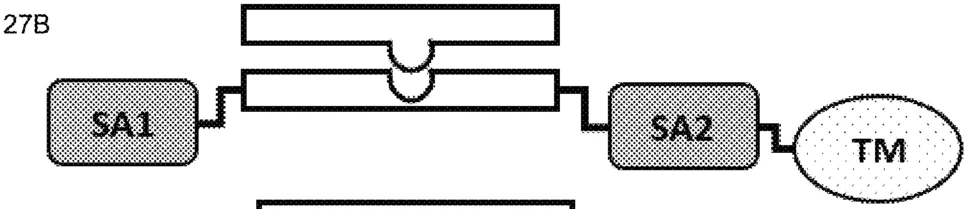
Figure 27C:
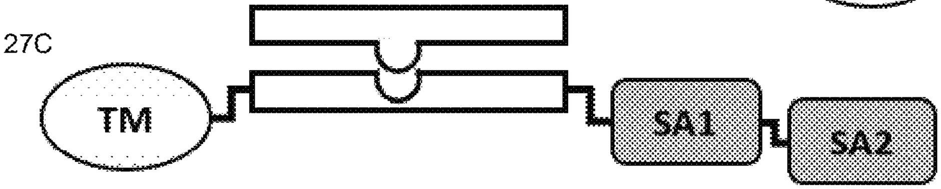
Figure 27D:
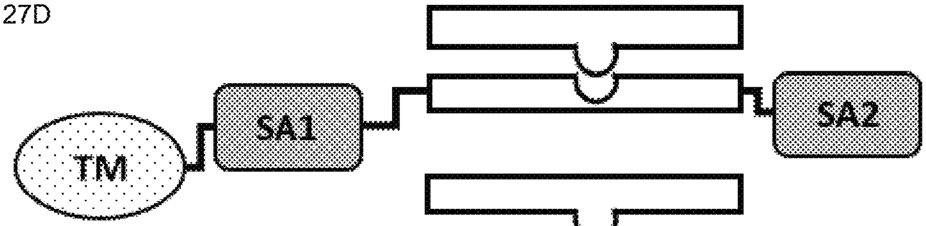
Figure 27E:
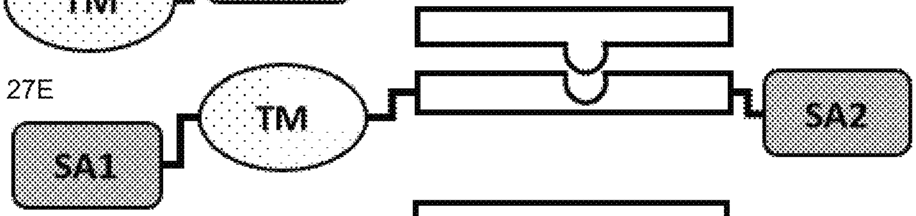
Figure 27F:
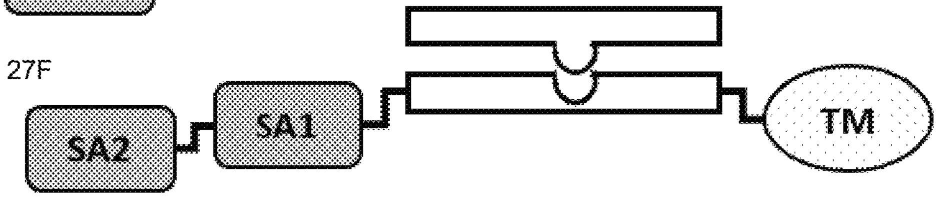
Figure 27G:
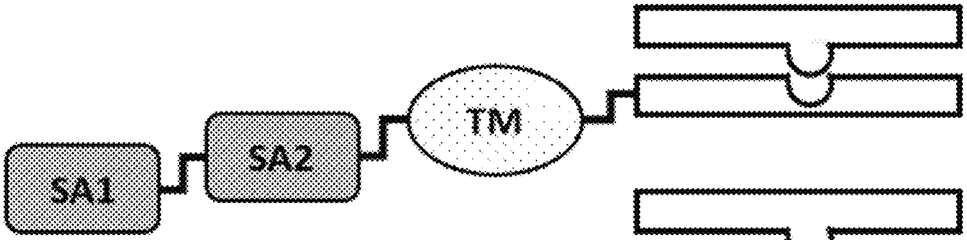
Figure 27H:
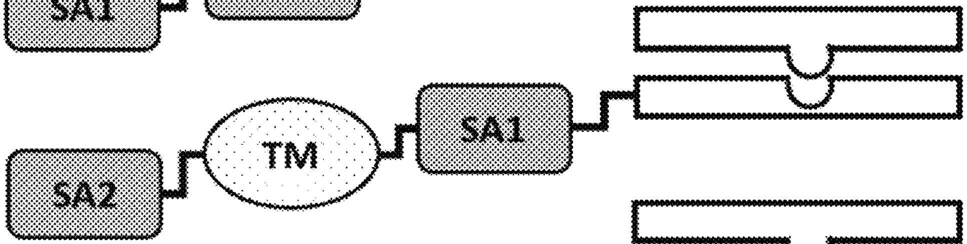
Figure 27I:
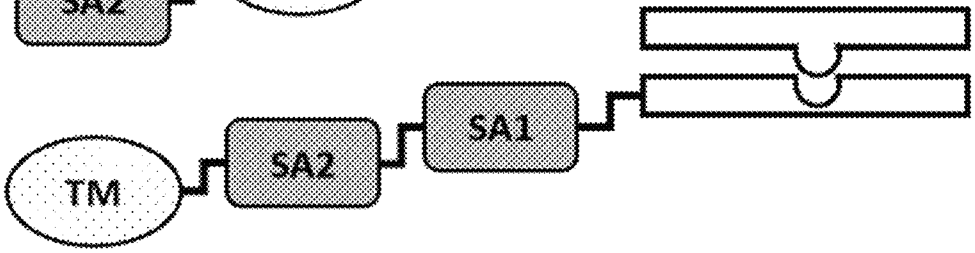
Figure 27J:
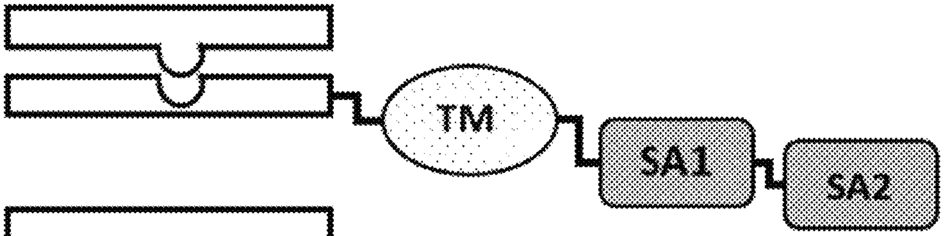
Figure 27K:
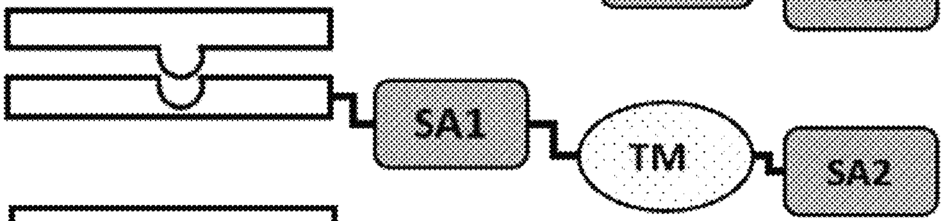
Figure 27L:
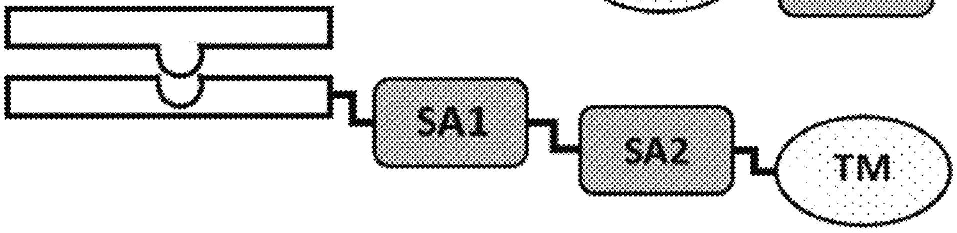
Figure 28A:
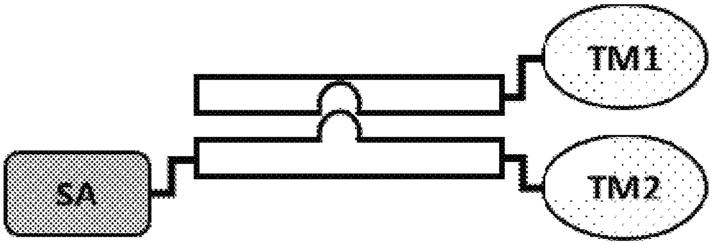
Figure 28B:
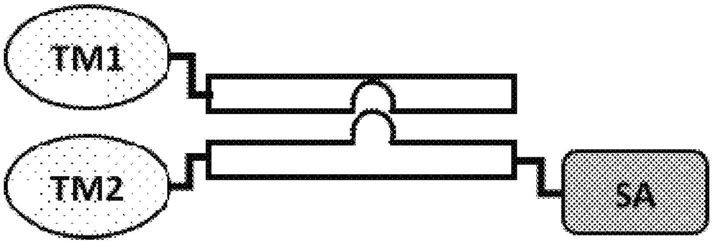
Figure 28C:
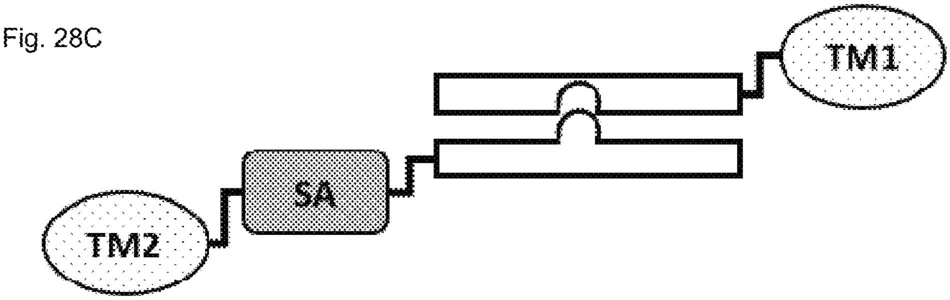
Figure 28D:
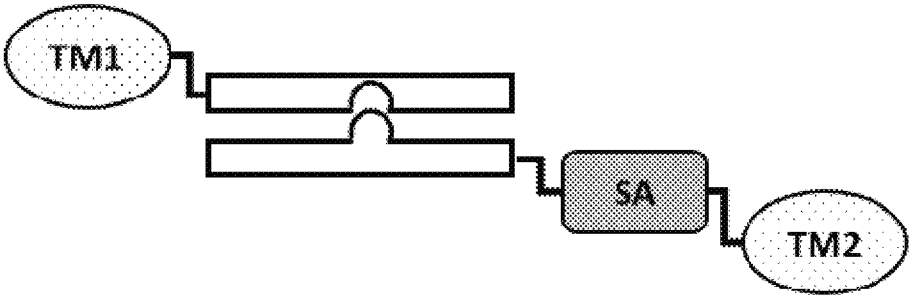
Figure 28E:
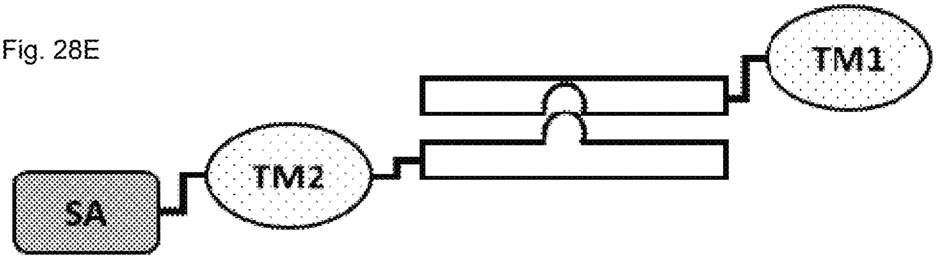
Figure 28F:
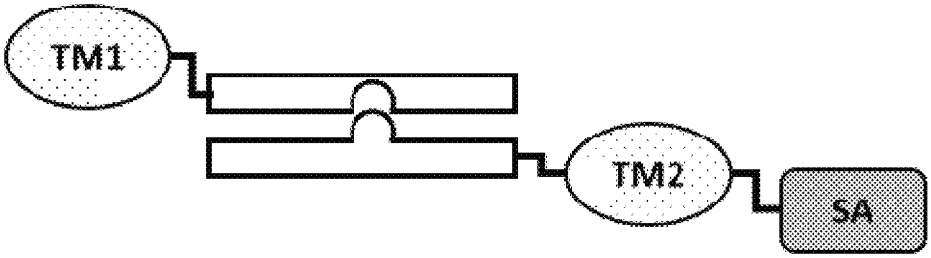
Figure 28G:
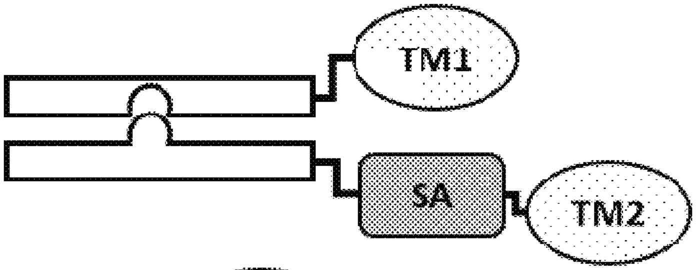
Figure 28H:
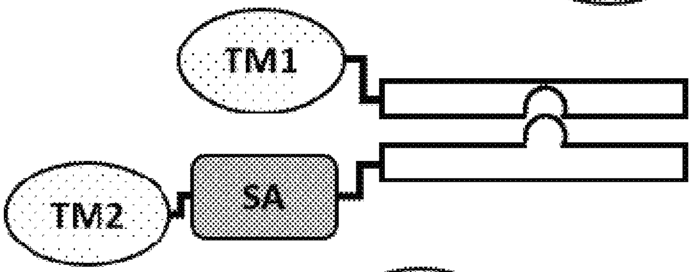
Figure 28I:
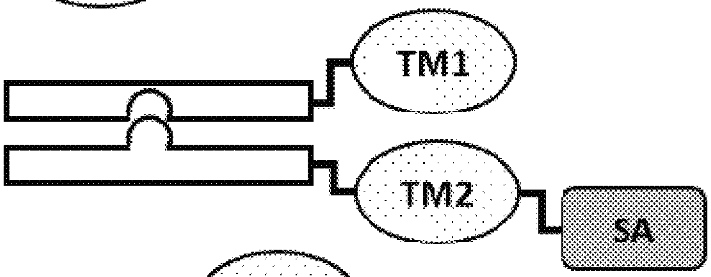
Figure 28J:
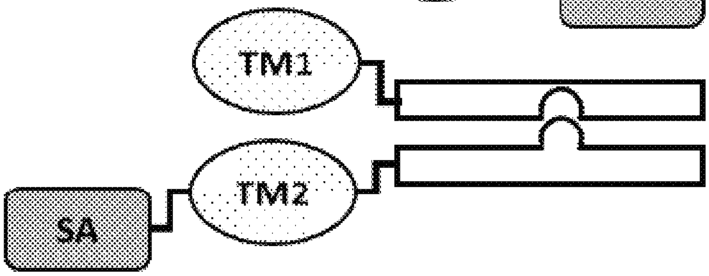
Figures 29A, 29B, 29C, 29D, 29E:
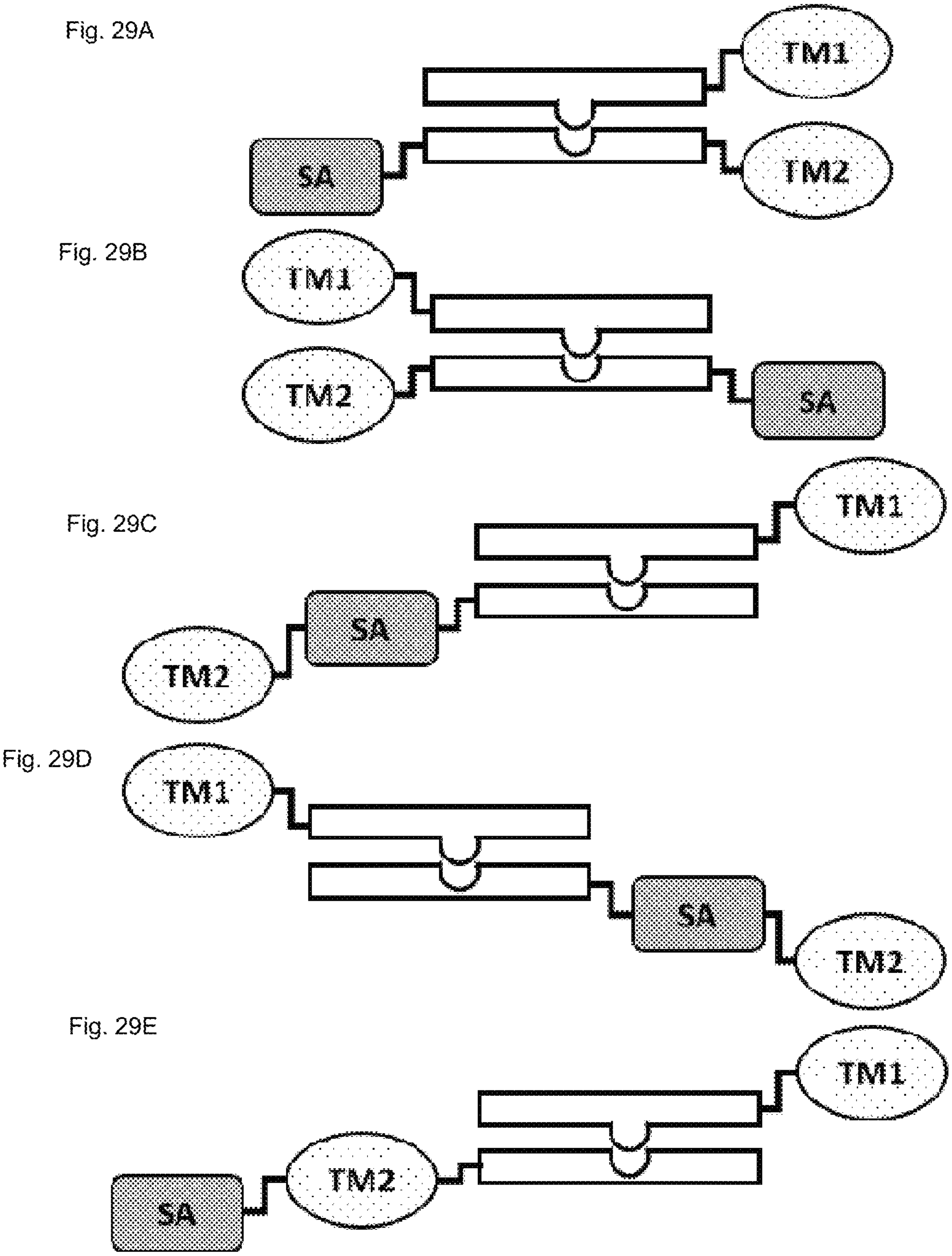
Figure 29F:
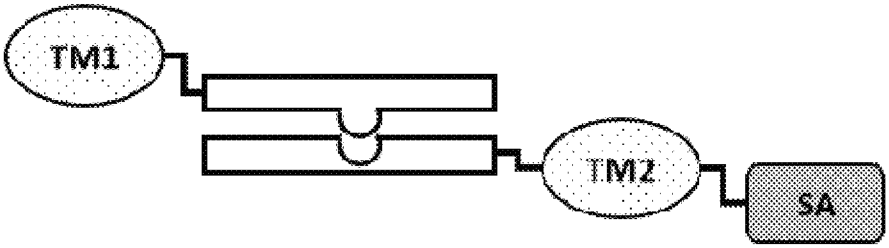
Figure 29G:
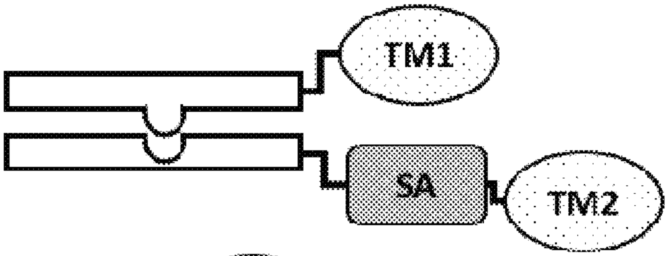
Figure 29H:
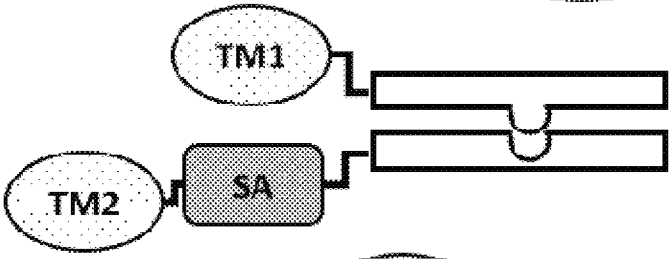
Figure 29I:
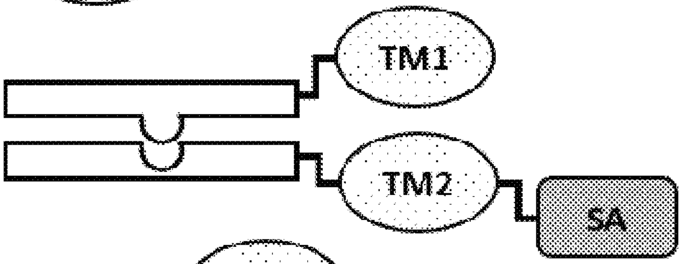
Figure 29J:
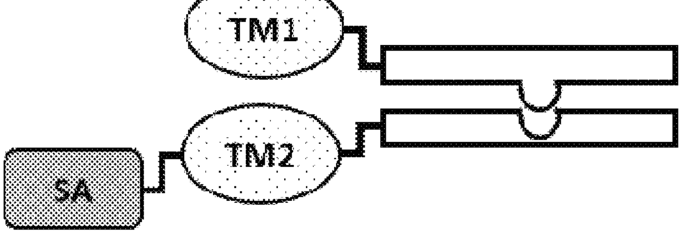
Figure 30A:
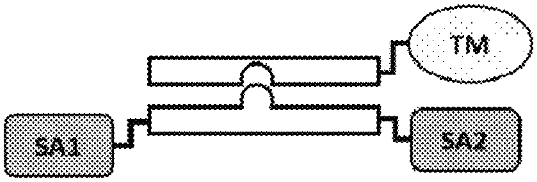
Figure 30B:
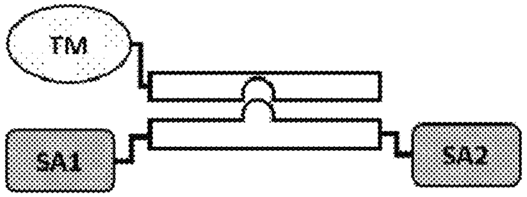
Figure 30C:
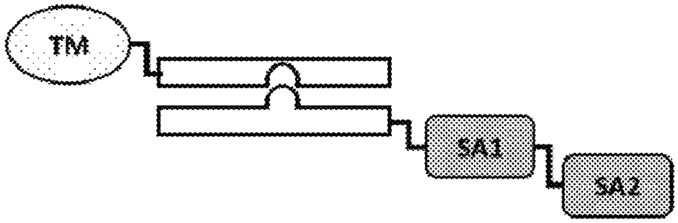
Figure 30D:
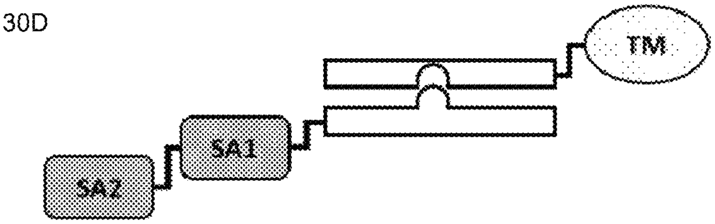
Figure 30E:
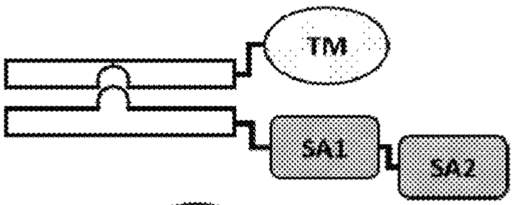
Figure 30F:
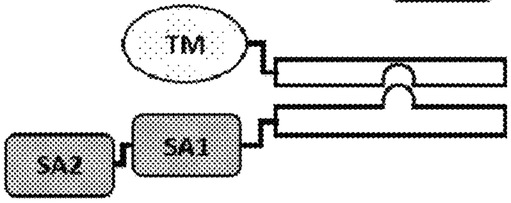
Figure 31A:
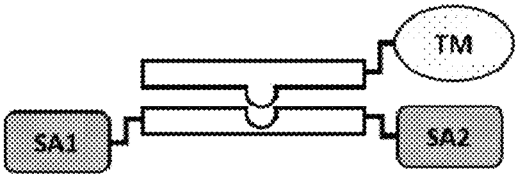
Figure 31B:
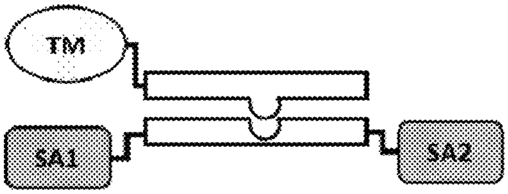
Figure 31C:
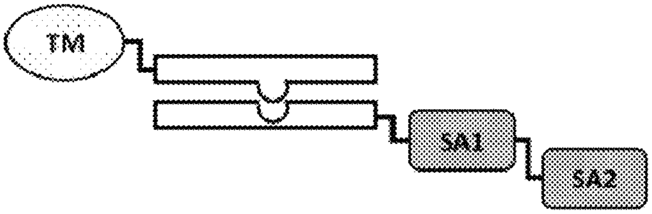
Figure 31D:
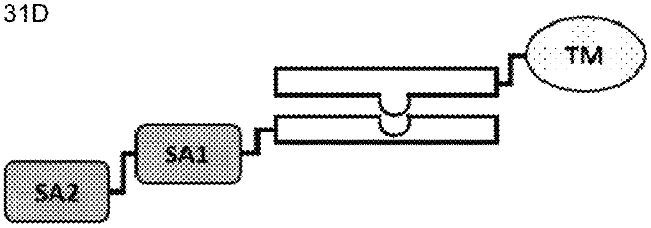
Figure 31E:
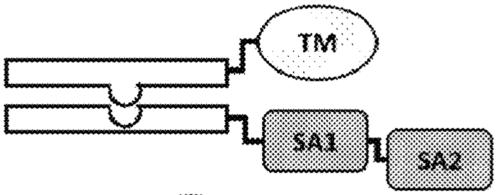
Figure 31F:
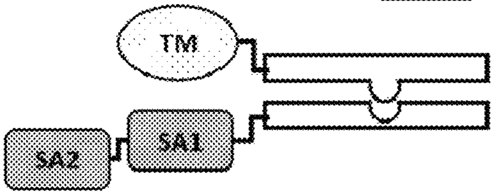

Based on the findings above, a type II AcTaferon (AFN-11) (FIG. 8D) was designed. Deletion of the eight (8) C-terminal amino acids reduced mIFN-γ activity approximately 7000-fold in an encephalomyocarditis virus (EMCV) cytopathic assay in L929 cells (FIG. 11), and more than 3000-fold in a TNF/IFN-γ cytotoxicity assay in B16BI6 cells (FIG. 8E). As seen for mCD20-AFN-11, the activity was completely recovered (FIG. 8E) and even surpassed that of wt mIFN-γ on B16BI6 cells expressing mCD20, predicting a more than 10000-fold AcTakine targeting efficiency. To target IFN-γ activity to tumor vasculature, the same mCD13 VHH as for AFR was used. In both the B16BI6 model and the human RL lymphoma model in immunodeficient NSG mice, daily treatment with mCD13-AFN-II resulted in significant tumor growth suppression (FIG. 12A and 12B). To evaluate the in vivo synergy between mCD13-AFR and mCD13-AFN-II, equimolar doses in combination treatments were used. In both tumor models, combination therapy induced very rapid tumor necrosis, resulting in complete regression within 6 days of treatment in all mice (FIGS. 12A and 12B), demonstrating the generic and direct effect on tumor vasculature, independent of an immune response. The kinetics and appearance of tumor necrosis induced by mCD13-AFN-II/mCD13-AFR combination therapy (FIGS. 12A and 12B) were similar to those observed during treatment with high-dose wtTNF alone, suggesting that mCD13-AFN-II is able to shift mCD13-AFR signaling towards cell death. This was further confirmed by the detection of selective endothelial apoptosis in B16BI6 tumors as soon as 3 to 5 hours after mCD13-AFN-II/mCD13-AFR treatment (FIG. 12C). Strikingly, even this synergistic mCD13-IFN-II/mCD13-AFR co-treatment did not evoke a detectable toxic response.

Equivalents

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims. Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties. The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A method for treating cancer comprising co-administering to a subject in need thereof an effective amount of:

(a) a chimeric protein or chimeric protein complex comprising:

(i) a targeting moiety comprising a recognition domain which recognizes and binds to CD13; and (ii) a modified tumor necrosis factor (TNF) signaling agent, the modified TNF signaling agent having one or more mutations that confer improved safety as compared to a wild type TNF signaling agent, and (b) a chimeric protein or chimeric protein complex comprising:

(i) a targeting moiety comprising a recognition domain that recognizes and binds to CD8 and (ii) a modified interferon (IFN) signaling agent, the modified IFN signaling agent having one or more mutations that confer improved safety relative to a wild type signaling agent as compared to a wild type signaling agent, and wherein the targeting moiety and modified IFN signaling agent are optionally connected with one or more linkers.

2. The method of claim 1, wherein the CD13 recognition domain recognizes and binds an antigen or receptor on an endothelial cell of tumor neovasculature and/or tumor cell.

3. The method of claim 1, wherein the modified TNF signaling agent comprises one or more mutations conferring reduced affinity or activity at the TNF signaling agent's receptor relative to a wild type TNF signaling agent.

4. The method of claim 1, wherein the modified TNF signaling agent comprises one or more mutations conferring substantially reduced or ablated affinity or activity for a receptor relative to a wild type TNF signaling agent.

5. The method of claim 1, wherein the modified IFN signaling agent comprises one or more mutations conferring reduced affinity or activity at the signaling agent's receptor relative to a wild type IFN signaling agent.

6. The method of claim 5, wherein the modified IFN signaling agent is a modified IFN-γ.

7. The method of claim 6, wherein the modified IFN-γ is a human IFN-γ.

8. The method of claim 7, wherein the modified IFN-γ exhibits reduced affinity and/or biological activity for IFN-γ receptor.

9. The method of claim 8, wherein the modified IFN-γ has a truncation at the C-terminus of about 5 to about 20 amino acid residues.

10. The method of claim 7, wherein the modified IFN-γ comprises one or more mutations at positions Q1, V5, E9, K12, H19, S20, V22, A23, D24, N25, G26, T27, L30, K108, H111, E112, 1114, Q115, A118, E119, and K125.

11. The method of claim 10, wherein the one or more mutations are substitutions selected from V5E, S20E, V22A, A23G, A23F, D24G, G26Q, H111A, H111D, 1114A, Q115A, and A118G.

* * * * *

SEQUENCE LISTING

```
<160> NUMBER OF SEQ ID NOS: 381

<210> SEQ ID NO 1
<211> LENGTH: 967
<212> TYPE: PRT
<213> ORGANISM: Artificial Sequence
```

<220> FEATURE:
<223> OTHER INFORMATION: Synthetic Sequence

<400> SEQUENCE: 1

```
Met Ala Lys Gly Phe Tyr Ile Ser Lys Ser Leu Gly Ile Leu Gly Ile
1               5                   10                  15

Leu Leu Gly Val Ala Ala Val Cys Thr Ile Ile Ala Leu Ser Val Val
            20                  25                  30

Tyr Ser Gln Glu Lys Asn Lys Asn Ala Asn Ser Ser Pro Val Ala Ser
        35                  40                  45

Thr Thr Pro Ser Ala Ser Ala Thr Thr Asn Pro Ala Ser Ala Thr Thr
    50                  55                  60

Leu Asp Gln Ser Lys Ala Trp Asn Arg Tyr Arg Leu Pro Asn Thr Leu
65                  70                  75                  80

Lys Pro Asp Ser Tyr Arg Val Thr Leu Arg Pro Tyr Leu Thr Pro Asn
                85                  90                  95

Asp Arg Gly Leu Tyr Val Phe Lys Gly Ser Ser Thr Val Arg Phe Thr
            100                 105                 110

Cys Lys Glu Ala Thr Asp Val Ile Ile Ile His Ser Lys Lys Leu Asn
        115                 120                 125

Tyr Thr Leu Ser Gln Gly His Arg Val Val Leu Arg Gly Val Gly Gly
    130                 135                 140

Ser Gln Pro Pro Asp Ile Asp Lys Thr Glu Leu Val Glu Pro Thr Glu
145                 150                 155                 160

Tyr Leu Val Val His Leu Lys Gly Ser Leu Val Lys Asp Ser Gln Tyr
                165                 170                 175

Glu Met Asp Ser Glu Phe Glu Gly Glu Leu Ala Asp Asp Leu Ala Gly
            180                 185                 190

Phe Tyr Arg Ser Glu Tyr Met Glu Gly Asn Val Arg Lys Val Val Ala
        195                 200                 205

Thr Thr Gln Met Gln Ala Ala Asp Ala Arg Lys Ser Phe Pro Cys Phe
    210                 215                 220

Asp Glu Pro Ala Met Lys Ala Glu Phe Asn Ile Thr Leu Ile His Pro
225                 230                 235                 240

Lys Asp Leu Thr Ala Leu Ser Asn Met Leu Pro Lys Gly Pro Ser Thr
                245                 250                 255

Pro Leu Pro Glu Asp Pro Asn Trp Asn Val Thr Glu Phe His Thr Thr
            260                 265                 270

Pro Lys Met Ser Thr Tyr Leu Leu Ala Phe Ile Val Ser Glu Phe Asp
        275                 280                 285

Tyr Val Glu Lys Gln Ala Ser Asn Gly Val Leu Ile Arg Ile Trp Ala
    290                 295                 300

Arg Pro Ser Ala Ile Ala Ala Gly His Gly Asp Tyr Ala Leu Asn Val
305                 310                 315                 320

Thr Gly Pro Ile Leu Asn Phe Phe Ala Gly His Tyr Asp Thr Pro Tyr
                325                 330                 335

Pro Leu Pro Lys Ser Asp Gln Ile Gly Leu Pro Asp Phe Asn Ala Gly
            340                 345                 350

Ala Met Glu Asn Trp Gly Leu Val Thr Tyr Arg Glu Asn Ser Leu Leu
        355                 360                 365

Phe Asp Pro Leu Ser Ser Ser Ser Ser Asn Lys Glu Arg Val Val Thr
    370                 375                 380

Val Ile Ala His Glu Leu Ala His Gln Trp Phe Gly Asn Leu Val Thr
385                 390                 395                 400
```

```
Ile Glu Trp Trp Asn Asp Leu Trp Leu Asn Glu Gly Phe Ala Ser Tyr
                405                 410                 415

Val Glu Tyr Leu Gly Ala Asp Tyr Ala Glu Pro Thr Trp Asn Leu Lys
            420                 425                 430

Asp Leu Met Val Leu Asn Asp Val Tyr Arg Val Met Ala Val Asp Ala
        435                 440                 445

Leu Ala Ser Ser His Pro Leu Ser Thr Pro Ala Ser Glu Ile Asn Thr
    450                 455                 460

Pro Ala Gln Ile Ser Glu Leu Phe Asp Ala Ile Ser Tyr Ser Lys Gly
465                 470                 475                 480

Ala Ser Val Leu Arg Met Leu Ser Ser Phe Leu Ser Glu Asp Val Phe
                485                 490                 495

Lys Gln Gly Leu Ala Ser Tyr Leu His Thr Phe Ala Tyr Gln Asn Thr
            500                 505                 510

Ile Tyr Leu Asn Leu Trp Asp His Leu Gln Glu Ala Val Asn Asn Arg
        515                 520                 525

Ser Ile Gln Leu Pro Thr Thr Val Arg Asp Ile Met Asn Arg Trp Thr
    530                 535                 540

Leu Gln Met Gly Phe Pro Val Ile Thr Val Asp Thr Ser Thr Gly Thr
545                 550                 555                 560

Leu Ser Gln Glu His Phe Leu Leu Asp Pro Asp Ser Asn Val Thr Arg
                565                 570                 575

Pro Ser Glu Phe Asn Tyr Val Trp Ile Val Pro Ile Thr Ser Ile Arg
            580                 585                 590

Asp Gly Arg Gln Gln Gln Asp Tyr Trp Leu Ile Asp Val Arg Ala Gln
        595                 600                 605

Asn Asp Leu Phe Ser Thr Ser Gly Asn Glu Trp Val Leu Leu Asn Leu
    610                 615                 620

Asn Val Thr Gly Tyr Tyr Arg Val Asn Tyr Asp Glu Glu Asn Trp Arg
625                 630                 635                 640

Lys Ile Gln Thr Gln Leu Gln Arg Asp His Ser Ala Ile Pro Val Ile
                645                 650                 655

Asn Arg Ala Gln Ile Ile Asn Asp Ala Phe Asn Leu Ala Ser Ala His
            660                 665                 670

Lys Val Pro Val Thr Leu Ala Leu Asn Asn Thr Leu Phe Leu Ile Glu
        675                 680                 685

Glu Arg Gln Tyr Met Pro Trp Glu Ala Ala Leu Ser Ser Leu Ser Tyr
    690                 695                 700

Phe Lys Leu Met Phe Asp Arg Ser Glu Val Tyr Gly Pro Met Lys Asn
705                 710                 715                 720

Tyr Leu Lys Lys Gln Val Thr Pro Leu Phe Ile His Phe Arg Asn Asn
                725                 730                 735

Thr Asn Asn Trp Arg Glu Ile Pro Glu Asn Leu Met Asp Gln Tyr Ser
            740                 745                 750

Glu Val Asn Ala Ile Ser Thr Ala Cys Ser Asn Gly Val Pro Glu Cys
        755                 760                 765

Glu Glu Met Val Ser Gly Leu Phe Lys Gln Trp Met Glu Asn Pro Asn
    770                 775                 780

Asn Asn Pro Ile His Pro Asn Leu Arg Ser Thr Val Tyr Cys Asn Ala
785                 790                 795                 800

Ile Ala Gln Gly Gly Glu Glu Glu Trp Asp Phe Ala Trp Glu Gln Phe
                805                 810                 815
```

Arg Asn Ala Thr Leu Val Asn Glu Ala Asp Lys Leu Arg Ala Ala Leu
820 825 830

Ala Cys Ser Lys Glu Leu Trp Ile Leu Asn Arg Tyr Leu Ser Tyr Thr
835 840 845

Leu Asn Pro Asp Leu Ile Arg Lys Gln Asp Ala Thr Ser Thr Ile Ile
850 855 860

Ser Ile Thr Asn Asn Val Ile Gly Gln Gly Leu Val Trp Asp Phe Val
865 870 875 880

Gln Ser Asn Trp Lys Lys Leu Phe Asn Asp Tyr Gly Gly Gly Ser Phe
885 890 895

Ser Phe Ser Asn Leu Ile Gln Ala Val Thr Arg Arg Phe Ser Thr Glu
900 905 910

Tyr Glu Leu Gln Gln Leu Glu Gln Phe Lys Lys Asp Asn Glu Glu Thr
915 920 925

Gly Phe Gly Ser Gly Thr Arg Ala Leu Glu Gln Ala Leu Glu Lys Thr
930 935 940

Lys Ala Asn Ile Lys Trp Val Lys Glu Asn Lys Glu Val Val Leu Gln
945 950 955 960

Trp Phe Thr Glu Asn Ser Lys
965

<210> SEQ ID NO 2
<211> LENGTH: 157
<212> TYPE: PRT
<213> ORGANISM: Artificial Sequence
<220> FEATURE:
<223> OTHER INFORMATION: Synthetic Sequence

<400> SEQUENCE: 2

Val Arg Ser Ser Ser Arg Thr Pro Ser Asp Lys Pro Val Ala His Val
1 5 10 15

Val Ala Asn Pro Gln Ala Glu Gly Gln Leu Gln Trp Leu Asn Arg Arg
20 25 30

Ala Asn Ala Leu Leu Ala Asn Gly Val Glu Leu Arg Asp Asn Gln Leu
35 40 45

Val Val Pro Ser Glu Gly Leu Tyr Leu Ile Tyr Ser Gln Val Leu Phe
50 55 60

Lys Gly Gln Gly Cys Pro Ser Thr His Val Leu Leu Thr His Thr Ile
65 70 75 80

Ser Arg Ile Ala Val Ser Tyr Gln Thr Lys Val Asn Leu Leu Ser Ala
85 90 95

Ile Lys Ser Pro Cys Gln Arg Glu Thr Pro Glu Gly Ala Glu Ala Lys
100 105 110

Pro Trp Tyr Glu Pro Ile Tyr Leu Gly Gly Val Phe Gln Leu Glu Lys
115 120 125

Gly Asp Arg Leu Ser Ala Glu Ile Asn Arg Pro Asp Tyr Leu Asp Phe
130 135 140

Ala Glu Ser Gly Gln Val Tyr Phe Gly Ile Ile Ala Leu
145 150 155

<210> SEQ ID NO 3
<211> LENGTH: 171
<212> TYPE: PRT
<213> ORGANISM: Artificial Sequence
<220> FEATURE:
<223> OTHER INFORMATION: Synthetic Sequence

<400> SEQUENCE: 3

```
Leu Pro Gly Val Gly Leu Thr Pro Ser Ala Ala Gln Thr Ala Arg Gln
1               5                   10                  15

His Pro Lys Met His Leu Ala His Ser Asn Leu Lys Pro Ala Ala His
            20                  25                  30

Leu Ile Gly Asp Pro Ser Lys Gln Asn Ser Leu Leu Trp Arg Ala Asn
        35                  40                  45

Thr Asp Arg Ala Phe Leu Gln Asp Gly Phe Ser Leu Ser Asn Asn Ser
    50                  55                  60

Leu Leu Val Pro Thr Ser Gly Ile Tyr Phe Val Tyr Ser Gln Val Val
65                  70                  75                  80

Phe Ser Gly Lys Ala Tyr Ser Pro Lys Ala Thr Ser Ser Pro Leu Tyr
                85                  90                  95

Leu Ala His Glu Val Gln Leu Phe Ser Ser Gln Tyr Pro Phe His Val
            100                 105                 110

Pro Leu Leu Ser Ser Gln Lys Met Val Tyr Pro Gly Leu Gln Glu Pro
        115                 120                 125

Trp Leu His Ser Met Tyr His Gly Ala Ala Phe Gln Leu Thr Gln Gly
    130                 135                 140

Asp Gln Leu Ser Thr His Thr Asp Gly Ile Pro His Leu Val Leu Ser
145                 150                 155                 160

Pro Ser Thr Val Phe Phe Gly Ala Phe Ala Leu
                165                 170


<210> SEQ ID NO 4
<211> LENGTH: 281
<212> TYPE: PRT
<213> ORGANISM: Artificial Sequence
<220> FEATURE:
<223> OTHER INFORMATION: Synthetic Sequence

<400> SEQUENCE: 4

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190
```

Gln Glu Glu Ile Lys Glu Asn Thr Lys Asn Asp Lys Gln Met Val Gln
195 200 205

Tyr Ile Tyr Lys Tyr Thr Ser Tyr Pro Asp Pro Ile Leu Leu Met Lys
210 215 220

Ser Ala Arg Asn Ser Cys Trp Ser Lys Asp Ala Glu Tyr Gly Leu Tyr
225 230 235 240

Ser Ile Tyr Gln Gly Gly Ile Phe Glu Leu Lys Glu Asn Asp Arg Ile
245 250 255

Phe Val Ser Val Thr Asn Glu His Leu Ile Asp Met Asp His Glu Ala
260 265 270

Ser Phe Phe Gly Ala Phe Leu Val Gly
275 280

<210> SEQ ID NO 5
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 5

Gly Gly Gly Gly Ser
1 5

<210> SEQ ID NO 6
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 6

Gly Gly Gly Gly Ser Gly Gly Gly Gly Ser
1 5 10

<210> SEQ ID NO 7
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 7

Gly Gly Gly Gly Ser Gly Gly Gly Gly Ser Gly Gly Gly Gly Ser
1 5 10 15

<210> SEQ ID NO 8
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 8

Gly Gly Gly Gly Ser Gly Gly Gly Gly Ser Gly Gly Gly Gly Ser Gly
1 5 10 15

Gly Gly Gly Ser
20

<210> SEQ ID NO 9
<211> LENGTH: 25
<212> TYPE: PRT
<213> ORGANISM: Artificial Sequence

```
<220> FEATURE:
<223> OTHER INFORMATION: Synthetic Sequence

<400> SEQUENCE: 9

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25


<210> SEQ ID NO 10
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 10

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30


<210> SEQ ID NO 11
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 11

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35


<210> SEQ ID NO 12
<211> LENGTH: 40
<212> TYPE: PRT
<213> ORGANISM: Artificial Sequence
<220> FEATURE:
<223> OTHER INFORMATION: Synthetic Sequence

<400> SEQUENCE: 12

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40


<210> SEQ ID NO 13
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 13

Gly Gly Ser Gly Gly Ser Gly Gly Gly Gly Ser Gly Gly Gly Gly Ser
1               5                   10                  15
```

<210> SEQ ID NO 14
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 14

Gly Gly Gly Gly Gly Gly Gly Gly
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 15

Gly Gly Gly Gly Gly Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 16

Glu Ala Ala Ala Lys
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 17

Glu Ala Ala Ala Lys Glu Ala Ala Ala Lys
1               5                   10

<210> SEQ ID NO 18
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 18

Glu Ala Ala Ala Lys Glu Ala Ala Ala Lys Glu Ala Ala Ala Lys
1               5                   10                  15

<210> SEQ ID NO 19
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 19

Ala Glu Ala Ala Ala Lys Glu Ala Ala Ala Lys Ala
1               5                   10

<210> SEQ ID NO 20

<211> LENGTH: 17
<212> TYPE: PRT
<213> ORGANISM: Artificial Sequence
<220> FEATURE:
<223> OTHER INFORMATION: Synthetic Sequence

<400> SEQUENCE: 20

Ala Glu Ala Ala Ala Lys Glu Ala Ala Ala Lys Glu Ala Ala Ala Lys
1 5 10 15

Ala

<210> SEQ ID NO 21
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 21

Ala Glu Ala Ala Ala Lys Glu Ala Ala Ala Lys Glu Ala Ala Ala Lys
1 5 10 15

Glu Ala Ala Ala Lys Ala
20

<210> SEQ ID NO 22
<211> LENGTH: 27
<212> TYPE: PRT
<213> ORGANISM: Artificial Sequence
<220> FEATURE:
<223> OTHER INFORMATION: Synthetic Sequence

<400> SEQUENCE: 22

Ala Glu Ala Ala Ala Lys Glu Ala Ala Ala Lys Glu Ala Ala Ala Lys
1 5 10 15

Glu Ala Ala Ala Lys Glu Ala Ala Ala Lys Ala
20 25

<210> SEQ ID NO 23
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 23

Ala Glu Ala Ala Ala Lys Glu Ala Ala Ala Lys Ala
1 5 10

<210> SEQ ID NO 24
<211> LENGTH: 46
<212> TYPE: PRT
<213> ORGANISM: Artificial Sequence
<220> FEATURE:
<223> OTHER INFORMATION: Synthetic Sequence

<400> SEQUENCE: 24

Ala Glu Ala Ala Ala Lys Glu Ala Ala Ala Lys Glu Ala Ala Ala Lys
1 5 10 15

Glu Ala Ala Ala Lys Ala Leu Glu Ala Glu Ala Ala Ala Lys Glu Ala
20 25 30

Ala Ala Lys Glu Ala Ala Ala Lys Glu Ala Ala Ala Lys Ala
35 40 45

<210> SEQ ID NO 25

<211> LENGTH: 5
<212> TYPE: PRT
<213> ORGANISM: Artificial Sequence
<220> FEATURE:
<223> OTHER INFORMATION: Synthetic Sequence

<400> SEQUENCE: 25

Pro Ala Pro Ala Pro
1 5

<210> SEQ ID NO 26
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 26

Lys Glu Ser Gly Ser Val Ser Ser Glu Gln Leu Ala Gln Phe Arg Ser
1 5 10 15

Leu Asp

<210> SEQ ID NO 27
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 27

Glu Gly Lys Ser Ser Gly Ser Gly Ser Glu Ser Lys Ser Thr
1 5 10

<210> SEQ ID NO 28
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 28

Gly Ser Ala Gly Ser Ala Ala Gly Ser Gly Glu Phe
1 5 10

<210> SEQ ID NO 29
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 29

Gly Gly Ser
1

<210> SEQ ID NO 30
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 30

Gly Gly Ser Gly Gly Ser
1 5

<210> SEQ ID NO 31
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 31

Gly Gly Ser Gly Gly Ser Gly Gly Ser
1               5

<210> SEQ ID NO 32
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 32

Gly Gly Ser Gly Gly Ser Gly Gly Ser Gly Gly Ser
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 33

Gly Gly Ser Gly Gly Ser Gly Gly Ser Gly Gly Ser Gly Gly Ser
1               5                   10                  15

<210> SEQ ID NO 34
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 34

Gly Gly Ser Gly Gly Ser Gly Gly Ser Gly Gly Ser Gly Gly Ser Gly
1               5                   10                  15

Gly Ser

<210> SEQ ID NO 35
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 35

Gly Gly Ser Gly Gly Ser Gly Gly Ser Gly Gly Ser Gly Gly Ser Gly
1               5                   10                  15

Gly Ser Gly Gly Ser
            20

<210> SEQ ID NO 36
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 36

Gly Gly Ser Gly Gly Ser Gly Gly Ser Gly Gly Ser Gly Gly Ser Gly
1 5 10 15

Gly Ser Gly Gly Ser Gly Gly Ser
20

<210> SEQ ID NO 37
<211> LENGTH: 27
<212> TYPE: PRT
<213> ORGANISM: Artificial Sequence
<220> FEATURE:
<223> OTHER INFORMATION: Synthetic Sequence

<400> SEQUENCE: 37

Gly Gly Ser Gly Gly Ser Gly Gly Ser Gly Gly Ser Gly Gly Ser Gly
1 5 10 15

Gly Ser Gly Gly Ser Gly Gly Ser Gly Gly Ser
20 25

<210> SEQ ID NO 38
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 38

Gly Gly Ser Gly Gly Ser Gly Gly Ser Gly Gly Ser Gly Gly Ser Gly
1 5 10 15

Gly Ser Gly Gly Ser Gly Gly Ser Gly Gly Ser Gly Gly Ser
20 25 30

<210> SEQ ID NO 39
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 39

Gly Gly Ser Gly Gly Ser Gly Gly Ser Gly Gly Ser Gly Gly Ser Gly
1 5 10 15

Gly Ser Gly Gly Ser Gly Gly Ser Gly Gly Ser Gly Gly Ser Gly Gly
20 25 30

Ser

<210> SEQ ID NO 40
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 40

Gly Gly Ser Gly Gly Ser Gly Gly Ser Gly Gly Ser Gly Gly Ser Gly
1 5 10 15

Gly Ser Gly Gly Ser Gly Gly Ser Gly Gly Ser Gly Gly Ser Gly Gly
20 25 30

Ser Gly Gly Ser
35

<210> SEQ ID NO 41
<211> LENGTH: 39
<212> TYPE: PRT

<213> ORGANISM: Artificial Sequence
<220> FEATURE:
<223> OTHER INFORMATION: Synthetic Sequence

<400> SEQUENCE: 41

```
Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser
        35
```

<210> SEQ ID NO 42
<211> LENGTH: 42
<212> TYPE: PRT
<213> ORGANISM: Artificial Sequence
<220> FEATURE:
<223> OTHER INFORMATION: Synthetic Sequence

<400> SEQUENCE: 42

```
Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser
        35                  40
```

<210> SEQ ID NO 43
<211> LENGTH: 45
<212> TYPE: PRT
<213> ORGANISM: Artificial Sequence
<220> FEATURE:
<223> OTHER INFORMATION: Synthetic Sequence

<400> SEQUENCE: 43

```
Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser
        35                  40                  45
```

<210> SEQ ID NO 44
<211> LENGTH: 48
<212> TYPE: PRT
<213> ORGANISM: Artificial Sequence
<220> FEATURE:
<223> OTHER INFORMATION: Synthetic Sequence

<400> SEQUENCE: 44

```
Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45
```

<210> SEQ ID NO 45
<211> LENGTH: 51
<212> TYPE: PRT
<213> ORGANISM: Artificial Sequence
<220> FEATURE:
<223> OTHER INFORMATION: Synthetic Sequence

<400> SEQUENCE: 45

Gly Gly Ser Gly Gly Ser Gly Gly Ser Gly Gly Ser Gly Gly Ser Gly
1 5 10 15

Gly Ser Gly Gly Ser Gly Gly Ser Gly Gly Ser Gly Gly Ser Gly Gly
20 25 30

Ser Gly Gly Ser Gly Gly Ser Gly Gly Ser Gly Gly Ser Gly Gly Ser
35 40 45

Gly Gly Ser
50

<210> SEQ ID NO 46
<211> LENGTH: 54
<212> TYPE: PRT
<213> ORGANISM: Artificial Sequence
<220> FEATURE:
<223> OTHER INFORMATION: Synthetic Sequence

<400> SEQUENCE: 46

Gly Gly Ser Gly Gly Ser Gly Gly Ser Gly Gly Ser Gly Gly Ser Gly
1 5 10 15

Gly Ser Gly Gly Ser Gly Gly Ser Gly Gly Ser Gly Gly Ser Gly Gly
20 25 30

Ser Gly Gly Ser Gly Gly Ser Gly Gly Ser Gly Gly Ser Gly Gly Ser
35 40 45

Gly Gly Ser Gly Gly Ser
50

<210> SEQ ID NO 47
<211> LENGTH: 57
<212> TYPE: PRT
<213> ORGANISM: Artificial Sequence
<220> FEATURE:
<223> OTHER INFORMATION: Synthetic Sequence

<400> SEQUENCE: 47

Gly Gly Ser Gly Gly Ser Gly Gly Ser Gly Gly Ser Gly Gly Ser Gly
1 5 10 15

Gly Ser Gly Gly Ser Gly Gly Ser Gly Gly Ser Gly Gly Ser Gly Gly
20 25 30

Ser Gly Gly Ser Gly Gly Ser Gly Gly Ser Gly Gly Ser Gly Gly Ser
35 40 45

Gly Gly Ser Gly Gly Ser Gly Gly Ser
50 55

<210> SEQ ID NO 48
<211> LENGTH: 60
<212> TYPE: PRT
<213> ORGANISM: Artificial Sequence
<220> FEATURE:
<223> OTHER INFORMATION: Synthetic Sequence

<400> SEQUENCE: 48

Gly Gly Ser Gly Gly Ser Gly Gly Ser Gly Gly Ser Gly Gly Ser Gly
1 5 10 15

Gly Ser Gly Gly Ser Gly Gly Ser Gly Gly Ser Gly Gly Ser Gly Gly
20 25 30

Ser Gly Gly Ser Gly Gly Ser Gly Gly Ser Gly Gly Ser Gly Gly Ser
35 40 45

Gly Gly Ser Gly Gly Ser Gly Gly Ser Gly Gly Ser 50 55 60

<210> SEQ ID NO 49
<211> LENGTH: 45
<212> TYPE: PRT
<213> ORGANISM: Artificial Sequence
<220> FEATURE:
<223> OTHER INFORMATION: Synthetic Sequence

<400> SEQUENCE: 49

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser
35 40 45

<210> SEQ ID NO 50
<211> LENGTH: 50
<212> TYPE: PRT
<213> ORGANISM: Artificial Sequence
<220> FEATURE:
<223> OTHER INFORMATION: Synthetic Sequence

<400> SEQUENCE: 50

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser Gly Gly Gly
35 40 45

Gly Ser
50

<210> SEQ ID NO 51
<211> LENGTH: 55
<212> TYPE: PRT
<213> ORGANISM: Artificial Sequence
<220> FEATURE:
<223> OTHER INFORMATION: Synthetic Sequence

<400> SEQUENCE: 51

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser Gly Gly Gly
35 40 45

Gly Ser Gly Gly Gly Gly Ser
50 55

<210> SEQ ID NO 52
<211> LENGTH: 60
<212> TYPE: PRT
<213> ORGANISM: Artificial Sequence
<220> FEATURE:
<223> OTHER INFORMATION: Synthetic Sequence

<400> SEQUENCE: 52

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly

```
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser
    50                  55                  60


<210> SEQ ID NO 53
<211> LENGTH: 65
<212> TYPE: PRT
<213> ORGANISM: Artificial Sequence
<220> FEATURE:
<223> OTHER INFORMATION: Synthetic Sequence

<400> SEQUENCE: 53

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser
65


<210> SEQ ID NO 54
<211> LENGTH: 70
<212> TYPE: PRT
<213> ORGANISM: Artificial Sequence
<220> FEATURE:
<223> OTHER INFORMATION: Synthetic Sequence

<400> SEQUENCE: 54

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser
65                  70


<210> SEQ ID NO 55
<211> LENGTH: 75
<212> TYPE: PRT
<213> ORGANISM: Artificial Sequence
<220> FEATURE:
<223> OTHER INFORMATION: Synthetic Sequence

<400> SEQUENCE: 55

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60
```

Ser Gly Gly Gly Gly Ser Gly Gly Gly Gly Ser
65 70 75

<210> SEQ ID NO 56
<211> LENGTH: 80
<212> TYPE: PRT
<213> ORGANISM: Artificial Sequence
<220> FEATURE:
<223> OTHER INFORMATION: Synthetic Sequence

<400> SEQUENCE: 56

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser Gly Gly Gly
35 40 45

Gly Ser Gly Gly Gly Gly Ser Gly Gly Gly Gly Ser Gly Gly Gly Gly
50 55 60

Ser Gly Gly Gly Gly Ser Gly Gly Gly Gly Ser Gly Gly Gly Gly Ser
65 70 75 80

<210> SEQ ID NO 57
<211> LENGTH: 85
<212> TYPE: PRT
<213> ORGANISM: Artificial Sequence
<220> FEATURE:
<223> OTHER INFORMATION: Synthetic Sequence

<400> SEQUENCE: 57

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser Gly Gly Gly
35 40 45

Gly Ser Gly Gly Gly Gly Ser Gly Gly Gly Gly Ser Gly Gly Gly Gly
50 55 60

Ser Gly Gly Gly Gly Ser Gly Gly Gly Gly Ser Gly Gly Gly Gly Ser
65 70 75 80

Gly Gly Gly Gly Ser
85

<210> SEQ ID NO 58
<211> LENGTH: 90
<212> TYPE: PRT
<213> ORGANISM: Artificial Sequence
<220> FEATURE:
<223> OTHER INFORMATION: Synthetic Sequence

<400> SEQUENCE: 58

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser Gly Gly Gly
35 40 45

Gly Ser Gly Gly Gly Gly Ser Gly Gly Gly Gly Ser Gly Gly Gly Gly
50 55 60

```
Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser
                85                  90


<210> SEQ ID NO 59
<211> LENGTH: 95
<212> TYPE: PRT
<213> ORGANISM: Artificial Sequence
<220> FEATURE:
<223> OTHER INFORMATION: Synthetic Sequence

<400> SEQUENCE: 59

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser
                85                  90                  95


<210> SEQ ID NO 60
<211> LENGTH: 100
<212> TYPE: PRT
<213> ORGANISM: Artificial Sequence
<220> FEATURE:
<223> OTHER INFORMATION: Synthetic Sequence

<400> SEQUENCE: 60

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100


<210> SEQ ID NO 61
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 61

Gly Gly Gly Ser Glu
1               5
```

<210> SEQ ID NO 62
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 62

Gly Ser Glu Ser Gly
1               5

<210> SEQ ID NO 63
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 63

Gly Ser Glu Gly Ser
1               5

<210> SEQ ID NO 64
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 64

Gly Glu Gly Gly Ser Gly Glu Gly Ser Ser Gly Glu Gly Ser Ser Ser
1               5                   10                  15

Glu Gly Gly Gly Ser Glu Gly Gly Gly Ser Glu Gly Gly Gly Ser Glu
            20                  25                  30

Gly Gly Ser
        35

<210> SEQ ID NO 65
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 65

Cys Pro Pro Cys
1

<210> SEQ ID NO 66
<211> LENGTH: 235
<212> TYPE: PRT
<213> ORGANISM: Artificial Sequence
<220> FEATURE:
<223> OTHER INFORMATION: Synthetic Sequence

<400> SEQUENCE: 66

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

```
Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235


<210> SEQ ID NO 67
<211> LENGTH: 198
<212> TYPE: PRT
<213> ORGANISM: Artificial Sequence
<220> FEATURE:
<223> OTHER INFORMATION: Synthetic Sequence

<400> SEQUENCE: 67

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Gly Asn Arg Arg Arg
                165                 170                 175

Val Cys Lys Cys Pro Arg Pro Val Val Lys Ser Gly Asp Lys Pro Ser
            180                 185                 190
```

Leu Ser Ala Arg Tyr Val
195

<210> SEQ ID NO 68
<211> LENGTH: 276
<212> TYPE: PRT
<213> ORGANISM: Artificial Sequence
<220> FEATURE:
<223> OTHER INFORMATION: Synthetic Sequence

<400> SEQUENCE: 68

Met Arg Asn Gln Ala Pro Gly Arg Pro Lys Gly Ala Thr Phe Pro Pro
1 5 10 15

Arg Arg Pro Thr Gly Ser Arg Ala Pro Pro Leu Ala Pro Glu Leu Arg
20 25 30

Ala Lys Gln Arg Pro Gly Glu Arg Val Met Ala Leu Pro Val Thr Ala
35 40 45

Leu Leu Leu Pro Leu Ala Leu Leu Leu His Ala Ala Arg Pro Ser Gln
50 55 60

Phe Arg Val Ser Pro Leu Asp Arg Thr Trp Asn Leu Gly Glu Thr Val
65 70 75 80

Glu Leu Lys Cys Gln Val Leu Leu Ser Asn Pro Thr Ser Gly Cys Ser
85 90 95

Trp Leu Phe Gln Pro Arg Gly Ala Ala Ala Ser Pro Thr Phe Leu Leu
100 105 110

Tyr Leu Ser Gln Asn Lys Pro Lys Ala Ala Glu Gly Leu Asp Thr Gln
115 120 125

Arg Phe Ser Gly Lys Arg Leu Gly Asp Thr Phe Val Leu Thr Leu Ser
130 135 140

Asp Phe Arg Arg Glu Asn Glu Gly Tyr Tyr Phe Cys Ser Ala Leu Ser
145 150 155 160

Asn Ser Ile Met Tyr Phe Ser His Phe Val Pro Val Phe Leu Pro Ala
165 170 175

Lys Pro Thr Thr Thr Pro Ala Pro Arg Pro Pro Thr Pro Ala Pro Thr
180 185 190

Ile Ala Ser Gln Pro Leu Ser Leu Arg Pro Glu Ala Cys Arg Pro Ala
195 200 205

Ala Gly Gly Ala Val His Thr Arg Gly Leu Asp Phe Ala Cys Asp Ile
210 215 220

Tyr Ile Trp Ala Pro Leu Ala Gly Thr Cys Gly Val Leu Leu Leu Ser
225 230 235 240

Leu Val Ile Thr Leu Tyr Cys Asn His Arg Asn Arg Arg Arg Val Cys
245 250 255

Lys Cys Pro Arg Pro Val Val Lys Ser Gly Asp Lys Pro Ser Leu Ser
260 265 270

Ala Arg Tyr Val
275

<210> SEQ ID NO 69
<211> LENGTH: 210
<212> TYPE: PRT
<213> ORGANISM: Artificial Sequence
<220> FEATURE:
<223> OTHER INFORMATION: Synthetic Sequence

<400> SEQUENCE: 69

Met Arg Pro Arg Leu Trp Leu Leu Leu Ala Ala Gln Leu Thr Val Leu
1 5 10 15

```
His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
            180                 185                 190

Leu Cys Cys Arg Arg Arg Arg Ala Arg Leu Arg Phe Met Lys Gln Phe
        195                 200                 205

Tyr Lys
    210
```

```
<210> SEQ ID NO 70
<211> LENGTH: 221
<212> TYPE: PRT
<213> ORGANISM: Artificial Sequence
<220> FEATURE:
<223> OTHER INFORMATION: Synthetic Sequence

<400> SEQUENCE: 70

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160
```

```
Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
            180                 185                 190

Leu Cys Cys Arg Arg Arg Arg Ala Arg Leu Arg Phe Met Lys Gln Leu
        195                 200                 205

Arg Leu His Pro Leu Glu Lys Cys Ser Arg Met Asp Tyr
    210                 215                 220


<210> SEQ ID NO 71
<211> LENGTH: 213
<212> TYPE: PRT
<213> ORGANISM: Artificial Sequence
<220> FEATURE:
<223> OTHER INFORMATION: Synthetic Sequence

<400> SEQUENCE: 71

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Arg Arg Arg Arg Ala Arg Leu Arg Phe Met Lys
                165                 170                 175

Gln Pro Gln Gly Glu Gly Ile Ser Gly Thr Phe Val Pro Gln Cys Leu
            180                 185                 190

His Gly Tyr Tyr Ser Asn Thr Thr Thr Ser Gln Lys Leu Leu Asn Pro
        195                 200                 205

Trp Ile Leu Lys Thr
    210


<210> SEQ ID NO 72
<211> LENGTH: 246
<212> TYPE: PRT
<213> ORGANISM: Artificial Sequence
<220> FEATURE:
<223> OTHER INFORMATION: Synthetic Sequence

<400> SEQUENCE: 72

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
```

```
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
            180                 185                 190

Leu Cys Cys Arg Arg Arg Arg Ala Arg Leu Arg Phe Met Lys Gln Lys
        195                 200                 205

Phe Asn Ile Val Cys Leu Lys Ile Ser Gly Phe Thr Thr Cys Cys Cys
    210                 215                 220

Phe Gln Ile Leu Gln Ile Ser Arg Glu Tyr Gly Phe Gly Val Leu Leu
225                 230                 235                 240

Gln Lys Asp Ile Gly Gln
                245


<210> SEQ ID NO 73
<211> LENGTH: 243
<212> TYPE: PRT
<213> ORGANISM: Artificial Sequence
<220> FEATURE:
<223> OTHER INFORMATION: Synthetic Sequence

<400> SEQUENCE: 73

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
```

130 135 140

Thr Lys Lys Ser Thr Leu Lys Lys Arg Val Cys Arg Leu Pro Arg Pro
145 150 155 160

Glu Thr Gln Lys Gly Pro Leu Cys Ser Pro Ile Thr Leu Gly Leu Leu
165 170 175

Val Ala Gly Val Leu Val Leu Leu Val Ser Leu Gly Val Ala Ile His
180 185 190

Leu Cys Cys Arg Arg Arg Arg Ala Arg Leu Arg Phe Met Lys Gln Pro
195 200 205

Gln Gly Glu Gly Ile Ser Gly Thr Phe Val Pro Gln Cys Leu His Gly
210 215 220

Tyr Tyr Ser Asn Thr Thr Thr Ser Gln Lys Leu Leu Asn Pro Trp Ile
225 230 235 240

Leu Lys Thr

<210> SEQ ID NO 74
<211> LENGTH: 180
<212> TYPE: PRT
<213> ORGANISM: Artificial Sequence
<220> FEATURE:
<223> OTHER INFORMATION: Synthetic Sequence

<400> SEQUENCE: 74

Met Arg Pro Arg Leu Trp Leu Leu Leu Ala Ala Gln Leu Thr Val Leu
1 5 10 15

His Gly Asn Ser Val Leu Gln Gln Thr Pro Ala Tyr Ile Lys Val Gln
20 25 30

Thr Asn Lys Met Val Met Leu Ser Cys Glu Ala Lys Ile Ser Leu Ser
35 40 45

Asn Met Arg Ile Tyr Trp Leu Arg Gln Arg Gln Ala Pro Ser Ser Asp
50 55 60

Ser His His Glu Phe Leu Ala Leu Trp Asp Ser Ala Lys Gly Thr Ile
65 70 75 80

His Gly Glu Glu Val Glu Gln Glu Lys Ile Ala Val Phe Arg Asp Ala
85 90 95

Ser Arg Phe Ile Leu Asn Leu Thr Ser Val Lys Pro Glu Asp Ser Gly
100 105 110

Ile Tyr Phe Cys Met Ile Val Gly Ser Pro Glu Leu Thr Phe Gly Lys
115 120 125

Gly Thr Gln Leu Ser Val Val Asp Phe Leu Pro Thr Thr Ala Gln Pro
130 135 140

Thr Lys Lys Ser Thr Leu Lys Lys Arg Val Cys Arg Leu Pro Arg Pro
145 150 155 160

Glu Thr Gln Lys Gly Arg Arg Arg Arg Ala Arg Leu Arg Phe Met Lys
165 170 175

Gln Phe Tyr Lys
180

<210> SEQ ID NO 75
<211> LENGTH: 206
<212> TYPE: PRT
<213> ORGANISM: Artificial Sequence
<220> FEATURE:
<223> OTHER INFORMATION: Synthetic Sequence

<400> SEQUENCE: 75

Met Arg Pro Arg Leu Trp Leu Leu Leu Ala Ala Gln Leu Thr Val Leu

```
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Asp Phe Thr Asn Lys Gln Arg Ile Gly Phe Trp Cys
                165                 170                 175

Pro Ala Thr Lys Arg His Arg Ser Val Met Ser Thr Met Trp Lys Asn
            180                 185                 190

Glu Arg Arg Asp Thr Phe Asn Pro Gly Glu Phe Asn Gly Cys
        195                 200                 205


<210> SEQ ID NO 76
<211> LENGTH: 198
<212> TYPE: PRT
<213> ORGANISM: Artificial Sequence
<220> FEATURE:
<223> OTHER INFORMATION: Synthetic Sequence

<400> SEQUENCE: 76

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Leu Lys Gly Lys Val Tyr Gln Glu Pro Leu Ser
```

165 170 175

Pro Asn Ala Cys Met Asp Thr Thr Ala Ile Leu Gln Pro His Arg Ser
180 185 190

Cys Leu Thr His Gly Ser
195

<210> SEQ ID NO 77
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 77

Gly Phe Thr Phe Asp Asp Tyr Ala Met Ser
1 5 10

<210> SEQ ID NO 78
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 78

Gly Phe Thr Phe Asp Asp Tyr Ala Ile Gly
1 5 10

<210> SEQ ID NO 79
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 79

Gly Arg Ser Phe Ser Ser Tyr Thr Leu Ala
1 5 10

<210> SEQ ID NO 80
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 80

Gly Arg Thr Phe Ser Ser Tyr Thr Met Gly
1 5 10

<210> SEQ ID NO 81
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 81

Gly Arg Thr Phe Ser Ser Tyr Ile Met Gly
1 5 10

<210> SEQ ID NO 82
<211> LENGTH: 10
<212> TYPE: PRT
<213> ORGANISM: Artificial Sequence
<220> FEATURE:

<223> OTHER INFORMATION: Synthetic Sequence

<400> SEQUENCE: 82

Gly Arg Thr Phe Ser Ser Tyr Thr Met Gly
1 5 10

<210> SEQ ID NO 83
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 83

Gly Arg Thr Ser Gly Arg Thr Phe Ser Ser Tyr Thr Met Gly
1 5 10

<210> SEQ ID NO 84
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 84

Gly Arg Thr Phe Ser Ser Tyr Ala Met Gly
1 5 10

<210> SEQ ID NO 85
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 85

Gly Leu Thr Phe Ser Asn Tyr Ile Met Gly
1 5 10

<210> SEQ ID NO 86
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 86

Gly Arg Thr Phe Ser Ser Tyr Thr Met Gly
1 5 10

<210> SEQ ID NO 87
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 87

Gly Arg Thr Phe Ser Ser Asp Thr Met Gly
1 5 10

<210> SEQ ID NO 88
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 88

Gly Leu Thr Phe Ser Asn Tyr Ile Met Gly
1 5 10

<210> SEQ ID NO 89
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 89

Gly Phe Thr Leu Asp Tyr Tyr Gly Ile Gly
1 5 10

<210> SEQ ID NO 90
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 90

Gly His Thr Phe Ser Ser Tyr Thr Met Gly
1 5 10

<210> SEQ ID NO 91
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 91

Gly Arg Thr Phe Ser Ser Tyr Val Ile Gly
1 5 10

<210> SEQ ID NO 92
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 92

Gly Phe Ala Phe Asp Gly Tyr Ala Ile Gly
1 5 10

<210> SEQ ID NO 93
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 93

Gly Phe Ala Phe Gly Phe Phe Asp Met Thr
1 5 10

<210> SEQ ID NO 94
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 94

Gly Arg Thr Phe Ser Asn Tyr Val Ile Gly
1 5 10

<210> SEQ ID NO 95
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 95

Gly Ser Ile Phe Ser Ile Asn Val Met Gly
1 5 10

<210> SEQ ID NO 96
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 96

Gly Arg Thr Phe Ser Asn Tyr Asn Val Gly
1 5 10

<210> SEQ ID NO 97
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 97

Gly His Thr Phe Ser Ser Tyr Thr Met Gly
1 5 10

<210> SEQ ID NO 98
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 98

Gly Arg Thr Phe Ser Thr Tyr Pro Val Gly
1 5 10

<210> SEQ ID NO 99
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 99

Gly Arg Thr Phe Ser Asn Tyr Ala Met Gly
1 5 10

<210> SEQ ID NO 100
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 100

Gly Arg Thr Phe Ser Asp Tyr Arg Met Gly
1 5 10

<210> SEQ ID NO 101
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 101

Gly Leu Thr Phe Ser Asn Tyr Ile Met Ala
1 5 10

<210> SEQ ID NO 102
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 102

Gly Arg Thr Phe Ser Asn Ser Val Met Gly
1 5 10

<210> SEQ ID NO 103
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 103

Gly Arg Thr Phe Ser Ser Tyr Ile Ile Gly
1 5 10

<210> SEQ ID NO 104
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 104

Gly Arg Thr Phe Ser Ser Tyr Val Met Gly
1 5 10

<210> SEQ ID NO 105
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 105

Gly Gly Thr Phe Ser Asn Tyr Val Met Gly
1 5 10

<210> SEQ ID NO 106
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 106

Gly Arg Thr Phe Ser Asn Tyr Gly Ile Gly
1 5 10

<210> SEQ ID NO 107
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 107

Gly Phe Thr Phe Asp Asp Tyr Ala Ile Ala
1 5 10

<210> SEQ ID NO 108
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 108

Gly Arg Thr Phe Ser Ser Tyr Thr Val Ala
1 5 10

<210> SEQ ID NO 109
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 109

Gly Phe Pro Phe Asp Asp Tyr Ala Ile Ala
1 5 10

<210> SEQ ID NO 110
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 110

Gly Arg Thr Phe Ser Ser Tyr Val Met Gly
1 5 10

<210> SEQ ID NO 111
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 111

Gly Arg Thr Leu Ser Ser Asn Pro Met Ala
1 5 10

<210> SEQ ID NO 112
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 112

Gly Phe Thr Phe Asp Asn Tyr Ala Ile Gly 1 5 10

<210> SEQ ID NO 113
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 113

Gly Arg Ala Phe Ser Ser Tyr Phe Met Gly
1 5 10

<210> SEQ ID NO 114
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 114

Thr Pro Thr Phe Ser Ser Tyr Asn Met Gly
1 5 10

<210> SEQ ID NO 115
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 115

Gly Phe Thr Phe Asp Asp Tyr Ala Ile Ala
1 5 10

<210> SEQ ID NO 116
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 116

Gly Gly Thr Phe Ser Gly Tyr Ile Met Gly
1 5 10

<210> SEQ ID NO 117
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 117

Gly Arg Ser Phe Ser Ser Tyr Thr Ile Ala
1 5 10

<210> SEQ ID NO 118
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 118

Gly Phe Ser Ser Asp Asp Tyr Thr Ile Gly
1 5 10

<210> SEQ ID NO 119
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 119

Gly Phe Thr Phe Asp Asp Tyr Thr Ile Gly
1 5 10

<210> SEQ ID NO 120
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 120

Gly Phe Ser Ser Asp Asp Tyr Thr Ile Gly
1 5 10

<210> SEQ ID NO 121
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 121

Gly Phe Thr Phe Asp Gln Tyr Thr Ile Ala
1 5 10

<210> SEQ ID NO 122
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 122

Gly Arg Thr Phe Ser Ser Tyr Ala Met Ala
1 5 10

<210> SEQ ID NO 123
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 123

Gly Phe Ala Phe Asp Gly Tyr Ala Ile Gly
1 5 10

<210> SEQ ID NO 124
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 124

Gly Phe Ser Ser Asp Asp Tyr Thr Ile Ala
1 5 10

```
<210> SEQ ID NO 125
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 125

Gly Phe Ser Ser Asp Asp Tyr Thr Ile Gly
1               5                   10


<210> SEQ ID NO 126
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 126

Gly Phe Thr Phe Asp Asp Tyr Thr Ile Gly
1               5                   10


<210> SEQ ID NO 127
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 127

Gly Phe Ser Ser Asp Asp Tyr Thr Ile Gly
1               5                   10


<210> SEQ ID NO 128
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 128

Gly Phe Ser Ser Asp Asp Tyr Thr Ile Gly
1               5                   10


<210> SEQ ID NO 129
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 129

Gly Phe Ser Phe Asp Asp Tyr Ala Ile Ala
1               5                   10


<210> SEQ ID NO 130
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 130

Gly Phe Ser Ser Asp Asp Tyr Thr Ile Gly
1               5                   10
```

<210> SEQ ID NO 131
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 131

Gly Phe Thr Gly Asn Asp Leu Ala Ile Gly
1               5                   10

<210> SEQ ID NO 132
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 132

Gly Phe Ser Ser Asp Asp Tyr Thr Ile Ala
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 133

Glu Gly Thr Leu Ser Ser Tyr Gly Ile Gly
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 134

Gly Phe Ser Ser Asp Asp Tyr Thr Ile Ala
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 135

Gly Phe Thr Phe Asp Asp Tyr Ala Ile Ala
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 136

Gly Leu Ser Ser Asp Asp Tyr Thr Ile Gly
1               5                   10

<210> SEQ ID NO 137

<211> LENGTH: 10
<212> TYPE: PRT
<213> ORGANISM: Artificial Sequence
<220> FEATURE:
<223> OTHER INFORMATION: Synthetic Sequence

<400> SEQUENCE: 137

Gly Leu Ser Ser Asp Asp Tyr Thr Ile Gly
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 138

Gly Phe Ser Ser Asp Asp Tyr Thr Ile Gly
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 139

Gly Phe Ser Phe Asp Asp Tyr Thr Ile Gly
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 140

Gly Phe Thr Phe Asp Asp Tyr Ala Ile Ala
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 141

Gly Phe Thr Phe Asp Asp Tyr Ala Ile Gly
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 142

Gly Phe Thr Phe Gly Asp Tyr Thr Ile Gly
1               5                   10

<210> SEQ ID NO 143
<211> LENGTH: 10

<212> TYPE: PRT
<213> ORGANISM: Artificial Sequence
<220> FEATURE:
<223> OTHER INFORMATION: Synthetic Sequence

<400> SEQUENCE: 143

Glu Gly Thr Phe Ser Ser Tyr Gly Ile Gly
1 5 10

<210> SEQ ID NO 144
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 144

Gly Phe Ser Ser Asp Asp Tyr Thr Ile Gly
1 5 10

<210> SEQ ID NO 145
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 145

Gly Val Ser Ile Gly Asp Tyr Asn Ile Gly
1 5 10

<210> SEQ ID NO 146
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 146

Gly Phe Thr Phe Asp Asp Tyr Thr Ile Ala
1 5 10

<210> SEQ ID NO 147
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 147

Gly Phe Thr Phe Asp Asp Tyr Thr Ile Ala
1 5 10

<210> SEQ ID NO 148
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 148

Thr Ile Asn Trp Asn Gly Gly Ser Ala Glu Tyr Ala Glu Pro Val Lys
1 5 10 15

Gly

<210> SEQ ID NO 149

<211> LENGTH: 17
<212> TYPE: PRT
<213> ORGANISM: Artificial Sequence
<220> FEATURE:
<223> OTHER INFORMATION: Synthetic Sequence

<400> SEQUENCE: 149

Cys Ile Arg Val Ser Asp Gly Ser Thr Tyr Tyr Ala Asp Pro Val Lys
1 5 10 15

Gly

<210> SEQ ID NO 150
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 150

Ala Ser Ile Thr Trp Gly Gly Gly Asn Thr Tyr
1 5 10

<210> SEQ ID NO 151
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 151

Ala Ala Thr Val Trp Thr Gly Ala Gly Thr Val
1 5 10

<210> SEQ ID NO 152
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 152

Ala Ala Ile Gly Trp Ser Ala Asp Ile Thr Val
1 5 10

<210> SEQ ID NO 153
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 153

Ala Phe Ile Asp Trp Ser Gly Gly Gly Thr Tyr
1 5 10

<210> SEQ ID NO 154
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 154

Ala Thr Ile Thr Trp Gly Gly Gly Ser Thr Tyr
1 5 10

<210> SEQ ID NO 155
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 155

Ala Ala Ile Ser Trp Ser Gly Gly Pro Thr Val
1 5 10

<210> SEQ ID NO 156
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 156

Ala Ala Ile Thr Trp Gly Gly Gly Ser Thr Val
1 5 10

<210> SEQ ID NO 157
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 157

Ala Ala Ile Thr Trp Ser Gly Val Ser Thr Val
1 5 10

<210> SEQ ID NO 158
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 158

Gly Ala Ile Met Trp Ser Gly Ala Phe Thr His
1 5 10

<210> SEQ ID NO 159
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 159

Ala Ala Ile Thr Trp Gly Gly Gly Ser Thr Val
1 5 10

<210> SEQ ID NO 160
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 160

Ser Cys Ile Ser Ser Ser Asp Arg Asn Thr Tyr
1 5 10

<210> SEQ ID NO 161

<211> LENGTH: 11
<212> TYPE: PRT
<213> ORGANISM: Artificial Sequence
<220> FEATURE:
<223> OTHER INFORMATION: Synthetic Sequence

<400> SEQUENCE: 161

Ala Phe Ile Asp Trp Ser Gly Gly Gly Thr Tyr
1 5 10

<210> SEQ ID NO 162
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 162

Ala Val Ile Thr Trp Ser Gly Asp Ser Thr Tyr
1 5 10

<210> SEQ ID NO 163
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 163

Ala Cys Ile Ser Ser Lys Asp Gly Ser Thr Tyr
1 5 10

<210> SEQ ID NO 164
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 164

Ser Gly Ile Asn Ser Ile Gly Gly Ser Thr Thr
1 5 10

<210> SEQ ID NO 165
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 165

Ala Val Val Thr Trp Ser Gly Asp Ser Thr Tyr
1 5 10

<210> SEQ ID NO 166
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 166

Ala Lys Ile Thr Asn Phe Gly Ile Thr Ser
1 5 10

<210> SEQ ID NO 167
<211> LENGTH: 11

<212> TYPE: PRT
<213> ORGANISM: Artificial Sequence
<220> FEATURE:
<223> OTHER INFORMATION: Synthetic Sequence

<400> SEQUENCE: 167

Ser Phe Ile Ser Trp Ile Ser Asp Ile Thr Tyr
1 5 10

<210> SEQ ID NO 168
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 168

Ala Phe Ile Asp Trp Ser Gly Gly Gly Thr Tyr
1 5 10

<210> SEQ ID NO 169
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 169

Ala Val Ile Leu Trp Ser Gly Val Ser Thr Tyr
1 5 10

<210> SEQ ID NO 170
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 170

Ala Ala Ile Val Trp Ser Gly Gly Ser Thr Tyr
1 5 10

<210> SEQ ID NO 171
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 171

Ala Ala Ile Ser Ser Ser Gly Tyr His Thr Tyr
1 5 10

<210> SEQ ID NO 172
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 172

Ser Cys Ile Ser Ser Pro Asp Gly Ser Thr Tyr
1 5 10

<210> SEQ ID NO 173
<211> LENGTH: 11
<212> TYPE: PRT

<213> ORGANISM: Artificial Sequence
<220> FEATURE:
<223> OTHER INFORMATION: Synthetic Sequence

<400> SEQUENCE: 173

Ala Ala Val Leu Trp Ser Gly Val Ser Thr Ala
1 5 10

<210> SEQ ID NO 174
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 174

Val Ala Ile Thr Trp Asp Gly Ser Ala Thr Thr
1 5 10

<210> SEQ ID NO 175
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 175

Ala Ala Ile Gly Trp Asn Gly Gly Ile Thr Tyr
1 5 10

<210> SEQ ID NO 176
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 176

Gly Phe Ile Thr Trp Ser Gly Ala Ser Thr Tyr
1 5 10

<210> SEQ ID NO 177
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 177

Ala Gly Ile Asn Trp Ser Gly Glu Ser Ala Asp
1 5 10

<210> SEQ ID NO 178
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 178

Ser Cys Ile Glu Arg Ser Asp Gly Ser Thr Tyr
1 5 10

<210> SEQ ID NO 179
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 179

Ser Cys Ile Ser Asn Thr Asp Ser Ser Thr Tyr
1 5 10

<210> SEQ ID NO 180
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 180

Ser Cys Ile Ser Asn Thr Asp Ser Ser Thr Tyr
1 5 10

<210> SEQ ID NO 181
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 181

Ala Gln Ile Ser Trp Ser Ala Gly Ser Ile Tyr
1 5 10

<210> SEQ ID NO 182
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 182

Ala Gly Met Ser Trp Asn Pro Gly Pro Ala Val
1 5 10

<210> SEQ ID NO 183
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 183

Ser Cys Ile Ser Arg Ser Asp Gly Ser Thr Tyr
1 5 10

<210> SEQ ID NO 184
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 184

Ala Asn Ile Gly Trp Thr Gly Asp Met Thr Tyr
1 5 10

<210> SEQ ID NO 185
<211> LENGTH: 11
<212> TYPE: PRT
<213> ORGANISM: Artificial Sequence
<220> FEATURE:

<223> OTHER INFORMATION: Synthetic Sequence

<400> SEQUENCE: 185

Ala Ala Ile Ile Trp Ser Gly Ser Met Thr Tyr
1 5 10

<210> SEQ ID NO 186
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 186

Ser Cys Ile Ser Asn Thr Asp Ser Ser Thr Tyr
1 5 10

<210> SEQ ID NO 187
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 187

Ala Ala Asn Thr Trp Ser Gly Gly Pro Thr Tyr
1 5 10

<210> SEQ ID NO 188
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 188

Ser Cys Ile Ser Ser Asp Gly Ser Thr Gly
1 5 10

<210> SEQ ID NO 189
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 189

Ser Cys Tyr Ser Ser Ser Asp Gly Ser Thr Gly
1 5 10

<210> SEQ ID NO 190
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 190

Ser Cys Ile Ser Ser Asp Gly Ser Thr Gly
1 5 10

<210> SEQ ID NO 191
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 191

Gly Cys Ile Lys Ser Ser Asp Gly Thr Thr Gly
1 5 10

<210> SEQ ID NO 192
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 192

Ser Cys Ile Ser Asn Thr Asp Ser Ser Thr Tyr
1 5 10

<210> SEQ ID NO 193
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 193

Ala Ala Ile Ala Trp Ser Ala Gly Ser Thr Tyr
1 5 10

<210> SEQ ID NO 194
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 194

Ser Cys Ile Ser Ser Lys Glu Gly Ser Thr Tyr
1 5 10

<210> SEQ ID NO 195
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 195

Ser Cys Ile Ser Ser Ser Asp Gly Ser Thr Gly
1 5 10

<210> SEQ ID NO 196
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 196

Ser Cys Tyr Ser Ser Arg Asp Gly Thr Thr Gly
1 5 10

<210> SEQ ID NO 197
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 197

Ser Cys Ile Ser Ser Asp Gly Ser Thr Gly
1 5 10

<210> SEQ ID NO 198
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 198

Ser Cys Tyr Ser Ser Ser Asp Gly Ser Thr Gly
1 5 10

<210> SEQ ID NO 199
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 199

Ser Cys Phe Ser Ser Ser Asp Gly Ser Thr Gly
1 5 10

<210> SEQ ID NO 200
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 200

Ser Cys Ile Ser Asn Thr Asp Ser Ser Thr Phe
1 5 10

<210> SEQ ID NO 201
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 201

Ser Cys Tyr Ser Ser Ser Asp Gly Ser Thr Gly
1 5 10

<210> SEQ ID NO 202
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 202

Ser Cys Ile Ser Asn Thr Asp Ser Ser Thr Tyr
1 5 10

<210> SEQ ID NO 203
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 203

Ser Cys Ile Ser Ser Ser Asp Gly Ser Thr Gly
1 5 10

<210> SEQ ID NO 204
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 204

Gly Gly Ile Asn Trp Ser Gly Asp Ser Thr Asp
1 5 10

<210> SEQ ID NO 205
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 205

Ser Cys Phe Ser Ser Ser Asp Gly Ser Ala Gly
1 5 10

<210> SEQ ID NO 206
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 206

Ser Cys Ile Ser Asn Thr Asp Ser Ser Thr Tyr
1 5 10

<210> SEQ ID NO 207
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 207

Ser Cys Phe Ser Thr Arg Asp Gly Asn Ala Gly
1 5 10

<210> SEQ ID NO 208
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 208

Ser Cys Phe Ser Ser Arg Asp Gly Ser Thr Gly
1 5 10

<210> SEQ ID NO 209
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 209

Ser Cys Phe Ser Ser Arg Asp Gly Ser Thr Gly
1 5 10

<210> SEQ ID NO 210
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 210

Ser Cys Ile Ser Ser Asp Gly Ser Thr Gly
1 5 10

<210> SEQ ID NO 211
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 211

Ser Cys Ile Ser Asn Thr Asp Ser Ser Thr Tyr
1 5 10

<210> SEQ ID NO 212
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 212

Ser Cys Ile Ser Ser Pro Asp Gly Ser Thr Tyr
1 5 10

<210> SEQ ID NO 213
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 213

Ser Cys Tyr Ser Ser Ser Asp Gly Asn Thr Gly
1 5 10

<210> SEQ ID NO 214
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 214

Gly Gly Ile Asn Trp Ser Gly Asp Ser Thr Asp
1 5 10

<210> SEQ ID NO 215
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 215

Ser Cys Phe Ser Ser Ser Asp Gly Ser Thr Gly 1 5 10

<210> SEQ ID NO 216
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 216

Ser Cys Ile Ser Ser Gly Asp Gly Thr Thr Tyr
1 5 10

<210> SEQ ID NO 217
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 217

Ser Cys Ile Ser Ser Asp Gly Ser Thr Gly
1 5 10

<210> SEQ ID NO 218
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 218

Ser Cys Ile Ser Ser Asp Gly Ser Thr Gly
1 5 10

<210> SEQ ID NO 219
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 219

Lys Asp Ala Asp Leu Val Trp Tyr Asn Leu Ser
1 5 10

<210> SEQ ID NO 220
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 220

Lys Asp Ala Asp Leu Val Trp Tyr Asn Leu Arg
1 5 10

<210> SEQ ID NO 221
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 221

Ala Gly Ser Leu Tyr Thr Cys Val Gln Ser Ile Val Val Val Pro Ala
1 5 10 15

Arg Pro Tyr Tyr Asp Met Asp Tyr
20

<210> SEQ ID NO 222
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 222

Ala Lys Gly Leu Arg Asn Ser Asp Trp Asp Leu Arg Arg Gly Tyr Glu
1 5 10 15

Tyr Asp Tyr

<210> SEQ ID NO 223
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 223

Ala Asp Gln Ala Ser Val Pro Pro Pro Tyr Gly Ser Glu Arg Tyr Asp
1 5 10 15

Ile Ala Ser Pro Ser Glu Tyr Asp Tyr
20 25

<210> SEQ ID NO 224
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 224

Ala Asn Ser Arg Ala Tyr Tyr Ser Ser Ser Tyr Asp Leu Gly Arg Leu
1 5 10 15

Ala Ser Tyr Asp Tyr
20

<210> SEQ ID NO 225
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 225

Ala Ala Gln Arg Leu Gly Ser Val Thr Asp Tyr Thr Lys Tyr Asp Tyr
1 5 10 15

<210> SEQ ID NO 226
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 226

Ala Ser Val Lys Val Val Ala Gly Ser Gly Ile Asp Ile Ser Gly Ser
1 5 10 15

Arg Asn Tyr Asp Tyr
20

<210> SEQ ID NO 227
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 227

Ala Lys Arg Leu Asp Tyr Ser Ala Thr Asp Lys Gly Val Asp Leu Ser
1 5 10 15

Asp Glu Tyr Asp Tyr
20

<210> SEQ ID NO 228
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 228

Ala Ala Gly Gly Ser Gly Arg Leu Arg Asp Leu Lys Val Gly Gln Asn
1 5 10 15

Tyr Asp Tyr

<210> SEQ ID NO 229
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 229

Ala Asp Ser Pro Pro Arg Thr Tyr Ser Ser Gly Ser Val Asn Leu Glu
1 5 10 15

Asp Gly Ser Glu Tyr Asp Tyr
20

<210> SEQ ID NO 230
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 230

Val Ile Pro Gly Arg Gly Ser Ala Leu Pro Ile Asp Val Gly Lys Ser
1 5 10 15

Asp Glu Tyr Glu Tyr
20

<210> SEQ ID NO 231
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 231

Ala Ala Gly Ala Ser Gly Arg Leu Arg Asp Leu Lys Val Gly Gln Asn
1 5 10 15

Tyr Asp Tyr

<210> SEQ ID NO 232
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 232

Ala Asp Gly Asn Val Trp Ser Pro Pro Ile Cys Gly Ser Ala Gly Pro
1               5                   10                  15

Pro Pro Gly Gly Met Asp Tyr
            20

<210> SEQ ID NO 233
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 233

Ala Ala Gln Arg Leu Gly Ser Val Thr Asp Tyr Thr Lys Tyr Asp Tyr
1               5                   10                  15

<210> SEQ ID NO 234
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 234

Ala Ile Pro Pro Arg Ala Tyr Ser Gly Gly Ser Tyr Ser Leu Lys Asp
1               5                   10                  15

Gln Ser Lys Tyr Glu Tyr
            20

<210> SEQ ID NO 235
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 235

Ala Asp Gly Asn Val Trp Ser Pro Pro Ile Cys Ser Ser Ala Gly Pro
1               5                   10                  15

Pro Pro Gly Gly Met Asp Tyr
            20

<210> SEQ ID NO 236
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 236

Lys Ser Arg Ser Ser Tyr Ser Asn Asn
1               5

<210> SEQ ID NO 237
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 237

Ala Met Pro Pro Arg Ala Tyr Thr Gly Arg Ser Val Ser Leu Lys Asp
1 5 10 15

Gln Ser Lys Tyr Glu Tyr
20

<210> SEQ ID NO 238
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 238

Leu Asp Thr Thr Gly Trp Gly Pro Pro Pro Tyr Gln Tyr
1 5 10

<210> SEQ ID NO 239
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 239

Ala His Pro Pro Asp Pro Ser Arg Gly Gly Glu Trp Arg Leu Gln Thr
1 5 10 15

Pro Ser Glu Tyr Asp Tyr
20

<210> SEQ ID NO 240
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 240

Ala Ala Gln Arg Leu Gly Ser Val Thr Asp Tyr Thr Lys Tyr Asp Tyr
1 5 10 15

<210> SEQ ID NO 241
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 241

Val Pro Arg Ser His Phe Thr Thr Ala Gln Asp Met Gly Gln Asp Met
1 5 10 15

Gly Ala Pro Ser Trp Tyr Glu Tyr
20

<210> SEQ ID NO 242
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 242

Ala Val Leu Ile Arg Tyr Tyr Ser Gly Gly Tyr Gln Gly Leu Ser Asp
1               5                   10                  15

Ala Asn Glu Tyr Asp Tyr
            20

<210> SEQ ID NO 243
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 243

Val Val Lys Tyr Leu Ser Gly Ser Tyr Ser Tyr Ala Gly Gln Tyr Asn
1               5                   10                  15

Phe

<210> SEQ ID NO 244
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 244

Ala Asp Phe Asn Val Trp Ser Pro Pro Ile Cys Gly Ser Val Gly Pro
1               5                   10                  15

Pro Pro Gly Gly Met Asp Tyr
            20

<210> SEQ ID NO 245
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 245

Ala His Glu Ser Thr Tyr Tyr Ser Gly Thr Tyr Tyr Leu Thr Asp Pro
1               5                   10                  15

Arg Arg Tyr Val Tyr
            20

<210> SEQ ID NO 246
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 246

Ala Val Pro Ala Arg Gly Leu Thr Met Asp Leu Glu Asn Ser Asp Ile
1               5                   10                  15

Tyr Asp His

<210> SEQ ID NO 247
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 247

Ala Ala Thr Leu Gln Val Thr Gly Ser Tyr Tyr Leu Asp Leu Ser Thr

```
1               5                   10                  15

Val Asp Ile Tyr Asp Asn
            20


<210> SEQ ID NO 248
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 248

Ala Thr Leu Phe Arg Ser Asn Gly Pro Lys Asp Leu Ser Ser Gly Tyr
1               5                   10                  15

Glu Tyr Asp Tyr
            20


<210> SEQ ID NO 249
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 249

Ala Gly Glu Ser Gly Val Trp Val Gly Gly Leu Asp Tyr
1               5                   10


<210> SEQ ID NO 250
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 250

Val Gly Ser Ala Asn Ser Gly Glu Phe Arg Phe Gly Trp Val Leu Lys
1               5                   10                  15

Pro Asp Leu Tyr Asn Tyr
            20


<210> SEQ ID NO 251
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 251

Ala Asp Gly Asn Val Trp Ser Pro Pro Ile Cys Gly Ser Ala Gly Pro
1               5                   10                  15

Pro Pro Gly Gly Met Asp Tyr
            20


<210> SEQ ID NO 252
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 252

Ala Asp Gly Asn Val Trp Ser Pro Pro Ile Cys Gly Ser Ala Gly Pro
1               5                   10                  15
```

Pro Pro Gly Gly Met Asp Tyr
20

<210> SEQ ID NO 253
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 253

Glu Arg Gly Tyr Ala Tyr Cys Ser Asp Asp Gly Cys Gln Arg Thr Gln
1 5 10 15

Asp Tyr Asp Tyr
20

<210> SEQ ID NO 254
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 254

Gly Ala Ala Arg Ala Trp Trp Ser Gly Ser Tyr Asp Tyr Thr Arg Met
1 5 10 15

Asn Asn Tyr Asp Tyr
20

<210> SEQ ID NO 255
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 255

Ala Glu Thr Ser Ala Asp Ser Gly Glu Phe Arg Phe Gly Trp Val Leu
1 5 10 15

Lys Pro Ser Leu Tyr Asp Tyr
20

<210> SEQ ID NO 256
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 256

Ala Ala Gly Ser Ala Tyr Ser Gly Ser Tyr Trp Asn Ile Thr Met Ala
1 5 10 15

Ala Asn Tyr Asp Tyr
20

<210> SEQ ID NO 257
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 257

Ala Gln Arg Ile Phe Gly Ala Gln Pro Met Asp Leu Ser Gly Asp Tyr
1 5 10 15

Glu Tyr

<210> SEQ ID NO 258
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 258

Ala Asp Gly Asn Val Trp Ser Pro Pro Ile Cys Gly Ser Ala Gly Pro
1 5 10 15

Pro Pro Gly Gly Met Asp Tyr
20

<210> SEQ ID NO 259
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 259

Ala Arg Asp Tyr Arg Gly Ile Lys Asp Leu Asp Leu Lys Gly Asp Tyr
1 5 10 15

Asp Tyr

<210> SEQ ID NO 260
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 260

Ala Asp Phe Asn Val Trp Ser Pro Pro Ile Cys Gly Ser Ile Trp Tyr
1 5 10 15

Gly Pro Pro Pro Arg Gly Met Asp Tyr
20 25

<210> SEQ ID NO 261
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 261

Ala Asp Ser Asn Val Trp Ser Pro Pro Ile Cys Gly Ser Arg Trp Tyr
1 5 10 15

Gly Pro Pro Pro Gly Gly Met Ala Tyr
20 25

<210> SEQ ID NO 262
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 262

Ala Asp Phe Asn Val Trp Ser Pro Pro Ile Cys Gly Ser Asn Trp Tyr
1 5 10 15

Gly Pro Pro Pro Gly Gly Met Asp Tyr
20 25

<210> SEQ ID NO 263
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 263

Ala Asp Phe Asn Val Trp Ser Pro Pro Ile Cys Gly Ser Ile Trp Tyr
1 5 10 15

Gly Pro Pro Pro Gly Gly Met Asp Tyr
20 25

<210> SEQ ID NO 264
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 264

Ala Asp Gly Asn Val Trp Ser Pro Pro Ile Cys Gly Ser Ala Gly Pro
1 5 10 15

Pro Pro Gly Gly Met Asp Tyr
20

<210> SEQ ID NO 265
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 265

Ala Arg Ile Ile Thr Val Ala Thr Met Arg Leu Asp Ser Asp Tyr Asp
1 5 10 15

Tyr

<210> SEQ ID NO 266
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 266

Ala Asp Gly Asn Val Trp Ser Pro Pro Ile Cys Gly Ser Ala Gly Pro
1 5 10 15

Pro Pro Gly Gly Met Asp Tyr
20

<210> SEQ ID NO 267
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 267

Ala Asp Ser Asn Val Trp Ser Pro Pro Ile Cys Gly Arg Thr Trp Tyr
1 5 10 15

```
Gly Pro Pro Pro Gly Gly Met Asp Tyr
            20                  25


<210> SEQ ID NO 268
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 268

Ala Asp Phe Asn Val Trp Ser Pro Pro Ile Cys Gly Ser Ile Trp Tyr
1               5                   10                  15

Gly Pro Pro Pro Gly Gly Met Ala Tyr
            20                  25


<210> SEQ ID NO 269
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 269

Ala Asp Phe Asn Val Trp Ser Pro Pro Ile Cys Gly Ser Asn Trp Tyr
1               5                   10                  15

Gly Pro Pro Pro Gly Gly Met Asp Tyr
            20                  25


<210> SEQ ID NO 270
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 270

Ala Asp Phe Asn Val Trp Ser Pro Pro Ile Cys Gly Ser Ser Trp Tyr
1               5                   10                  15

Gly Pro Pro Pro Gly Gly Met Asp Tyr
            20                  25


<210> SEQ ID NO 271
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 271

Ala Asp Phe Asn Val Trp Ser Pro Pro Ile Cys Gly Ser Arg Trp Tyr
1               5                   10                  15

Gly Pro Pro Pro Gly Gly Met Glu Tyr
            20                  25


<210> SEQ ID NO 272
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 272

Ala Asp Gly Asn Val Trp Ser Pro Pro Ile Cys Gly Ser Ala Gly Pro
1               5                   10                  15
```

Pro Pro Gly Gly Met Asp Tyr
20

<210> SEQ ID NO 273
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 273

Ala Asp Phe Asn Val Trp Ser Pro Pro Ile Cys Gly Ser Arg Trp Tyr
1 5 10 15

Gly Pro Pro Pro Gly Gly Met Ala Tyr
20 25

<210> SEQ ID NO 274
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 274

Ala Asp Gly Asn Val Trp Ser Pro Pro Ile Cys Gly Ser Ala Gly Pro
1 5 10 15

Pro Pro Gly Gly Met Asp Tyr
20

<210> SEQ ID NO 275
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 275

Ala Asp Ser Asn Val Trp Ser Pro Pro Ile Cys Gly Lys Thr Trp Tyr
1 5 10 15

Gly Pro Pro Pro Gly Gly Met Asp Tyr
20 25

<210> SEQ ID NO 276
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 276

Ala Gly Glu Ser Gly Val Trp Val Gly Gly Leu Asp Tyr
1 5 10

<210> SEQ ID NO 277
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 277

Ala Asp Ser Asn Val Trp Ser Pro Pro Ile Cys Gly Ser Thr Trp Tyr
1 5 10 15

Gly Pro Pro Pro Gly Gly Met Ala Tyr 20 25

<210> SEQ ID NO 278
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 278

Ala Asp Gly Asn Val Trp Ser Pro Pro Ile Cys Gly Ser Ala Gly Pro
1 5 10 15

Pro Pro Gly Gly Met Asp Tyr
20

<210> SEQ ID NO 279
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 279

Ala Asp Phe Asn Val Trp Ser Pro Pro Ile Cys Gly Ser Arg Trp Tyr
1 5 10 15

Gly Pro Pro Pro Gly Gly Met Asp Tyr
20 25

<210> SEQ ID NO 280
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 280

Ala Asp Phe Asn Val Trp Ser Pro Pro Ile Cys Gly Ser Arg Trp Tyr
1 5 10 15

Gly Pro Pro Pro Gly Gly Met Asp Tyr
20 25

<210> SEQ ID NO 281
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 281

Ala Asp Phe Asn Val Trp Ser Pro Pro Ile Cys Gly Ser Arg Trp Tyr
1 5 10 15

Gly Pro Pro Pro Gly Gly Met Asp Tyr
20 25

<210> SEQ ID NO 282
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 282

Ala Asp Phe Asn Val Trp Ser Pro Pro Ile Cys Gly Ser Ile Trp Tyr
1 5 10 15

Gly Pro Pro Pro Gly Gly Met Asp Tyr
20 25

<210> SEQ ID NO 283
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 283

Ala Asp Gly Asn Val Trp Ser Pro Pro Ile Cys Gly Ser Ala Gly Pro
1 5 10 15

Pro Pro Gly Gly Met Asp Tyr
20

<210> SEQ ID NO 284
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 284

Ala Asp Phe Asn Val Trp Ser Pro Pro Ile Cys Gly Ser Val Gly Pro
1 5 10 15

Pro Pro Gly Gly Met Asp Tyr
20

<210> SEQ ID NO 285
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 285

Ala Asp Phe Asn Val Trp Ser Pro Pro Ile Cys Gly Ser Ser Trp Tyr
1 5 10 15

Gly Pro Pro Pro Gly Gly Met Ala Tyr
20 25

<210> SEQ ID NO 286
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 286

Ala Gly Glu Ser Gly Val Trp Val Gly Gly Leu Asp Tyr
1 5 10

<210> SEQ ID NO 287
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 287

Ala Asp Phe Asn Val Trp Ser Pro Pro Ile Cys Gly Ser Ser Trp Tyr
1 5 10 15

Gly Pro Pro Pro Gly Gly Met Glu Tyr
20 25

<210> SEQ ID NO 288
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 288

Ala Asp Gly Asn Val Trp Ser Pro Pro Ile Cys Gly Ser Ala Gly Pro
1 5 10 15

Pro Pro Gly Gly Met Asp Tyr
20

<210> SEQ ID NO 289
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 289

Ala Asp Phe Asn Val Trp Ser Pro Pro Ile Cys Ser Ser Asn Trp Tyr
1 5 10 15

Gly Pro Pro Pro Arg Gly Met Asp Tyr
20 25

<210> SEQ ID NO 290
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 290

Ala Asp Phe Asn Val Trp Ser Pro Pro Ile Cys Gly Ser Ile Trp Tyr
1 5 10 15

Gly Pro Pro Pro Arg Gly Met Asp Tyr
20 25

<210> SEQ ID NO 291
<211> LENGTH: 132
<212> TYPE: PRT
<213> ORGANISM: Artificial Sequence
<220> FEATURE:
<223> OTHER INFORMATION: Synthetic Sequence

<400> SEQUENCE: 291

Gln Val Gln Leu Gln Glu Ser Gly Gly Gly Ser Val Gln Pro Gly Gly
1 5 10 15

Ser Leu Arg Leu Ser Cys Ala Ala Ser Gly Phe Thr Phe Asp Asp Tyr
20 25 30

Ala Met Ser Trp Val Arg Gln Val Pro Gly Lys Gly Leu Glu Trp Val
35 40 45

Ser Thr Ile Asn Trp Asn Gly Gly Ser Ala Glu Tyr Ala Glu Pro Val
50 55 60

Lys Gly Arg Phe Thr Ile Ser Arg Asp Asn Ala Lys Asn Thr Val Tyr
65 70 75 80

Leu Gln Met Asn Ser Leu Lys Leu Glu Asp Thr Ala Val Tyr Tyr Cys
85 90 95

Ala Lys Asp Ala Asp Leu Val Trp Tyr Asn Leu Ser Thr Gly Gln Gly
100 105 110

```
Thr Gln Val Thr Val Ser Ser Ala Ala Ala Tyr Pro Tyr Asp Val Pro
        115                 120                 125

Asp Tyr Gly Ser
    130


<210> SEQ ID NO 292
<211> LENGTH: 132
<212> TYPE: PRT
<213> ORGANISM: Artificial Sequence
<220> FEATURE:
<223> OTHER INFORMATION: Synthetic Sequence

<400> SEQUENCE: 292

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Val Pro Gly Lys Gly Leu Glu Trp Val
        35                  40                  45

Ser Thr Ile Asn Trp Asn Gly Gly Ser Ala Glu Tyr Ala Glu Pro Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Leu Glu Asp Thr Ala Val Tyr Tyr Cys
                85                  90                  95

Ala Lys Asp Ala Asp Leu Val Trp Tyr Asn Leu Arg Thr Gly Gln Gly
            100                 105                 110

Thr Gln Val Thr Val Ser Ser Ala Ala Ala Tyr Pro Tyr Asp Val Pro
        115                 120                 125

Asp Tyr Gly Ser
    130


<210> SEQ ID NO 293
<211> LENGTH: 145
<212> TYPE: PRT
<213> ORGANISM: Artificial Sequence
<220> FEATURE:
<223> OTHER INFORMATION: Synthetic Sequence

<400> SEQUENCE: 293

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Cys Ile Arg Val Ser Asp Gly Ser Thr Tyr Tyr Ala Asp Pro Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Ala Ala Val Tyr Tyr Cys
                85                  90                  95

Ala Ala Gly Ser Leu Tyr Thr Cys Val Gln Ser Ile Val Val Val Pro
            100                 105                 110

Ala Arg Pro Tyr Tyr Asp Met Asp Tyr Trp Gly Lys Gly Thr Gln Val
        115                 120                 125

Thr Val Ser Ser Ala Ala Ala Tyr Pro Tyr Asp Val Pro Asp Tyr Gly
```

130 135 140

Ser
145

<210> SEQ ID NO 294
<211> LENGTH: 146
<212> TYPE: PRT
<213> ORGANISM: Artificial Sequence
<220> FEATURE:
<223> OTHER INFORMATION: Synthetic Sequence

<400> SEQUENCE: 294

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Ser Phe Ser Ser Tyr
20 25 30

Thr Leu Ala Trp Phe Arg Gln Ala Pro Gly Lys Glu Arg Glu Phe Val
35 40 45

Ala Ser Ile Thr Trp Gly Gly Gly Asn Thr Tyr Tyr Pro Asp Ser Val
50 55 60

Lys Gly Arg Phe Thr Ile Ser Arg Asp Asp Ala Lys Asn Thr Val Tyr
65 70 75 80

Leu Gln Met Asn Ser Leu Lys Pro Glu Asp Thr Ala Val Tyr Tyr Cys
85 90 95

Ala Ala Lys Gly Leu Arg Asn Ser Asp Trp Asp Leu Arg Arg Gly Tyr
100 105 110

Glu Tyr Asp Tyr Trp Gly Gln Gly Thr Gln Val Thr Val Ser Ser Ala
115 120 125

Ala Ala Tyr Pro Tyr Asp Val Pro Asp Tyr Gly Ser His His His His
130 135 140

His His
145

<210> SEQ ID NO 295
<211> LENGTH: 152
<212> TYPE: PRT
<213> ORGANISM: Artificial Sequence
<220> FEATURE:
<223> OTHER INFORMATION: Synthetic Sequence

<400> SEQUENCE: 295

Gln Val Gln Leu Gln Glu Ser Gly Gly Gly Leu Val Gln Asp Gly Gly
1 5 10 15

Ser Leu Arg Leu Ser Cys Ala Phe Ser Gly Arg Thr Phe Ser Ser Tyr
20 25 30

Thr Met Gly Trp Phe Arg Gln Gly Pro Gly Lys Glu Arg Glu Phe Val
35 40 45

Ala Ala Thr Val Trp Thr Gly Ala Gly Thr Val Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Arg Pro Glu Asp Thr Ala Val Tyr Tyr Cys
85 90 95

Ala Ala Asp Gln Ala Ser Val Pro Pro Pro Tyr Gly Ser Glu Arg Tyr
100 105 110

Asp Ile Ala Ser Pro Ser Glu Tyr Asp Tyr Trp Gly Gln Gly Thr Gln
115 120 125

```
Val Thr Val Ser Ser Ala Ala Ala Tyr Pro Tyr Asp Val Pro Asp Tyr
    130                 135                 140

Gly Ser His His His His His His
145                 150


<210> SEQ ID NO 296
<211> LENGTH: 148
<212> TYPE: PRT
<213> ORGANISM: Artificial Sequence
<220> FEATURE:
<223> OTHER INFORMATION: Synthetic Sequence

<400> SEQUENCE: 296

Gln Val Gln Leu Gln Glu Ser Gly Gly Gly Leu Val Gln Ala Gly Ala
1               5                   10                  15

Ser Leu Arg Leu Ser Cys Ala Ala Ser Gly Arg Thr Phe Ser Ser Tyr
            20                  25                  30

Ile Met Gly Trp Phe Arg Gln Ala Pro Gly Lys Glu Arg Glu Phe Val
        35                  40                  45

Ala Ala Ile Gly Trp Ser Ala Asp Ile Thr Val Tyr Ala Asp Ser Val
    50                  55                  60

Lys Gly Arg Phe Thr Ile Ser Arg Asp Asn Ala Glu Asn Met Val Tyr
65                  70                  75                  80

Leu Gln Met Asn Ser Leu Asn Pro Glu Asp Thr Ala Val Tyr Tyr Cys
                85                  90                  95

Ala Ala Asn Ser Arg Ala Tyr Tyr Ser Ser Ser Tyr Asp Leu Gly Arg
            100                 105                 110

Leu Ala Ser Tyr Asp Tyr Trp Gly Gln Gly Thr Gln Val Thr Val Ser
        115                 120                 125

Ser Ala Ala Ala Tyr Pro Tyr Asp Val Pro Asp Tyr Gly Ser His His
    130                 135                 140

His His His His
145


<210> SEQ ID NO 297
<211> LENGTH: 143
<212> TYPE: PRT
<213> ORGANISM: Artificial Sequence
<220> FEATURE:
<223> OTHER INFORMATION: Synthetic Sequence

<400> SEQUENCE: 297

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Thr Met Gly Trp Phe Arg Gln Ala Pro Gly Lys Glu Arg Glu Phe Val
        35                  40                  45

Ala Phe Ile Asp Trp Ser Gly Gly Gly Thr Tyr Tyr Asp Asp Ser Val
    50                  55                  60

Lys Gly Arg Phe Thr Ile Ser Arg Asp Asn Ala Glu Asn Thr Val Tyr
65                  70                  75                  80

Leu Gln Met Asn Asn Leu Glu Pro Glu Asp Thr Ala Val Tyr Tyr Cys
                85                  90                  95

Ala Ala Ala Gln Arg Leu Gly Ser Val Thr Asp Tyr Thr Lys Tyr Asp
            100                 105                 110

Tyr Trp Gly Gln Gly Thr Gln Val Thr Val Ser Ser Ala Ala Ala Tyr
        115                 120                 125
```

```
Pro Tyr Asp Val Pro Asp Tyr Gly Ser His His His His His His
    130                 135                 140


<210> SEQ ID NO 298
<211> LENGTH: 152
<212> TYPE: PRT
<213> ORGANISM: Artificial Sequence
<220> FEATURE:
<223> OTHER INFORMATION: Synthetic Sequence

<400> SEQUENCE: 298

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Ser Gly Arg Thr
            20                  25                  30

Phe Ser Ser Tyr Thr Met Gly Trp Phe Arg Gln Ala Pro Gly Lys Glu
        35                  40                  45

Arg Glu Phe Val Ala Thr Ile Thr Trp Gly Gly Gly Ser Thr Tyr Tyr
    50                  55                  60

Ala Asp Ser Val Lys Gly Arg Phe Thr Ile Ser Arg Asp Asn Ala Asn
65                  70                  75                  80

Asn Thr Val Tyr Leu Gln Met Asn Ser Leu Lys Pro Glu Asp Thr Ala
                85                  90                  95

Val Tyr Tyr Cys Ala Ala Ser Val Lys Val Val Ala Gly Ser Gly Ile
            100                 105                 110

Asp Ile Ser Gly Ser Arg Asn Tyr Asp Tyr Trp Gly Gln Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 299
<211> LENGTH: 148
<212> TYPE: PRT
<213> ORGANISM: Artificial Sequence
<220> FEATURE:
<223> OTHER INFORMATION: Synthetic Sequence

<400> SEQUENCE: 299

Gln Val Gln Leu Gln Glu Ser Gly Gly Gly Leu Val Gln Pro Gly Gly
1               5                   10                  15

Ser Leu Arg Leu Ser Cys Leu Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Pro Thr Val Tyr Ala Asp His Val
    50                  55                  60

Lys Gly Arg Phe Thr Ile Ser Arg Asp Asn Ala Lys Asn Thr Val Tyr
65                  70                  75                  80

Leu Gln Val Asn Ser Leu Lys Pro Glu Asp Thr Ala Asp Tyr Tyr Cys
                85                  90                  95

Ala Ala Lys Arg Leu Asp Tyr Ser Ala Thr Asp Lys Gly Val Asp Leu
            100                 105                 110

Ser Asp Glu Tyr Asp Tyr Trp Gly Gln Gly Thr Gln Val Thr Val Ser
        115                 120                 125

Ser Ala Ala Ala Tyr Pro Tyr Asp Val Pro Asp Tyr Gly Ser His His
```

```
    130                 135                 140

His His His His
145


<210> SEQ ID NO 300
<211> LENGTH: 146
<212> TYPE: PRT
<213> ORGANISM: Artificial Sequence
<220> FEATURE:
<223> OTHER INFORMATION: Synthetic Sequence

<400> SEQUENCE: 300

Gln Val Gln Leu Gln Glu Ser Gly Gly Gly Leu Val Gln Ala Gly Asp
1               5                   10                  15

Ser Leu Arg Leu Ser Cys Ala Ala Ser Gly Leu Thr Phe Ser Asn Tyr
            20                  25                  30

Ile Met Gly Trp Phe Arg Gln Ala Pro Gly Lys Glu Arg Glu Phe Val
        35                  40                  45

Ala Ala Ile Thr Trp Gly Gly Gly Ser Thr Val Tyr Ala Asp Ser Val
    50                  55                  60

Glu Gly Arg Phe Thr Ile Ser Arg Asp Gly Thr Lys Asn Thr Val Ser
65                  70                  75                  80

Leu Gln Met Asn Ser Leu Leu Pro Glu Asp Thr Ala Val Tyr Tyr Cys
                85                  90                  95

Ala Ala Ala Gly Gly Ser Gly Arg Leu Arg Asp Leu Lys Val Gly Gln
            100                 105                 110

Asn Tyr Asp Tyr Trp Gly Gln Gly Thr Gln Val Thr Val Ser Ser Ala
        115                 120                 125

Ala Ala Tyr Pro Tyr Asp Val Pro Asp Tyr Gly Ser His His His His
    130                 135                 140

His His
145


<210> SEQ ID NO 301
<211> LENGTH: 150
<212> TYPE: PRT
<213> ORGANISM: Artificial Sequence
<220> FEATURE:
<223> OTHER INFORMATION: Synthetic Sequence

<400> SEQUENCE: 301

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Thr Met Gly Trp Phe Arg Gln Ala Pro Gly Arg Glu Arg Glu Phe Val
        35                  40                  45

Ala Ala Ile Thr Trp Ser Gly Val Ser Thr Val Tyr Thr Asp Ser Val
    50                  55                  60

Lys Gly Arg Phe Thr Val Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Ser Pro Pro Arg Thr Tyr Ser Ser Gly Ser Val Asn Leu
            100                 105                 110

Glu Asp Gly Ser Glu Tyr Asp Tyr Trp Gly Gln Gly Thr Gln Val Thr
        115                 120                 125
```

```
Val Ser Ser Ala Ala Ala Tyr Pro Tyr Asp Val Pro Asp Tyr Gly Ser
    130                 135                 140

His His His His His His
145                 150


<210> SEQ ID NO 302
<211> LENGTH: 148
<212> TYPE: PRT
<213> ORGANISM: Artificial Sequence
<220> FEATURE:
<223> OTHER INFORMATION: Synthetic Sequence

<400> SEQUENCE: 302

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Asp
            20                  25                  30

Thr Met Gly Trp Phe Arg Gln Ala Pro Gly Lys Glu Arg Glu Phe Val
        35                  40                  45

Gly Ala Ile Met Trp Ser Gly Ala Phe Thr His Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ala Leu Lys Pro Glu Asp Thr Ala Val Tyr Tyr Cys
                85                  90                  95

Ala Val Ile Pro Gly Arg Gly Ser Ala Leu Pro Ile Asp Val Gly Lys
            100                 105                 110

Ser Asp Glu Tyr Glu Tyr Trp Gly Gln Gly Thr Gln Val Thr Val Ser
        115                 120                 125

Ser Ala Ala Ala Tyr Pro Tyr Asp Val Pro Asp Tyr Gly Ser His His
    130                 135                 140

His His His His
145


<210> SEQ ID NO 303
<211> LENGTH: 146
<212> TYPE: PRT
<213> ORGANISM: Artificial Sequence
<220> FEATURE:
<223> OTHER INFORMATION: Synthetic Sequence

<400> SEQUENCE: 303

Gln Val Gln Leu Gln Glu Ser Gly Gly Gly Leu Val Gln Ala Gly Asp
1               5                   10                  15

Ser Leu Arg Leu Ser Cys Ala Ala Ser Gly Leu Thr Phe Ser Asn Tyr
            20                  25                  30

Ile Met Gly Trp Phe Arg Gln Ala Pro Gly Lys Glu Arg Glu Phe Val
        35                  40                  45

Ala Ala Ile Thr Trp Gly Gly Gly Ser Thr Val Tyr Ala Asp Ser Val
    50                  55                  60

Glu Gly Arg Phe Thr Ile Ser Arg Asp Gly Thr Lys Asn Thr Val Ser
65                  70                  75                  80

Leu Gln Met Asn Ser Leu Gln Pro Glu Asp Thr Ala Val Tyr Tyr Cys
                85                  90                  95

Ala Ala Ala Gly Ala Ser Gly Arg Leu Arg Asp Leu Lys Val Gly Gln
            100                 105                 110

Asn Tyr Asp Tyr Trp Gly Gln Gly Thr Gln Val Thr Val Ser Ser Ala
        115                 120                 125
```

```
Ala Ala Tyr Pro Tyr Asp Val Pro Asp Tyr Gly Ser His His His His
    130                 135                 140

His His
145


<210> SEQ ID NO 304
<211> LENGTH: 150
<212> TYPE: PRT
<213> ORGANISM: Artificial Sequence
<220> FEATURE:
<223> OTHER INFORMATION: Synthetic Sequence

<400> SEQUENCE: 304

Gln Val Gln Leu Gln Glu Ser Gly Gly Gly Leu Val Gln Ala Gly Gly
1               5                   10                  15

Ser Leu Arg Leu Ser Cys Ala Gly Ser Gly Phe Thr Leu Asp Tyr Tyr
            20                  25                  30

Gly Ile Gly Trp Phe Arg Gln Ala Pro Gly Lys Glu Arg Glu Gly Val
        35                  40                  45

Ser Cys Ile Ser Ser Ser Asp Arg Asn Thr Tyr Tyr Ala Asp Ser Val
    50                  55                  60

Lys Gly Arg Phe Thr Ile Ser Gly Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Ala Asp Gly Asn Val Trp Ser Pro Pro Ile Cys Gly Ser Ala Gly
            100                 105                 110

Pro Pro Pro Gly Gly Met Asp Tyr Trp Gly Lys Gly Thr Gln Val Thr
        115                 120                 125

Val Ser Ser Ala Ala Ala Tyr Pro Tyr Asp Val Pro Asp Tyr Gly Ser
    130                 135                 140

His His His His His His
145                 150


<210> SEQ ID NO 305
<211> LENGTH: 143
<212> TYPE: PRT
<213> ORGANISM: Artificial Sequence
<220> FEATURE:
<223> OTHER INFORMATION: Synthetic Sequence

<400> SEQUENCE: 305

Gln Val Gln Leu Gln Glu Ser Gly Gly Gly Leu Val Gln Ala Gly Gly
1               5                   10                  15

Ser Leu Arg Leu Ser Cys Val Ala Ser Gly His Thr Phe Ser Ser Tyr
            20                  25                  30

Thr Met Gly Trp Phe Arg Gln Ala Pro Gly Lys Glu Arg Glu Phe Val
        35                  40                  45

Ala Phe Ile Asp Trp Ser Gly Gly Gly Thr Tyr Tyr Ala Asn Ser Val
    50                  55                  60

Lys Gly Arg Phe Thr Ile Ser Arg Asp Asn Ala Glu Asn Thr Val Tyr
65                  70                  75                  80

Leu Gln Met Asn Asn Leu Lys Pro Glu Asp Thr Ala Val Tyr Tyr Cys
                85                  90                  95

Ala Ala Ala Gln Arg Leu Gly Ser Val Thr Asp Tyr Thr Lys Tyr Asp
            100                 105                 110

Tyr Trp Gly Gln Gly Thr Gln Val Thr Val Ser Ser Ala Ala Ala Tyr
```

```
        115                 120                 125

Pro Tyr Asp Val Pro Asp Tyr Gly Ser His His His His His His
    130                 135                 140


<210> SEQ ID NO 306
<211> LENGTH: 149
<212> TYPE: PRT
<213> ORGANISM: Artificial Sequence
<220> FEATURE:
<223> OTHER INFORMATION: Synthetic Sequence

<400> SEQUENCE: 306

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Val Ile Gly Trp Phe Arg Gln Ala Pro Gly Lys Glu Arg Glu Phe Val
        35                  40                  45

Ala Val Ile Thr Trp Ser Gly Asp Ser Thr Tyr Ser Ser Asp Ser Leu
    50                  55                  60

Lys Gly Arg Phe Thr Ile Ser Arg Asp Asn Ala Lys Asn Thr Val Tyr
65                  70                  75                  80

Leu Gln Met Asn Ala Leu Asn Pro Glu Asp Thr Ala Val Tyr Tyr Cys
                85                  90                  95

Ala Ala Ile Pro Pro Arg Ala Tyr Ser Gly Gly Ser Tyr Ser Leu Lys
            100                 105                 110

Asp Gln Ser Lys Tyr Glu Tyr Trp Gly Gln Gly Thr Gln Val Thr Val
        115                 120                 125

Ser Ser Ala Ala Ala Tyr Pro Tyr Asp Val Pro Asp Tyr Gly Ser His
    130                 135                 140

His His His His His
145


<210> SEQ ID NO 307
<211> LENGTH: 149
<212> TYPE: PRT
<213> ORGANISM: Artificial Sequence
<220> FEATURE:
<223> OTHER INFORMATION: Synthetic Sequence

<400> SEQUENCE: 307

Gln Val Gln Leu Gln Glu Ser Gly Gly Gly Leu Val Gln Ala Glu Gly
1               5                   10                  15

Ser Leu Lys Leu Ser Cys Ile Ser Gly Phe Ala Phe Asp Gly Tyr Ala
            20                  25                  30

Ile Gly Trp Phe Arg Gln Ala Pro Gly Lys Glu Arg Glu Gly Val Ala
        35                  40                  45

Cys Ile Ser Ser Lys Asp Gly Ser Thr Tyr Tyr Ala Asp Ser Val Lys
    50                  55                  60

Gly Arg Phe Thr Met Ser Val Asp Lys Thr Lys Asn Thr Val Tyr Leu
65                  70                  75                  80

Gln Met Ser Ser Leu Lys Pro Glu Asp Thr Ala Val Tyr Tyr Cys Ala
                85                  90                  95

Ala Asp Gly Asn Val Trp Ser Pro Pro Ile Cys Ser Ser Ala Gly Pro
            100                 105                 110

Pro Pro Gly Gly Met Asp Tyr Trp Gly Lys Gly Thr Gln Val Thr Val
        115                 120                 125
```

Ser Ser Ala Ala Ala Tyr Pro Tyr Asp Val Pro Asp Tyr Gly Ser His
130 135 140

His His His His His
145

<210> SEQ ID NO 308
<211> LENGTH: 139
<212> TYPE: PRT
<213> ORGANISM: Artificial Sequence
<220> FEATURE:
<223> OTHER INFORMATION: Synthetic Sequence

<400> SEQUENCE: 308

Gln Val Gln Leu Gln Glu Ser Gly Gly Gly Leu Val Gln Pro Gly Gly
1 5 10 15

Ser Leu Thr Leu Ser Cys Ala Ala Ser Gly Phe Ala Phe Gly Phe Phe
20 25 30

Asp Met Thr Trp Val Arg Gln Ala Pro Gly Lys Gly Leu Glu Trp Val
35 40 45

Ser Gly Ile Asn Ser Ile Gly Gly Ser Thr Thr Tyr Ala Asp Ser Val
50 55 60

Lys Gly Arg Phe Thr Ile Ser Arg Asp Asn Ala Lys Asn Glu Leu Tyr
65 70 75 80

Leu Gln Met Asn Ser Leu Lys Pro Asp Asp Thr Ala Val Tyr Tyr Cys
85 90 95

Ala Lys Ser Arg Ser Ser Tyr Ser Asn Asn Trp Arg Pro Pro Gly Gln
100 105 110

Gly Thr Gln Val Thr Val Ser Ser Ala Ala Ala Tyr Pro Tyr Asp Val
115 120 125

Pro Asp Tyr Gly Ser His His His His His His
130 135

<210> SEQ ID NO 309
<211> LENGTH: 149
<212> TYPE: PRT
<213> ORGANISM: Artificial Sequence
<220> FEATURE:
<223> OTHER INFORMATION: Synthetic Sequence

<400> SEQUENCE: 309

Gln Val Gln Leu Gln Glu Ser Gly Gly Gly Leu Val Gln Ala Arg Gly
1 5 10 15

Ser Leu Thr Leu Ser Cys Ala Ala Ser Gly Arg Thr Phe Ser Asn Tyr
20 25 30

Val Ile Gly Trp Phe Arg Gln Ala Pro Gly Glu Glu Arg Glu Phe Val
35 40 45

Ala Val Val Thr Trp Ser Gly Asp Ser Thr Tyr Ser Ser Asp Ser Leu
50 55 60

Lys Gly Arg Phe Thr Ile Ser Arg Asp Asn Ala Lys Asn Thr Val Tyr
65 70 75 80

Leu Gln Met Asn Asn Leu Asn Pro Glu Asp Thr Ala Val Tyr Tyr Cys
85 90 95

Ala Ala Met Pro Pro Arg Ala Tyr Thr Gly Arg Ser Val Ser Leu Lys
100 105 110

Asp Gln Ser Lys Tyr Glu Tyr Trp Gly Gln Gly Thr Gln Val Thr Val
115 120 125

Ser Ser Ala Ala Ala Tyr Pro Tyr Asp Val Pro Asp Tyr Gly Ser His
130 135 140

His His His His His
145

<210> SEQ ID NO 310
<211> LENGTH: 139
<212> TYPE: PRT
<213> ORGANISM: Artificial Sequence
<220> FEATURE:
<223> OTHER INFORMATION: Synthetic Sequence

<400> SEQUENCE: 310

Gln Val Gln Leu Gln Glu Ser Gly Gly Gly Leu Val Gln Pro Gly Gly
1 5 10 15

Ser Leu Arg Leu Ser Cys Ala Ala Ser Gly Ser Ile Phe Ser Ile Asn
20 25 30

Val Met Gly Trp Tyr Arg Gln Thr Pro Gly Lys Glu Arg Glu Leu Val
35 40 45

Ala Lys Ile Thr Asn Phe Gly Ile Thr Ser Tyr Ala Asp Ser Ala Gln
50 55 60

Gly Arg Phe Thr Ile Ser Arg Gly Asn Ala Lys Asn Thr Val Tyr Leu
65 70 75 80

Gln Met Asn Ser Leu Lys Pro Glu Asp Thr Ala Val Tyr Tyr Cys Asn
85 90 95

Leu Asp Thr Thr Gly Trp Gly Pro Pro Pro Tyr Gln Tyr Trp Gly Gln
100 105 110

Gly Thr Gln Val Thr Val Ser Ser Ala Ala Ala Tyr Pro Tyr Asp Val
115 120 125

Pro Asp Tyr Gly Ser His His His His His His
130 135

<210> SEQ ID NO 311
<211> LENGTH: 149
<212> TYPE: PRT
<213> ORGANISM: Artificial Sequence
<220> FEATURE:
<223> OTHER INFORMATION: Synthetic Sequence

<400> SEQUENCE: 311

Gln Val Gln Leu Gln Glu Ser Gly Gly Gly Leu Val Gln Ala Gly Ala
1 5 10 15

Ser Leu Arg Leu Ser Cys Ala Ala Ser Gly Arg Thr Phe Ser Asn Tyr
20 25 30

Asn Val Gly Trp Phe Arg Gln Ala Pro Gly Lys Glu Arg Glu Phe Val
35 40 45

Ser Phe Ile Ser Trp Ile Ser Asp Ile Thr Tyr Tyr Ser Asp Ser Val
50 55 60

Lys Gly Arg Phe Ile Ile Ser Arg Asp Asn Ala Lys Asn Met Val Tyr
65 70 75 80

Leu Gln Met Asn Ser Leu Lys Pro Glu Asp Thr Ala Val Tyr Tyr Cys
85 90 95

Ala Ala His Pro Pro Asp Pro Ser Arg Gly Gly Glu Trp Arg Leu Gln
100 105 110

Thr Pro Ser Glu Tyr Asp Tyr Trp Gly Gln Gly Thr Gln Val Thr Val
115 120 125

Ser Ser Ala Ala Ala Tyr Pro Tyr Asp Val Pro Asp Tyr Gly Ser His
130 135 140

His His His His His

145

<210> SEQ ID NO 312
<211> LENGTH: 143
<212> TYPE: PRT
<213> ORGANISM: Artificial Sequence
<220> FEATURE:
<223> OTHER INFORMATION: Synthetic Sequence

<400> SEQUENCE: 312

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly His Thr Phe Ser Ser Tyr
            20                  25                  30

Thr Met Gly Trp Phe Arg Gln Ala Pro Gly Lys Glu Arg Glu Phe Val
        35                  40                  45

Ala Phe Ile Asp Trp Ser Gly Gly Gly Thr Tyr Tyr Ala Asp Ser Val
    50                  55                  60

Lys Gly Arg Phe Thr Ile Ser Arg Asp Asn Ala Glu Asn Thr Val Tyr
65                  70                  75                  80

Leu Gln Met Asn Asn Leu Lys Pro Glu Asp Thr Ala Val Tyr Tyr Cys
                85                  90                  95

Ala Ala Ala Gln Arg Leu Gly Ser Val Thr Asp Tyr Thr Lys Tyr Asp
            100                 105                 110

Tyr Trp Gly Gln Gly Thr Gln Val Thr Val Ser Ser Ala Ala Ala Tyr
        115                 120                 125

Pro Tyr Asp Val Pro Asp Tyr Gly Ser His His His His His His
    130                 135                 140
```

<210> SEQ ID NO 313
<211> LENGTH: 151
<212> TYPE: PRT
<213> ORGANISM: Artificial Sequence
<220> FEATURE:
<223> OTHER INFORMATION: Synthetic Sequence

<400> SEQUENCE: 313

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Thr Tyr
            20                  25                  30

Pro Val Gly Trp Phe Arg Gln Ala Pro Gly Lys Glu Arg Glu Phe Val
        35                  40                  45

Ala Val Ile Leu Trp Ser Gly Val Ser Thr Tyr Tyr Ala Asp Ser Val
    50                  55                  60

Lys Gly Arg Phe Thr Ile Ser Arg Asp Asn Ala Gln Asn Thr Val Tyr
65                  70                  75                  80

Leu Gln Met Asp Ser Leu Lys Pro Glu Asp Thr Ala Val Tyr Tyr Cys
                85                  90                  95

Ala Val Pro Arg Ser His Phe Thr Thr Ala Gln Asp Met Gly Gln Asp
            100                 105                 110

Met Gly Ala Pro Ser Trp Tyr Glu Tyr Trp Gly Gln Gly Thr Gln Val
        115                 120                 125

Thr Val Ser Ser Ala Ala Ala Tyr Pro Tyr Asp Val Pro Asp Tyr Gly
    130                 135                 140

Ser His His His His His His
145                 150
```

<210> SEQ ID NO 314
<211> LENGTH: 149
<212> TYPE: PRT
<213> ORGANISM: Artificial Sequence
<220> FEATURE:
<223> OTHER INFORMATION: Synthetic Sequence

<400> SEQUENCE: 314

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Thr Phe Ser Asn Tyr
20 25 30

Ala Met Gly Trp Phe Arg Gln Ala Pro Gly Lys Glu Arg Glu Phe Val
35 40 45

Ala Ala Ile Val Trp Ser Gly Gly Ser Thr Tyr Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Val Leu Ile Arg Tyr Tyr Ser Gly Gly Tyr Gln Gly Leu Ser
100 105 110

Asp Ala Asn Glu Tyr Asp Tyr Trp Gly Gln Gly Thr Gln Val Thr Val
115 120 125

Ser Ser Ala Ala Ala Tyr Pro Tyr Asp Val Pro Asp Tyr Gly Ser His
130 135 140

His His His His His
145

<210> SEQ ID NO 315
<211> LENGTH: 144
<212> TYPE: PRT
<213> ORGANISM: Artificial Sequence
<220> FEATURE:
<223> OTHER INFORMATION: Synthetic Sequence

<400> SEQUENCE: 315

Gln Val Gln Leu Gln Glu Ser Gly Gly Gly Leu Val Gln Ala Gly Ala
1 5 10 15

Ser Leu Arg Leu Ser Cys Ser Ala Ser Gly Arg Thr Phe Ser Asp Tyr
20 25 30

Arg Met Gly Trp Phe Arg Gln Ala Pro Gly Lys Glu Arg Glu Trp Val
35 40 45

Ala Ala Ile Ser Ser Ser Gly Tyr His Thr Tyr Tyr Ala Asp Ser Val
50 55 60

Lys Gly Arg Phe Thr Ile Ser Arg Asp Asn Ala Lys Asn Thr Gly Tyr
65 70 75 80

Leu Gln Met Ser Ser Leu Lys Pro Glu Asp Thr Ala Val Tyr Tyr Cys
85 90 95

Ala Val Val Lys Tyr Leu Ser Gly Ser Tyr Ser Tyr Ala Gly Gln Tyr
100 105 110

Asn Phe Trp Gly Gln Gly Thr Gln Val Thr Val Ser Ser Ala Ala Ala
115 120 125

Tyr Pro Tyr Asp Val Pro Asp Tyr Gly Ser His His His His His His
130 135 140

<210> SEQ ID NO 316

<211> LENGTH: 150
<212> TYPE: PRT
<213> ORGANISM: Artificial Sequence
<220> FEATURE:
<223> OTHER INFORMATION: Synthetic Sequence

<400> SEQUENCE: 316

```
Gln Val Gln Leu Gln Glu Ser Gly Gly Gly Leu Val Gln Ala Gly Asp
1               5                   10                  15

Ser Leu Lys Leu Ser Cys Ala Ala Ser Gly Leu Thr Phe Ser Asn Tyr
            20                  25                  30

Ile Met Ala Trp Phe Arg Gln Ala Pro Gly Lys Glu Arg Glu Gly Val
        35                  40                  45

Ser Cys Ile Ser Ser Pro Asp Gly Ser Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Phe Asn Val Trp Ser Pro Pro Ile Cys Gly Ser Val Gly
            100                 105                 110

Pro Pro Pro Gly Gly Met Asp Tyr Trp Gly Lys Gly Thr Gln Val Thr
        115                 120                 125

Val Ser Ser Ala Ala Ala Tyr Pro Tyr Asp Val Pro Asp Tyr Gly Ser
    130                 135                 140

His His His His His His
145                 150
```

<210> SEQ ID NO 317
<211> LENGTH: 148
<212> TYPE: PRT
<213> ORGANISM: Artificial Sequence
<220> FEATURE:
<223> OTHER INFORMATION: Synthetic Sequence

<400> SEQUENCE: 317

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Asn Ser
            20                  25                  30

Val Met Gly Trp Phe Arg Gln Pro Pro Gly Lys Glu Arg Glu Phe Val
        35                  40                  45

Ala Ala Val Leu Trp Ser Gly Val Ser Thr Ala Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Pro Asp Asp Thr Ala Val Tyr Tyr Cys
                85                  90                  95

Ala Ala His Glu Ser Thr Tyr Tyr Ser Gly Thr Tyr Tyr Leu Thr Asp
            100                 105                 110

Pro Arg Arg Tyr Val Tyr Trp Gly Gln Gly Thr Gln Val Thr Val Ser
        115                 120                 125

Ser Ala Ala Ala Tyr Pro Tyr Asp Val Pro Asp Tyr Gly Ser His His
    130                 135                 140

His His His His
145
```

<210> SEQ ID NO 318
<211> LENGTH: 146
<212> TYPE: PRT
<213> ORGANISM: Artificial Sequence
<220> FEATURE:
<223> OTHER INFORMATION: Synthetic Sequence

<400> SEQUENCE: 318

```
Gln Val Gln Leu Gln Glu Ser Gly Gly Gly Leu Val Gln Ala Gly Gly
1               5                   10                  15

Ser Leu Arg Leu Ser Cys Val Gly Asp Gly Arg Thr Phe Ser Ser Tyr
            20                  25                  30

Ile Ile Gly Trp Phe Arg Gln Ala Pro Gly Asn Glu Arg Glu Phe Val
        35                  40                  45

Val Ala Ile Thr Trp Asp Gly Ser Ala Thr Thr Tyr Ala Asp Ser Val
    50                  55                  60

Lys Gly Arg Phe Thr Val Ser Arg Asp Ser Ala Lys Asn Thr Ala Tyr
65                  70                  75                  80

Leu Gln Met Asn Ser Leu Lys Pro Glu Asp Thr Ala Val Tyr Tyr Cys
                85                  90                  95

Ala Ala Val Pro Ala Arg Gly Leu Thr Met Asp Leu Glu Asn Ser Asp
            100                 105                 110

Ile Tyr Asp His Trp Gly Arg Gly Thr Gln Val Thr Val Ser Ser Ala
        115                 120                 125

Ala Ala Tyr Pro Tyr Asp Val Pro Asp Tyr Gly Ser His His His His
    130                 135                 140

His His
145
```

<210> SEQ ID NO 319
<211> LENGTH: 149
<212> TYPE: PRT
<213> ORGANISM: Artificial Sequence
<220> FEATURE:
<223> OTHER INFORMATION: Synthetic Sequence

<400> SEQUENCE: 319

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Val Met Gly Trp Phe Arg Gln Ala Leu Gly Lys Glu Arg Glu Phe Val
        35                  40                  45

Ala Ala Ile Gly Trp Asn Gly Gly Ile Thr Tyr Tyr Ala Asp Ser Val
    50                  55                  60

Lys Gly Arg Phe Ala Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Thr Leu Gln Val Thr Gly Ser Tyr Tyr Leu Asp Leu Ser
            100                 105                 110

Thr Val Asp Ile Tyr Asp Asn Trp Gly Gln Gly Thr Gln Val Thr Val
        115                 120                 125

Ser Ser Ala Ala Ala Tyr Pro Tyr Asp Val Pro Asp Tyr Gly Ser His
    130                 135                 140

His His His His His
145
```

<210> SEQ ID NO 320
<211> LENGTH: 147
<212> TYPE: PRT
<213> ORGANISM: Artificial Sequence
<220> FEATURE:
<223> OTHER INFORMATION: Synthetic Sequence

<400> SEQUENCE: 320

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Gly Thr Phe Ser Asn Tyr
            20                  25                  30

Val Met Gly Trp Phe Arg Gln Ala Pro Gly Lys Glu Arg Glu Phe Val
        35                  40                  45

Gly Phe Ile Thr Trp Ser Gly Ala Ser Thr Tyr Tyr Ala Asp Ser Val
    50                  55                  60

Lys Gly Arg Phe Thr Ile Ser Arg Asp Asn Ala Glu Asn Thr Val Tyr
65                  70                  75                  80

Leu Gln Met Asn Ser Leu Lys Pro Glu Asp Thr Ala Val Tyr Tyr Cys
                85                  90                  95

Ala Ala Thr Leu Phe Arg Ser Asn Gly Pro Lys Asp Leu Ser Ser Gly
            100                 105                 110

Tyr Glu Tyr Asp Tyr Trp Gly Gln Gly Thr Gln Val Thr Val Ser Ser
        115                 120                 125

Ala Ala Ala Tyr Pro Tyr Asp Val Pro Asp Tyr Gly Ser His His His
    130                 135                 140

His His His
145
```

<210> SEQ ID NO 321
<211> LENGTH: 140
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (112)..(112)
<223> OTHER INFORMATION: Xaa can be any naturally occurring amino acid

<400> SEQUENCE: 321

```
Gln Val Gln Leu Gln Glu Ser Gly Gly Gly Leu Val Gln Ala Gly Asp
1               5                   10                  15

Ser Leu Arg Leu Thr Cys Thr Ala Ser Gly Arg Thr Phe Ser Asn Tyr
            20                  25                  30

Gly Ile Gly Trp Phe Arg Gln Ala Pro Gly Lys Glu Arg Glu Phe Val
        35                  40                  45

Ala Gly Ile Asn Trp Ser Gly Glu Ser Ala Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Glu Ser Gly Val Trp Val Gly Gly Leu Asp Tyr Trp Xaa
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
```

130 135 140

<210> SEQ ID NO 322
<211> LENGTH: 149
<212> TYPE: PRT
<213> ORGANISM: Artificial Sequence
<220> FEATURE:
<223> OTHER INFORMATION: Synthetic Sequence

<400> SEQUENCE: 322

Gln Val Gln Leu Gln Glu Ser Gly Gly Gly Leu Val Gln Ala Gly Gly
1 5 10 15

Ser Leu Arg Leu Ser Cys Ala Ala Ser Gly Phe Thr Phe Asp Asp Tyr
20 25 30

Ala Ile Ala Trp Phe Arg Gln Ala Pro Gly Lys Glu Arg Glu Gly Val
35 40 45

Ser Cys Ile Glu Arg Ser Asp Gly Ser Thr Tyr Tyr Ala Asp Ser Val
50 55 60

Lys Gly Arg Phe Thr Ile Ser Ser Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Val Gly Ser Ala Asn Ser Gly Glu Phe Arg Phe Gly Trp Val Leu
100 105 110

Lys Pro Asp Leu Tyr Asn Tyr Trp Gly Gln Gly Thr Gln Val Thr Val
115 120 125

Ser Ser Ala Ala Ala Tyr Pro Tyr Asp Val Pro Asp Tyr Gly Ser His
130 135 140

His His His His His
145

<210> SEQ ID NO 323
<211> LENGTH: 150
<212> TYPE: PRT
<213> ORGANISM: Artificial Sequence
<220> FEATURE:
<223> OTHER INFORMATION: Synthetic Sequence

<400> SEQUENCE: 323

Gln Val Gln Leu Gln Glu Ser Gly Gly Gly Leu Val Gln Ala Gly Gly
1 5 10 15

Ser Leu Arg Leu Ser Cys Thr Ala Ser Gly Arg Thr Phe Ser Ser Tyr
20 25 30

Thr Val Ala Trp Phe Arg Gln Ser Pro Gly Lys Glu Arg Glu Gly Ile
35 40 45

Ser Cys Ile Ser Asn Thr Asp Ser Ser Thr Tyr Tyr Ala Asp Ser Val
50 55 60

Lys Gly Arg Phe Thr Ile Ser Ser Asp Asn Ala Lys Ser Thr Val His
65 70 75 80

Leu Gln Met Ser Ser Leu Lys Pro Glu Asp Thr Ala Val Tyr Tyr Cys
85 90 95

Ala Ala Asp Gly Asn Val Trp Ser Pro Pro Ile Cys Gly Ser Ala Gly
100 105 110

Pro Pro Pro Gly Gly Met Asp Tyr Trp Gly Lys Gly Thr Gln Val Thr
115 120 125

Val Ser Ser Ala Ala Ala Tyr Pro Tyr Asp Val Pro Asp Tyr Gly Ser
130 135 140

His His His His His His
145 150

<210> SEQ ID NO 324
<211> LENGTH: 150
<212> TYPE: PRT
<213> ORGANISM: Artificial Sequence
<220> FEATURE:
<223> OTHER INFORMATION: Synthetic Sequence

<400> SEQUENCE: 324

Gln Val Gln Leu Gln Glu Ser Gly Gly Gly Leu Val Gln Pro Gly Gly
1 5 10 15

Ser Leu Arg Leu Ser Cys Ala Thr Phe Gly Phe Pro Phe Asp Asp Tyr
20 25 30

Ala Ile Ala Trp Phe Arg Gln Ala Pro Gly Lys Glu Arg Glu Gly Val
35 40 45

Ser Cys Ile Ser Asn Thr Asp Ser Ser Thr Tyr Tyr Ala Asp Ser Val
50 55 60

Lys Gly Arg Phe Thr Ile Ser Ser Asp Asn Ala Lys Asn Thr Val His
65 70 75 80

Leu Gln Met Ser Ser Leu Lys Pro Glu Asp Thr Ala Val Tyr Tyr Cys
85 90 95

Ala Ala Asp Gly Asn Val Trp Ser Pro Pro Ile Cys Gly Ser Ala Gly
100 105 110

Pro Pro Pro Gly Gly Met Asp Tyr Trp Gly Lys Gly Thr Gln Val Thr
115 120 125

Val Ser Ser Ala Ala Ala Tyr Pro Tyr Asp Val Pro Asp Tyr Gly Ser
130 135 140

His His His His His His
145 150

<210> SEQ ID NO 325
<211> LENGTH: 147
<212> TYPE: PRT
<213> ORGANISM: Artificial Sequence
<220> FEATURE:
<223> OTHER INFORMATION: Synthetic Sequence

<400> SEQUENCE: 325

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Thr Phe Ser Ser Tyr
20 25 30

Val Met Gly Trp Phe Arg Gln Ala Pro Gly Lys Glu Arg Glu Phe Val
35 40 45

Ala Gln Ile Ser Trp Ser Ala Gly Ser Ile Tyr Tyr Ala Asp Ser Val
50 55 60

Lys Gly Arg Phe Thr Ile Ser Asn Asp Asn Ala Lys Arg Thr Val Tyr
65 70 75 80

Leu Gln Met Asn Ser Leu Lys Pro Glu Asp Thr Ala Val Tyr Tyr Cys
85 90 95

Ala Glu Arg Gly Tyr Ala Tyr Cys Ser Asp Asp Gly Cys Gln Arg Thr
100 105 110

Gln Asp Tyr Asp Tyr Trp Gly Gln Gly Thr Gln Val Thr Val Ser Ser
115 120 125

Ala Ala Ala Tyr Pro Tyr Asp Val Pro Asp Tyr Gly Ser His His His
130 135 140

```
His His His
145


<210> SEQ ID NO 326
<211> LENGTH: 148
<212> TYPE: PRT
<213> ORGANISM: Artificial Sequence
<220> FEATURE:
<223> OTHER INFORMATION: Synthetic Sequence

<400> SEQUENCE: 326

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Leu Ser Ser Asn
            20                  25                  30

Pro Met Ala Trp Phe Arg Gln Ala Ala Gly Lys Glu Arg Glu Phe Val
        35                  40                  45

Ala Gly Met Ser Trp Asn Pro Gly Pro Ala Val Tyr Ala Asp Ser Val
    50                  55                  60

Lys Gly Arg Phe Thr Ile Ser Arg Asp Ser Ala Glu Asn Thr Val Tyr
65                  70                  75                  80

Leu Gln Met Asn Ser Leu Lys Pro Glu Asp Thr Ala Val Tyr Tyr Cys
                85                  90                  95

Ala Gly Ala Ala Arg Ala Trp Trp Ser Gly Ser Tyr Asp Tyr Thr Arg
            100                 105                 110

Met Asn Asn Tyr Asp Tyr Trp Gly Pro Gly Thr Gln Val Thr Val Ser
        115                 120                 125

Ser Ala Ala Ala Tyr Pro Tyr Asp Val Pro Asp Tyr Gly Ser His His
    130                 135                 140

His His His His
145


<210> SEQ ID NO 327
<211> LENGTH: 150
<212> TYPE: PRT
<213> ORGANISM: Artificial Sequence
<220> FEATURE:
<223> OTHER INFORMATION: Synthetic Sequence

<400> SEQUENCE: 327

Gln Val Gln Leu Gln Glu Ser Gly Gly Gly Leu Val Gln Ala Gly Gly
1               5                   10                  15

Ser Leu Arg Leu Ser Cys Ala Val Ser Gly Phe Thr Phe Asp Asn Tyr
            20                  25                  30

Ala Ile Gly Trp Phe Arg Gln Ala Pro Gly Lys Glu Arg Glu Gly Val
        35                  40                  45

Ser Cys Ile Ser Arg Ser Asp Gly Ser Thr Tyr Tyr Ala Asp Ser Val
    50                  55                  60

Arg Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Thr Ser Ala Asp Ser Gly Glu Phe Arg Phe Gly Trp Val
            100                 105                 110

Leu Lys Pro Ser Leu Tyr Asp Tyr Trp Gly Gln Gly Thr Gln Val Thr
        115                 120                 125

Val Ser Ser Ala Ala Ala Tyr Pro Tyr Asp Val Pro Asp Tyr Gly Ser
```

130 135 140

His His His His His His
145 150

<210> SEQ ID NO 328
<211> LENGTH: 148
<212> TYPE: PRT
<213> ORGANISM: Artificial Sequence
<220> FEATURE:
<223> OTHER INFORMATION: Synthetic Sequence

<400> SEQUENCE: 328

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Ala Phe Ser Ser Tyr
20 25 30

Phe Met Gly Trp Phe Arg Gln Thr Pro Gly Lys Glu Arg Glu Phe Val
35 40 45

Ala Asn Ile Gly Trp Thr Gly Asp Met Thr Tyr Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Ala Gly Ser Ala Tyr Ser Gly Ser Tyr Trp Asn Ile Thr Met
100 105 110

Ala Ala Asn Tyr Asp Tyr Trp Gly Gln Gly Thr Gln Val Thr Val Ser
115 120 125

Ser Ala Ala Ala Tyr Pro Tyr Asp Val Pro Asp Tyr Gly Ser His His
130 135 140

His His His His
145

<210> SEQ ID NO 329
<211> LENGTH: 145
<212> TYPE: PRT
<213> ORGANISM: Artificial Sequence
<220> FEATURE:
<223> OTHER INFORMATION: Synthetic Sequence

<400> SEQUENCE: 329

Gln Val Gln Leu Gln Glu Ser Gly Gly Gly Leu Val Gln Ala Gly Gly
1 5 10 15

Ser Leu Arg Leu Ser Cys Ala Ala Ser Thr Pro Thr Phe Ser Ser Tyr
20 25 30

Asn Met Gly Trp Phe Arg Gln Ala Pro Gly Lys Glu Arg Glu Phe Val
35 40 45

Ala Ala Ile Ile Trp Ser Gly Ser Met Thr Tyr Tyr Ala Asp Ser Met
50 55 60

Lys Gly Arg Phe Thr Val Ser Ile Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Gln Arg Ile Phe Gly Ala Gln Pro Met Asp Leu Ser Gly Asp
100 105 110

Tyr Glu Tyr Trp Gly Gln Gly Thr Gln Val Thr Val Ser Ser Ala Ala
115 120 125

```
Ala Tyr Pro Tyr Asp Val Pro Asp Tyr Gly Ser His His His His His
    130                 135                 140

His
145


<210> SEQ ID NO 330
<211> LENGTH: 150
<212> TYPE: PRT
<213> ORGANISM: Artificial Sequence
<220> FEATURE:
<223> OTHER INFORMATION: Synthetic Sequence

<400> SEQUENCE: 330

Gln Val Gln Leu Gln Glu Ser Gly Gly Gly Leu Val Gln Ala Gly Gly
1               5                   10                  15

Ser Leu Arg Leu Ser Cys Ala Thr Phe Gly Phe Thr Phe Asp Asp Tyr
            20                  25                  30

Ala Ile Ala Trp Phe Arg Gln Ala Pro Gly Lys Glu Arg Glu Gly Ile
        35                  40                  45

Ser Cys Ile Ser Asn Thr Asp Ser Ser Thr Tyr Tyr Ala Asp Ser Val
    50                  55                  60

Lys Gly Arg Phe Thr Ile Ser Ser Asp Ser Ala Lys Asn Thr Val His
65                  70                  75                  80

Leu Gln Met Ser Ser Leu Lys Pro Glu Asp Thr Ala Val Tyr Tyr Cys
                85                  90                  95

Ala Ala Asp Gly Asn Val Trp Ser Pro Pro Ile Cys Gly Ser Ala Gly
            100                 105                 110

Pro Pro Pro Gly Gly Met Asp Tyr Trp Gly Lys Gly Thr Gln Val Thr
        115                 120                 125

Val Ser Ser Ala Ala Ala Tyr Pro Tyr Asp Val Pro Asp Tyr Gly Ser
    130                 135                 140

His His His His His His
145                 150


<210> SEQ ID NO 331
<211> LENGTH: 145
<212> TYPE: PRT
<213> ORGANISM: Artificial Sequence
<220> FEATURE:
<223> OTHER INFORMATION: Synthetic Sequence

<400> SEQUENCE: 331

Gln Val Gln Leu Gln Glu Ser Gly Gly Gly Leu Val Gln Ala Gly Gly
1               5                   10                  15

Ser Leu Arg Leu Ser Cys Lys Ala Ser Gly Gly Thr Phe Ser Gly Tyr
            20                  25                  30

Ile Met Gly Trp Phe Arg Gln Ala Pro Gly Lys Glu Arg Glu Phe Val
        35                  40                  45

Ala Ala Asn Thr Trp Ser Gly Gly Pro Thr Tyr Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Glu Asp Thr Ala Val Tyr Gln Cys
                85                  90                  95

Ala Ala Arg Asp Tyr Arg Gly Ile Lys Asp Leu Asp Leu Lys Gly Asp
            100                 105                 110

Tyr Asp Tyr Trp Gly Gln Gly Thr Gln Val Thr Val Ser Ser Ala Ala
        115                 120                 125
```

Ala Tyr Pro Tyr Asp Val Pro Asp Tyr Gly Ser His His His His His
130 135 140

His
145

<210> SEQ ID NO 332
<211> LENGTH: 151
<212> TYPE: PRT
<213> ORGANISM: Artificial Sequence
<220> FEATURE:
<223> OTHER INFORMATION: Synthetic Sequence

<400> SEQUENCE: 332

Gln Val Gln Leu Gln Glu Ser Gly Gly Gly Leu Val Gln Ala Gly Asp
1 5 10 15

Ser Leu Lys Leu Ser Cys Ala Thr Ser Gly Arg Ser Phe Ser Ser Tyr
20 25 30

Thr Ile Ala Trp Phe Arg Gln Ala Pro Gly Lys Glu Arg Glu Gly Ile
35 40 45

Ser Cys Ile Ser Ser Asp Gly Ser Thr Gly Tyr Ala Asp Ser Val Arg
50 55 60

Gly Arg Phe Thr Ile Ser Ser Asp Asn Ala Lys Asn Thr Val Tyr Leu
65 70 75 80

Gln Met Asn Ser Leu Lys Pro Glu Asp Thr Ala Val Tyr Tyr Cys Ala
85 90 95

Ala Asp Phe Asn Val Trp Ser Pro Pro Ile Cys Gly Ser Ile Trp Tyr
100 105 110

Gly Pro Pro Pro Arg Gly Met Asp Tyr Trp Gly Lys Gly Thr Gln Val
115 120 125

Thr Val Ser Ser Ala Ala Ala Tyr Pro Tyr Asp Val Pro Asp Tyr Gly
130 135 140

Ser His His His His His His
145 150

<210> SEQ ID NO 333
<211> LENGTH: 152
<212> TYPE: PRT
<213> ORGANISM: Artificial Sequence
<220> FEATURE:
<223> OTHER INFORMATION: Synthetic Sequence

<400> SEQUENCE: 333

Gln Val Gln Leu Gln Glu Ser Gly Gly Gly Leu Val Gln Ala Gly Gly
1 5 10 15

Tyr Leu Arg Leu Ser Cys Ala Ala Ser Gly Phe Ser Ser Asp Asp Tyr
20 25 30

Thr Ile Gly Trp Phe Arg Gln Ala Pro Gly Lys Glu Arg Glu Gly Ile
35 40 45

Ser Cys Tyr Ser Ser Ser Asp Gly Ser Thr Gly Phe Ala Asp Ser Val
50 55 60

Lys Gly Arg Phe Thr Ile Ser Ser Asp Asn Ala Lys Asn Thr Val Tyr
65 70 75 80

Leu Gln Met Asn Asn Leu Arg Pro Glu Asp Thr Ala Val Tyr Tyr Cys
85 90 95

Ala Ala Asp Ser Asn Val Trp Ser Pro Pro Ile Cys Gly Ser Arg Trp
100 105 110

Tyr Gly Pro Pro Pro Gly Gly Met Ala Tyr Trp Gly Lys Gly Thr Gln

```
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 334
<211> LENGTH: 151
<212> TYPE: PRT
<213> ORGANISM: Artificial Sequence
<220> FEATURE:
<223> OTHER INFORMATION: Synthetic Sequence

<400> SEQUENCE: 334

Gln Val Gln Leu Gln Glu Ser Gly Gly Gly Leu Ala Gln Val Gly Gly
1               5                   10                  15

Ser Leu Arg Leu Ser Cys Thr Ala Ser Gly Phe Thr Phe Asp Asp Tyr
            20                  25                  30

Thr Ile Gly Trp Phe Arg Gln Ala Pro Gly Lys Glu Arg Glu Gly Ile
        35                  40                  45

Ser Cys Ile Ser Ser Asp Gly Ser Thr Gly Tyr Ala Asp Ser Val Lys
    50                  55                  60

Gly Arg Phe Thr Ile Ser Ser Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Asp Phe Asn Val Trp Ser Pro Pro Ile Cys Gly Ser Asn Trp Tyr
            100                 105                 110

Gly Pro Pro Pro Gly Gly Met Asp Tyr Trp Gly Lys Gly Thr Gln Val
        115                 120                 125

Thr Val Ser Ser Ala Ala Ala Tyr Pro Tyr Asp Val Pro Asp Tyr Gly
    130                 135                 140

Ser His His His His His His
145                 150


<210> SEQ ID NO 335
<211> LENGTH: 152
<212> TYPE: PRT
<213> ORGANISM: Artificial Sequence
<220> FEATURE:
<223> OTHER INFORMATION: Synthetic Sequence

<400> SEQUENCE: 335

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ser Ser Asp Asp Tyr
            20                  25                  30

Thr Ile Gly Trp Phe Arg Gln Ala Pro Gly Lys Glu Arg Glu Gly Ile
        35                  40                  45

Gly Cys Ile Lys Ser Ser Asp Gly Thr Thr Gly Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Phe Asn Val Trp Ser Pro Pro Ile Cys Gly Ser Ile Trp
            100                 105                 110
```

```
Tyr Gly Pro Pro Pro Gly Gly Met Asp Tyr Trp Gly Lys Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 336
<211> LENGTH: 150
<212> TYPE: PRT
<213> ORGANISM: Artificial Sequence
<220> FEATURE:
<223> OTHER INFORMATION: Synthetic Sequence

<400> SEQUENCE: 336

Gln Val Gln Leu Gln Glu Ser Gly Gly Gly Leu Ala Gln Ala Gly Gly
1               5                   10                  15

Ser Leu Arg Leu Ser Cys Ala Ala Ser Gly Phe Thr Phe Asp Gln Tyr
            20                  25                  30

Thr Ile Ala Trp Phe Arg Gln Ala Pro Gly Lys Glu Arg Glu Gly Val
        35                  40                  45

Ser Cys Ile Ser Asn Thr Asp Ser Ser Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Ser Ser Leu Lys Pro Glu Asp Thr Ala Val Tyr Tyr Cys
                85                  90                  95

Ala Ala Asp Gly Asn Val Trp Ser Pro Pro Ile Cys Gly Ser Ala Gly
            100                 105                 110

Pro Pro Pro Gly Gly Met Asp Tyr Trp Gly Lys Gly Thr Gln Val Thr
        115                 120                 125

Val Ser Ser Ala Ala Ala Tyr Pro Tyr Asp Val Pro Asp Tyr Gly Ser
    130                 135                 140

His His His His His His
145                 150


<210> SEQ ID NO 337
<211> LENGTH: 144
<212> TYPE: PRT
<213> ORGANISM: Artificial Sequence
<220> FEATURE:
<223> OTHER INFORMATION: Synthetic Sequence

<400> SEQUENCE: 337

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Ala Trp Phe Arg Gln Ala Pro Gly Lys Glu Arg Glu Phe Val
        35                  40                  45

Ala Ala Ile Ala Trp Ser Ala Gly Ser Thr Tyr Tyr Ala Asp Ser Val
    50                  55                  60

Lys Gly Arg Phe Ala Ile Ser Arg Asp Asn Ala Glu Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Ile Ile Thr Val Ala Thr Met Arg Leu Asp Ser Asp Tyr
            100                 105                 110
```

```
Asp Tyr Trp Gly Gln Gly Thr Gln Val Thr Val Ser Ser Ala Ala Ala
        115                 120                 125

Tyr Pro Tyr Asp Val Pro Asp Tyr Gly Ser His His His His His His
    130                 135                 140


<210> SEQ ID NO 338
<211> LENGTH: 150
<212> TYPE: PRT
<213> ORGANISM: Artificial Sequence
<220> FEATURE:
<223> OTHER INFORMATION: Synthetic Sequence

<400> SEQUENCE: 338

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ala Phe Asp Gly Tyr
            20                  25                  30

Ala Ile Gly Trp Phe Arg Gln Ala Pro Gly Lys Glu Arg Glu Gly Val
        35                  40                  45

Ser Cys Ile Ser Ser Lys Glu Gly Ser Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Ser Ser Leu Lys Pro Glu Asp Thr Ala Val Tyr Tyr Cys
                85                  90                  95

Ala Ala Asp Gly Asn Val Trp Ser Pro Pro Ile Cys Gly Ser Ala Gly
            100                 105                 110

Pro Pro Pro Gly Gly Met Asp Tyr Trp Gly Lys Gly Thr Gln Val Thr
        115                 120                 125

Val Ser Ser Ala Ala Ala Tyr Pro Tyr Asp Val Pro Asp Tyr Gly Ser
    130                 135                 140

His His His His His His
145                 150


<210> SEQ ID NO 339
<211> LENGTH: 152
<212> TYPE: PRT
<213> ORGANISM: Artificial Sequence
<220> FEATURE:
<223> OTHER INFORMATION: Synthetic Sequence

<400> SEQUENCE: 339

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ser Ser Asp Asp Tyr
            20                  25                  30

Thr Ile Ala Trp Phe Arg Arg Ala Pro Gly Lys Glu Arg Glu Gly Ile
        35                  40                  45

Ser Cys Ile Ser Ser Ser Asp Gly Ser Thr Gly Tyr Ala Asp Ser Val
    50                  55                  60

Lys Gly Arg Phe Thr Ile Thr Ser Asp Ser Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Ser Asn Val Trp Ser Pro Pro Ile Cys Gly Arg Thr Trp
            100                 105                 110

Tyr Gly Pro Pro Pro Gly Gly Met Asp Tyr Trp Gly Lys Gly Thr Gln
```

```
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 340
<211> LENGTH: 152
<212> TYPE: PRT
<213> ORGANISM: Artificial Sequence
<220> FEATURE:
<223> OTHER INFORMATION: Synthetic Sequence

<400> SEQUENCE: 340

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Ser Asp Asp Tyr
            20                  25                  30

Thr Ile Gly Trp Phe Arg Gln Ala Pro Gly Lys Glu Arg Glu Gly Ile
        35                  40                  45

Ser Cys Tyr Ser Ser Arg Asp Gly Thr Thr Gly Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Phe Asn Val Trp Ser Pro Pro Ile Cys Gly Ser Ile Trp
            100                 105                 110

Tyr Gly Pro Pro Pro Gly Gly Met Ala Tyr Trp Gly Gln Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 341
<211> LENGTH: 151
<212> TYPE: PRT
<213> ORGANISM: Artificial Sequence
<220> FEATURE:
<223> OTHER INFORMATION: Synthetic Sequence

<400> SEQUENCE: 341

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Thr Ile Gly Trp Phe Arg Gln Ala Pro Gly Lys Glu Arg Glu Gly Ile
        35                  40                  45

Ser Cys Ile Ser Ser Asp Gly Ser Thr Gly Tyr Ala Asp Ser Val Lys
    50                  55                  60

Gly Arg Phe Thr Ile Ser Ser Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Asp Phe Asn Val Trp Ser Pro Pro Ile Cys Gly Ser Asn Trp Tyr
            100                 105                 110
```

Gly Pro Pro Pro Gly Gly Met Asp Tyr Trp Gly Lys Gly Thr Gln Val
115 120 125

Thr Val Ser Ser Ala Ala Ala Tyr Pro Tyr Asp Val Pro Asp Tyr Gly
130 135 140

Ser His His His His His His
145 150

<210> SEQ ID NO 342
<211> LENGTH: 152
<212> TYPE: PRT
<213> ORGANISM: Artificial Sequence
<220> FEATURE:
<223> OTHER INFORMATION: Synthetic Sequence

<400> SEQUENCE: 342

Gln Val Gln Leu Gln Glu Ser Gly Gly Gly Leu Val Gln Ala Gly Gly
1 5 10 15

Ser Leu Arg Leu Ser Cys Ala Ala Ser Gly Phe Ser Ser Asp Asp Tyr
20 25 30

Thr Ile Gly Trp Phe Arg Gln Ala Pro Gly Lys Glu Arg Glu Gly Ile
35 40 45

Ser Cys Tyr Ser Ser Ser Asp Gly Ser Thr Gly Tyr Ala Asp Ser Val
50 55 60

Lys Gly Arg Phe Thr Ile Ser Ser Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Asp Phe Asn Val Trp Ser Pro Pro Ile Cys Gly Ser Ser Trp
100 105 110

Tyr Gly Pro Pro Pro Gly Gly Met Asp Tyr Trp Gly Lys Gly Thr Gln
115 120 125

Val Thr Val Ser Ser Ala Ala Ala Tyr Pro Tyr Asp Val Pro Asp Tyr
130 135 140

Gly Ser His His His His His His
145 150

<210> SEQ ID NO 343
<211> LENGTH: 152
<212> TYPE: PRT
<213> ORGANISM: Artificial Sequence
<220> FEATURE:
<223> OTHER INFORMATION: Synthetic Sequence

<400> SEQUENCE: 343

Gln Val Gln Leu Gln Glu Ser Gly Gly Gly Leu Val Gln Ala Gly Gly
1 5 10 15

Ser Leu Arg Leu Ser Cys Ala Ala Ser Gly Phe Ser Ser Asp Asp Tyr
20 25 30

Thr Ile Gly Trp Phe Arg Gln Ala Pro Gly Lys Glu Arg Glu Gly Ile
35 40 45

Ser Cys Phe Ser Ser Ser Asp Gly Ser Thr Gly Phe Ala Asp Ser Val
50 55 60

Lys Gly Arg Phe Thr Ile Ser Ser Asp Asn Ala Thr Asn Thr Val Tyr
65 70 75 80

Leu Glu Met Asn Ser Leu Lys Pro Glu Asp Thr Ala Val Tyr Tyr Cys
85 90 95

Ala Ala Asp Phe Asn Val Trp Ser Pro Pro Ile Cys Gly Ser Arg Trp
100 105 110

```
Tyr Gly Pro Pro Pro Gly Gly Met Glu Tyr Trp Gly Lys Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 344
<211> LENGTH: 150
<212> TYPE: PRT
<213> ORGANISM: Artificial Sequence
<220> FEATURE:
<223> OTHER INFORMATION: Synthetic Sequence

<400> SEQUENCE: 344

Gln Val Gln Leu Gln Glu Ser Gly Gly Gly Leu Val Gln Ala Gly Gly
1               5                   10                  15

Ser Leu Arg Leu Ser Cys Ala Thr Phe Gly Phe Ser Phe Asp Asp Tyr
            20                  25                  30

Ala Ile Ala Trp Phe Arg Gln Ala Pro Gly Lys Glu Arg Glu Gly Ile
        35                  40                  45

Ser Cys Ile Ser Asn Thr Asp Ser Ser Thr Phe Tyr Ala Asp Ser Val
    50                  55                  60

Lys Gly Arg Phe Thr Ile Ser Ser Asp Asn Ala Lys Asn Thr Val His
65                  70                  75                  80

Leu Gln Met Ser Ser Leu Lys Pro Glu Asp Thr Ala Val Tyr Tyr Cys
                85                  90                  95

Ala Ala Asp Gly Asn Val Trp Ser Pro Pro Ile Cys Gly Ser Ala Gly
            100                 105                 110

Pro Pro Pro Gly Gly Met Asp Tyr Trp Gly Lys Gly Thr Gln Val Thr
        115                 120                 125

Val Ser Ser Ala Ala Ala Tyr Pro Tyr Asp Val Pro Asp Tyr Gly Ser
    130                 135                 140

His His His His His His
145                 150


<210> SEQ ID NO 345
<211> LENGTH: 152
<212> TYPE: PRT
<213> ORGANISM: Artificial Sequence
<220> FEATURE:
<223> OTHER INFORMATION: Synthetic Sequence

<400> SEQUENCE: 345

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ser Ser Asp Asp Tyr
            20                  25                  30

Thr Ile Gly Trp Phe Arg Gln Ala Pro Gly Lys Glu Arg Glu Gly Ile
        35                  40                  45

Ser Cys Tyr Ser Ser Ser Asp Gly Ser Thr Gly Phe Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Phe Asn Val Trp Ser Pro Pro Ile Cys Gly Ser Arg Trp
```

```
            100                 105                 110

Tyr Gly Pro Pro Pro Gly Gly Met Ala Tyr Trp Gly Lys Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 346
<211> LENGTH: 151
<212> TYPE: PRT
<213> ORGANISM: Artificial Sequence
<220> FEATURE:
<223> OTHER INFORMATION: Synthetic Sequence

<400> SEQUENCE: 346

Gln Val Gln Leu Gln Glu Ser Gly Gly Gly Leu Val Gln Val Gly Gly
1               5                   10                  15

Ser Leu Arg Leu Ser Cys Thr Ile Ser Gly Phe Thr Gly Asn Asp Leu
            20                  25                  30

Ala Ile Gly Trp Phe Arg Gln Ala Pro Gly Lys Asp Gln Arg Glu Gly
        35                  40                  45

Ile Ser Cys Ile Ser Asn Thr Asp Ser Ser Thr Tyr Tyr Ala Asp Ser
    50                  55                  60

Val Lys Gly Arg Phe Thr Ile Ser Ser Asp Asn Ala Lys Asn Thr Val
65                  70                  75                  80

His Leu Gln Met Ser Ser Leu Lys Pro Glu Asp Thr Ala Val Tyr Tyr
                85                  90                  95

Cys Ala Ala Asp Gly Asn Val Trp Ser Pro Pro Ile Cys Gly Ser Ala
            100                 105                 110

Gly Pro Pro Pro Gly Gly Met Asp Tyr Trp Gly Lys Gly Thr Gln Val
        115                 120                 125

Thr Val Ser Ser Ala Ala Ala Tyr Pro Tyr Asp Val Pro Asp Tyr Gly
    130                 135                 140

Ser His His His His His His
145                 150


<210> SEQ ID NO 347
<211> LENGTH: 152
<212> TYPE: PRT
<213> ORGANISM: Artificial Sequence
<220> FEATURE:
<223> OTHER INFORMATION: Synthetic Sequence

<400> SEQUENCE: 347

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ser Ser Asp Asp Tyr
            20                  25                  30

Thr Ile Ala Trp Phe Arg Arg Ala Pro Gly Lys Glu Arg Glu Gly Ile
        35                  40                  45

Ser Cys Ile Ser Ser Ser Asp Gly Ser Thr Gly Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Thr Ser Leu Lys Pro Glu Asp Thr Ala Val Tyr Tyr Cys
                85                  90                  95
```

```
Ala Ala Asp Ser Asn Val Trp Ser Pro Pro Ile Cys Gly Lys Thr Trp
            100                 105                 110

Tyr Gly Pro Pro Pro Gly Gly Met Asp Tyr Trp Gly Lys Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150
```

<210> SEQ ID NO 348
<211> LENGTH: 140
<212> TYPE: PRT
<213> ORGANISM: Artificial Sequence
<220> FEATURE:
<223> OTHER INFORMATION: Synthetic Sequence

<400> SEQUENCE: 348

```
Gln Val Gln Leu Gln Glu Ser Gly Gly Gly Leu Val Gln Ala Gly Asp
1               5                   10                  15

Ser Leu Arg Leu Ser Cys Ala Gly Ser Glu Gly Thr Leu Ser Ser Tyr
            20                  25                  30

Gly Ile Gly Trp Phe Arg Gln Ala Pro Gly Lys Glu Arg Glu Phe Val
        35                  40                  45

Gly Gly Ile Asn Trp Ser Gly Asp Ser Thr Asp Tyr Ala Asp Ser Val
    50                  55                  60

Lys Gly Arg Phe Thr Ile Ser Arg Asp Ser Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Glu Ser Gly Val Trp Val Gly Gly Leu Asp Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
    130                 135                 140
```

<210> SEQ ID NO 349
<211> LENGTH: 152
<212> TYPE: PRT
<213> ORGANISM: Artificial Sequence
<220> FEATURE:
<223> OTHER INFORMATION: Synthetic Sequence

<400> SEQUENCE: 349

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ser Ser Asp Asp Tyr
            20                  25                  30

Thr Ile Ala Trp Phe Arg Arg Ala Pro Gly Lys Glu Arg Glu Gly Ile
        35                  40                  45

Ser Cys Phe Ser Ser Ser Asp Gly Ser Ala Gly Tyr Ala Asp Ser Val
    50                  55                  60

Lys Gly Arg Phe Thr Val Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Ser Asn Val Trp Ser Pro Pro Ile Cys Gly Ser Thr Trp
            100                 105                 110
```

Tyr Gly Pro Pro Pro Gly Gly Met Ala Tyr Trp Gly Lys Gly Thr Gln
115 120 125

Val Thr Val Ser Ser Ala Ala Ala Tyr Pro Tyr Asp Val Pro Asp Tyr
130 135 140

Gly Ser His His His His His His
145 150

<210> SEQ ID NO 350
<211> LENGTH: 150
<212> TYPE: PRT
<213> ORGANISM: Artificial Sequence
<220> FEATURE:
<223> OTHER INFORMATION: Synthetic Sequence

<400> SEQUENCE: 350

Gln Val Gln Leu Gln Glu Ser Gly Gly Gly Leu Val Gln Ala Gly Gly
1 5 10 15

Ser Leu Arg Leu Ser Cys Ala Thr Ser Gly Phe Thr Phe Asp Asp Tyr
20 25 30

Ala Ile Ala Trp Phe Arg Gln Ala Pro Gly Lys Glu Arg Glu Gly Val
35 40 45

Ser Cys Ile Ser Asn Thr Asp Ser Ser Thr Tyr Tyr Ala Asp Ser Val
50 55 60

Lys Gly Arg Phe Thr Ile Ser Ser Asp Asn Ala Lys Asn Thr Val Tyr
65 70 75 80

Leu Gln Met Ser Ser Leu Lys Pro Glu Asp Thr Ala Val Tyr Tyr Cys
85 90 95

Ala Ala Asp Gly Asn Val Trp Ser Pro Pro Ile Cys Gly Ser Ala Gly
100 105 110

Pro Pro Pro Gly Gly Met Asp Tyr Trp Gly Lys Gly Thr Gln Val Thr
115 120 125

Val Ser Ser Ala Ala Ala Tyr Pro Tyr Asp Val Pro Asp Tyr Gly Ser
130 135 140

His His His His His His
145 150

<210> SEQ ID NO 351
<211> LENGTH: 152
<212> TYPE: PRT
<213> ORGANISM: Artificial Sequence
<220> FEATURE:
<223> OTHER INFORMATION: Synthetic Sequence

<400> SEQUENCE: 351

Gln Val Gln Leu Gln Glu Ser Gly Gly Gly Leu Val Gln Ala Gly Gly
1 5 10 15

Ser Leu Arg Leu Ser Cys Glu Val Ser Gly Leu Ser Ser Asp Asp Tyr
20 25 30

Thr Ile Gly Trp Phe Arg Gln Ala Pro Gly Lys Glu Arg Glu Gly Phe
35 40 45

Ser Cys Phe Ser Thr Arg Asp Gly Asn Ala Gly Tyr Ala Asp Ser Val
50 55 60

Lys Gly Arg Phe Thr Ile Ser Ser Asp Asn Ala Lys Asn Thr Val Tyr
65 70 75 80

Leu Gln Met Asn Asn Leu Lys Pro Glu Asp Thr Ala Val Tyr Tyr Cys
85 90 95

Ala Ala Asp Phe Asn Val Trp Ser Pro Pro Ile Cys Gly Ser Arg Trp

```
            100                 105                 110

Tyr Gly Pro Pro Pro Gly Gly Met Asp Tyr Trp Gly Lys Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 352
<211> LENGTH: 152
<212> TYPE: PRT
<213> ORGANISM: Artificial Sequence
<220> FEATURE:
<223> OTHER INFORMATION: Synthetic Sequence

<400> SEQUENCE: 352

Gln Val Gln Leu Gln Glu Ser Gly Gly Gly Leu Val Gln Ala Gly Gly
1               5                   10                  15

Ser Leu Arg Leu Ser Cys Glu Val Ser Gly Leu Ser Ser Asp Asp Tyr
            20                  25                  30

Thr Ile Gly Trp Phe Arg Gln Ala Pro Gly Lys Lys Arg Glu Gly Phe
        35                  40                  45

Ser Cys Phe Ser Ser Arg Asp Gly Ser Thr Gly Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Phe Asn Val Trp Ser Pro Pro Ile Cys Gly Ser Arg Trp
            100                 105                 110

Tyr Gly Pro Pro Pro Gly Gly Met Asp Tyr Trp Gly Lys Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 353
<211> LENGTH: 152
<212> TYPE: PRT
<213> ORGANISM: Artificial Sequence
<220> FEATURE:
<223> OTHER INFORMATION: Synthetic Sequence

<400> SEQUENCE: 353

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ser Ser Asp Asp Tyr
            20                  25                  30

Thr Ile Gly Trp Phe Arg Gln Ala Pro Gly Lys Glu Arg Glu Gly Phe
        35                  40                  45

Ser Cys Phe Ser Ser Arg Asp Gly Ser Thr Gly Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95
```

Ala Ala Asp Phe Asn Val Trp Ser Pro Pro Ile Cys Gly Ser Arg Trp
100 105 110

Tyr Gly Pro Pro Pro Gly Gly Met Asp Tyr Trp Gly Lys Gly Thr Gln
115 120 125

Val Thr Val Ser Ser Ala Ala Ala Tyr Pro Tyr Asp Val Pro Asp Tyr
130 135 140

Gly Ser His His His His His His
145 150

<210> SEQ ID NO 354
<211> LENGTH: 151
<212> TYPE: PRT
<213> ORGANISM: Artificial Sequence
<220> FEATURE:
<223> OTHER INFORMATION: Synthetic Sequence

<400> SEQUENCE: 354

Gln Val Gln Leu Gln Glu Ser Gly Gly Gly Leu Val Gln Ala Gly Gly
1 5 10 15

Ser Leu Arg Leu Ser Cys Ala Ala Ser Gly Phe Ser Phe Asp Asp Tyr
20 25 30

Thr Ile Gly Trp Phe Arg Gln Val Pro Gly Lys Glu Arg Glu Gly Ile
35 40 45

Ser Cys Ile Ser Ser Asp Gly Ser Thr Gly Tyr Ala Asp Ser Val Lys
50 55 60

Gly Arg Phe Thr Ile Ser Ser Asp Asn Ala Lys Asn Thr Val Tyr Leu
65 70 75 80

Gln Ile Asn Ser Leu Lys Pro Glu Asp Thr Ala Val Tyr Tyr Cys Ala
85 90 95

Ala Asp Phe Asn Val Trp Ser Pro Pro Ile Cys Gly Ser Ile Trp Tyr
100 105 110

Gly Pro Pro Pro Gly Gly Met Asp Tyr Trp Gly Lys Gly Thr Gln Val
115 120 125

Thr Val Ser Ser Ala Ala Ala Tyr Pro Tyr Asp Val Pro Asp Tyr Gly
130 135 140

Ser His His His His His His
145 150

<210> SEQ ID NO 355
<211> LENGTH: 150
<212> TYPE: PRT
<213> ORGANISM: Artificial Sequence
<220> FEATURE:
<223> OTHER INFORMATION: Synthetic Sequence

<400> SEQUENCE: 355

Gln Val Gln Leu Gln Glu Ser Gly Gly Gly Leu Val Gln Ala Gly Gly
1 5 10 15

Ser Leu Arg Leu Ser Cys Ala Thr Phe Gly Phe Thr Phe Asp Asp Tyr
20 25 30

Ala Ile Ala Trp Phe Arg Gln Ala Pro Gly Lys Glu Arg Glu Gly Ile
35 40 45

Ser Cys Ile Ser Asn Thr Asp Ser Ser Thr Tyr Tyr Ala Asp Ser Val
50 55 60

Lys Gly Arg Phe Thr Ile Ser Ser Asp Asn Ala Lys Asn Thr Val His
65 70 75 80

Leu Gln Met Ser Ser Leu Lys Pro Glu Asp Thr Ala Val Tyr Tyr Cys
85 90 95

```
Ala Ala Asp Gly Asn Val Trp Ser Pro Pro Ile Cys Gly Ser Ala Gly
            100                 105                 110

Pro Pro Pro Gly Gly Met Asp Tyr Trp Gly Lys Gly Thr Gln Val Thr
        115                 120                 125

Val Ser Ser Ala Ala Ala Tyr Pro Tyr Asp Val Pro Asp Tyr Gly Ser
    130                 135                 140

His His His His His His
145                 150
```

```
<210> SEQ ID NO 356
<211> LENGTH: 150
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (19)..(19)
<223> OTHER INFORMATION: Xaa can be any naturally occurring amino acid

<400> SEQUENCE: 356

Gln Val Gln Leu Gln Glu Ser Gly Gly Gly Leu Val Gln Ala Gly Gly
1               5                   10                  15

Ser Leu Xaa Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Cys Ile Ser Ser Pro Asp Gly Ser Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Phe Asn Val Trp Ser Pro Pro Ile Cys Gly Ser Val Gly
            100                 105                 110

Pro Pro Pro Gly Gly Met Asp Tyr Trp Gly Lys Gly Thr Gln Val Thr
        115                 120                 125

Val Ser Ser Ala Ala Ala Tyr Pro Tyr Asp Val Pro Asp Tyr Gly Ser
    130                 135                 140

His His His His His His
145                 150
```

```
<210> SEQ ID NO 357
<211> LENGTH: 152
<212> TYPE: PRT
<213> ORGANISM: Artificial Sequence
<220> FEATURE:
<223> OTHER INFORMATION: Synthetic Sequence

<400> SEQUENCE: 357

Gln Val Gln Leu Gln Glu Ser Gly Gly Gly Leu Val Gln Ala Gly Ala
1               5                   10                  15

Ser Leu Arg Leu Ser Cys Lys Ala Ser Gly Phe Thr Phe Gly Asp Tyr
            20                  25                  30

Thr Ile Gly Trp Phe Arg Gln Ala Pro Gly Lys Glu Arg Glu Gly Ile
        35                  40                  45

Ser Cys Tyr Ser Ser Ser Asp Gly Asn Thr Gly Tyr Ala Asp Ser Val
    50                  55                  60
```

```
Lys Gly Arg Phe Thr Ile Ser Ser Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Phe Asn Val Trp Ser Pro Pro Ile Cys Gly Ser Ser Trp
            100                 105                 110

Tyr Gly Pro Pro Pro Gly Gly Met Ala Tyr Trp Gly Lys Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150
```

```
<210> SEQ ID NO 358
<211> LENGTH: 140
<212> TYPE: PRT
<213> ORGANISM: Artificial Sequence
<220> FEATURE:
<223> OTHER INFORMATION: Synthetic Sequence

<400> SEQUENCE: 358

Gln Val Gln Leu Gln Glu Ser Gly Gly Gly Leu Val Gln Ala Gly Asp
1               5                   10                  15

Ser Leu Arg Leu Ser Cys Ala Gly Ser Glu Gly Thr Phe Ser Ser Tyr
            20                  25                  30

Gly Ile Gly Trp Phe Arg Gln Ala Pro Gly Lys Glu Arg Glu Phe Val
        35                  40                  45

Gly Gly Ile Asn Trp Ser Gly Asp Ser Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Glu Ser Gly Val Trp Val Gly Gly Leu Asp Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
    130                 135                 140
```

```
<210> SEQ ID NO 359
<211> LENGTH: 152
<212> TYPE: PRT
<213> ORGANISM: Artificial Sequence
<220> FEATURE:
<223> OTHER INFORMATION: Synthetic Sequence

<400> SEQUENCE: 359

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ser Ser Asp Asp Tyr
            20                  25                  30

Thr Ile Gly Trp Phe Arg Gln Ala Pro Gly Lys Glu Arg Glu Gly Ile
        35                  40                  45

Ser Cys Phe Ser Ser Ser Asp Gly Ser Thr Gly Phe Ala Asp Ser Val
    50                  55                  60

Lys Gly Arg Phe Thr Ile Ser Ser Asp Asn Ala Thr Asn Thr Val Tyr
65                  70                  75                  80
```

Leu Gln Met Asn Ser Leu Lys Pro Glu Asp Thr Ala Val Tyr Tyr Cys
85 90 95

Ala Ala Asp Phe Asn Val Trp Ser Pro Pro Ile Cys Gly Ser Ser Trp
100 105 110

Tyr Gly Pro Pro Pro Gly Gly Met Glu Tyr Trp Gly Lys Gly Thr Gln
115 120 125

Val Thr Val Ser Ser Ala Ala Ala Tyr Pro Tyr Asp Val Pro Asp Tyr
130 135 140

Gly Ser His His His His His His
145 150

<210> SEQ ID NO 360
<211> LENGTH: 150
<212> TYPE: PRT
<213> ORGANISM: Artificial Sequence
<220> FEATURE:
<223> OTHER INFORMATION: Synthetic Sequence

<400> SEQUENCE: 360

Gln Val Gln Leu Gln Glu Ser Gly Gly Gly Leu Val Gln Ala Gly Asp
1 5 10 15

Ser Leu Arg Leu Ser Cys Thr Ala Ser Gly Val Ser Ile Gly Asp Tyr
20 25 30

Asn Ile Gly Trp Phe Arg Gln Ala Pro Gly Lys Glu Arg Glu Gly Val
35 40 45

Ser Cys Ile Ser Ser Gly Asp Gly Thr Thr Tyr Tyr Thr Asp Ser Val
50 55 60

Lys Gly Arg Phe Thr Ile Ser Thr Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Asp Gly Asn Val Trp Ser Pro Pro Ile Cys Gly Ser Ala Gly
100 105 110

Pro Pro Pro Gly Gly Met Asp Tyr Trp Gly Lys Gly Thr Gln Val Thr
115 120 125

Val Ser Ser Ala Ala Ala Tyr Pro Tyr Asp Val Pro Asp Tyr Gly Ser
130 135 140

His His His His His His
145 150

<210> SEQ ID NO 361
<211> LENGTH: 152
<212> TYPE: PRT
<213> ORGANISM: Artificial Sequence
<220> FEATURE:
<223> OTHER INFORMATION: Synthetic Sequence

<400> SEQUENCE: 361

Gln Val Gln Leu Gln Glu Ser Gly Gly Gly Leu Val Gln Ala Gly Gly
1 5 10 15

Ser Leu Arg Leu Ser Cys Ala Ala Ser Gly Phe Thr Phe Asp Asp Tyr
20 25 30

Thr Ile Ala Trp Phe Arg Gln Ala Pro Gly Gly Lys Glu Arg Glu Gly
35 40 45

Ile Ser Cys Ile Ser Ser Asp Gly Ser Thr Gly Tyr Ala Asp Ser Val
50 55 60

Lys Gly Arg Phe Thr Ile Ser Ser Asp Asn Ala Lys Asn Met Val Tyr

```
65                  70                  75                  80

Leu Gln Met Asn Ser Leu Lys Pro Glu Asp Thr Ala Leu Tyr Tyr Cys
                85                  90                  95

Ala Ala Asp Phe Asn Val Trp Ser Pro Pro Ile Cys Ser Ser Asn Trp
            100                 105                 110

Tyr Gly Pro Pro Pro Arg Gly Met Asp Tyr Trp Gly Lys Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 362
<211> LENGTH: 151
<212> TYPE: PRT
<213> ORGANISM: Artificial Sequence
<220> FEATURE:
<223> OTHER INFORMATION: Synthetic Sequence

<400> SEQUENCE: 362

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Thr Ile Ala Trp Phe Arg Gln Ala Pro Gly Lys Glu Arg Glu Gly Ile
        35                  40                  45

Ser Cys Ile Ser Ser Asp Gly Ser Thr Gly Tyr Ala Asp Ser Val Arg
    50                  55                  60

Gly Arg Phe Thr Ile Ser Ser Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Asp Phe Asn Val Trp Ser Pro Pro Ile Cys Gly Ser Ile Trp Tyr
            100                 105                 110

Gly Pro Pro Pro Arg Gly Met Asp Tyr Trp Gly Lys Gly Thr Gln Val
        115                 120                 125

Thr Val Ser Ser Ala Ala Ala Tyr Pro Tyr Asp Val Pro Asp Tyr Gly
    130                 135                 140

Ser His His His His His His
145                 150


<210> SEQ ID NO 363
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 363

His His His His His His
1               5


<210> SEQ ID NO 364
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 364
```

Tyr Pro Tyr Asp Val Pro Asp Tyr Gly Ser
1 5 10

<210> SEQ ID NO 365
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 365

Ala Ala Ala Tyr Pro Tyr Asp Val Pro Asp Tyr Gly Ser His His His
1 5 10 15

His His His

<210> SEQ ID NO 366
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 366

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Asp Pro Ala Asn Asp Asn Thr Leu Tyr Ala Ser Lys Phe
50 55 60

Gln Gly Arg Ala Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Gly Arg Gly Tyr Gly Tyr Tyr Val Phe Asp His Trp Gly Gln Gly Thr
100 105 110

Leu Val Thr Val Ser Ser
115

<210> SEQ ID NO 367
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 367

Gln Val Gln Leu Val Gln Ser Gly Ala Glu Val Lys Lys Pro Gly Ala
1 5 10 15

Thr Val Lys Ile Ser Cys Lys Val Ser Gly Phe Asn Ile Lys Asp Thr
20 25 30

Tyr Ile His Trp Val Gln Gln Ala Pro Gly Lys Gly Leu Glu Trp Met
35 40 45

Gly Arg Ile Asp Pro Ala Asn Asp Asn Thr Leu Tyr Ala Ser Lys Phe
50 55 60

Gln Gly Arg Val Thr Ile Thr Ala Asp Thr Ser Thr Asp Thr Ala Tyr
65 70 75 80

Met Glu Leu Ser Ser Leu Arg Ser Glu Asp Thr Ala Val Tyr Tyr Cys

```
                85                  90                  95

Ala Arg Gly Tyr Gly Tyr Tyr Val Phe Asp His Trp Gly Gln Gly Thr
            100                 105                 110

Leu Val Thr Val Ser Ser
        115


<210> SEQ ID NO 368
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 368

Asp Val Gln Ile Thr Gln Ser Pro Ser Ser Leu Ser Ala Ser Val Gly
1               5                   10                  15

Asp Arg Val Thr Ile Thr Cys Arg Thr Ser Arg Ser Ile Ser Gln Tyr
            20                  25                  30

Leu Ala Trp Tyr Gln Gln Lys Pro Gly Lys Val Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Asn Glu Asn Pro Leu
                85                  90                  95

Thr Phe Gly Gly Gly Thr Lys Val Glu Ile Lys
            100                 105


<210> SEQ ID NO 369
<211> LENGTH: 165
<212> TYPE: PRT
<213> ORGANISM: Artificial Sequence
<220> FEATURE:
<223> OTHER INFORMATION: Synthetic Sequence

<400> SEQUENCE: 369

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160
```

Leu Arg Ser Lys Glu
165

<210> SEQ ID NO 370
<211> LENGTH: 165
<212> TYPE: PRT
<213> ORGANISM: Artificial Sequence
<220> FEATURE:
<223> OTHER INFORMATION: Synthetic Sequence

<400> SEQUENCE: 370

Cys Asp Leu Pro Gln Thr His Ser Leu Gly Ser Arg Arg Thr Leu Met
1 5 10 15

Leu Leu Ala Gln Met Arg Arg Ile Ser Leu Phe Ser Cys Leu Lys Asp
20 25 30

Arg His Asp Phe Gly Phe Pro Gln Glu Glu Phe Gly Asn Gln Phe Gln
35 40 45

Lys Ala Glu Thr Ile Pro Val Leu His Glu Met Ile Gln Gln Ile Phe
50 55 60

Asn Leu Phe Ser Thr Lys Asp Ser Ser Ala Ala Trp Asp Glu Thr Leu
65 70 75 80

Leu Asp Lys Phe Tyr Thr Glu Leu Tyr Gln Gln Leu Asn Asp Leu Glu
85 90 95

Ala Cys Val Ile Gln Gly Val Gly Val Thr Glu Thr Pro Leu Met Lys
100 105 110

Glu Asp Ser Ile Leu Ala Val Arg Lys Tyr Phe Gln Arg Ile Thr Leu
115 120 125

Tyr Leu Lys Glu Lys Lys Tyr Ser Pro Cys Ala Trp Glu Val Val Arg
130 135 140

Ala Glu Ile Met Arg Ser Phe Ser Leu Ser Thr Asn Leu Gln Glu Ser
145 150 155 160

Leu Arg Ser Lys Glu
165

<210> SEQ ID NO 371
<211> LENGTH: 166
<212> TYPE: PRT
<213> ORGANISM: Artificial Sequence
<220> FEATURE:
<223> OTHER INFORMATION: Synthetic Sequence

<400> SEQUENCE: 371

Met Ser Tyr Asn Leu Leu Gly Phe Leu Gln Arg Ser Ser Asn Phe Gln
1 5 10 15

Cys Gln Lys Leu Leu Trp Gln Leu Asn Gly Arg Leu Glu Tyr Cys Leu
20 25 30

Lys Asp Arg Met Asn Phe Asp Ile Pro Glu Glu Ile Lys Gln Leu Gln
35 40 45

Gln Phe Gln Lys Glu Asp Ala Ala Leu Thr Ile Tyr Glu Met Leu Gln
50 55 60

Asn Ile Phe Ala Ile Phe Arg Gln Asp Ser Ser Ser Thr Gly Trp Asn
65 70 75 80

Glu Thr Ile Val Glu Asn Leu Leu Ala Asn Val Tyr His Gln Ile Asn
85 90 95

His Leu Lys Thr Val Leu Glu Glu Lys Leu Glu Lys Glu Asp Phe Thr
100 105 110

Arg Gly Lys Leu Met Ser Ser Leu His Leu Lys Arg Tyr Tyr Gly Arg
115 120 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 372
<211> LENGTH: 167
<212> TYPE: PRT
<213> ORGANISM: Artificial Sequence
<220> FEATURE:
<223> OTHER INFORMATION: Synthetic Sequence

<400> SEQUENCE: 372

Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
            20                  25                  30

Asp Arg His Asp Phe Gly Phe Pro Gln Glu Glu Phe Asp Gly Asn Gln
        35                  40                  45

Phe Gln Lys Ala Gln Ala Ile Ser Val Leu His Glu Met Ile Gln Gln
    50                  55                  60

Thr Phe Asn Leu Phe Ser Thr Lys Asp Ser Ser Ala Ala Trp Asp Glu
65                  70                  75                  80

Ser Leu Leu Glu Lys Phe Tyr Thr Glu Leu Tyr Gln Gln Leu Asn Asp
                85                  90                  95

Leu Glu Ala Cys Val Ile Gln Glu Val Gly Val Glu Glu Thr Pro Leu
            100                 105                 110

Met Asn Val Asp Ser Ile Leu Ala Val Lys Lys Tyr Phe Gln Arg Ile
        115                 120                 125

Thr Leu Tyr Leu Thr Glu Lys Lys Tyr Ser Pro Cys Ala Trp Glu Val
    130                 135                 140

Val Arg Ala Glu Ile Met Arg Ser Phe Ser Leu Ser Thr Asn Leu Gln
145                 150                 155                 160

Glu Arg Leu Arg Arg Lys Glu
                165

<210> SEQ ID NO 373
<211> LENGTH: 166
<212> TYPE: PRT
<213> ORGANISM: Artificial Sequence
<220> FEATURE:
<223> OTHER INFORMATION: Synthetic Sequence

<400> SEQUENCE: 373

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Trp Asp Glu Ser
65                  70                  75                  80

Leu Leu Glu Lys Phe Tyr Thr Glu Leu Tyr Gln Gln Leu Asn Asp Leu

```
                85                  90                  95

Glu Ala Cys Val Ile Gln Glu Val Gly Val Glu Glu Thr Pro Leu Met
            100                 105                 110

Asn Val Asp Ser Ile Leu Ala Val Lys Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Arg Leu Arg Arg Lys Glu
                165


<210> SEQ ID NO 374
<211> LENGTH: 166
<212> TYPE: PRT
<213> ORGANISM: Artificial Sequence
<220> FEATURE:
<223> OTHER INFORMATION: Synthetic Sequence

<400> SEQUENCE: 374

Cys Asp Leu Pro Gln Thr His Ser Leu Gly Asn Arg Arg Thr Leu Met
1               5                   10                  15

Leu Leu Ala Gln Met Arg Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Trp Asp Glu Ser
65                  70                  75                  80

Leu Leu Glu Lys Phe Tyr Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Lys Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Arg Leu Arg Arg Lys Glu
                165


<210> SEQ ID NO 375
<211> LENGTH: 166
<212> TYPE: PRT
<213> ORGANISM: Artificial Sequence
<220> FEATURE:
<223> OTHER INFORMATION: Synthetic Sequence

<400> SEQUENCE: 375

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45
```

```
Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Trp Asp Glu Ser
65                  70                  75                  80

Leu Leu Glu Lys Phe Tyr Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Arg Leu Arg Arg Lys Glu
                165


<210> SEQ ID NO 376
<211> LENGTH: 167
<212> TYPE: PRT
<213> ORGANISM: Artificial Sequence
<220> FEATURE:
<223> OTHER INFORMATION: Synthetic Sequence

<400> SEQUENCE: 376

Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
            20                  25                  30

Asp Arg His Asp Phe Gly Phe Pro Gln Glu Glu Phe Asp Gly Asn Gln
        35                  40                  45

Phe Gln Lys Ala Gln Ala Ile Ser Val Leu His Glu Met Ile Gln Gln
    50                  55                  60

Thr Phe Asn Leu Phe Ser Thr Lys Asp Ser Ser Ala Ala Trp Asp Glu
65                  70                  75                  80

Ser Leu Leu Glu Lys Phe Tyr Thr Glu Leu Tyr Gln Gln Leu Asn Asp
                85                  90                  95

Leu Glu Ala Cys Val Ile Gln Glu Val Gly Val Glu Glu Thr Pro Leu
            100                 105                 110

Met Asn Glu Asp Ser Ile Leu Ala Val Arg Lys Tyr Phe Gln Arg Ile
        115                 120                 125

Thr Leu Tyr Leu Thr Glu Lys Lys Tyr Ser Pro Cys Ala Trp Glu Val
    130                 135                 140

Val Arg Ala Glu Ile Met Arg Ser Phe Ser Leu Ser Thr Asn Leu Gln
145                 150                 155                 160

Glu Arg Leu Arg Arg Lys Glu
                165


<210> SEQ ID NO 377
<211> LENGTH: 167
<212> TYPE: PRT
<213> ORGANISM: Artificial Sequence
<220> FEATURE:
<223> OTHER INFORMATION: Synthetic Sequence

<400> SEQUENCE: 377

Met Cys Asp Leu Pro Gln Thr His Ser Leu Gly Asn Arg Arg Ala Leu
1               5                   10                  15
```

Ile Leu Leu Ala Gln Met Arg Arg Ile Ser Pro Phe Ser Cys Leu Lys
20 25 30

Asp Arg His Asp Phe Gly Phe Pro Gln Glu Glu Phe Asp Gly Asn Gln
35 40 45

Phe Gln Lys Ala Gln Ala Ile Ser Val Leu His Glu Met Ile Gln Gln
50 55 60

Thr Phe Asn Leu Phe Ser Thr Lys Asp Ser Ser Ala Ala Trp Asp Glu
65 70 75 80

Ser Leu Leu Glu Lys Phe Tyr Thr Glu Leu Tyr Gln Gln Leu Asn Asp
85 90 95

Leu Glu Ala Cys Val Ile Gln Glu Val Gly Val Glu Glu Thr Pro Leu
100 105 110

Met Asn Glu Asp Ser Ile Leu Ala Val Arg Lys Tyr Phe Gln Arg Ile
115 120 125

Thr Leu Tyr Leu Thr Glu Lys Lys Tyr Ser Pro Cys Ala Trp Glu Val
130 135 140

Val Arg Ala Glu Ile Met Arg Ser Phe Ser Leu Cys Thr Asn Leu Gln
145 150 155 160

Glu Arg Leu Arg Arg Lys Glu
165

<210> SEQ ID NO 378
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 378

Glu Glu Phe Gly Asn Gln
1 5

<210> SEQ ID NO 379
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 379

Glu Glu Phe Asp Gly Asn Gln
1 5

<210> SEQ ID NO 380
<211> LENGTH: 166
<212> TYPE: PRT
<213> ORGANISM: Artificial Sequence
<220> FEATURE:
<223> OTHER INFORMATION: Synthetic Sequence

<400> SEQUENCE: 380

Met Lys Tyr Thr Ser Tyr Ile Leu Ala Phe Gln Leu Cys Ile Val Leu
1 5 10 15

Gly Ser Leu Gly Cys Tyr Cys Gln Asp Pro Tyr Val Lys Glu Ala Glu
20 25 30

Asn Leu Lys Lys Tyr Phe Asn Ala Gly His Ser Asp Val Ala Asp Asn
35 40 45

Gly Thr Leu Phe Leu Gly Ile Leu Lys Asn Trp Lys Glu Glu Ser Asp
50 55 60

-continued

```
Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165


<210> SEQ ID NO 381
<211> LENGTH: 143
<212> TYPE: PRT
<213> ORGANISM: Artificial Sequence
<220> FEATURE:
<223> OTHER INFORMATION: Synthetic Sequence

<400> SEQUENCE: 381

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly Arg Arg Ala Ser Gln
    130                 135                 140
```